United States Patent
Yang et al.

(10) Patent No.: US 7,671,062 B2
(45) Date of Patent: *Mar. 2, 2010

(54) MODULATORS OF CHEMOKINE RECEPTOR ACTIVITY, CRYSTALLINE FORMS AND PROCESS

(75) Inventors: Michael G. Yang, Narbeth, PA (US); Robert J. Cherney, Newtown, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 70 days.

This patent is subject to a terminal disclaimer.

(21) Appl. No.: 11/782,704

(22) Filed: Jul. 25, 2007

(65) Prior Publication Data

US 2008/0027083 A1      Jan. 31, 2008

Related U.S. Application Data

(60) Provisional application No. 60/834,235, filed on Jul. 28, 2006, provisional application No. 60/896,026, filed on Mar. 21, 2007.

(51) Int. Cl.
*A61K 31/517* (2006.01)
(52) U.S. Cl. .................. 514/266.2; 544/283
(58) Field of Classification Search ............. 514/266.2; 544/283
See application file for complete search history.

(56) References Cited

U.S. PATENT DOCUMENTS

| | | | |
|---|---|---|---|
| 6,706,712 B2 | 3/2004 | Cherney |
| 6,974,836 B2 | 12/2005 | Carter et al. |
| 7,087,604 B2 | 8/2006 | Cherney |
| 7,157,470 B2 | 1/2007 | Smallheer et al. |
| 7,163,937 B2 | 1/2007 | Carter et al. |
| 7,183,270 B2 | 2/2007 | Cherney et al. |
| 7,230,133 B2 | 6/2007 | Carter |
| 2003/0171218 A1 | 9/2003 | Bojack et al. |
| 2004/0186143 A1 | 9/2004 | Carter et al. |
| 2004/0235836 A1 | 11/2004 | Cherney |
| 2005/0043392 A1 | 2/2005 | Carter |
| 2005/0054626 A1 | 3/2005 | Carter et al. |
| 2005/0054627 A1 | 3/2005 | Carter et al. |
| 2005/0065147 A1 | 3/2005 | Carter |
| 2006/0069123 A1 | 3/2006 | Xia et al. |
| 2007/0197516 A1 | 8/2007 | Carter |

FOREIGN PATENT DOCUMENTS

EP      0 550 924      7/1993

(Continued)

OTHER PUBLICATIONS

Abbadie, C. et al., "Impaired neuropathic pain responses in mice lacking the chemokine receptor CCR2", Proceedings of the National Academy of Sciences, vol. 100, No. 13, pp. 7947-7952 (2003).

(Continued)

Primary Examiner—James O Wilson
Assistant Examiner—Douglas M Willis
(74) *Attorney, Agent, or Firm*—Terence J. Bogie; Laurelee A. Duncan

(57) ABSTRACT

The present invention provides a novel antagonist or partial agonists/antagonists of MCP-1 receptor activity: N-((1R,2S,5R)-5-(isopropyl(methyl)amino)-2-((S)-2-oxo-3-(6-(trifluoromethyl)quinazolin-4-ylamino)pyrrolidin-1-yl)cyclohexyl) acetamide,

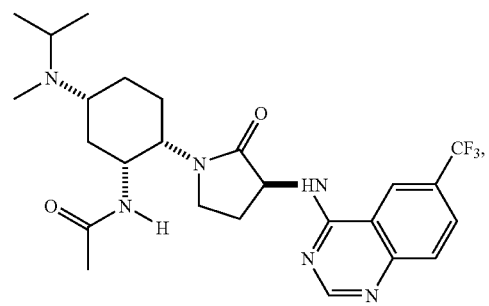

or a pharmaceutically acceptable salt, solvate or prodrug, thereof, having an unexpected combination of desirable pharmacological characteristics. Crystalline forms of the present invention are also provided. Pharmaceutical compositions containing the same and methods of using the same as agents for the treatment of inflammatory diseases, allergic, autoimmune, metabolic, cancer and/or cardiovascular diseases is also an objective of this invention. The present disclosure also provides a process for preparing compounds of Formula (I), including N-((1R,2S,5R)-5-(isopropyl(methyl)amino)-2-((S)-2-oxo-3-(6-(trifluoromethyl)quinazolin-4-ylamino)pyrrolidin-1-yl)cyclohexyl)acetamide:

I

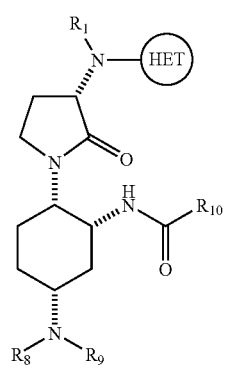

wherein $R^1$, $R^8$, $R^9$, $R^{10}$, and

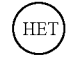

are as described herein. Compounds that are useful intermediates of the process are also provided herein.

9 Claims, 16 Drawing Sheets

FOREIGN PATENT DOCUMENTS

| | | |
|---|---|---|
| JP | 63-83082 | 4/1988 |
| WO | WO 97/05111 | 2/1997 |
| WO | WO 97/43257 | 11/1997 |
| WO | WO 98/01426 | 1/1998 |
| WO | WO 99/00362 | 1/1999 |
| WO | WO 99/07678 | 2/1999 |
| WO | WO 99/37304 | 7/1999 |
| WO | WO 99/38844 | 8/1999 |
| WO | WO 99/40914 | 8/1999 |
| WO | WO 99/46991 | 9/1999 |
| WO | WO 01/10799 | 2/2001 |
| WO | WO 01/17992 | 3/2001 |
| WO | WO 02/04416 | 1/2002 |
| WO | WO 02/060859 | 8/2002 |
| WO | WO 02/078679 | 10/2002 |
| WO | WO 02/102372 | 12/2002 |
| WO | WO 03/005824 | 1/2003 |
| WO | WO 03/075853 | 9/2003 |
| WO | WO 2004/022536 | 3/2004 |
| WO | WO 2004/071460 | 8/2004 |
| WO | WO 2004/098516 | 11/2004 |
| WO | WO 2004/110376 | 12/2004 |
| WO | WO 2005/021500 | 3/2005 |
| WO | WO 2006/013427 | 2/2006 |

OTHER PUBLICATIONS

Abdi, R. et al., "Differential Role of CCR2 in Islet and Heart Allograft Rejection: Tissue Specificity of Chemokine/Chemokine Receptor Function In Vivo", The Journal of Immunology, vol. 172, pp. 767-775 (2004).

Andres, P.G. et al., "Mice with a Selective Deletion of the CC Chemokine Receptors 5 or 2 are Protected from Dextran Sodium Sulfate-Mediated Colitis: Lack of CC Chemokine Receptor 5 Expression Results in a NK1.1$^+$Lymphocyte-Associated Th2-Type Immune Response in the Intestine", The Journal of Immunology, vol. 164, pp. 6303-6312 (2000).

Antoniades, H.N. et al., "Expression of monocyte chemoattractant protein 1 mRNA in human idiopathic pulmonary fibrosis", Proc. Natl. Acad. Sci. USA, vol. 89, pp. 5371-5375 (1992).

Baba, M. et al., "Identification of CCR6, the Specific Receptor for a Novel Lymphocyte-directed CC Chemokine LARC", The Journal of Biological Chemistry, vol. 272, No. 23, pp. 14893-14898 (1997).

Belperio, J.A. et al., "Critical role for the chemokine MCP-1/CCR2 in the pathogenesis of bronchiolitis obliterans syndrome", The Journal of Clinical Investigation, vol. 108, No. 4, pp. 547-556 (2001).

Berman, J.W. et al., "Localization of Monocyte Chemoattractant Peptide-1 Expression in the Central Nervous System in Experimental Autoimmune Encephalomyelitis and Trauma in the Rat", The Journal of Immunology, vol. 156, pp. 3017-3023 (1996).

Bonini, J.A. et al., "Cloning, Expression, and Chromosomal Mapping of a Novel Human CC-Chemokine Receptor (CCR10) that Displays High-Affinity Binding for MCP-1 and MCP-3", DNA and Cell Biology, vol. 16, No. 10, pp. 1249-1256 (1997).

Boring, L. et al., "Decreased lesion formation in CCR2$^{-/-}$ mice reveals a role for chemokines in the initiation of atherosclerosis", Nature, vol. 394, pp. 894-897 (1998).

Boring, L. et al., "Impaired Monocyte Migration and Reduced Type 1 (Th1) Cytokine Responses in C-C Chemokine Receptor 2 Knockout Mice", The Journal of Clinical Investigation, vol. 100, No. 10, pp. 2552-2561 (1997).

Brodmerkel, C.M. et al., "Discovery and Pharmacological Characterization of a Novel Rodent-Active CCR2 Antagonist, INCB3344", The Journal of Immunology, vol. 175, pp. 5370-5378 (2005).

Brühl, H. et al., "Dual Role of CCR2 during Initiation and Progression of Collagen-Induced Arthritis: Evidence for Regulatory Activity of CCR2$^+$ T Cells", The Journal of Immunology, vol. 172, pp. 890-898 (2004).

Bruun, J.M. et al., "Monocyte Chemoattractant Protein-1 Release is Higher in Visceral than Subcutaneous Human Adipose Tissue (AT): Implication of Macrophages Resident in the AT", The Journal of Clinical Endocrinology & Metabolism, vol. 90, No. 4, pp. 2282-2289 (2005).

Bush, E. et al., "CC Chemokine Receptor 2 is Required for Macrophage Infiltration and Vascular Hypertrophy in Angiotensin II-Induced Hypertension", Hypertension, vol. 36, pp. 360-363 (2000).

Carter, P.H., "Chemokine receptor antagonism as an approach to anti-inflammatory therapy: 'just right' or plain wrong?", Current Opinion in Chemical Biology, vol. 6, pp. 510-525 (2002).

Charo, I.F. et al., "Molecular cloning and functional expression of two monocyte chemoattractant protein 1 receptors reveals alternative splicing of the carboxyl-terminal tails", Proc. Natl. Acad. Sci. USA, vol. 91, pp. 2752-2756 (1994).

Charo, I.F. et al., "The Many Roles of Chemokines and Chemokine Receptors in Inflammation", The New England Journal of Medicine, vol. 354, No. 6, pp. 610-621 (2006).

Chen, A. et al., "Diet Induction of Monocyte Chemoattractant Protein-1 and its Impact on Obesity", Obesity Research, vol. 13, No. 8, pp. 1311-1320 (2005).

Chen, H., "Cellular inflammatory responses: Novel insights for obesity and insulin resistance", Pharmacological Research, vol. 53, pp. 469-477 (2006).

Chow, F.Y. et al., "Monocyte chemoattractant protein-1-induced tissue inflammation is critical for the development of renal injury but not type 2 diabetes in obese db/db mice", Diabetologia, vol. 50, pp. 471-480 (2007).

Cipollone, F. et al., "Elevated Circulating Levels of Monocyte Chemoattractant Protein-1 in Patients with Restenosis After Coronary Angioplasty", Arterioscler. Thromb. Vasc. Biol., vol. 21, pp. 327-334 (2001).

Combadiere, C. et al., "Cloning and Functional Expression of a Human Eosinophil CC Chemokine Receptor", The Journal of Biological Chemistry, vol. 270, No. 27, pp. 16491-16494 (1995).

Connor, R.I. et al., "Change in Coreceptor Use Correlates with Disease Progression in HIV-1-Infected Individuals", J. Exp. Med., vol. 185, No. 4, pp. 621-628 (1997).

Connor, S.J. et al., "CCR2 expressing CD4$^+$ lymphocytes are preferentially recruited to the ileum in Crohn's disease", Gut, vol. 53, pp. 1287-1294 (2004).

Conti, I. et al., "CCL2 (monocyte chemoattractant protein-1) and cancer", Seminars in Cancer Biology, vol. 14, pp. 149-154 (2004).

Costain, W.J. et al., "Modulatory effects of PLG and its peptidomimetics on haloperidol-induced catalepsy in rats", Peptides, vol. 20, pp. 761-767 (1999).

Craig, M.J. et al., "CCL2 (Monocyte Chemoattractant Protein-1) in cancer bone metastases", Cancer Metastasis Rev., vol. 25, pp. 611-619 (2006).

Dandona, P. et al., "A Rational Approach to Pathogenesis and Treatment of Type 2 Diabetes Mellitus, Insulin Resistance, Inflammation, and Atherosclerosis", The American Journal of Cardiology, vol. 90, No. 5A, pp. 27G-33G (2002).

Dawson, J. et al., "Targeting monocyte chemoattractant protein-1 signalling in disease", Expert Opin. Ther. Targets, vol. 7, No. 1, pp. 35-48 (2003).

Dawson, T.C. et al., "Absence of CC chemokine receptor-2 reduces atherosclerosis in apolipoprotein E-deficient mice", Atherosclerosis, vol. 143, pp. 205-211 (1999).

Deleuran, M. et al., "Localization of monocyte chemotactic and activating factor (MCAF/MCP-1) in psoriasis", Journal of Dermatological Science, vol. 13, pp. 228-236 (1996).

Dimitrijevic, O.B. et al., "Absence of the Chemokine Receptor CCR2 Protects Against Cerebral Ischemia/Reperfusion Injury in Mice", Stroke, vol. 38, pp. 1345-1353 (2007).

Doranz, B.J. et al., "A Dual-Tropic Primary HIV-1 Isolate that Uses Fusin and the β-Chemokine Receptors CKR-5, CKR-3, and CKR-2b as Fusion Cofactors", Cell, vol. 85, pp. 1149-1158 (1996).

Dresser, G.K. et al., "Pharmacokinetic-Pharmacodynamic Consequences and Clinical Relevance of Cytochrome P450 3A4 Inhibition", Clin. Pharmacokinet., vol. 38, No. 1, pp. 41-57 (2000).

Eckel, R.H. et al., "The metabolic syndrome", The Lancet, vol. 365, pp. 1415-1428 (2005).

Egashira, K. et al., "Importance of Monocyte Chemoattractant Protein-1 Pathway in Neointimal Hyperplasia After Periarterial Injury in Mice and Monkeys", Circulation Research, vol. 90, pp. 1167-1172 (2002).

Evans, M.C. et al., "Synthesis and Dopamine Receptor Modulating Activity of Novel Peptidomimetics of $_L$-Prolyl-$_L$-leucyl-glycinamide Featuring α,α-Disubstituted Amino Acids", Journal of Medicinal Chemistry, vol. 42, No. 8, pp. 1441-1447 (1999).

Feria, M. et al., "The CCR2 receptor as a therapeutic target", Expert Opin. Ther. Patents, vol. 16, No. 1, pp. 49-57 (2006).

Ferreira, A.M. et al., "Diminished Induction of Skin Fibrosis in Mice with MCP-1 Deficiency", Journal of Investigative Dermatology, vol. 126, pp. 1900-1908 (2006).

Fife, B.T. et al., "CC Chemokine Receptor 2 is Critical for Induction of Experimental Autoimmune Encephalomyelitis", J. Exp. Med., vol. 192, No. 6, pp. 899-905 (2000).

Frangogiannis, N. G. et al., "Critical Role of Monocyte Chemoattractant Protein-1/CC Chemokine Ligand 2 in the Pathogenesis of Ischemic Cardiomyopathy", Circulation, vol. 115, pp. 584-592 (2007).

Gao, Z. et al., "Unraveling the Chemistry of Chemokine Receptor Ligands", Chemical Reviews, vol. 103, No. 9, pp. 3733-3752 (2003).

Gaupp, S. et al., "Experimental Autoimmune Encephalomyelitis (EAE) in CCR2$^{-/-}$ Mice", American Journal of Pathology, vol. 162, No. 1, pp. 139-150 (2003).

Gerhardt, C.C. et al., "Chemokines control fat accumulation and leptin secretion by cultured human adipocytes", Molecular and Cellular Endocrinology, vol. 175, pp. 81-92 (2001).

Gharaee-Kermani, M. et al., "CC-chemokine receptor 2 required for bleomycin-induced pulmonary fibrosis", Cytokine, vol. 24, pp. 266-276 (2003).

Giles, R. et al., "Can We Target the Chemokine Network for Cancer Therapeutics?", Current Cancer Drug Targets, vol. 6, No. 8, pp. 659-670 (2006).

Gillitzer, R. et al., "MCP-1 mRNA Expression in Basal Keratinocytes of Psoriatic Lesions", The Journal of Investigative Dermatology, vol. 101, No. 2, pp. 127-131 (1993).

Gong, J.-H. et al., "An Antagonist of Monocyte Chemoattractant Protein 1 (MCP-1) Inhibits Arthritis in the MRL-*lpr* Mouse Model", J. Exp. Med., vol. 186, No. 1, pp. 131-137 (1997).

Gonzalo, J.-A. et al., "The Coordinated Action of CC Chemokines in the Lung Orchestrates Allergic Inflammation and Airway Hyperresponsiveness", J. Exp. Med., vol. 188, No. 1, pp. 157-167 (1998).

Gosling, J. et al., "MCP-1 deficiency reduces susceptibility to atherosclerosis in mice that overexpress human apolipoprotein B", The Journal of Clinical Investigation, vol. 103, No. 6, pp. 773-778 (1999).

Grimm, M.C. et al., "Enhanced expression and production of monocyte chemoattractant protein-1 in inflammatory bowel disease mucosa", Journal of Leukocyte Biology, vol. 59, pp. 804-812 (1996).

Gu, L. et al., "Absence of Monocyte Chemoattractant Protein-1 Reduces Atherosclerosis in Low Density Lipoprotein Receptor-Deficient Mice", Molecular Cell, vol. 2, pp. 275-281 (1998).

Guo, J. et al., "Repopulation of Apolipoprotein E Knockout Mice with CCR2-Deficient Bone Marrow Progenitor Cells Does Not Inhibit Ongoing Atherosclerotic Lesion Development", Arterioscler. Thromb. Vasc. Biol., vol. 25, pp. 1014-1019 (2005).

Guo, J. et al., "Transplantation of Monocyte CC-Chemokine Receptor 2-Deficient Bone Marrow into ApoE3-Leiden Mice Inhibits Atherogenesis", Arterioscler. Thromb. Vasc. Biol., vol. 23, pp. 447-453 (2003).

Hasegawa, H. et al., "Antagonist of Monocyte Chemoattractant Protein 1 Ameliorates the Initiation and Progression of Lupus Nephritis and Renal Vasculitis in MRL/1pr Mice", Arthritis & Rheumatism, vol. 48, No. 9, pp. 2555- 2566 (2003).

Hayashidani, S. et al., "Anti-Monocyte Chemoattractant Protein-1 Gene Therapy Attenuates Left Ventricular Remodeling and Failure After Experimental Myocardial Infarction", Circulation, vol. 108, pp. 2134-2140 (2003).

Horiguchi, K. et al., "Selective Chemokine and Receptor Gene Expressions in Allografts that Develop Transplant Vasculopathy", The Journal of Heart and Lung Transplantation, vol. 21, No. 10, pp. 1090-1100 (2002).

Horuk, R., "Molecular properties of the chemokine receptor family", Trends in Pharmacological Sciences, vol. 15, pp. 159-165 (1994).

Horvath, C. et al., "Targeting CCR2 or CD18 Inhibits Experimental In-Stent Restenosis in Primates: Inhibitory Potential Depends on Type of Injury and Leukocytes Targeted", Circulation Research, vol. 90, pp. 488-494 (2002).

Hughes, P.M. et al., "Monocyte Chemoattractant Protein-1 Deficiency is Protective in a Murine Stroke Model", Journal of Cerebral Blood Flow & Metabolism, Vol. 22, No. 3, pp. 308-317 (2002).

Iarlori, C. et al., "Interferon β-1b modulates MCP-1 expression and production in relapsing-remitting multiple sclerosis", Journal of Neuroimmunology, vol. 123, pp. 170-179 (2002).

Ishibashi, M. et al., "Critical Role of Monocyte Chemoattractant Protein-1 Receptor CCR2 on Monocytes in Hypertension-Induced Vascular Inflammation and Remodeling", Circulation Research, vol. 94, pp. 1203-1210 (2004).

Izikson, L. et al., "Resistance to Experimental Autoimmune Encephalomyelitis in Mice Lacking the CC Chemokine Receptor (CCR)2", J. Exp. Med., vol. 192, No. 7, pp. 1075-1080 (2000).

Jones, M.L. et al., "Potential Role of Monocyte Chemoattractant Protein 1/JE in Monocyte/Macrophage-Dependent IgA Immune Complex Alveolitis in the Rat", The Journal of Immunology, vol. 149, No. 6, pp. 2147-2154 (1992).

Kamei, N. et al., "Overexpression of Monocyte Chemoattractant Protein-1 in Adipose Tissues Causes Macrophage Recruitment and Insulin Resistance", The Journal of Biological Chemistry, vol. 281, No. 36, pp. 26602-26614 (2006).

Kanda, H. et al., "MCP-1 contributes to macrophage infiltration into adipose tissue, insulin resistance, and hepatic steatosis in obesity", The Journal of Clinical Investigation, vol. 116, No. 6, pp. 1494-1505 (2006).

Karrer, S. et al., "The -2518 Promotor Polymorphism in the MCP-1 Gene is Associated with Systemic Sclerosis", The Journal of Investigative Dermatology, vol. 124, vol. 1, pp. 92-98 (2005).

Kennedy, K.J. et al., "Acute and relapsing experimental autoimmune encephalomyelitis are regulated by differential expression of the CC chemokines macrophage inflammatory protein-1α and monocyte chemotactic protein-1", Journal of Neuroimmunology, vol. 92, pp. 98-108 (1998).

Khan, W.I. et al., "Critical role of MCP-1 in the pathogenesis of experimental colitis in the context of immune and enterochromaffin cells", Am. J. Physiol. Gastrointest. Liver Physiol., vol. 291, pp. G803-G811 (2006).

Kim, J.S. et al., "Expression of monocyte chemoattractant protein-1 and macrophage inflammatory protein-1 after focal cerebral ischemia in the rat", Journal of Neuroimmunology, vol. 56, pp. 127-134 (1995).

Kim, W.J.H. et al., "MCP-1 deficiency is associated with reduced intimal hyperplasia after arterial injury", Biochemical and Biophysical Research Communications, vol. 310, pp. 936-942 (2003).

Kitagawa, K. et al., "Blockade of CCR2 Ameliorates Progressive Fibrosis in Kidney", American Journal of Pathology, vol. 165, No. 1, pp. 237-246 (2004).

Koch, A.E. et al., "Enhanced Production of Monocyte Chemoattractant Protein-1 in Rheumatoid Arthritis", The Journal of Clinical Investigation, vol. 90, pp. 772-779 (1992).

Kurihara, T. et al., "Defects in Macrophage Recruitment and Host Defense in Mice Lacking the CCR2 Chemokine Receptor", J. Exp. Med., vol. 186, No. 10, pp. 1757-1762 (1997).

Kuziel, W.A. et al., "Severe reduction in leukocyte adhesion and monocyte extravasation in mice deficient in CC chemokine receptor 2", Proc. Natl. Acad. Sci. USA, vol. 94, pp. 12053-12058 (1997).

Lee, I. et al., "Blocking the Monocyte Chemoattractant Protein-1/CCR2 Chemokine Pathway Induces Permanent Survival of Islet Allografts through a Programmed Death-1 Ligand-1-Dependent Mechanism", The Journal of Immunology, vol. 171, pp. 6929-6935 (2003).

Liu, T. et al., "Depletion of macrophages reduces axonal degeneration and hyperalgesia following nerve injury", Pain, vol. 86, pp. 25-32 (2000).

Lloyd, C.M. et al., "RANTES and Monocyte Chemoattractant Protein-1 (MCP-1) Play an Important Role in the Inflammatory Phase of Crescentic Nephritis, but Only MCP-1 is Involved in Crescent Formation and Interstitial Fibrosis", J. Exp. Med., vol. 185, No. 7, pp. 1371-1380 (1997).

Lu, B. et al., "Abnormalities in Monocyte Recruitment and Cytokine Expression in Monocyte Chemoattractant Protein 1-deficient Mice", J. Exp. Med., vol. 187, No. 4, pp. 601-608 (1998).

Lu, Y. et al., "CCR2 Expression Correlates with Prostate Cancer Progression", Journal of Cellular Biochemistry, vol. 101, pp. 676-685 (2007).

Lu, Y. et al., "Monocyte Chemotactic Protein-1 (MCP-1) Acts as a Paracrine and Autocrine Factor for Prostate Cancer Growth and Invasion", The Prostate, vol. 66, pp. 1311-1318 (2006).

Lu, Y. et al., "Monocyte Chemotactic Protein-1 Mediates Prostate Cancer-Induced Bone Resorption", Cancer Research, vol. 67, No. 8, pp. 3646-3653 (2007).

Lukacs, N.W. et al., "Differential Recruitment of Leukocyte Populations and Alteration of Airway Hyperreactivity by C-C Family Chemokines in Allergic Airway Inflammation", The Journal of Immunology, vol. 158, pp. 4398-4404 (1997).

Lumeng, C.N. et al., "Increased Inflammatory Properties of Adipose Tissue Macrophages Recruited During Diet-Induced Obesity", Diabetes, vol. 56, pp. 16-23 (2007).

Lumeng, C.N. et al., "Obesity induces a phenotypic switch in adipose tissue macrophage polarization", The Journal of Clinical Investigation, vol. 117, No. 1, pp. 175-184 (2007).

Luster, A.D., "Chemokines—Chemotactic Cytokines that Mediate Inflammation", The New England Journal of Medicine, vol. 338, No. 7, pp. 436-445 (1998).

Napolitano, M. et al., "Molecular Cloning of TER1, a Chemokine Receptor-Like Gene Expressed by Lymphoid Tissues", The Journal of Immunology, vol. 157, pp. 2759-2763 (1996).

Neels, J.G. et al., "Inflamed fat: what starts the fire?", The Journal of Clinical Investigation, vol. 116, No. 1, pp. 33-35 (2006).

Neote, K. et al., "Molecular Cloning, Functional Expression, and Signaling Characteristics of a C-C Chemokine Receptor", Cell, vol. 72, pp. 415-425 (1993).

Ni, W. et al., "New Anti-Monocyte Chemoattractant Protein-1 Gene Therapy Attenuates Atherosclerosis in Apolipoprotein E-Knockout Mice", Circulation, vol. 103, pp. 2096-2101 (2001).

Nomura, S. et al., "Significance of chemokines and activated platelets in patients with diabetes", Clinical and Experimental Immunology, vol. 121, pp. 437-443 (2000).

Ogata, H. et al., "The Role of Monocyte Chemoattractant Protein-1 (MCP-1) in the Pathogenesis of Collagen-Induced Arthritis in Rats", Journal of Pathology, vol. 182, pp. 106-114 (1997).

Okuma, T. et al., "C-C chemokine receptor 2 (CCR2) deficiency improves bleomycin-induced pulmonary fibrosis by attenuation of both macrophage infiltration and production of macrophage-derived matrix metalloproteinases", Journal of Pathology, vol. 204, pp. 594-604 (2004).

Pérez de Lema, G. et al., "Chemokine Receptor Ccr2 Deficiency Reduces Renal Disease and Prolongs Survival in MRL/1pr Lupus-Prone Mice", Journal of the American Society of Nephrology, vol. 16, pp. 3592-3601 (2005).

Pickup, J.C. et al., "Is Type II diabetes mellitus a disease of the innate immune system?", Diabetologia, vol. 41, pp. 1241-1248 (1998).

Power, C.A. et al., "Molecular Cloning and Functional Expression of a Novel CC Chemokine Receptor cDNA from a Human Basophilic Cell Line", The Journal of Biological Chemistry, vol. 270, No. 33, pp. 19495-19500 (1995).

Premack, B.A. et al., "Chemokine receptors: Gateways to inflammation and infection", Nature Medicine, vol. 2, No. 11, pp. 1174-1178 (1996).

Quinones, M.P. et al., "CC chemokine receptor (CCR)-2 prevents arthritis development following infection by Mycobacterium avium", J. Mol. Med., vol. 84, pp. 503-512 (2006).

Quinones, M.P. et al., "Experimental arthritis in CC chemokine receptor 2-null mice closely mimics severe human rheumatoid arthritis", The Journal of Clinical Investigation, vol. 113, No. 6, pp. 856-866 (2004).

Reinecker, H.-C. et al., "Monocyte-Chemoattractant Protein 1 Gene Expression in Intestinal Epithelial Cells and Inflammatory Bowel Disease Mucosa", Gastroenterology, vol. 108, No. 1, pp. 40-50 (1995).

Reynaud-Gaubert, M. et al., "Upregulation of Chemokines in Bronchoalveolar Lavage Fluid as a Predictive Marker of Post-Transplant Airway Obliteration", The Journal of Heart and Lung Transplantation, vol. 21, No. 7, pp. 721-730 (2002).

Rezaie-Majd, A. et al., "Simvastatin Reduces Expression of Cytokines Interleukin-6, Interleukin-8, and Monocyte Chemoattractant Protein-1 in Circulating Monocytes from Hypercholesterolemic Patients", Arterioscler. Thromb. Vasc. Biol., vol. 22, pp. 1194-1199 (2002).

Rollins, B.J., "Chemokines", Blood, vol. 90, No. 3, pp. 909-928 (1997).

Roque, M. et al., "CCR2 Deficiency Decreases Intimal Hyperplasia After Arterial Injury", Arterioscler. Thromb. Vasc. Biol., vol. 22, pp. 554-559 (2002).

Russell, M.E. et al., "Early and persistent induction of monocyte chemoattractant protein 1 in rat cardiac allografts", Proc. Natl. Acad. Sci. USA, vol. 90, pp. 6086-6090 (1993).

Saiura, A. et al., "Antimonocyte Chemoattractant Protein-1 Gene Therapy Attenuates Graft Vasculopathy", Arterioscler. Thromb. Vasc. Biol., vol. 24, pp. 1886-1890 (2004).

Salcedo, R. et al., "Human endothelial cells express CCR2 and respond to MCP-1: direct role of MCP-1 in angiogenesis and tumor progression", Blood, vol. 96, No. 1, pp. 34-40 (2000).

Samad, F. et al., "Tumor necrosis factor $\alpha$ is a key component in the obesity-linked elevation of plasminogen activator inhibitor 1", Proc. Natl. Acad. Sci. USA, vol. 96, pp. 6902-6907 (1999).

Samson, M. et al., "Molecular Cloning and Functional Expression of a New Human CC-Chemokine Receptor Gene", Biochemistry, vol. 35, No. 11, pp. 3362-3367 (1996).

Sartipy, P. et al., "Monocyte chemoattractant protein 1 in obesity and insulin resistance", Proceedings of the National Academy of Sciences, vol. 100, No. 12, pp. 7265-7270 (2003).

Saunders, J. et al., "Opportunities for novel therapeutic agents acting at chemokine receptors", Drug Discovery Today, vol. 4, No. 2, pp. 80-92 (1999).

Schimmer, R.C. et al., "Streptococcal Cell Wall-Induced Arthritis: Requirements for IL-4, IL-10, IFN-$\gamma$, and Monocyte Chemoattractant Protein-1", The Journal of Immunology, vol. 160, pp. 1466-1471 (1998).

Schober, A. et al., "Crucial Role of the CCL2/CCR2 Axis in Neointimal Hyperplasia After Arterial Injury in Hyperlipidemic Mice Involves Early Monocyte Recruitment and CCL2 Presentation on Platelets", Circulation Research, vol. 95, pp. 1125-1133 (2004).

Schweickart, V.L. et al., "CCR11 is a Functional Receptor for the Monocyte Chemoattractant Protein Family of Chemokines", The Journal of Biological Chemistry, vol. 275, No. 13, pp. 9550-9556 (2000), and vol. 276, No. 1, p. 856 (2001) (errata sheet).

Shimizu, S. et al., "Anti-monocyte chemoattractant protein-1 gene therapy attenuates nephritis in MRL/1pr mice", Rheumatology, vol. 43, pp. 1121-1128 (2004).

Smith, M.W. et al., "Contrasting Genetic Influence of CCR2 and CCR5 Variants on HIV-1 Infection and Disease Progression", Science, vol. 277, pp. 959-965 (1997).

Spagnolo, P. et al., "C-C Chemokine Receptor 2 and Sarcoidosis: Association with Löfgren's Syndrome", American Journal of Respiratory and Critical Care Medicine, vol. 168, pp. 1162-1166 (2003).

Tacke, F. et al., "Monocyte subsets differentially employ CCR2, CCR5, and CX3CR1 to accumulate within atherosclerotic plaques", The Journal of Clinical Investigation, vol. 117, No. 1, pp. 185-194 (2007).

Tatewaki, H. et al., "Blockade of monocyte chemoattractant protein-1 by adenoviral gene transfer inhibits experimental vein graft neointimal formation", Journal of Vascular Surgery, vol. 45, No. 6, pp. 1236-1243 (2007).

Tesch, G.H. et al., "Monocyte Chemoattractant Protein 1-dependent Leukocyte Infiltrates are Responsible for Autoimmune Disease in MRL-$Fas^{lpr}$ Mice", J. Exp. Med., vol. 190, No. 12, pp. 1813-1824 (1999).

Tesch, G.H. et al., "Monocyte chemoattractant protein-1 promotes macrophage-mediated tubular injury, but not glomerular injury, in nephrotoxic serum nephritis", The Journal of Clinical Investigation, vol. 103, No. 1, pp. 73-80 (1999).

Tokuyama, H. et al., "The simultaneous blockade of chemokine receptors CCR2, CCR5 and CXCR3 by a non-peptide chemokine receptor antagonist protects mice from dextran sodium sulfate-mediated colitis", International Immunology, vol. 17, No. 8, pp. 1023-1034 (2005).

Trivedi, B.K. et al., Chapter 17: "Chemokines: Targets for Novel Therapeutics", Annual Reports in Medicinal Chemistry, vol. 35, Academic Press, publ., pp. 191-200 (2000).

Tsou, C.-L. et al., "Critical roles for CCR2 and MCP-3 in monocyte mobilization from bone marrow and recruitment to inflammatory sites", The Journal of Clinical Investigation, vol. 117, No. 4, pp. 902-909 (2007).

Tsuruta, S. et al., "Anti-monocyte chemoattractant protein-1 gene therapy prevents dimethylnitrosamine-induced hepatic fibrosis in rats", International Journal of Molecular Medicine, vol. 14, pp. 837-842 (2004).

Vestergaard, C. et al., "Expression of CCR2 on Monocytes and Macrophages in Chronically Inflamed Skin in Atopic Dermatitis and Psoriasis", Acta Derm. Venereol., vol. 84, pp. 353-358 (2004).

Wada, T. et al., "Gene Therapy via Blockade of Monocyte Chemoattractant Protein-1 for Renal Fibrosis", Journal of the American Society of Nephrology, vol. 15, pp. 940-948 (2004).

Weisberg, S.P. et al., "CCR2 modulates inflammatory and metabolic effects of high-fat feeding", The Journal of Clinical Investigation, vol. 116, No. 1, pp. 115-124 (2006).

Weisberg, S.P. et al., "Obesity is associated with macrophage accumulation in adipose tissue", The Journal of Clinical Investigation, vol. 112, No. 12, pp. 1796-1808 (2003).

Wells, T.N.C. et al., "Plagiarism of the host immune system: lessons about chemokine immunology from viruses", Current Opinion in Biotechnology, vol. 8, pp. 741-748 (1997).

Xu, H. et al., "Chronic inflammation in fat plays a crucial role in the development of obesity-related insulin resistance", The Journal of Clinical Investigation, vol. 112, No. 12, pp. 1821-1830 (2003).

Yamamoto, T. et al., "Role of Monocyte Chemoattractant Protein-1 and its Receptor, CCR-2, in the Pathogenesis of Bleomycin-Induced Scleroderma", The Journal of Investigative Dermatology, vol. 121, No. 3, pp. 510-516 (2003).

Yoshie, O. et al., "Novel lymphocyte-specific CC chemokines and their receptors", Journal of Leukocyte Biology, vol. 62, pp. 634-644 (1997).

Youssef, S. et al., "C-C chemokine-encoding DNA vaccines enhance breakdown of tolerance to their gene products and treat ongoing adjuvant arthritis", The Journal of Clinical Investigation, vol. 106, No. 3, pp. 361-371 (2000).

Zlotnik, A. et al., "Chemokines: A New Classification System and Their Role in Immunity", Immunity, vol. 12, pp. 127-127 (2000).

Experimental and simulated powder patterns of N-((1R,2S,5R)-5-(isopropyl(methyl)amino)-2-((S)-2-oxo-3-(6-(trifluoromethyl)quinazolin-4-ylamino)pyrrolidin-1-yl)cyclohexyl)acetamide, di-benzenesulfonic acid salt Form N-1 (Example 2a)

Experimental and simulated powder patterns of N-((1R,2S,5R)-5-(isopropyl(methyl)amino)-2-((S)-2-oxo-3-(6-(trifluoromethyl)quinazolin-4-ylamino)pyrrolidin-1-yl)cyclohexyl)acetamide, free base Form N-2, (Example 2f)

Experimental and simulated powder patterns of N-((1R,2S,5R)-5-(isopropyl(methyl)amino)-2-((S)-2-oxo-3-(6-(trifluoromethyl)quinazolin-4-ylamino)pyrrolidin-1-yl)cyclohexyl)acetamide, free base Form E-1 (mono-ethanolate), (Example 2d)

Experimental and simulated powder patterns of N-((1R,2S,5R)-5-(isopropyl(methyl)amino)-2-((S)-2-oxo-3-(6-(trifluoromethyl)quinazolin-4-ylamino)pyrrolidin-1-yl)cyclohexyl)acetamide, HCl Salt Form H4-1 (tetrahydrate), (Example 2h)

Experimental and simulated powder patterns of N-((1R,2S,5R)-5-(isopropyl(methyl)amino)-2-((S)-2-oxo-3-(6-(trifluoromethyl)quinazolin-4-ylamino)pyrrolidin-1-yl)cyclohexyl)acetamide, free base Form A-1 (mono-acetone solvate), (Example 2e)

Experimental and simulated powder patterns of N-((1R,2S,5R)-5-(isopropyl(methyl)amino)-2-((S)-2-oxo-3-(6-(trifluoromethyl)quinazolin-4-ylamino)pyrrolidin-1-yl)cyclohexyl)acetamide, free base Form DC-1 (mono-dichloromethane solvate), (Example 2b)

Experimental and simulated powder patterns of N-((1R,2S,5R)-5-(isopropyl(methyl)amino)-2-((S)-2-oxo-3-(6-(trifluoromethyl)quinazolin-4-ylamino)pyrrolidin-1-yl)cyclohexyl)acetamide, free base Form AN-3 (mono-acetonitrile solvate), (Example 2g)

DSC of the N-((1R,2S,5R)-5-(isopropyl(methyl)amino)-2-((S)-2-oxo-3-(6-(trifluoromethyl)quinazolin-4-ylamino)pyrrolidin-1-yl)cyclohexyl)acetamide, di-besylate salt Form N-1 (Example 2a)

TGA of N-((1R,2S,5R)-5-(isopropyl(methyl)amino)-2-((S)-2-oxo-3-(6-(trifluoromethyl)quinazolin-4-ylamino)pyrrolidin-1-yl)cyclohexyl)acetamide, di-besylate salt Form N-1 (Example 2a)

DSC of N-((1R,2S,5R)-5-(isopropyl(methyl)amino)-2-((S)-2-oxo-3-(6-(trifluoromethyl)quinazolin-4-ylamino)pyrrolidin-1-yl)cyclohexyl)acetamide, free base Form N-2 (Example 2f)

TGA of N-((1R,2S,5R)-5-(isopropyl(methyl)amino)-2-((S)-2-oxo-3-(6-(trifluoromethyl)quinazolin-4-ylamino)pyrrolidin-1-yl)cyclohexyl)acetamide, free base Form N-2 (Example 2f)

Moisture Sorption Isotherm of N-((1R,2S,5R)-5-(isopropyl(methyl)amino)-2-((S)-2-oxo-3-(6-(trifluoromethyl)quinazolin-4-ylamino)pyrrolidin-1-yl)cyclohexyl)acetamide, free base Form N-2 (Example 2f)

X-ray crystal structure of *tert*-butyl (1*R*,3*R*,4*S*)-3-acetamido-4-((*S*)-3-(benzyloxycarbonylamino)-2-oxopyrrolidin-1-yl)cyclohexylcarbamate 48-hour TG peritonitis model in hCCR2 KI mice: Example 1 inhibition of monocyte/macrophage infiltration into peritoneal cavity (differential cell count)

Example 1 mg/kg p.o. BID 48-hour TG peritonitis model in hCCR2 KI mice: Example 1 inhibition of monocyte/macrophage infiltration into peritoneal cavity (FACS analysis)

EAE in hCCR2 KI mice: clinical score of Example 1 treatment

MODULATORS OF CHEMOKINE RECEPTOR ACTIVITY, CRYSTALLINE FORMS AND PROCESS

CROSS-REFERENCE TO RELATED APPLICATIONS

This application claims priority from U.S. Provisional Application Nos. 60/834,235, and 60/896,026 filed Jul. 28, 2006 and Mar. 21, 2007, respectively, the disclosures of both of which are incorporated herein by reference.

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC

Not Applicable

BACKGROUND OF THE INENTION (1) Field of Invention

The present invention provides N-((1R,2S,5R)-5-(isopropyl(methyl)amino)-2-((S)-2-oxo-3-(6-(trifluoromethyl)quinazolin-4-ylamino)pyrrolidin-1-yl)cyclohexyl)acetamide, or a pharmaceutically acceptable salt, solvate or prodrug, thereof, having an unexpected combination of desirable pharmacological characteristics. Crystalline forms of the present invention are also provided. Pharmaceutical compositions containing the same and methods of using the same as agents for the treatment of inflammatory diseases, allergic, autoimmune, metabolic, cancer and/or cardiovascular diseases is also an objective of this invention. The present disclosure also provides a process for preparing compounds of Formula (I), including N-((1R,2S,5R)-5-(isopropyl(methyl)amino)-2-((S)-2-oxo-3-(6-(trifluoromethyl)quinazolin-4-ylamino)pyrrolidin-1-yl)cyclohexyl)acetamide:

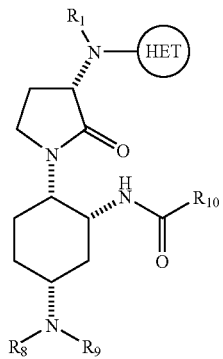

I wherein $R^1$, $R^8$, $R^9$, $R^{10}$, and are as described herein. Compounds that are useful intermediates of the process are also provided herein.

(2) Description of Related Art

Chemokines are chemotactic cytokines, of molecular weight 6-15 kDa, that are released by a wide variety of cells to attract and activate, among other cell types, macrophages, T and B lymphocytes, eosinophils, basophils and neutrophils (reviewed in: Charo and Rasonhoff, *New Eng. J. Med.* 2006, 354, 610-621; Luster, *New Eng. J. Med.* 1998, 338, 436-445; and Rollins, *Blood* 1997, 90, 909-928). There are two major classes of chemokines, CXC and CC, depending on whether the first two cysteines in the amino acid sequence are separated by a single amino acid (CXC) or are adjacent (CC). The CXC chemokines, such as interleukin-8 (IL-8), neutrophil-activating protein-2 (NAP-2) and melanoma growth stimulatory activity protein (MGSA) are chemotactic primarily for neutrophils and T lymphocytes, whereas the CC chemokines, such as RANTES, MIP-1α, MIP-1β, the monocyte chemotactic proteins (MCP-1, MCP-2, MCP-3, MCP-4, and MCP-5) and the eotaxins (-1 and -2) are chemotactic for, among other cell types, macrophages, T lymphocytes, eosinophils, dendritic cells, and basophils. There also exist the chemokines lymphotactin-1, lymphotactin-2 (both C chemokines), and fractalkine (a $CX_3C$ chemokine) that do not fall into either of the major chemokine subfamilies.

The chemokines bind to specific cell-surface receptors belonging to the family of G-protein-coupled seven-transmembrane-domain proteins (reviewed in: Horuk, *Trends Pharm. Sci.* 1994, 15, 159-165) which are termed "chemokine receptors." On binding their cognate ligands, chemokine receptors transduce an intracellular signal though the associated trimeric G proteins, resulting in, among other responses, a rapid increase in intracellular calcium concentration, changes in cell shape, increased expression of cellular adhesion molecules, degranulation, and promotion of cell migration. There are at least ten human chemokine receptors that bind or respond to CC chemokines with the following characteristic patterns (reviewed in Zlotnik and Oshie *Immunity* 2000, 12, 121): CCR-1 (or "CKR-1" or "CC-CKR-1") [MIP-1α, MCP-3, MCP-4, RANTES] (Ben-Barruch, et al., *Cell* 1993, 72, 415-425, and Luster, *New Eng. J. Med.* 1998, 338, 436-445); CCR-2A and CCR-2B (or "CKR-2A"/"CKR-2B" or "CC-CKR-2A"/"CC-CKR-2B") [MCP-1, MCP-2, MCP-3, MCP-4, MCP-5] (Charo, et al., *Proc. Natl. Acad. Sci. USA* 1994, 91, 2752-2756, and Luster, *New Eng. J. Med.* 1998, 338, 436-445); CCR-3 (or "CKR-3" or "CC-CKR-3") [eotaxin-1, eotaxin-2, RANTES, MCP-3, MCP-4] (Combadiere, et al., *J. Biol. Chem.* 1995, 270, 16491-16494, and Luster, *New Eng. J. Med.* 1998, 338, 436-445); CCR-4 (or "CKR-4" or "CC-CKR-4") [TARC, MDC] (Power, et al., *J. Biol. Chem.* 1995, 270, 19495-19500, and Luster, *New Eng. J. Med.* 1998, 338, 436-445); CCR-5 (or "CKR-5" OR "CC-CKR-5") [MIP-1α, RANTES, MIP-1β] (Sanson, et al., *Biochemistry* 1996, 35, 3362-3367); CCR-6 (or "CKR-6" or "CC-CKR-6") [LARC] (Baba, et al., *J. Biol. Chem.* 1997, 272, 14893-14898); CCR-7 (or "CKR-7" or "CC-CKR-7") [ELC] (Yoshie et al., *J. Leukoc. Biol.* 1997, 62, 634-644); CCR-8 (or "CKR-8" or "CC-CKR-8") [I-309] (Napolitano et al., J. Immunol., 1996, 157, 2759-2763); CCR-10 (or "CKR-10" or "CC-CKR-10") [MCP-1, MCP-3] (Bonini, et al., *DNA and*

*Cell Biol.* 1997, 16, 1249-1256); and CCR-11 [MCP-1, MCP-2, and MCP-4] (Schweickert, et al., *J. Biol. Chem.* 2000, 275, 90550).

In addition to the mammalian chemokine receptors, mammalian cytomegaloviruses, herpesviruses and poxviruses have been shown to express, in infected cells, proteins with the binding properties of chemokine receptors (reviewed in: Wells and Schwartz, *Curr. Opin. Biotech.* 1997, 8, 741-748). Human CC chemokines, such as RANTES and MCP-3, can cause rapid mobilization of calcium via these virally encoded receptors. Receptor expression may be permissive for infection by allowing for the subversion of normal immune system surveillance and response to infection. Additionally, human chemokine receptors, such as CXCR4, CCR2, CCR3, CCR5 and CCR8, can act as co-receptors for the infection of mammalian cells by microbes as with, for example, the human immunodeficiency viruses (HIV).

The chemokines and their cognate receptors have been implicated as being important mediators of inflammatory, infectious, and immunoregulatory disorders and diseases, including asthma and allergic diseases; as well as autoimmune pathologies, such as rheumatoid arthritis and multiple sclerosis; and metabolic diseases, such as atherosclerosis and diabetes (reviewed in: Charo and Rasonhoff, *New Eng. J. Med.* 2006, 354, 610-621; Z. Gao and W. A. Metz, *Chem. Rev.* 2003, 103, 3733; P. H. Carter, *Current Opinion in Chemical Biology* 2002, 6, 510; Trivedi, et al, *Ann. Reports Med. Chem.* 2000, 35, 191; Saunders and Tarby, *Drug Disc. Today* 1999, 4, 80; Premack and Schall, *Nature Medicine* 1996, 2, 1174). For example, the chemokine monocyte chemoattractant-1 (MCP-1) and its receptor CC Chemokine Receptor 2 (CCR-2) play a pivotal role in attracting leukocytes to sites of inflammation and in subsequently activating these cells. When the chemokine MCP-1 binds to CCR-2, it induces a rapid increase in intracellular calcium concentration, increased expression of cellular adhesion molecules, and the promotion of leukocyte migration. Demonstration of the importance of the MCP-1/CCR-2 interaction has been provided by experiments with genetically modified mice. MCP-1$^{-/-}$ mice were unable to recruit monocytes into sites of inflammation after several different types of immune challenge (Bao Lu, et al., *J. Exp. Med.* 1998, 187, 601). Likewise, CCR-2 –/– mice were unable to recruit monocytes or produce interferon-γ when challenged with various exogenous agents; moreover, the leukocytes of CCR-2 null mice did not migrate in response to MCP-1 (Landin Boring, et al., *J. Clin. Invest.* 1997, 100, 2552), thereby demonstrating the specificity of the MCP-1/CCR-2 interaction. Two other groups have independently reported equivalent results with different strains of CCR-2 –/– mice (William A. Kuziel, et al., *Proc. Natl. Acad. Sci. USA* 1997, 94, 12053, and Takao Kurihara, et al., *J. Exp. Med.* 1997, 186, 1757). The viability and generally normal health of the MCP-1 –/– and CCR-2 –/– animals is noteworthy, in that disruption of the MCP-1/CCR-2 interaction does not induce physiological crisis. Taken together, these data lead one to the conclusion that molecules that block the actions of MCP-1/CCR2 would be useful in treating a number of inflammatory and autoimmune disorders (reviewed in: M. Feria and F. Díaz-González, *Exp. Opin. Ther. Patents* 2006, 16, 49; and J. Dawson, W. Miltz, and C. Wiessner, C. *Exp. Opin. Ther. Targets* 2003, 7, 35). This hypothesis has now been validated in a number of different animal disease models, as described below.

It is known that MCP-1 is upregulated in patients with rheumatoid arthritis (Alisa Koch, et al., *J. Clin. Invest.* 1992, 90, 772-779). Moreover, several preclinical studies have demonstrated the potential therapeutic value of antagonism of the MCP-1/CCR2 interaction in treating rheumatoid arthritis. A DNA vaccine encoding MCP-1 was shown recently to ameliorate chronic polyadjuvant-induced arthritis in rats (Sawsan Youssef, et al., *J. Clin. Invest.* 2000, 106, 361). Likewise, the disease symptoms could be controlled via direct administration of antibodies for MCP-1 to rats with collagen-induced arthritis (Hiroomi Ogata, et al., *J. Pathol.* 1997, 182, 106), or streptococcal cell wall-induced arthritis (Ralph C. Schimmer, et al., *J. Immunol.* 1998, 160, 1466). Perhaps most significantly, a peptide antagonist of MCP-1, MCP-1(9-76), was shown both to prevent disease onset and to reduce disease symptoms (depending on the time of administration) in the MRL-1pr mouse model of arthritis (Jiang-Hong Gong, et al., *J. Exp. Med.* 1997, 186, 131). Moreover, it has been demonstrated the administration of small molecule CCR2 antagonists reduced clinical score in rodent models of arthritis (C. M. Brodmerkel, et al, *J. Immunol.* 2005, 175, 5370; and M. Xia, et al. US Patent Application 0069123, 2006). Administration of an anti-CCR2 antibody had varying effects on murine CIA, depending on the time of administration (H. Bruhl, et al. *J. Immunol.* 2004, 172, 890). Recent studies with CCR2–/– mice have suggested that deletion of CCR2 can exacerbate rodent arthritis models in specific experimental circumstances (M. P. Quinones, et al. *J. Clin. Invest.* 2004, 113, 856; M. P. Quinones, et al. *J. Mol. Med.* 2006, 84, 503).

It is known that MCP-1 is upregulated in atherosclerotic lesions, and it has been shown that circulating levels of MCP-1 are reduced through treatment with therapeutic agents (Abdolreza Rezaie-Majd, et al, *Arterioscler. Thromb. Vasc. Biol.* 2002, 22, 1194-1199). Several key studies have demonstrated the potential therapeutic value of antagonism of the MCP-1/CCR2 interaction in treating atherosclerosis. For example, when MCP-1 –/– mice are crossed with LDL receptor-deficient mice, an 83% reduction in aortic lipid deposition was observed (Long Gu, et al., *Mol. Cell* 1998, 2, 275). Similarly, when MCP-1 was genetically ablated from mice which already overexpressed human apolipoprotein B, the resulting mice were protected from atherosclerotic lesion formation relative to the MCP-1 +/+ apoB control mice (Jennifa Gosling, et al., *J. Clin. Invest.* 1999, 103, 773). Likewise, when CCR-2 –/– mice are crossed with apolipoprotein E –/– mice, a significant decrease in the incidence of atherosclerotic lesions was observed (Landin Boring, et al, *Nature* 1998, 394, 894; T. C. Dawson, et al. *Atherosclerosis* 1999, 143, 205). Finally, when apolipoprotein E –/– mice are administered a gene encoding a peptide antagonist of CCR2, then lesion size is decreased and plaque stability is increased (W. Ni, et al. *Circulation* 2001, 103, 2096-2101). Transplantation of bone marrow from CCR2–/– mice into ApoE3-Leiden mice inhibited early atherogenesis (J. Guo, et al. *Arterioscler. Thromb. Vasc. Biol.* 2003, 23, 447), but had minimal effects on advanced lesions (J. Guo, et al. *Arterioscler. Thromb. Vasc. Biol.* 2005, 25, 1014).

Patients with type 2 diabetes mellitus typically exhibit insulin resistance as one of the hallmark features of the disease. Insulin resistance is also associated with the grouping of abnormalities known as the "metabolic syndrome" or "syndrome X," which includes obesity, atherosclerosis, hypertension, and dyslipidemia (reviewed in: Eckel, et al. *Lancet* 2005, 365, 1415). It is well-recognized that inflammation plays a role in exacerbating the disease process in type 2 diabetes and the "syndrome X" pathologies (reviewed in: Chen, *Pharmacological Research* 2006, 53, 469; Neels and Olefsky, *J. Clin. Invest.* 2006, 116, 33; Danadona and Aljada, *Am J Cardiol.* 2002 90, 27G-33G; Pickup and Crook, *Diabetologia* 1998, 41, 1241). MCP-1 is recognized as playing a role in obesity-induced insulin resistance. In culture, human preadipocytes constitutively expressed MCP-1 (Gerhardt, *Mol. Cell. Endocrinology* 2001, 175, 81). CCR2 is expressed on adipocytes; Addition of MCP-1 to differentiated adipocytes in vitro decreases insulin-stimulated glucose uptake and the expression of several adipogenic genes (LpL, adipsin, GLU-4), aP2, β3-adrenergic receptor, and PPARγ) (P. Sartipy and D. Loskutoff, *Proc. Natl. Acad. Sci USA* 1999, 96, 6902). Patients with type 2 diabetes had greater levels of circulating MCP-1 than non-diabetic controls (S. Nomura, et al. *Clin. Exp. Immunol.* 2000, 121, 437), and release of MCP-1 from adipose tissue could be reduced by treatment with anti-diabetic therapies such as metformin or thiazolidinediones (J. M. Bruun, et al. *J. Clin. Endocrinol. Metab.* 2005, 90, 2282). Likewise, MCP-1 was also overexpressed in murine experimental models of obesity, and was primarily produced by adipose tissue (Sartipy and Loskutoff, *Proc. Natl. Acad. Sci. USA* 2003, 100, 7265). In obese mice, the expression of MCP-1 both preceded and occurred concurrently with the onset of insulin resistance (H. Xu, et al. *J. Clin. Invest.* 2003, 112, 1821). Another study showed that the expression of MCP-1 positively correlated with body mass in the perigonadal adipose tissue of mice (Weisberg, et al. *J. Clin. Invest.* 2003, 112, 1796). Consistent with these data, the development of insulin resistance in db/db mice was ameliorated either via genetic deletion of MCP-1 or by gene-induced expression of a dominant negative peptide (H. Kanda, et al. *J. Clin. Invest.* 2006, 116, 1494). The logical converse could also be demonstrated: overexpression of MCP-1 in adipose tissue promoted insulin resistance (N. Kamei, et al. *J. Biol. Chem.* 2006, 281, 26602). One conflicting result showing that genetic deletion of MCP-1 does not effect insulin resistance in the db/db mouse has also appeared (F. Y. Chow, et al. *Diabetologia* 2007, 50, 471). Consistent with the data on MCP-1, direct studies with CCR2 (the MCP-1 receptor) have showed that it plays a role in the formation of obesity and obesity-induced insulin resistance. Maintenance of a high fat diet increased the numbers of circulating $CCR2^+$ inflammatory monocytes in both wild-type (C. L. Tsou, et al. *J. Clin. Invest.* 2007, 117, 902) and $ApoE^{-/-}$ mice (F. Tacke, et al. *J. Clin. Invest.* 2007, 117, 185). Genetic deletion of CCR2 reduced numbers of activated macrophages in murine adipose tissue (C. N. Lumeng, et al. *Diabetes* 2007, 56, 16), but did not affect a population of M2 adipose macrophages thought to maintain the "lean" state (C. N. Lumeng, et al. *J. Clin. Invest.* 2007, 117, 175). Genetic deletion of CCR2 reduced diet-induced obesity and improved insulin sensitivity in diet-induced obesity model (S. P. Weisberg, et al. *J. Clin. Invest.* 2006, 116, 115; P Cornelius, R P Gladue, R S Sebastian, WO patent 2006/013427 A2), 2006), depending on experimental conditions (A. Chen, et al. *Obes. Res.* 2005, 13, 1311). Administration of a small molecule CCR2 antagonist also improved insulin sensitivity in this same model (S. P. Weisberg, et al. *J. Clin. Invest.* 2006, 116, 115).

Two studies described the important role of CCR2 in hypertension-induced vascular inflammation, remodeling, and hypertrophy (E Bush et al., *Hypertension* 2000, 36, 360; M Ishibashi, et al. *Circ. Res.* 2004, 94, 1203).

It is known that MCP-1 is upregulated in human multiple sclerosis, and it has been shown that effective therapy with interferon β-1b reduces MCP-1 expression in peripheral blood mononuclear cells, suggesting that MCP-1 plays a role in disease progression (Carla Jarlori, et al., *J. Neuroimmunol.* 2002, 123, 170-179). Other studies have demonstrated the potential therapeutic value of antagonism of the MCP-1/CCR-2 interaction in treating multiple sclerosis; all of these studies have been demonstrated in experimental autoimmune encephalomyelitis (EAE), the conventional animal model for multiple scelerosis. Administration of antibodies for MCP-1 to animals with EAE significantly diminished disease relapse (K. J. Kennedy, et al., *J. Neuroimmunol.* 1998, 92, 98). Furthermore, two reports have shown that CCR-2 −/− mice are resistant to EAE (B. T. Fife, et al., *J. Exp. Med.* 2000, 192, 899; L. Izikson, et al., *J. Exp. Med.* 2000, 192, 1075). A subsequent report extended these initial observations by examining the effects of CCR2 deletion in mice from different strains (S. Gaupp, et al. *Am. J. Pathol.* 2003, 162, 139). Notably, administration of a small molecule CCR2 antagonist also blunted disease progression in C57BL/6 mice (C. M. Brodmerkel, et al. *J. Immunol.* 2005, 175, 5370).

It is known that MCP-1 is upregulated in patients who develop bronchiolitis obliterans syndrome after lung transplantation (Martine Reynaud-Gaubert, et al., *J. of Heart and Lung Transplant.*, 2002, 21, 721-730; John Belperio, et al., *J. Clin. Invest.* 2001, 108, 547-556). In a murine model of bronchiolitis obliterans syndrome, administration of an antibody to MCP-1 led to attenuation of airway obliteration; likewise, CCR2 −/− mice were resistant to airway obliteration in this same model (John Belperio, et al., *J. Clin. Invest.* 2001, 108, 547-556). These data suggest that antagonism of MCP-1/ CCR2 may be beneficial in treating rejection of organs following transplantation. In addition, studies have shown that disruption of MCP-1/CCR2 axis was able to prolong the survival of islet transplant (I Lee et al. *J Immunol* 2003, 171, 6929; R Abdi et al., *J Immunol* 2004, 172, 767). In rat graft models, CCR2 and MCP-1 was shown to be upregulated in grafts that devlop graft vasculopathy (K Horiguchi et al., *J Heart Lung Transplant.* 2002, 21, 1090). In another study, anti-MCP-1 gene therapy attenuated graft vasculopathy (A Saiura et al., *Artherioscler Thromb Vasc Biol* 2004, 24, 1886). One study described inhibition of experimental vein graft neoinitimal formation by blockage of MCP-1 (H Tatewaki et al., *J Vasc Surg.* 2007, 45, 1236).

Other studies have demonstrated the potential therapeutic value of antagonism of the MCP-1/CCR2 interaction in treating asthma. Sequestration of MCP-1 with a neutralizing antibody in ovalbumin-challenged mice resulted in marked decrease in bronchial hyperresponsiveness and inflammation (Jose-Angel Gonzalo, et al., *J. Exp. Med.* 1998, 188, 157). It proved possible to reduce allergic airway inflammation in *Schistosoma mansoni* egg-challenged mice through the administration of antibodies for MCP-1 (Nicholas W. Lukacs, et al., J. Immunol. 1997, 158, 4398). Consistent with this, MCP-1 −/− mice displayed a reduced response to challenge with *Schistosoma mansoni* egg (Bao Lu, et al., *J. Exp. Med.* 1998, 187, 601).

Other studies have demonstrated the potential therapeutic value of antagonism of the MCP-1/CCR2 interaction in treating kidney disease. Administration of antibodies for MCP-1 in a murine model of glomerulamephritis resulted in a marked decrease in glomerular crescent formation and deposition of type I collagen (Clare M. Lloyd, et al., *J. Exp. Med.* 1997, 185, 1371). In addition, MCP-1 −/− mice with induced nephrotoxic serum nephritis showed significantly less tubular damage than their MCP-1 +/+ counterparts (Gregory H. Tesch, et al., *J. Clin. Invest.* 1999, 103, 73).

Several studies have demonstrated the potential therapeutic value of antagonism of the MCP-1/CCR2 interaction in treating systemic lupus erythematosus. $CCR2^{-/-}$ mice exhibited prolonged survival and reduced renal disease relative to their WT counterparts in a murine model of systemic lupus erythematosus (G. Perez de Lema, et al. *J. Am. Soc. Neph.* 2005, 16, 3592). These data are consistent with the disease-modifying activity found in recent studies on genetic deletion of MCP-1 (S. Shimizu, et al. *Rheumatology (Oxford)* 2004, 43, 1121; Gregory H. Tesch, et al., *J. Exp. Med.* 1999, 190, 1813) or administration of a peptide antagonist of CCR2 (H. Hasegawa, et al. *Arthritis & Rheumatism* 2003, 48, 2555) in rodent models of lupus.

A remarkable 30-fold increase in CCR2$^+$ lamina propria lymphocytes was observed in the small bowels from Crohn's patients relative to non-diseased ileum (S. J. Connor, et al. *Gut* 2004, 53, 1287). Also of note, there was an expansion in the subset of circulating CCR2$^+$/CD14$^+$/CD56$^+$ monocytes in patients with active Crohn's disease relative to controls. Several rodent studies have demonstrated the potential therapeutic value of antagonism of the MCP-1/CCR2 interaction in treating Crohn's disease/colitis. CCR-2$^{-/-}$ mice were protected from the effects of dextran sodium sulfate-induced colitis (Pietro G. Andres, et al., *J. Immunol.* 2000, 164, 6303). Administration of a small molecule antagonist of CCR2, CCR5, and CXCR3 (murine binding affinities=24, 236, and 369 nM, respectively) also protected against dextran sodium sulfate-induced colitis (H. Tokuyama, et al. *Int. Immunol.* 2005, 17, 1023). Finally, MCP-1−/− mice showed substantially reduced colonic damage (both macroscopic and histological) in a hapten-induced model of colitis (W. I. Khan, et al. *Am. J. Physiol. Gastrointest. Liver Physiol.* 2006, 291, G803).

Two reports described the overexpression of MCP-1 in the intestinal epithelial cells and bowel mucosa of patients with inflammatory bowel disease (H. C. Reinecker, et al., *Gastroenterology* 1995, 108, 40, and Michael C. Grimm, et al., *J. Leukoc. Biol.* 1996, 59, 804).

One study described the association of promoter polymorphism in the MCP-1 gene with sceroderma (systemic sclerosis) (S Karrer et al., *J Invest Dermatol.* 2005, 124, 92). In related models of tissue fibrosis, inhibition of CCR2/MCP-1 axis reduced fibrosis in skin (T Yamamoto and K Nishioka, *J Invest Dermatol* 2003, 121, 510; A M Ferreira et al., *J Invest Dermatol.* 2006, 126, 1900), lung (T Okuma et al., *J Pathol.* 2004, 204, 594; M Gharaee-Kermani et al., *Cytokine* 2003, 24, 266), kidney (K Kitagawa et al., *Am J Pathol.* 2004, 165, 237; T Wada et al., *J Am Soc Nephrol* 2004, 15, 940), heart (S Hayashidani et al., *Circulation* 2003, 108, 2134), and liver (S Tsuruta et al., *Int J Mol Med.* 2004, 14, 837).

One study has demonstrated the potential therapeutic value of antagonism of the MCP-1/CCR2 interaction in treating alveolitis. When rats with IgA immune complex lung injury were treated intravenously with antibodies raised against rat MCP-1 (JE), the symptoms of alveolitis were partially alleviated (Michael L. Jones, et al., *J. Immunol.* 1992, 149, 2147).

Several studies have shown the potential therapeutic value of antagonism of the MCP-1/CCR2 interaction in treating cancer (reviewed in: M. J. Craig and R. D. Loberg, *Cancer Metastasis Rev.* 2006, 25, 611; I. Conti and B. Rollins, *Seminars in Cancer Biology* 2004, 14, 149; R. Giles and R. D. Loberg, *Curr. Cancer Drug Targets* 2006, 6, 659). When immunodeficient mice bearing human breast carcinoma cells were treated with an anti-MCP-1 antibody, inhibition of lung micrometastases and increases in survival were observed (Rosalba Salcedo, et al., *Blood* 2000, 96, 34-40). Using human clinical tumor specimens, CCR2 expression was associated with prostrate cancer progression (Y. Lu, et al. *J. Cell. Biochem.* 2007, 101, 676). In vitro, MCP-1 expression has been shown to mediate prostrate cancer cell growth and invasion (Y. Lu, et al. *Prostate* 2006, 66, 1311); furthermore, MCP-1 expressed by prostate cancer cells induced human bone marrow progenitors for bone resorption (Y. Lu, et al., *Cancer Res.* 2007, 67, 3646).

Multiple studies have described the potential therapeutic value of antagonism of the MCP-1/CCR2 interaction in treating restenosis. In humans, MCP-1 levels correlate directly with risk for restenosis (F. Cipollone, et al. *Arterioscler. Thromb. Vasc. Biol.* 2001, 21, 327). Mice deficient in CCR2 or in MCP-1 showed reductions in the intimal area and in the intima/media ratio (relative to wildtype littermates) after arterial injury (Merce Roque, et al. *Arterioscler. Thromb. Vasc. Biol.* 2002, 22, 554; A. Schober, et al. *Circ. Res.* 2004, 95, 1125; W. J. Kim, et al. *Biochem Biophys Res Commun.* 2003, 310, 936). In mice, transfection of a dominant negative inhibitor of MCP-1 in the skeletal muscle (K. Egashira, et al. *Circ. Res.* 2002, 90, 1167) also reduced intimal hyperplasia after arterial injury. Blockade of CCR2 using a neutralizing antibody reduced neointimal hyperplasia after stenting in primates (C. Horvath, et al. *Circ. Res.* 2002, 90, 488).

Two reports describe the overexpression of MCP-1 rats with induced brain trauma (J. S. King, et al., *J. Neuroimmunol.* 1994, 56, 127, and Joan W. Berman, et al., *J. Immunol.* 1996, 156, 3017). In addition, studies have shown that both CCR2$^{-/-}$ (O. B. Dimitrijevic, et al. *Stroke* 2007, 38, 1345) and MCP-1$^{-/-}$ mice (P. M. Hughes, et al. *J. Cereb. Blood Flow Metab.* 2002, 22, 308) are partially protected from ischemia/reperfusion injury.

It is known that monocytes/macrophages play an important role in the development of neuropathic pain (Liu T, van Rooijen N, Tracey D J, *Pain* 2000, 86, 25). Consistent with this notion, a potential role for CCR2 in the treatment of both inflammatory and neuropathic pain has been described recently. CCR2$^{-/-}$ mice showed altered responses to inflammatory pain relative to their WT counterparts, including reduced pain behavior after intraplantar formalin injection and slightly reduced mechanical allodynia after intraplantar CFA injection (C. Abbadie, et al. *Proc. Natl. Acad. Sci., USA* 2003, 100, 7947). In addition, CCR2$^{-/-}$ mice did not display significant mechanical allodynia after sciatic nerve injury. Likewise, a small molecule CCR2 antagonist reduced mechanical allodynia to ~80% of pre-injury levels after oral administration (C. Abbadie, J. A. Lindia, and H. Wang, WO PCT 110376, 2004).

One study described the critical role of MCP-1 in ischemic cardiomyopathy (N. G. Frangogiannis, et al., *Circulation* 2007, 115, 584). Another study described the attenuation of experimetal heart failure following inhibition of MCP-1 (S Hayashidani et al., *Circulation* 2003, 108, 2134).

Other studies have provided evidence that MCP-1 is overexpressed in various disease states not mentioned above. These reports provide correlative evidence that MCP-1 antagonists could be useful therapeutics for such diseases. Another study has demonstrated the overexpression of MCP-1 in rodent cardiac allografts, suggesting a role for MCP-1 in the pathogenesis of transplant arteriosclerosis (Mary E. Russell, et al. *Proc. Natl. Acad. Sci. USA* 1993, 90, 6086). The overexpression of MCP-1 has been noted in the lung endothelial cells of patients with idiopathic pulmonary fibrosis (Harry N. Antoniades, et al., *Proc. Natl. Acad. Sci. USA* 1992, 89, 5371). Similarly, the overexpression of MCP-1 has been noted in the skin from patients with psoriasis (M. Deleuran, et al., *J. Dermatol. Sci.* 1996, 13, 228, and R. Gillitzer, et al., *J. Invest. Dermatol.* 1993, 101, 127); correlative findings with predominance of CCR2+ cells have also been reported (C. Vestergaard, et al. *Acta Derm. Venerol.* 2004, 84, 353). Finally, a recent report has shown that MCP-1 is overexpressed in the brains and cerebrospinal fluid of patients with HIV-1-associated dementia (Alfredo Garzino-Demo, WO 99/46991).

In addition, CCR2 polymorphism has been shown to be associated with sarcoidosis at least in one subset of patients (P. Spagnolo, et al. *Am J Respir Crit Care Med.* 2003, 168, 1162).

It should also be noted that CCR-2 has been implicated as a co-receptor for some strains of HIV (B. J. Doranz, et al., *Cell* 1996, 85, 1149). It has also been determined that the use of CCR-2 as an HIV co-receptor can be correlated with disease progression (Ruth I. Connor, et al., *J. Exp. Med.* 1997, 185, 621). This finding is consistent with the recent finding that the presence of a CCR-2 mutant, CCR2-64I, is positively correlated with delayed onset of HIV in the human population (Michael W. Smith, et al., *Science* 1997, 277, 959). Although MCP-1 has not been implicated in these processes, it may be that MCP-1 antagonists that act via binding to CCR-2 may have beneficial therapeutic effects in delaying the disease progression to AIDS in HIV-infected patients.

It should be noted that CCR2 is also the receptor for the human chemokines MCP-2, MCP-3, and MCP-4 (Luster, *New Eng. J. Med.* 1998, 338, 436-445). Since the new compounds of formula (I) described herein antagonize MCP-1 by binding to the CCR-2 receptor, it may be that these compounds of formula (I) are also effective antagonists of the actions of MCP-2, MCP-3, and MCP-4 that are mediated by CCR-2. Accordingly, when reference is made herein to "antagonism of MCP-1," it is to be assumed that this is equivalent to "antagonism of chemokine stimulation of CCR-2."

Accordingly, compounds that modulate chemokine activity could demonstrate a wide range of utilities in treating inflammatory, allergic, autoimmune, metabolic, cancer and/or cardiovascular diseases. U.S. Patent Application Publication WO2005021500 A1 (incorporated herein by reference and assigned to present applicant) discloses compounds that modulate MCP-1, MCP-2, MCP-3 and MCP-4 activity via CCR2. The reference also discloses various processes to prepare these compounds including multistep syntheses that include the introduction and subsequent removal of protecting groups.

It is desirable to find new compounds with improved pharmacological characteristics compared with known chemokine modulators. For example, it is desirable to find new compounds with improved CCR-2 inhibitory activity and selectivity for CCR-2 versus other G protein-coupled receptors (i.e. 5HT2A receptor). It is also desirable to find compounds with advantageous and improved characteristics in one or more of the following categories:

(a) pharmaceutical properties (i.e. solubility, permeability, amenability to sustained release formulations);

(b) dosage requirements (e.g., lower dosages and/or once-daily dosing);

(c) factors which decrease blood concentration peak-to-trough characteristics (i.e. clearance and/or volume of distribution);

(d) factors that increase the concentration of active drug at the receptor (i.e. protein binding, volume of distribution);

(e) factors that decrease the liability for clinical drug-drug interactions (cytochrome P450 enzyme inhibition or induction, such as CYP 2D6 inhibition, see G. K. Dresser, J. D. Spence, D. G. Bailey, *Clin. Pharmacokinet.* 2000, 38, 41-57, which is hereby incorporated by reference);

(f) factors that decrease the potential for adverse side-effects (e.g. pharmacological selectivity beyond G protein-coupled receptors, potential chemical or metabolic reactivity, limited CNS penetration, ion-channel selectivity). It is especially desirable to find compounds having a desirable combination of the aforementioned pharmacological characteristics.

It is also desirable in the art to provide new and/or improved processes to prepare such compounds. These processes may be characterized, without limitation, by a) facile adaptation to larger scale production, such as pilot plant or manufacturing scales; b) process steps and/or techniques enabling improvements in the purity (including chiral purity), stability and/or ease of handling of intermediates and/or final compounds; and/or c) fewer process steps.

BRIEF SUMMARY OF THE INVENTION

The present invention provides a novel antagonist or partial agonist/antagonist of MCP-1 receptor activity: N-((1R,2S,5R)-5-(isopropyl(methyl)amino)-2-((S)-2-oxo-3-(6-(trifluoromethyl)quinazolin-4-ylamino)pyrrolidin-1-yl)cyclohexyl)acetamide, or a pharmaceutically acceptable salt, solvate or prodrug, thereof, having an unexpected combination of desirable pharmacological characteristics. Crystalline forms of the present invention are also provided. Pharmaceutical compositions containing the same and methods of using the same as agents for the treatment of inflammatory diseases, allergic, autoimmune, metabolic, cancer and/or cardiovascular diseases is also an objective of this invention. The present disclosure also provides a process for preparing compounds of Formula (I), including N-((1R,2S,5R)-5-(isopropyl(methyl)amino)-2-((S)-2-oxo-3-(6-(trifluoromethyl)quinazolin-4-ylamino)pyrrolidin-1-yl)cyclohexyl)acetamide:

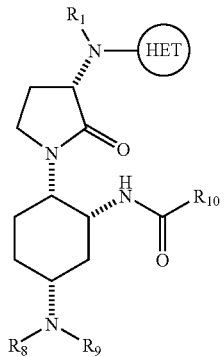

I wherein $R^1$, $R^8$, $R^9$, $R^{10}$, and

are as described herein. Compounds that are useful intermediates of the process are also provided herein.

The present disclosure also provides the use of N-((1R,2S,5R)-5-(isopropyl(methyl)amino)-2-((S)-2-oxo-3-(6-(trifluoromethyl)quinazolin-4-ylamino)pyrrolidin-1-yl)cyclohexyl)acetamide, or a pharmaceutically acceptable salt, solvate or prodrug, for the manufacture of a medicament for the treatment of inflammatory diseases, allergic, autoimmune, metabolic, cancer and/or cardiovascular diseases.

DETAILED DESCRIPTION OF THE INVENTION

Figure 1:
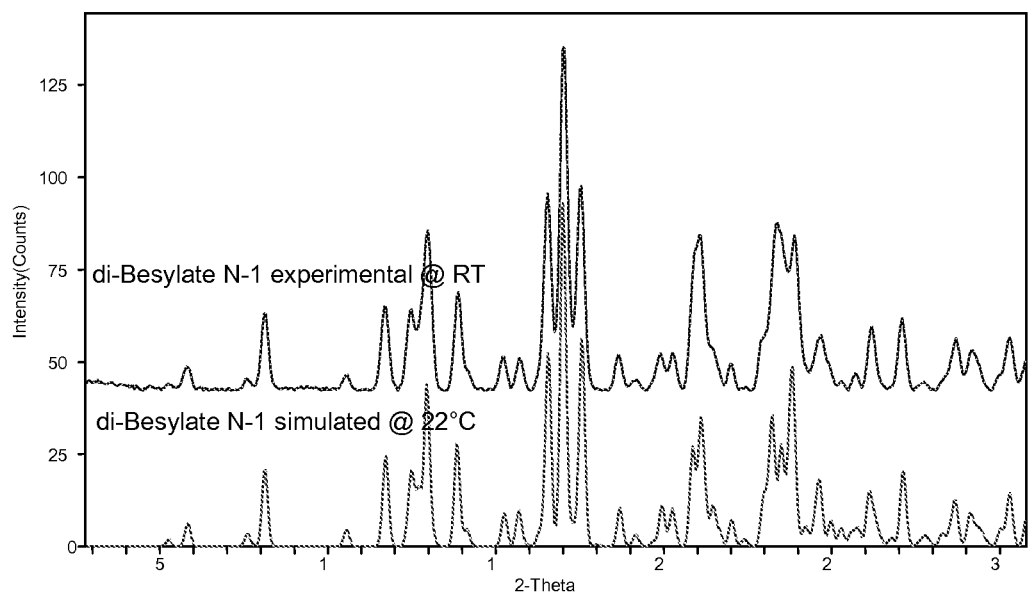
FIG. 1 discloses the experimental and simulated powder patterns of for N-((1R,2S,5R)-5-(isopropyl(methyl)amino)-2-((S)-2-oxo-3-(6-(trifluoromethyl)quinazolin-4-ylamino)pyrrolidin-1-yl)cyclohexyl)acetamide, di-benzenesulfonic acid salt Form N-1.

The present invention provides a novel antagonist or partial agonist/antagonist of MCP-1 receptor activity: N-((1R,2S,5R)-5-(isopropyl(methyl)amino)-2-((S)-2-oxo-3-(6-(trifluoromethyl)quinazolin-4-ylamino)pyrrolidin-1-yl)cyclohexyl)acetamide, or a pharmaceutically acceptable salt, solvate or prodrug, thereof, having an unexpected combination of desirable pharmacological characteristics. Crystalline forms of the present invention are also provided. Pharmaceutical compositions containing the same and methods of using the same as agents for the treatment of inflammatory diseases, allergic, autoimmune, metabolic, cancer and/or cardiovascular diseases is also an objective of this invention. The present disclosure also provides a process for preparing compounds of Formula (I), including N-((1R,2S,5R)-5-(isopropyl(methyl)amino)-2-((S)-2-oxo-3-(6-(trifluoromethyl)quinazolin-4-ylamino)pyrrolidin-1-yl)cyclohexyl)acetamide:

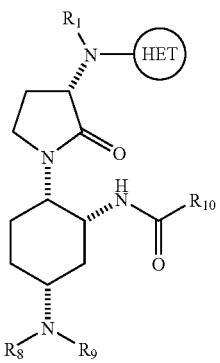

wherein $R^1$, $R^8$, $R^9$, $R^{10}$, and

are as described herein. Compounds that are useful intermediates of the process are also provided herein.

N-((1R,2S,5R)-5-(isopropyl(methyl)amino)-2-((S)-2-oxo-3-(6-(trifluoromethyl)quinazolin-4-ylamino)pyrrolidin-1-yl)cyclohexyl)acetamide, unexpectedly demonstrates a desirable combination of pharmacological characteristics including a surprisingly high degree of oral bioavailability in combination with indications that it is highly efficacious and has excellent safety criteria.

Known modulators of CCR2 receptors, such as those disclosed in patent publication WO2005021500 A1 published Mar. 10, 2005 (U.S. Pat. No. 7,163,937, issued Jan. 16, 2007, assigned to present Applicant) that demonstrate an adequate degree of membrane permeability (a critical factor of oral bioavailability), are not sufficiently efficacious, as measured by their CCR2-binding ability (a measure of efficacy), and/or they lack appropriate criteria for safety as indicated by ion channel selectivity as measured by hERG and Na+ ion channel studies.

In contrast, as illustrated by the data presented herein in the section titled "Comparative Pharmacological Characteristics", infra, the relatively polar molecule, N-((1R,2S,5R)-5-(isopropyl(methyl)amino)-2-((S)-2-oxo-3-(6-(trifluoromethyl)quinazolin-4-ylamino)pyrrolidin-1-yl)cyclohexyl)acetamide demonstrates a surprisingly high degree of membrane permeability, and yet maintains potent CCR2 binding ability along with excellent ion channel selectivity.

Accordingly, the present invention provides a new chemokine modulator having improved pharmacological characteristics that is expected to be useful in treating inflammatory, allergic, autoimmune, metabolic, cancer and/or cardiovascular diseases.

Embodiments

In one embodiment, the disclosure is directed to N-((1R,2S,5R)-5-(isopropyl(methyl)amino)-2-((S)-2-oxo-3-(6-(trifluoromethyl)quinazolin-4-ylamino)pyrrolidin-1-yl)cyclohexyl)acetamide, and pharmaceutically acceptable salts, thereof.

Another embodiment is a crystalline form of N-((1R,2S,5R)-5-(isopropyl(methyl)amino)-2-((S)-2-oxo-3-(6-(trifluoromethyl)quinazolin-4-ylamino)pyrrolidin-1-yl)cyclohexyl)acetamide, free base.

Another embodiment is a crystalline form of N-((1R,2S,5R)-5-(isopropyl(methyl)amino)-2-((S)-2-oxo-3-(6-(trifluoromethyl)quinazolin-4-ylamino)pyrrolidin-1-yl)cyclohexyl)acetamide, free base, the crystalline form comprising the N-2 Form.

Another embodiment is the N-2 Form characterized by (or having) unit cell parameters substantially equal to the following:

Cell dimensions:
a=11.8427(3)
b=18,1503(7)
c=12.7923(4)
α=90
β=105.362(2)
γ=90
Space group P2$_1$
Molecules/unit cell 2 wherein said crystal is at a temperature of about +22° C. (RT).

Another embodiment is the N-2 Form characterized by (or having) a powder x-ray diffraction pattern comprising three or more of 2θ values (CuKα λ=1.541 Å) selected from 7.2, 8.7, 9.7, 12.5, 12.8, 13.3, 16.0, 16.6, 18.2, and 18.8, at a temperature of about 22° C.

Another embodiment is the N-2 Form characterized by (or having) an powder x-ray diffraction pattern further comprising four or more of 2θ values (CuKα λ=1.541 Å) selected from the group consisting of 7.2, 8.7, 9.7, 12.5, 12.8, 13.3, 16.0, 16.6, 18.2, and 18.8, at a temperature of about 22° C.

Another embodiment is the N-2 Form characterized by (or having) fractional atomic coordinates substantially as listed in Table 7.

Figure 2:
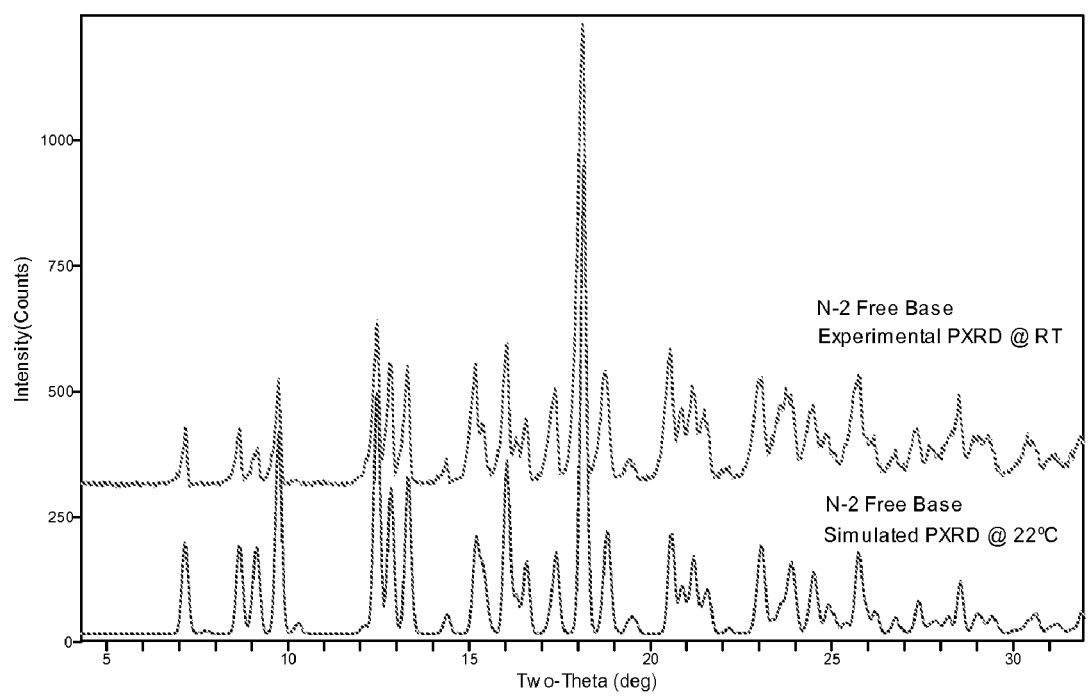
FIG. 2 discloses the experimental and simulated powder patterns of N-((1R,2S,5R)-5-(isopropyl(methyl)amino)-2-((S)-2-oxo-3-(6-(trifluoromethyl)quinazolin-4-ylamino)pyrrolidin-1-yl)cyclohexyl)acetamide, free base Form N-2.

Another embodiment is the N-2 Form characterized by (or having) a power x ray diffraction pattern substantially according to FIG. 2.

Another embodiment is a crystalline form of N-((1R,2S,5R)-5-(isopropyl(methyl)amino)-2-((S)-2-oxo-3-(6-(trifluoromethyl)quinazolin-4-ylamino)pyrrolidin-1-yl)cyclohexyl)acetamide, di-benzenesulfonic acid salt, comprising Form N-1, characterized by the unit cell parameters found in Table 1; 3 or 4 or more 2θ values (CuKα λ=1.541 Å) selected from Table 10; fractional atomic coordinates substantially as listed in Table 2, and/or a powder x-ray diffraction pattern substantially according to FIG. 1.

Figure 3:
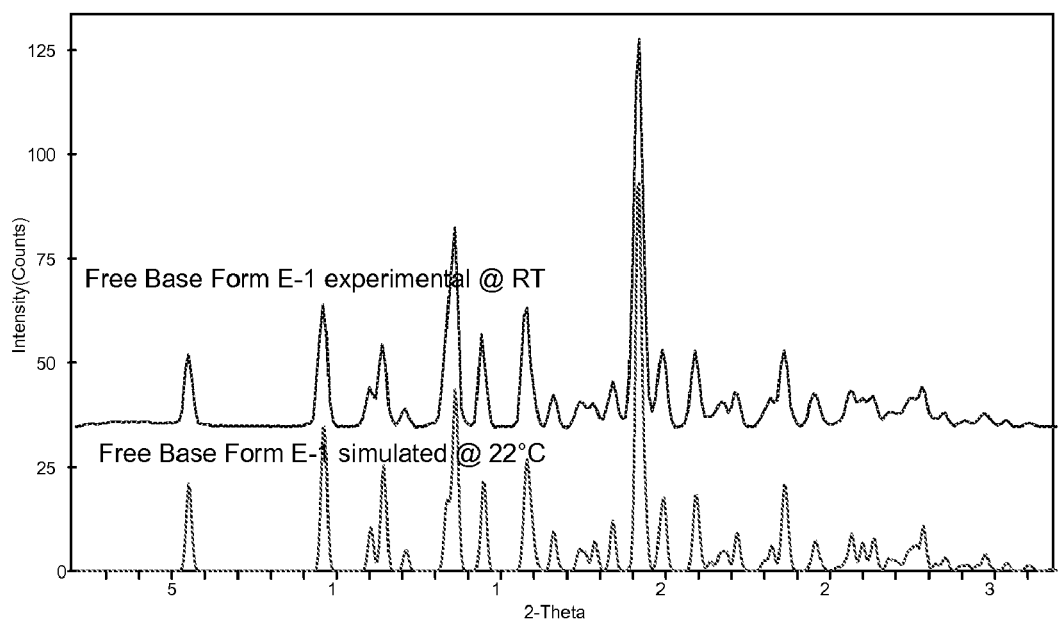
FIG. 3 discloses the experimental and simulated powder patterns of N-((1R,2S,5R)-5-(isopropyl(methyl)amino)-2-((S)-2-oxo-3-(6-(trifluoromethyl)quinazolin-4-ylamino)pyrrolidin-1-yl)cyclohexyl)acetamide, free base Form E-1 (mono-ethanolate).

Another embodiment is a crystalline form of N-((1R,2S,5R)-5-(isopropyl(methyl)amino)-2-((S)-2-oxo-3-(6-(trifluoromethyl)quinazolin-4-ylamino)pyrrolidin-1-yl)cyclohexyl)acetamide, free base, comprising Form E-1 (mono-ethanolate), characterized by the unit cell parameters found in Table 1; 3 or 4 or more 2θ values (CuKα λ=1.541 Å) selected from Table 10; fractional atomic coordinates substantially as listed in Table 5, and/or a powder x-ray diffraction pattern substantially according to FIG. 3.

Figure 4:
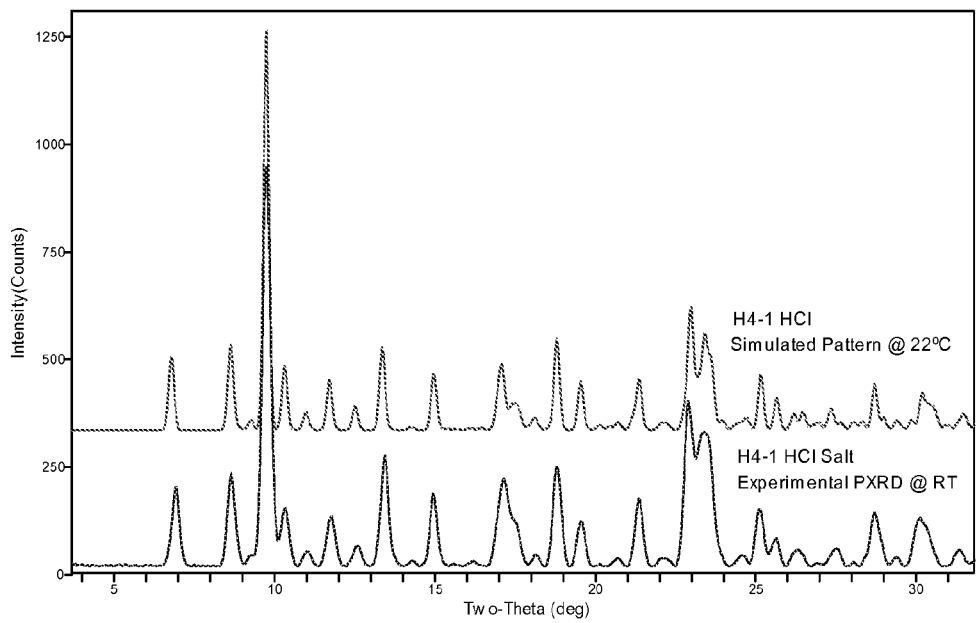
FIG. 4 discloses the experimental and simulated powder patterns of N-((1R,2S,5R)-5-(isopropyl(methyl)amino)-2-((S)-2-oxo-3-(6-(trifluoromethyl)quinazolin-4-ylamino)pyrrolidin-1-yl)cyclohexyl)acetamide, HCl Salt Form H4-1 (tetrahydrate).

Another embodiment is a crystalline form of N-((1R,2S,5R)-5-(isopropyl(methyl)amino)-2-((S)-2-oxo-3-(6-(trifluoromethyl)quinazolin-4-ylamino)pyrrolidin-1-yl)cyclohexyl)acetamide, HCl Salt, comprising Form H4-1 (tetrahydrate), characterized by the unit cell parameters found in Table 1; 3 or 4 or more 2θ values (CuKα λ=1.541 Å) selected from Table 10; fractional atomic coordinates substantially as listed in Table 9, and/or a powder x-ray diffraction pattern substantially according to FIG. 4.

Figure 5:
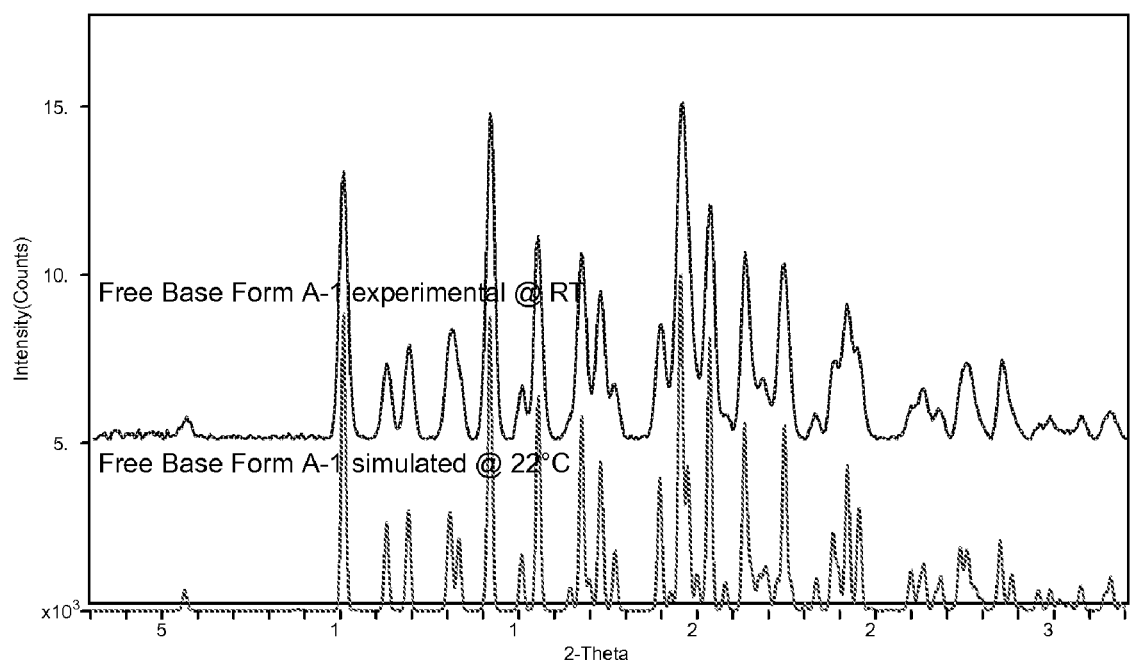
FIG. 5 discloses the experimental and simulated powder patterns of N-((1R,2S,5R)-5-(isopropyl(methyl)amino)-2-((S)-2-oxo-3-(6-(trifluoromethyl)quinazolin-4-ylamino)pyrrolidin-1-yl)cyclohexyl)acetamide, free base Form A-1 (mono-acetone solvate).

Another embodiment is a crystalline form patterns of N-((1R,2S,5R)-5-(isopropyl(methyl)amino)-2-((S)-2-oxo-3-(6-(trifluoromethyl)quinazolin-4-ylamino)pyrrolidin-1-yl)cyclohexyl)acetamide, free base, comprising Form A-1 (mono-acetone solvate), characterized by the unit cell parameters found in Table 1; 3 or 4 or more 2θ values (CuKα λ=1.541 Å) selected from Table 10; fractional atomic coordinates substantially as listed in Table 6, and/or a powder x-ray diffraction pattern substantially according to FIG. 5.

Figure 6:
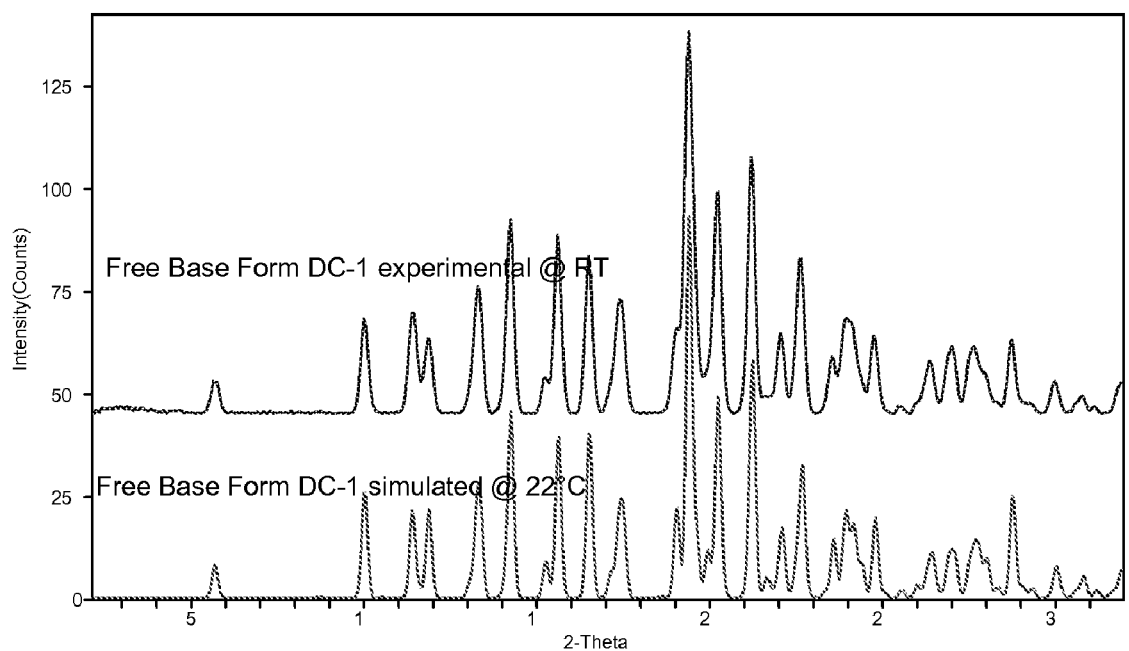
FIG. 6 discloses the experimental and simulated powder patterns of N-((1R,2S,5R)-5-(isopropyl(methyl)amino)-2-((S)-2-oxo-3-(6-(trifluoromethyl)quinazolin-4-ylamino)pyrrolidin-1-yl)cyclohexyl)acetamide, free base Form DC-1 (mono-dichloromethane solvate).

Another embodiment is a crystalline form of N-((1R,2S,5R)-5-(isopropyl(methyl)amino)-2-((S)-2-oxo-3-(6-(trifluoromethyl)quinazolin-4-ylamino)pyrrolidin-1-yl)cyclohexyl)acetamide, free base, comprising Form DC-1 (mono-dichloromethane solvate), characterized by the unit cell parameters found in Table 1; 3 or 4 or more 2θ values (CuKα λ=1.541 Å) selected from Table 10; fractional atomic coordinates substantially as listed in Table 3, and/or a powder x-ray diffraction pattern substantially according to FIG. 6.

Figure 7:
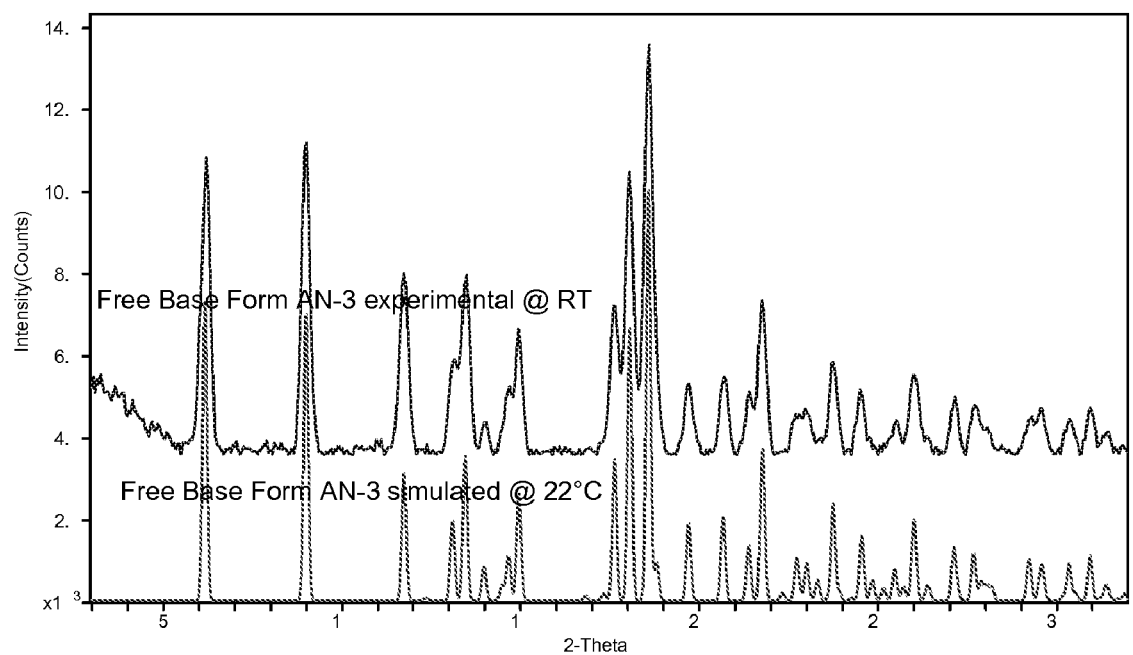
FIG. 7 discloses the experimental and simulated powder patterns of N-((1R,2S,5R)-5-(isopropyl(methyl)amino)-2-((S)-2-oxo-3-(6-(trifluoromethyl)quinazolin-4-ylamino)pyrrolidin-1-yl)cyclohexyl)acetamide, free base Form AN-3 (mono-acetonitrile solvate).

Another embodiment is a crystalline form of N-((1R,2S,5R)-5-(isopropyl(methyl)amino)-2-((S)-2-oxo-3-(6-(trifluoromethyl)quinazolin-4-ylamino)pyrrolidin-1-yl)cyclohexyl)acetamide, free base comprising Form AN-3 (mono-acetonitrile solvate), characterized by the unit cell parameters found in Table 1; 3 or 4 or more 2θ values (CuKα λ=1.541 Å) selected from Table 10; fractional atomic coordinates substantially as listed in Table 8, and/or a powder x-ray diffraction pattern substantially according to FIG. 7.

Another embodiment is a crystalline form of N-((1R,2S,5R)-5-(isopropyl(methyl)amino)-2-((S)-2-oxo-3-(6-(trifluoromethyl)quinazolin-4-ylamino)pyrrolidin-1-yl)cyclohexyl)acetamide, free base comprising Form THOO-1 (mono-tetrahydrofuran solvate), characterized by the unit cell parameters found in Table 1; 3 or 4 or more 2θ values (CuKα λ=1.541 Å) selected from Table 10; and/or fractional atomic coordinates substantially as listed in Table 4.

Another embodiment is a pharmaceutical composition, comprising a pharmaceutically acceptable carrier and a compound of the Examples Another embodiment is a method for modulation of chemokine or chemokine receptor activity comprising administering to a patient in need thereof a therapeutically effective amount of a compound of the Examples Another embodiment is a method for modulation of CCR-2 receptor activity comprising administering to a patient in need thereof a therapeutically effective amount of a compound of the Examples.

Another embodiment is a method for modulation of MCP-1, MCP-2, MCP-3 and MCP-4, and MCP-5 activity that is mediated by the CCR2 receptor comprising administering to a patient in need thereof a therapeutically effective amount of a compound of the Examples.

Another embodiment is a method for modulation of MCP-1 activity comprising administering to a patient in need thereof a therapeutically effective amount of a compound of the Examples.

Another embodiment is a method for treating disorders, comprising administering to a patient in need thereof a therapeutically effective amount of a compound of the Examples, said disorders being selected from another embodiment is a method for treating disorders, comprising administering to a patient in need thereof a therapeutically effective amount of a compound of the Examples, said disorders being selected from diabetes, obesity, metabolic syndrome, stroke, neuropathic pain, ischemic cardiomyopathy, psoriasis, hypertension, scheroderma, osteoarthritis, aneurism, fever, cardiovascular disease, Crohn's disease, congestive heart failure, autoimmune diseases, HIV-infection, HIV-associated dementia, psoriasis, idiopathic pulmonary fibrosis, transplant arteriosclerosis, physically- or chemically-induced brain trauma, inflammatory bowel disease, alveolitis, colitis, systemic lupus erythematosus, nephrotoxic serum nephritis, glomerulonephritis, asthma, multiple sclerosis, atherosclerosis, vasculitis, vulnerable plaques, rheumatoid arthritis, restenosis, venous neointimal hyperplasia, dialysis-graft neointimal hyperplasia, arterio-venous shunt intimal hyperplasia, organ transplantation, chronic allograft nephropathy, and cancer.

Another embodiment is a method for treating disorders, comprising administering to a patient in need thereof a therapeutically effective amount of a compound of the Examples, wherein said disorders being selected from diabetes, obesity, Crohn's disease, psoriasis, idiopathic pulmonary fibrosis, transplant arteriosclerosis, physically- or chemically-induced brain trauma, inflammatory bowel disease, alveolitis, colitis, systemic lupus erythematosus, nephrotoxic serum nephritis, glomerulonephritis, asthma, multiple sclerosis, atherosclerosis, and rheumatoid arthritis, restenosis, organ transplantation, and cancer.

Another embodiment is a method for treating disorders, comprising administering to a patient in need thereof a therapeutically effective amount of a compound of the Examples, wherein said disorders being selected from diabetes, obesity, Crohn's disease, systemic lupus erythematosus, glomerulonephritis, multiple sclerosis, atherosclerosis, restenosis, and organ transplantation.

Another embodiment is a method for treating disorders, comprising administering to a patient in need thereof a therapeutically effective amount of a compound of the Examples, wherein said disorders being selected from multiple sclerosis, atherosclerosis, Crohn's disease, and diabetes.

Another embodiment is a method for treating disorders, comprising administering to a patient in need thereof a therapeutically effective amount of a compound of the Examples, wherein said disorders being selected from restenosis, organ transplantation, and cancer.

Another embodiment is a method for treating diabetes, comprising administering to a patient in need thereof a therapeutically effective amount of a compound of the Examples.

Another embodiment is a method for treating Crohn's disease, comprising administering to a patient in need thereof a therapeutically effective amount of a compound of the Examples.

Another embodiment is a method for treating multiple sclerosis, comprising administering to a patient in need thereof a therapeutically effective amount of a compound of the Examples.

Another embodiment is a method for treating atherosclerosis, comprising administering to a patient in need thereof a therapeutically effective amount of a compound of the Examples.

Another embodiment is a method for treating restenosis, comprising administering to a patient in need thereof a therapeutically effective amount of a compound of the Examples.

Another embodiment is a method for treating organ transplantation, comprising administering to a patient in need thereof a therapeutically effective amount of a compound of Example 1.

Another embodiment is a method for treating cancer, comprising administering to a patient in need thereof a therapeutically effective amount of a compound of Example 1.

Another embodiment is a method for treating cancer, wherein the cancer is selected from breast cancer, liver cancer, prostate cancer and melanoma.

Another embodiment is a method for treating inflammatory diseases, allergic, autoimmune, metabolic, cancer and/or cardiovascular diseases comprising administering to a patient in need thereof a therapeutically effective amount of a compound of Example 1.

Another embodiment is a method for treating diseases which are at least partially mediated by CCR-2, comprising administering to a patient in need thereof a therapeutically effective amount of a compound of Example 1.

Another embodiment is a method for modulation of CCR2 activity comprising administering to a patient in need thereof a therapeutically effective amount of a compound of Example 1.

Another embodiment is a compound of Example 1 in the preparation of a medicament for the treatment of diabetes, obesity, metabolic syndrome, stroke, neuropathic pain, ischemic cardiomyopathy, psoriasis, hypertension, scheroderma, osteoarthritis, aneurism, fever, cardiovascular disease, Crohn's disease, congestive heart failure, autoimmune diseases, HIV-infection, HIV-associated dementia, psoriasis, idiopathic pulmonary fibrosis, transplant arteriosclerosis, physically- or chemically-induced brain trauma, inflammatory bowel disease, alveolitis, colitis, systemic lupus erythematosus, nephrotoxic serum nephritis, glomerulonephritis, asthma, multiple sclerosis, atherosclerosis, vasculitis, vulnerable plaques, rheumatoid arthritis, restenosis, venous neointimal hyperplasia, dialysis-graft neointimal hyperplasia, arterio-venous shunt intimal hyperplasia, organ transplantation, chronic allograft nephropathy, and cancer.

Another embodiment is a compound of the Examples for use in therapy.

The invention may be embodied in other specific forms without departing from the spirit or essential attributes thereof. This invention also encompasses all combinations of alternative aspects and embodiments of the invention noted herein. It is understood that any and all embodiments may be taken in conjunction with any other embodiment to describe additional embodiments of the present invention. Furthermore, any elements of an embodiment are meant to be combined with any and all other elements from any of the embodiments to describe additional embodiments.

Process Embodiments

In a 1st embodiment, the disclosure provides a process for preparing a compound of formula IV, or a salt thereof:

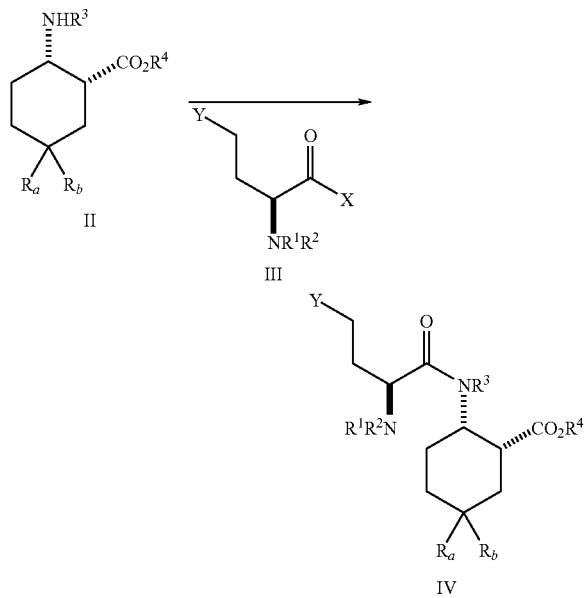

the process comprising the steps of:

coupling a β-aminoester of formula II, or a salt thereof, with a suitably protected chiral α-aminoacid of formula III to give amide IV (See WO2005021500); wherein:

$R_a$ and $R_b$ are independently $C_{1-6}$alkoxy;

or $R_a$ and $R_b$ together with the carbon to which they are both attached combine to form a carbonyl, a thiocarbonyl, a cyclic acetal or cyclic thioacetal, wherein the cyclic acetal or cyclic thioacetal is selected from —O-Z-O— and —S-Z-S—, Z is —$(CT_1T_2)_2$-, —$(CT_1T_2)_3$-, or

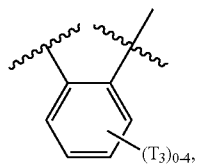

and $T_1$, $T_2$ and $T_3$ at each occurrence is independently selected from hydrogen, $C_{1-4}$alkyl, $C_{2-4}$alkenyl, halogen, hydroxy, cyano, nitro, $CF_3$, $OC_{1-4}$alkyl, $OCF_3$, C(=O)$C_{1-4}$alkyl, and $CO_2C_{1-4}$alkyl (preferably $T_1$, $T_2$ and $T_3$ are each hydrogen);

$R_1$, $R_2$ and $R_3$ are independently hydrogen or an amine-protecting group selected from a carbobenzyloxy (Cbz) group, a tert-butyloxycarbonyl (BOC), a fluorenylmethyloxycarbonyl (FMOC) group, a benzyl (Bn) group, and a p-methoxybenzyl (PMB) group (preferably the amine-protecting group is Cbz, Bn or BOC, especially Cbz or Bn);

$R_4$ is lower $C_{1-6}$alkyl or a benzyl optionally substituted by $C_{1-4}$alkyl, $C_{2-4}$alkenyl, halogen, hydroxy, cyano, nitro, $CF_3$, $OC_{1-4}$alkyl, $OCF_3$, and C(=O)$C_{1-4}$alkyl;

Y is halogen, $SR_{12}$ or $OSO_2R_{13}$;

X is OH, halogen or $OCOR_{14}$;

$R_{12}$ is $C_{1-6}$alkyl, —$(CH_2)C(O)OR_{13}$, or —$(CH_2)C(O)R_{13}$;

$R_{13}$ at each occurrence is $C_{1-6}$alkyl or a benzyl optionally substituted by $C_{1-4}$alkyl, $C_{2-4}$alkenyl, halogen, hydroxy, cyano, nitro, $CF_3$, $OC_{1-4}$alkyl, $OCF_3$, and C(=O)$C_{1-4}$alkyl; and $R_{14}$ at each occurrence is hydrogen, $C_{1-6}$alkyl or a benzyl optionally substituted by $C_{1-4}$alkyl, $C_{2-4}$alkenyl, halogen, hydroxy, cyano, nitro, $CF_3$, $OC_{1-4}$alkyl, $OCF_3$, and C(=O) $C_{1-4}$alkyl.

An optionally substituted benzyl as used herein designates a benzyl group that is connected through its methylene group (—$CH_2$—) and optionally substituted on the phenyl ring attached to the methylene group.

In a 2nd embodiment, the disclosure provides a process for forming a product of formula IV, or a salt thereof, wherein:

$R_a$ and $R_b$ together with the carbon atom to which they are both attached combine to form carbonyl or a 1,3-dioxolane group (preferably $R_a$ and $R_b$ together with the carbon atoms to which they are both attached combine to form a 1,3-dioxolane group);

$R_1$ is hydrogen;

$R_2$ is Cbz;

$R_3$ is hydrogen;

$R_4$ is $C_{1-6}$alkoxy;

Y is S(Me); and

X is OH.

In a 3rd embodiment, the disclosure provides a process wherein the the β-aminoester of formula II is a toluenesulfonate or hydrobromide salt. A preferable salt of the β-aminoester of formula II is the toluemesulfonate salt of

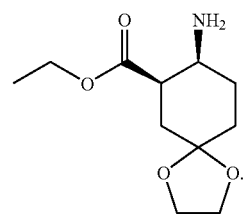

In a 4th embodiment, the disclosure provides a process for forming a compound of formula IV, or a salt thereof, wherein the coupling is conducted under an inert atmosphere, such as nitrogen or argon (preferably nitrogen) in an aprotic solvent such as proprionitrile, isopropyl acetate, n-butyl acetate, tert-butyl acetate or acetonitrile (especially acetonitrile and/or ethyl acetate).

In a 5th embodiment, the disclosure provides a process for forming a compound of formula IV, or a salt thereof, wherein the coupling is achieved by contacting the β-aminoester of formula II with a diimide coupling reagent in the presence of an activator, the protected β-aminoester of formula II, and a tertiary amine base. The diimide coupling reagent includes, for example, reagents such as EDAC. Examples of activators include 1-hydroxybenzotriazole (HOBt; said term includes hydrates thereof) and N',N'-4-dimethylamino-pyridine. A tertiary amine base, includes for example, trialkylamines such as triethylamine, N—N-diisopropyl-N-ethyl amine and tri-n-propylamine.

In a 6th embodiment, the disclosure provides a process for forming a compound of formula IV, or a salt thereof, wherein the diimide coupling reagent is EDAC, the activator, is HOBt, and the tertiary amine base is triethylamine or N—N-diisopropyl-N-ethyl amine.

In a 7th embodiment, the disclosure provides a process for formula a compound of formula IV, or a salt thereof, wherein the molar ratios of the aminoester of formula II to the diimide coupling reagent to the activator to the tertiary amine is one to about 0.90-1.50 to about 0.95-1.50 to about 2.00 to 3.00, respectively. Said mole ratios are preferably one to about 0.95-1.05 to about 0.95-1.10 and to about 2.10 to 2.30, respectively.

In an 8th embodiment, the disclosure provides a process for preparing a compound of formula V, or a salt thereof:

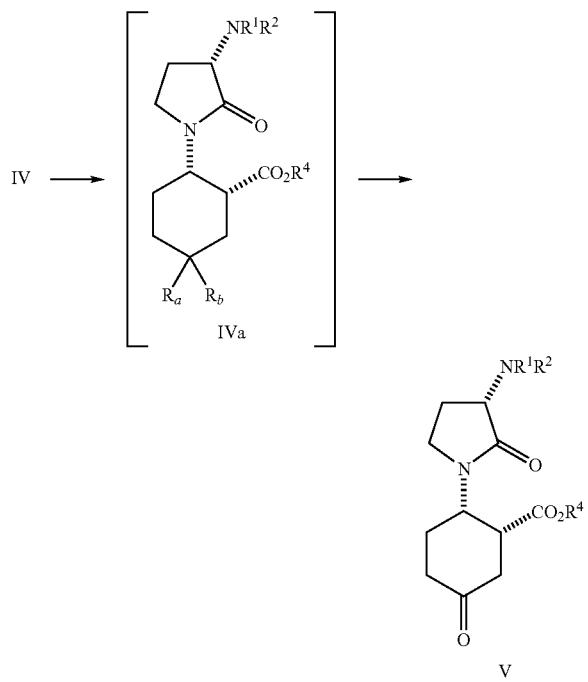

the process, comprising the steps of:
a) alkylating a compound of formula IV with an alkylating agent to form an activated compound; and
b) cyclizing the activated compound in situ to give a compound of formula IVa.

In a 9th embodiment, the disclosure provides a process for preparing a compound of formula V, or a salt thereof, wherein the alkylating agent of step a) is a sulfur alkylating agent such as an $C_{1-6}$alkyl halide and the activated compound is a sulfonium salt of compound IV wherein Y is $S^{\oplus}$ $(C_{1-6}alkyl)R_{12}$. Preferably, the alkylating agent is methyl iodide and Y is $S^{\oplus}$ $(CH_3)_2$.

In a 10th embodiment, the disclosure provides a process for forming a compound of formula V, or a salt thereof, wherein the cyclizing step comprises combining the activated compound, or a salt thereof, with a base in the presence of a solvent. The base is selected from cesium carbonate, cesium bicarbonate, potassium carbonate, sodium tert-butylate, or sodium hexamethyldisilazide, (preferably the base is cesium carbonate).

In a 11th embodiment, the disclosure provides a process for forming a compound of formula V, or a salt thereof, wherein the cyclizing step is conducted under an inert atmosphere, such as nitrogen or argon, in a solvent selected from DMSO, DMF, DMA, N-methylpyrrolidone, and sulfolane. Preferably the inert atmosphere is nitrogen and the solvent is selected from DMSO and/or DMF.

In an 12th embodiment, where the compound of formula IVa has an acetal moiety, i.e. where $R_a$ and $R_b$ are independently $C_{1-6}$alkoxy, or together with the atom to which they are attached $R_a$ and $R_b$ combine to form a cyclic acetal or cyclic thioacetal, the disclosure provides a process for forming a compound of formula V, or a salt thereof, further comprising the step of hydrolyzing a compound of formula IVa having an acetal moiety:

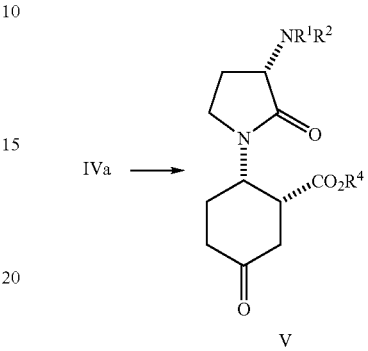

to form the compound of formula V.

The hydrolyzing step can be conducted according to procedures for hydrolyzing acetal groups known by those of skill in the art. For example, the hydrolyzing step may comprise treating the compound of formula IVa in a solvent such as acetone, butanone, acetonitrile and isopropanol, or aqueous solutions thereof with an acid. The hydrolyzying step preferably comprises treating the compound of formula IVa in a solution of aqueous acetone with hydrochloric acid.

In a 13th embodiment, the present disclosure provides a process for preparing a compound of formula VI having an ester moiety, or a salt thereof:

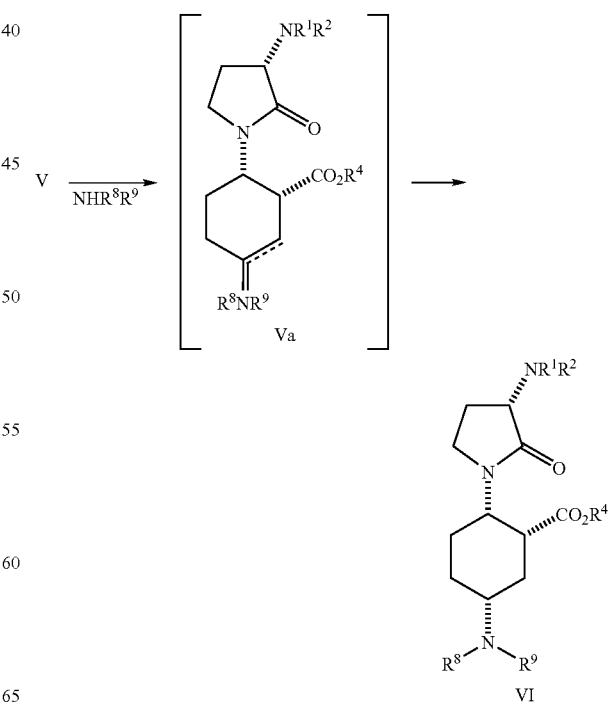

the process comprising the step of:
reductively aminating a compound of formula V with an amine having the formula, $NH(R^8)(R^9)$, to afford an imine/enamine of formula Va wherein $R_8$ and $R_9$ are independently selected from hydrogen and $C_{1-6}$alkyl. Preferably, $R_8$ and $R_9$ are selected independently from $C_{1-6}$alkyl. More preferably, the amine is N-methyl-N-isopropylamine.

In a 14th embodiment, the disclosure provides a process for forming a product of formula VI comprising the reductively aminating steps of:
(a) adding the amine of formula $NH(R^8)(R^9)$ and a dehydrating agent to a compound of formula V in an aprotic solvent at a temperature from about −20° to about +50° C. to form the imine/enamine of formula Va; and
(b) treating a solution of the imine/enamine of formula Va and a platinum catalyst, 5% Pt/S/C, with a pressure of hydrogen gas to afford a compound of formula VI.

In a 15th embodiment, the disclosure provides a process for forming a compound of formula VI, or a salt thereof, wherein the dehydrating agent of step a) is a Lewis acid/Bronsted acid (preferably titanium tetraisopropoxide) and the aprotic solvent is selected from dichloroethane, dichloromethane, acetonitrile, DMSO, DMF, and N-methyl-pyrrolidinone (preferably dichloromethane).

In a 16th embodiment, the disclosure provides a process for forming a compound of formula VI, or a salt thereof, wherein in step b) the 5% Pt/S/C catalyst is present at approximately 0.5 to 50% (wt/wt) relative to compound Va. Preferably, the hydrogen gas is at a pressure of from about 15 to about 35 psig.

In a 17th embodiment, the present invention provides a process for preparing a compound of formula VII, or a salt thereof:

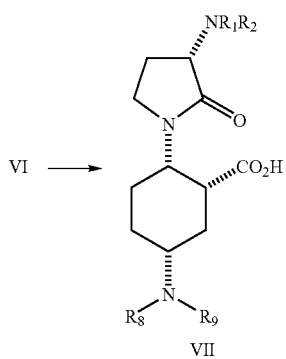

the process comprising step of:
hydrolyzing the ester compound of formula VI, to afford an acid compound of formula VII. The temperature ranges from about 40° C. to about 100° C. (a temperature range of from about 50° C. to about 70° C. is most preferred). Acids are selected from sulfuric acid, toluenesulfonic acid, nitric acid, methanesulfonic acid, hydrobromic acid and hydrochloric acid. Hydrodrochloric acid is most preferred. Preferably, the hydrolyzing step is performed in a solution of aqueous hydrochloric acid to obtain the compound of formula VII.

In a 18th embodiment, the disclosure provides a process for preparing a salt of the compound of formula VII further comprising the step of mixing a base with a solution of the acid compound of formula VII, optionally in situ. The base is preferably an alkali hydroxide, for example, sodium hydroxide.

In a 19th embodiment, the disclosure provides a process for preparing a carbamate compound of formula VIII, or a salt thereof:

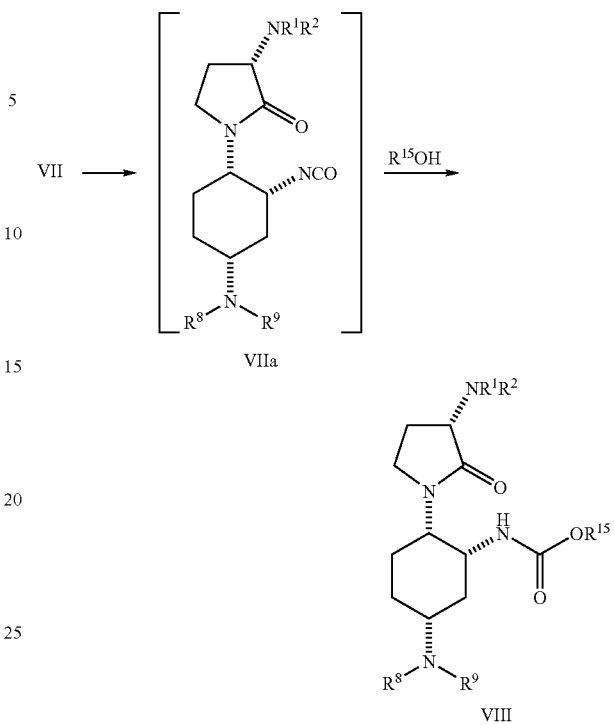

the process, comprising the steps of:
a) converting an acid compound of formula VII to an isocyanate compound of formula VIIa; and
b) reacting the isocyanate compound of formula VIIa with an alcohol of formula $R^{15}OH$ to afford a carbamate compound of formula VIII;
wherein $R^{15}$ is $C_{1-6}$alkyl or a benzyl optionally substituted by $C_{1-4}$alkyl, $C_{2-4}$alkenyl, halogen, hydroxy, cyano, nitro, $CF_3$, $OC_{1-4}$alkyl, $OCF_3$, and $C(=O)C_{1-4}$alkyl. $R^{15}$ is preferably tert-butyl or unsubstituted benzyl.

In a 20th embodiment, the disclosure provides a process for preparing a compound of formula VIII, or a salt thereof, via a Curtius rearrangement comprising contacting the sodium salt of the compound of formula VII with an azide reagent (preferably diphenylphosphoryl azide) in a solvent (preferably tert-butyl alcohol) containing toluene at a temperature above the trigger point of thermal rearrangement. The temperature is preferably a greater than 50° C.

In a 21st embodiment, the disclosure provides a process for preparing a compound of formula IX, or a salt thereof:

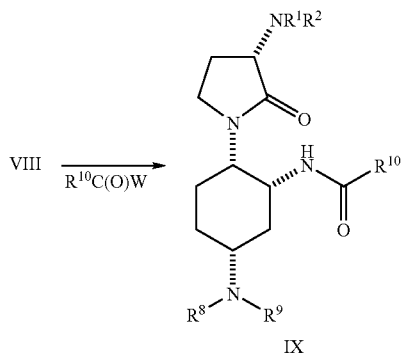

the process comprising the steps of:
a) transforming the carbamate compound of formula VIII to a free amine intermediate; and
b) acylating the free amine intermediate in situ with a reagent, $R^{10}C(O)W$, to give a compound of formula IX; wherein:
$R^{10}$ is independently $C_{1-6}$alkyl or a benzyl optionally substituted by $C_{1-4}$alkyl, $C_{2-4}$alkenyl, halogen, hydroxy, cyano, nitro, $CF_3$, $OC_{1-4}$alkyl, $OCF_3$, and $C(=O)C_{1-4}$alkyl; and
W is a halogen or $R^{10}C(O)$—.
Preferably, $R^{10}C(O)W$ is acetic anhydride.

In a $22^{nd}$ embodiment, the disclosure provides a process for preparing a compound of formula IX, or a salt thereof, wherein the transforming step comprises the steps of:
a) treating a solution of a compound of formula VIII with an acid; and
b) adding a base to the solution to give a free amine intermediate.

Preferably the acid is selected from sulfuric acid, toluenesulfonic acid, nitric acid, methanesulfonic acid, hydrobromic acid and hydrochloric acid, more preferably methanesulfonic acid. Preferably the base is a trialkylamine, preferably triethylamine.

In a $23^{rd}$ embodiment, the disclosure provides an alternative process for preparing a compound of formula IX, or a salt thereof:

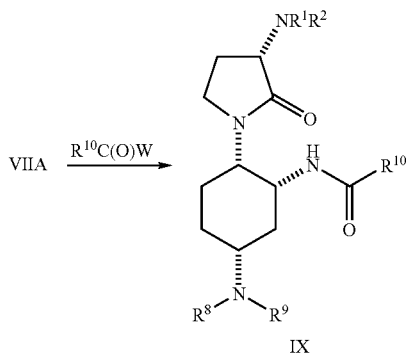

the process comprising the step of adding the isocyanate compound of formula VIIa, optionally in situ, to an acylating agent agent, $(R^{10}C(O))_2O$ in the presence of its corresponding acid, $R^{10}C(O)OH$, wherein $R^{10}$ is independently $C_{1-6}$alkyl or a benzyl optionally substituted by $C_{1-4}$alkyl, $C_{2-4}$alkenyl, halogen, hydroxy, cyano, nitro, $CF_3$, $OC_{1-4}$alkyl, $OCF_3$, and $C(=O)C_{1-4}$alkyl. Preferably, $R^{10}$ is $C_{1-6}$alkyl, especially methyl.

In a $24^{th}$ embodiment, the disclosure provides a process for preparing a compound of formula X, or a salt thereof:

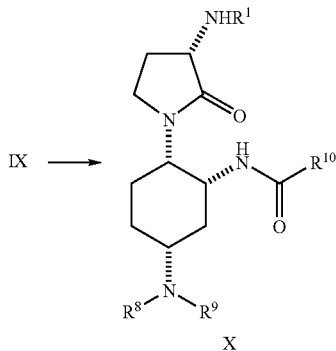

the process comprising the step of:
deprotecting the protected amine compound of formula IX to provide a compound of formula X. Preferably, where $R^2$ is Cbz, deprotection comprises hydrogenating the protected amine compound of formula IX in the presence of a palladium catalyst. The palladium catalyst is preferably 10% Pd/C.

In a $25^{th}$ embodiment, the disclosure provides a process for preparing a compound of formula I:

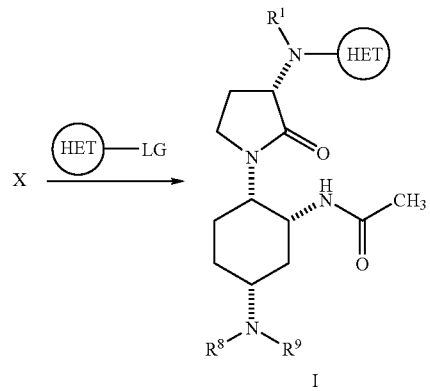

the process comprising the step of:
coupling a compound of formula X with a compound of formula:

to give a compound of formula I;
wherein:
HET is an optionally substituted 3-14 membered heterocyclo or heteroaryl ring having one to four heteroatoms selected from N, O or S (preferably one to three heteroatoms, especially one to two nitrogen atoms) in at least one of the rings (HET is preferably a 6-substituted quinazolin-4-yl, more preferably 6-trifluoromethyl-quinazolin-4-yl); and
LG is a leaving group selected from halogen or $OSO_2R_{16}$ (LG is preferably a halogen, more preferably chloro), wherein $R_{16}$ is $C_{1-6}$alkyl, phenyl, a 5- to 7-membered heteroaryl having one or more atoms selected from N, S, or O, or a 3- to 7-membered cycloalkyl, all of which are optionally substituted (preferably, optional substituents for $R_{16}$ are one to three groups selected from halogen, $CF_3$ and $C_{1-6}$alkyl).

In a $26^{th}$ embodiment, the present invention provides a novel process for preparing a compound of formula VIII, or a salt thereof:

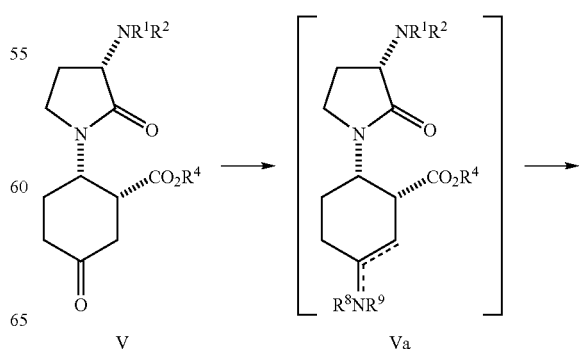

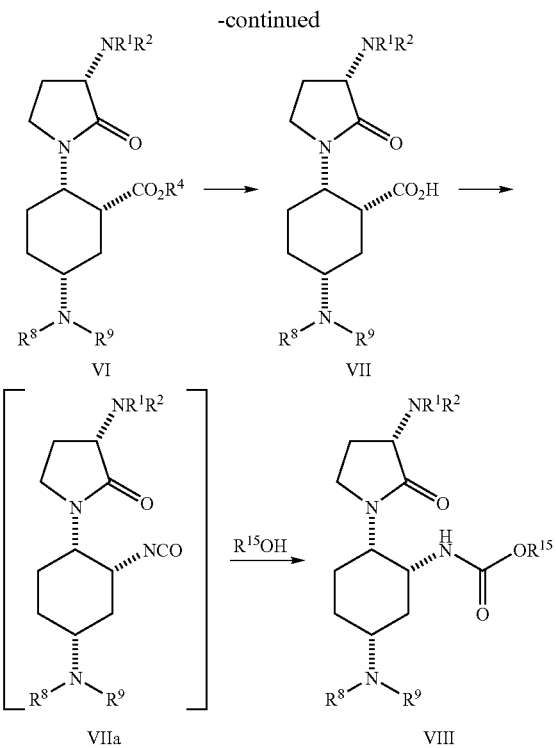

the process comprising the steps of:
reductively aminating a compound of formula V with an amine of formula, NH($R^8$)($R^9$), to give a compound of formula VI comprising the steps of:
(a) adding the amine and a dehydrating agent to a compound of formula V in an aprotic solvent at a temperature from about −20° to about +50° C. to form the imine/enamine compound of formula Va; and
(b) treating a solution of the imine/enamine compound of formula Va and a platinum catalyst, 5% Pt/S/C, with a pressure of hydrogen gas to give an ester compound of formula VI;

hydrolyzing the ester compound of formula VI to give an acid compound of formula VII;
converting an acid compound of formula VII to an isocyanate compound of formula VIIa; and
reacting the isocyanate compound of formula VIIa with an alcohol of formula $R^{15}OH$ to afford a carbamate compound of formula VIII;

wherein:
$R_1$ and $R_2$ are independently hydrogen or an amine-protecting group selected from a carbobenzyloxy (Cbz) group, a tert-butyloxycarbonyl (BOC), a fluorenylmethyloxycarbonyl (FMOC) group, a benzyl (Bn) group, and a p-methoxybenzyl (PMB) group (preferably the amine-protecting group is Cbz, Bn or BOC, especially Cbz or Bn);

$R_4$ is lower $C_{1-6}$alkyl or a benzyl optionally substituted by $C_{1-4}$alkyl, $C_{2-4}$alkenyl, halogen, hydroxy, cyano, nitro, $CF_3$, $OC_{1-4}$alkyl, $OCF_3$, and $C(=O)C_{1-4}$alkyl;

$R_8$ and $R_9$ are independently hydrogen or $C_{1-6}$alkyl;

$R^{15}$ is $C_{1-6}$alkyl or a benzyl optionally substituted by $C_{1-4}$alkyl, $C_{2-4}$alkenyl, halogen, hydroxy, cyano, nitro, $CF_3$, $OC_{1-4}$alkyl, $OCF_3$, and $C(=O)C_{1-4}$alkyl ($R^{15}$ is preferably tert-butyl or unsubstituted benzyl, more preferably tert-butyl);

HET is an optionally substituted 3-14 membered heterocyclo or heteroaryl ring having one to four heteroatoms selected from N, O or S (preferably one to three heteroatoms, especially one to two nitrogen atoms) in at least one of the rings (HET is preferably a 6-substituted quinazolin-4-yl, more preferably 6-trifluoromethyl-quinazolin-4-yl); and LG is a leaving group selected from halogen or $OSO_2R_{16}$ (LG is preferably a halogen, more preferably chloro), wherein $R_{16}$ is $C_{1-6}$alkyl, phenyl, a 5- to 7-membered heteroaryl having one or more atoms selected from N, S, or O, or a 3- to 7-membered cycloalkyl, all of which are optionally substituted (preferably, optional substituents for $R_{16}$ are one to three groups selected from halogen, $CF_3$ and $C_{1-6}$alkyl).

In a 27$^{th}$ embodiment, the present invention provides a novel process for preparing a compound of formula I, or a salt thereof:

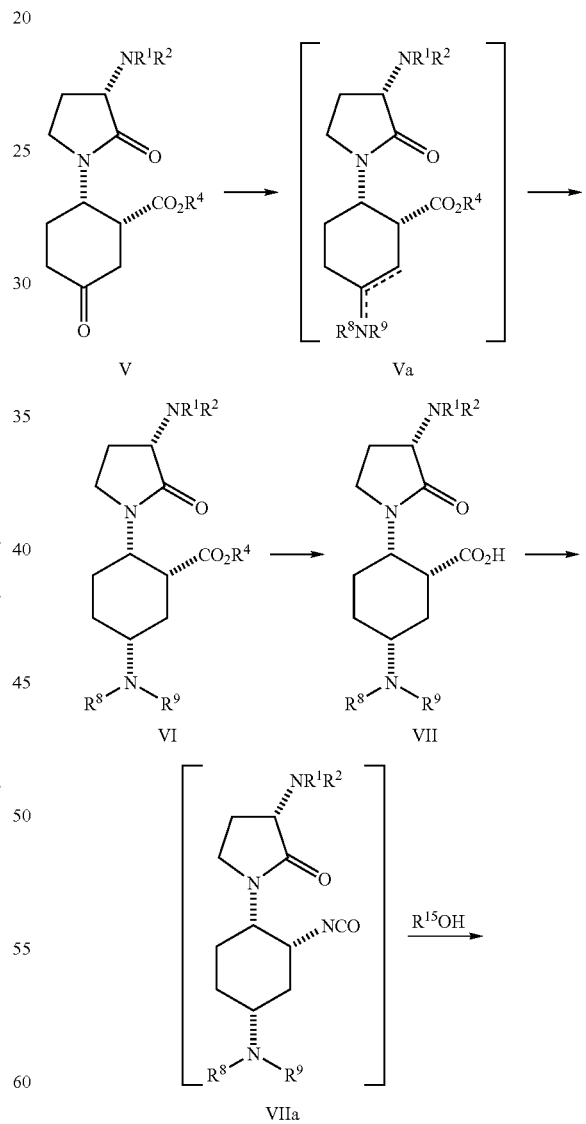

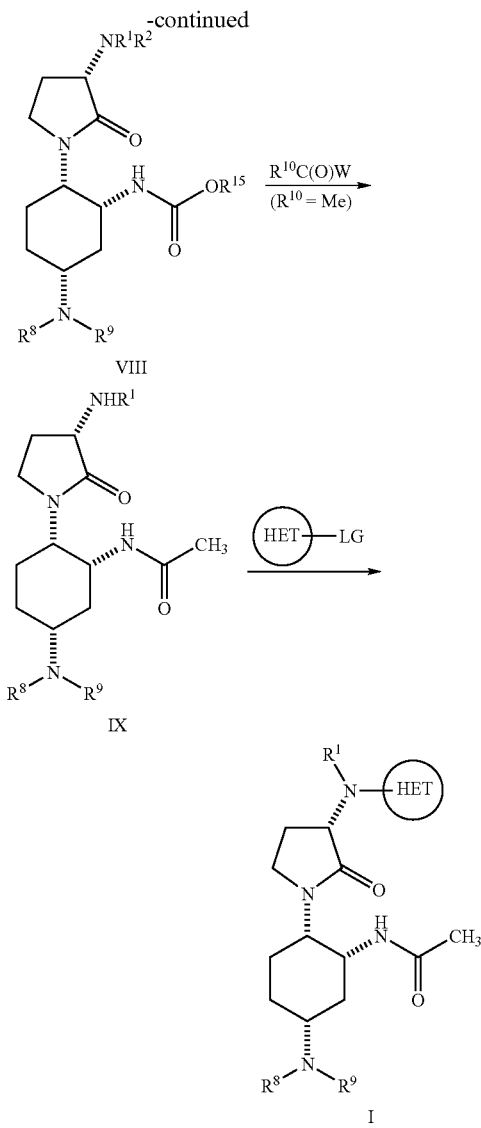

the process comprising the steps of:

reductively aminating a compound of formula V with an amine of formula, $NH(R^8)(R^9)$, to give a compound of formula VI, reductively aminating comprising the steps of:

(a) adding the amine and a dehydrating agent to a compound of formula V in an aprotic solvent at a temperature from about −20° to about +50° C. to form the imine/enamine compound of formula Va; and (b) treating a solution of the imine/enamine compound of formula Va and a platinum catalyst, 5% Pt/S/C, with a pressure of hydrogen gas to give an ester compound of formula VI;

hydrolyzing the ester compound of formula VI to give an acid compound of formula VII;

converting an acid compound of formula VII to an isocyanate compound of formula VIIa;

reacting the isocyanate compound of formula VIIa with an alcohol of formula $R^{15}OH$ to afford a carbamate compound of formula VIII;

transforming the carbamate compound of formula VIII to a free amine intermediate; and acylating the free amine intermediate in situ with a reagent, $R^{10}C(O)W$, to give a protected amine compound of formula IX;

deprotecting the protected amine compound of formula IX to give a compound of formula X; and coupling a compound of formula X with a compound of formula $$\text{HET}-\text{LG}$$

to give a compound of formula I;

wherein:

$R_1$ and $R_2$ are independently hydrogen or an amine-protecting group selected from a carbobenzyloxy (Cbz) group, a tert-butyloxycarbonyl (BOC), a fluorenylmethyloxycarbonyl (FMOC) group, a benzyl (Bn) group, and a p-methoxybenzyl (PMB) group (preferably the amine-protecting group is Cbz, Bn or BOC, especially Cbz or Bn);

$R_4$ is lower $C_{1-6}$alkyl or a benzyl optionally substituted by $C_{1-4}$alkyl, $C_{2-4}$alkenyl, halogen, hydroxy, cyano, nitro, $CF_3$, $OC_{1-4}$alkyl, $OCF_3$, and $C(=O)C_{1-4}$alkyl;

$R_8$ and $R_9$ are independently hydrogen or $C_{1-6}$alkyl;

$R^{10}$ is independently $C_{1-6}$alkyl or a benzyl optionally substituted by $C_{1-4}$alkyl, $C_{2-4}$alkenyl, halogen, hydroxy, cyano, nitro, $CF_3$, $OC_{1-4}$alkyl, $OCF_3$, and $C(=O)C_{1-4}$alkyl (preferably $C_{1-6}$alkyl, more preferably methyl);

W is halogen or $R^{10}C(O)$—;

$R^{15}$ is $C_{1-6}$alkyl or a benzyl optionally substituted by $C_{1-4}$alkyl, $C_{2-4}$alkenyl, halogen, hydroxy, cyano, nitro, $CF_3$, $OC_{1-4}$alkyl, $OCF_3$, and $C(=O)C_{1-4}$alkyl ($R^{15}$ is preferably tert-butyl or unsubstituted benzyl, more preferably tert-butyl);

HET is an optionally substituted 3-14 membered heterocyclo or heteroaryl ring having one to four heteroatoms selected from N, O or S (preferably one to three heteroatoms, especially one to two nitrogen atoms) in at least one of the rings (HET is preferably a 6-substituted quinazolin-4-yl, more preferably 6-trifluoromethyl-quinazolin-4-yl); and LG is a leaving group selected from halogen or $OSO_2R_{16}$ (LG is preferably a halogen, more preferably chloro), wherein $R_{16}$ is $C_{1-6}$alkyl, phenyl, a 5- to 7-membered heteroaryl having one or more atoms selected from N, S, or O, or a 3- to 7-membered cycloalkyl, all of which are optionally substituted (preferably, optional substituents for $R_{16}$ are one to three groups selected from halogen, $CF_3$ and $C_{1-6}$alkyl).

In a 28$^{th}$ embodiment, the present invention provides an alternate novel process for preparing a compound of formula I, or a salt thereof:

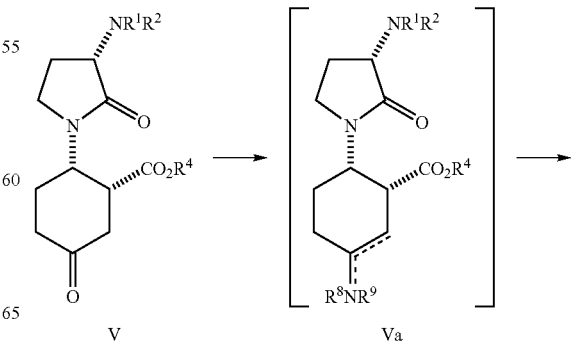

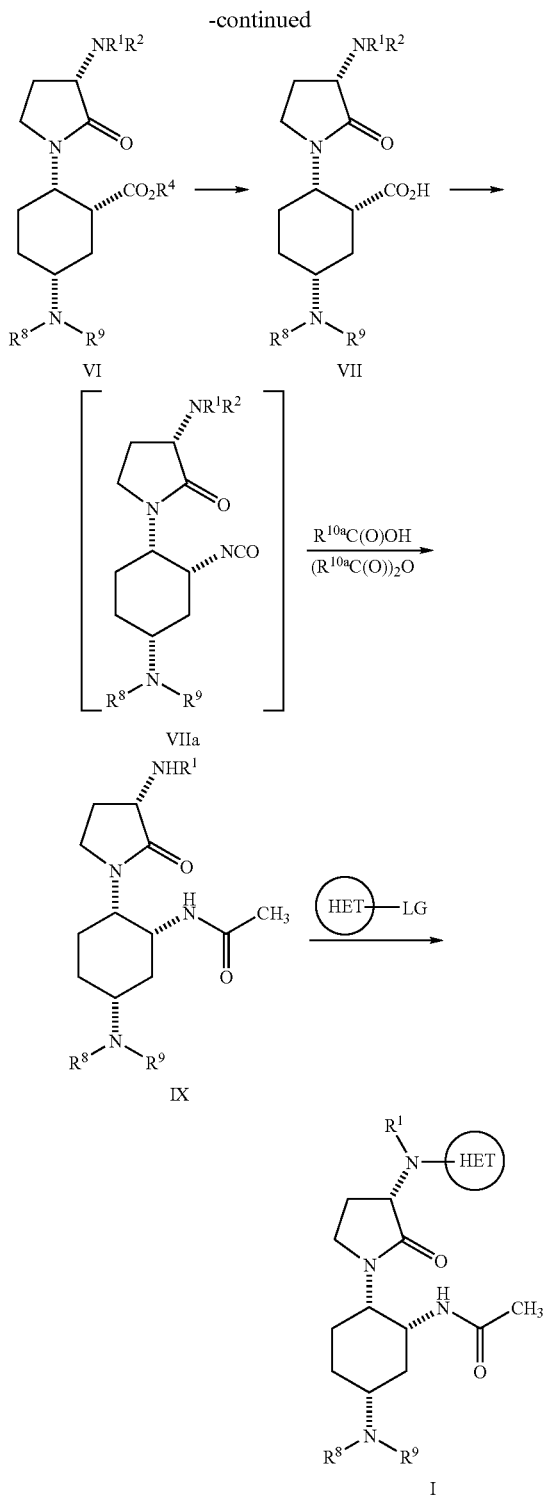

the process comprising the steps of:
 reductively aminating a compound of formula V with an amine of formula, $NH(R^8)(R^9)$, to give a compound of formula VI, reductively aminating comprising the steps of:
 (a) adding the amine and a dehydrating agent to a compound of formula V in an aprotic solvent at a temperature from about −20° to about +50° C. to form the imine/enamine compound of formula Va; and
 (b) treating a solution of the imine/enamine compound of formula Va and a platinum catalyst, 5% Pt/S/C, with a pressure of hydrogen gas to give an ester compound of formula VI;
 hydrolyzing the ester compound of formula VI to give an acid compound of formula VII;
 converting an acid compound of formula VII to an isocyanate compound of formula VIIa;
 adding the isocyanate compound of formula VIIa, optionally in situ, to an acylating agent agent, $(R^{10a}C(O))_2O$ in the presence of its corresponding acid, $R^{10a}C(O)OH$ to give the protected amine compound of formula IX;
 deprotecting the protected amine compound of formula IX to give a compound of formula X; and
 coupling a compound of formula X with a compound of formula

to give a compound of formula I;

wherein:
 $R_1$ and $R_2$ are independently hydrogen or an amine-protecting group selected from a carbobenzyloxy (Cbz) group, a tert-butyloxycarbonyl (BOC), a fluorenylmethyloxycarbonyl (FMOC) group, a benzyl (Bn) group, and a p-methoxybenzyl (PMB) group (preferably the amine-protecting group is Cbz, Bn or BOC, especially Cbz or Bn);
 $R_4$ is lower $C_{1-6}$alkyl or a benzyl optionally substituted by $C_{1-4}$alkyl, $C_{2-4}$alkenyl, halogen, hydroxy, cyano, nitro, $CF_3$, $OC_{1-4}$alkyl, $OCF_3$, and $C(=O)C_{1-4}$alkyl;
 $R_8$ and $R_9$ are independently hydrogen or $C_{1-6}$alkyl;
 wherein $R^{10a}$ is independently $C_{1-6}$alkyl or optionally substituted benzyl (preferably $R^{10a}$ is methyl);
 HET is an optionally substituted 3-14 membered heterocyclo or heteroaryl ring having one to four heteroatoms selected from N, O or S (preferably one to three heteroatoms, especially one to two nitrogen atoms) in at least one of the rings (HET is preferably a 6-substituted quinazolin-4-yl, more preferably 6-trifluoromethyl-quinazolin-4-yl); and
 LG is a leaving group selected from halogen or $OSO_2R_{16}$ (LG is preferably a halogen, more preferably chloro), wherein $R_{16}$ is $C_{1-6}$alkyl, phenyl, a 5- to 7-membered heteroaryl having one or more atoms selected from N, S, or O, or a 3- to 7-membered cycloalkyl, all of which are optionally substituted (preferably, optional substituents for $R_{16}$ are one to three groups selected from halogen, $CF_3$ and $C_{1-6}$alkyl).

In a 29$^{th}$ embodiment, the disclosure provides a process according to any of the foregoing embodiments wherein:
 the compound of formula V is

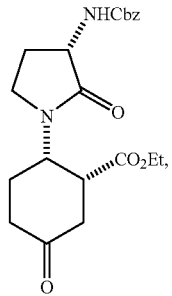

or a salt thereof;

the compound of formula VI is

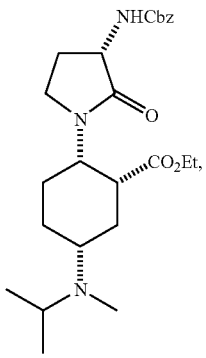

or a salt thereof;

the compound of formula VII is

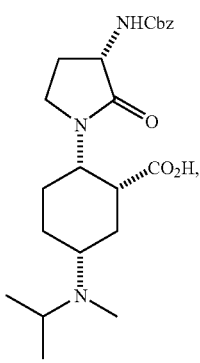

or a salt thereof (preferably the sodium salt);

the carbamate compound of formula VIII is

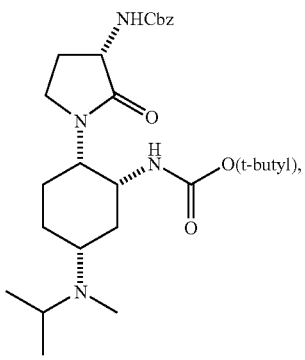

or a salt thereof;

the protected amine compound of formula IX is

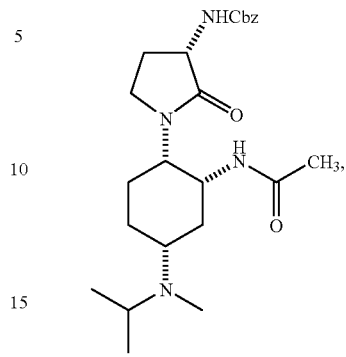

or a salt the deprotected compound of formula X is

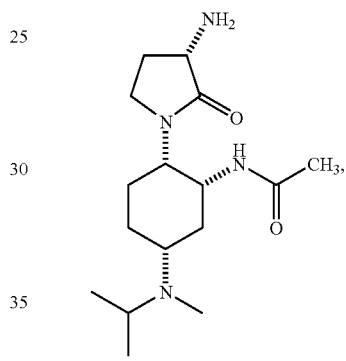

or a salt thereof, and the compound of formula I is N-((1R, 2S,5R)-5-(isopropyl(methyl)amino)-2-((S)-2-oxo-3-(6-(trifluoromethyl)quinazolin-4-ylamino)pyrrolidin-1-yl)cyclohexyl)acetamide, or a salt thereof.

In a 30$^{th}$ embodiment, the disclosure provides a compound of formula V, or a salt thereof:

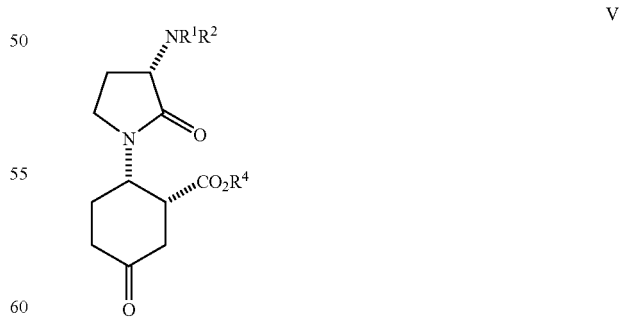

wherein:

$R^1$ and $R^2$ are hydrogen or an amine-protecting group selected from BOC, Cbz, or benzyl; and $R^4$ is lower $C_{1-6}$ alkyl.

A preferred compound of formula V is

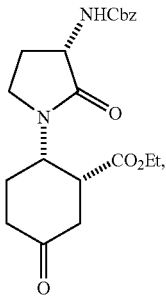

or a salt thereof.

In a 31$^{st}$ embodiment the disclosure provides a compound of formula VI, or a salt thereof:

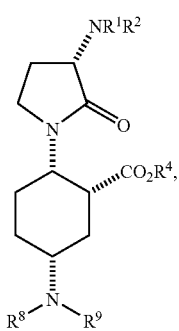

VI wherein:

R$^1$ and R$^2$ are independently hydrogen or an amine-protecting group selected from BOC, Cbz, or benzyl; and R$^4$ is C$_{1-6}$alkyl; and R$^8$ and R$^9$ are independently selected from hydrogen or C$_{1-6}$alkyl.

A preferred compound of formula VI is

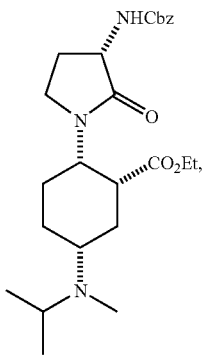

or a salt thereof

In a 32$^{nd}$ embodiment, the disclosure provides a compound of formula VII, or a salt thereof:

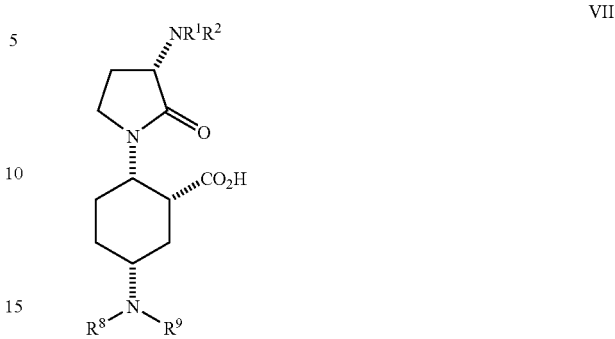

VII wherein:

R$^1$ and R$^2$ are independently hydrogen or an amine-protecting group selected from BOC, Cbz, or benzyl; and R$^8$ and R$^9$ are independently selected from hydrogen or C$_{1-6}$alkyl.

A preferred compound of formula VII is

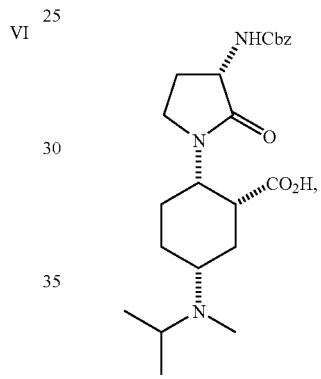

or a salt thereof. Preferable salts thereof include the alkali salts such as the sodium salt of the compound of formula VII.

In a 33$^{rd}$ embodiment, the disclosure provides a compound of formula VII, or a salt thereof:

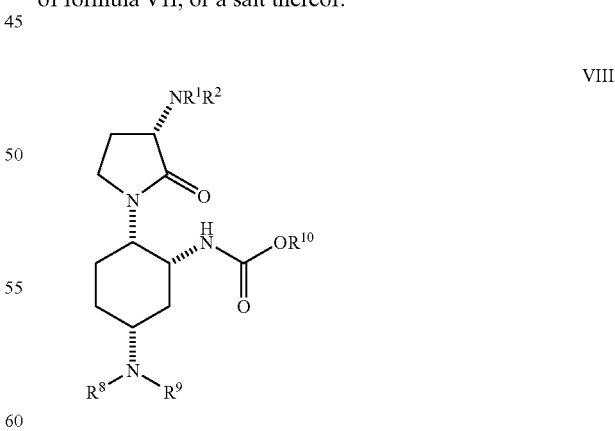

VIII wherein:

R$^1$ and R$^2$ are independently hydrogen or an amine-protecting group selected from BOC, Cbz, or benzyl;

R$^8$ and R$^9$ are independently selected from hydrogen or C$_{1-6}$alkyl; and

R$_{10}$ is C$_{1-6}$alkyl or benzyl.

A preferred compound of formula VIII is

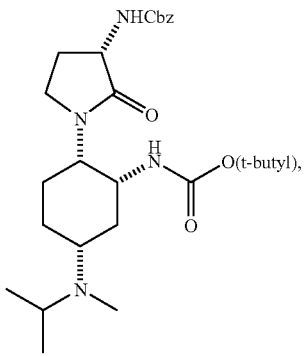

or a salt thereof.

In a 34th embodiment, the disclosure provides a compound of formula IX, or a salt thereof:

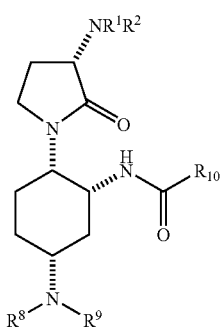

IX wherein:

$R^1$ and $R^2$ are independently hydrogen or an amine-protecting group selected from BOC, Cbz, or benzyl;

$R^8$ and $R^9$ are independently selected from hydrogen or $C_{1-6}$alkyl; and $R_{10}$ is $C_{1-6}$alkyl or optionally substituted benzyl.

A preferred compound of formula IX is

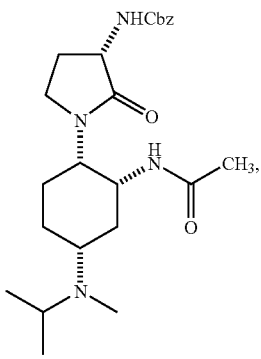

or a salt thereof.

In a 35th embodiment, the disclosure provides a compound of formula X, or a salt thereof:

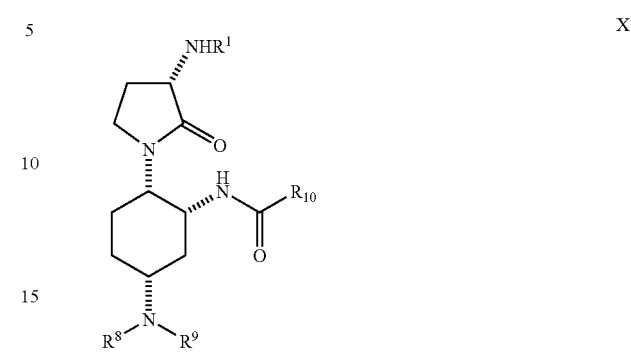

X wherein:

$R^1$ is independently hydrogen or an amine-protecting group selected from BOC, Cbz, or benzyl;

$R^8$ and $R^9$ are independently selected from hydrogen or $C_{1-6}$alkyl; and $R_{10}$ is $C_{1-6}$alkyl or optionally substituted benzyl.

A preferred compound of formula X is

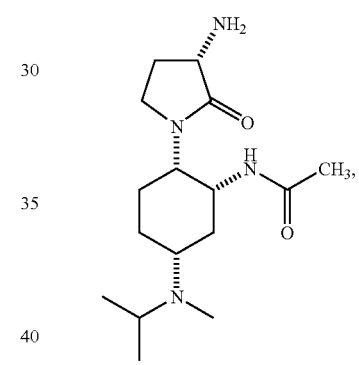

or a salt thereof.

In a 36th embodiment, the disclosure provides a compound of formula II, or a salt thereof:

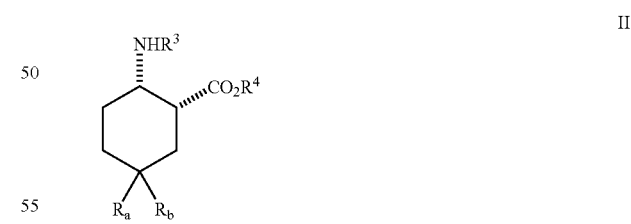

II wherein:

$R_a$ and $R_b$ together with the carbon atom to which they are both attached combine to form carbonyl or a 1,3-dioxolane group (preferably $R_a$ and $R_b$ together with the carbon atoms to which they are both attached combine to form a 1,3-dioxolane group);

$R_1$ is hydrogen;

$R_2$ is Cbz;

$R_3$ is hydrogen; and $R_4$ is $C_{1-6}$alkoxy.

A preferred compound of formula II is

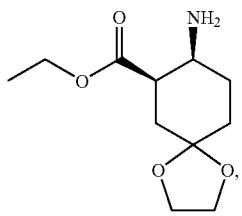

or a salt thereof. Preferable salts are the toluenesulfonate or hydrobromide salt, especially the toluemensulfonate salt.

In a 46th embodiment, the disclosure provides a process wherein a compound of formula I is N-((1R,2S,5R)-5-(isopropyl(methyl)amino)-2-((S)-2-oxo-3-(6-(trifluoromethyl)quinazolin-4-ylamino)pyrrolidin-1-yl)cyclohexyl)acetamide or a salt thereof.

The present invention may be embodied in other specific forms without departing from the spirit or essential attributes thereof. Thus, the above embodiments should not be considered limiting. Any and all embodiments of the present invention may be taken in conjunction with any other embodiment or embodiments to describe additional embodiments. Each individual element (e.g. preferable or special aspects) of the embodiments is its own independent embodiment. Furthermore, any element of an embodiment is meant to be combined with any and all other elements from any embodiment to describe an additional embodiment. In addition, the present invention encompasses combinations of different embodiment, parts of embodiments, definitions, descriptions, and examples of the invention noted herein.

DEFINITIONS

The following are definitions of terms used in this specification and appended claims. The initial definition provided for a group or term herein applies to that group or term throughout the specification and claims, individually or as part of another group, unless otherwise indicated.

The term "alkyl" refers to straight or branched chain hydrocarbon groups having 1 to 12 carbon atoms, preferably 1 to 6 carbon atoms. When numbers appear in a subscript after the symbol "C", the subscript defines with more specificity the number of carbon atoms that a particular group may contain. For example, "$C_{1-6}$alkyl" refers to straight and branched chain alkyl groups with one to six carbon atoms, such as methyl, ethyl, n-propyl, isopropyl, n-butyl, t-butyl, n-pentyl, and so forth. The subscript "0" refers to a bond. Thus, the term hydroxy($C_{0-2}$)alkyl or ($C_{0-2}$)hydroxyalkyl includes hydroxy, hydroxymethyl and hydroxyethyl. Alkyl groups may be substituted with one to three groups selected from ($C_{1-6}$)alkyl, ($C_{2-6}$)alkenyl, hydroxy, halogen, cyano, nitro, $CF_3$, O($C_{1-6}$ alkyl), $OCF_3$, C(=O)H, C(=O)($C_{1-6}$alkyl), $CO_2H$, $CO_2$($C_{1-6}$ alkyl), $NHCO_2$($C_{1-6}$alkyl), —S($C_{1-6}$alkyl), $NH_2$, NH($C_{1-6}$ alkyl), N($C_{1-6}$alkyl)$_2$, N($CH_3$)$_3^+$, $SO_2$($C_{1-6}$alkyl), C(=O)($C_{1-4}$alkylene)$NH_2$, C(=O)($C_{1-4}$alkylene)NH(alkyl), C(=O)($C_{1-4}$alkylene)N($C_{1-4}$alkyl)$_2$, $C_{3-7}$cycloalkyl, phenyl, benzyl, phenylethyl, phenyloxy, benzyloxy, napthyl, a four- to seven-membered heterocylo, and/or a five- to six-membered heteroaryl. When a substituted alkyl is substituted with an aryl, heterocyclo, cycloalkyl, or heteroaryl group, said ringed systems are as defined below and thus may have zero, one, two, or three substituents, also as defined below.

When the term "alkyl" is used together with another group, such as in "arylalkyl", this conjunction defines with more specificity at least one of the substituents that the substituted alkyl will contain. For example, "arylalkyl" refers to a substituted alkyl group as defined above where at least one of the substituents is an aryl, such as benzyl. Thus, the term aryl ($C_{0-4}$)alkyl includes a substituted lower alkyl having at least one aryl substituent and also includes an aryl directly bonded to another group, i.e., aryl($C_0$)alkyl.

The term "alkenyl" refers to straight or branched chain hydrocarbon groups having 2 to 12 carbon atoms and at least one double bond. Alkenyl groups of 2 to 6 carbon atoms and having one double bond are most preferred. Alkenyl groups may be substituted as described above for alkyl groups.

The term "alkynyl" refers to straight or branched chain hydrocarbon groups having 2 to 12 carbon atoms and at least one triple bond. Alkynyl groups of 2 to 6 carbon atoms and having one triple bond are most preferred. Alkynyl groups may be substituted as described above for alkyl groups.

The term "alkylene" refers to bivalent straight or branched chain hydrocarbon groups having 1 to 12 carbon atoms, preferably 1 to 8 carbon atoms, e.g., {—$CH_2$—}$_n$, wherein n is 1 to 12, preferably 1-8. Lower alkylene groups, that is, alkylene groups of 1 to 2 carbon atoms, are most preferred. The terms "alkenylene" and "alkynylene" refer to bivalent radicals of alkenyl and alkynyl groups, respectively, as defined above. Alkenylene groups may be substituted as described above for alkyl groups.

The term "alkoxy" refers to an oxygen atom substituted by alkyl, as defined herein. For example, the term "alkoxy" or includes the group —O—$C_{1-6}$alkyl.

When a subscript is used with reference to an alkoxy, thioalkyl or aminoalkyl, the subscript refers to the number of carbon atoms that the group may contain in addition to heteroatoms.

It should be understood that the selections for all groups, including for examples, alkoxy, thioalkyl, and aminoalkyl, will be made by one skilled in the field to provide stable compounds.

The term "carbonyl" refers to a bivalent carbonyl group —C(=O)—.

The term "acyl" refers to a carbonyl group linked to an organic radical, more particularly, the group C(=O)$R_e$, as well as the bivalent group —C(=O)$R_e$—, which are linked to organic radicals. The group $R_e$ can be selected from alkyl, alkenyl, alkynyl, cycloalkyl, heterocyclo, aryl, or heteroaryl as defined herein, or when appropriate, the corresponding bivalent group, e.g. alkylene.

The term "cycloalkyl" refers to fully saturated and partially unsaturated hydrocarbon rings (and therefore includes "cycloalkenyl rings") of 3 to 9, preferably 3 to 7 carbon atoms. The term "cycloalkyl" includes such rings having zero, one, two, or three substituents selected from ($C_{1-4}$)alkyl, ($C_{2-4}$)alkenyl, halogen, hydroxy, cyano, nitro, $CF_3$, O($C_{1-4}$ alkyl), $OCF_3$, C(=O)H, C(=O)($C_{1-4}$alkyl), $CO_2H$, $CO_2$ ($C_{1-4}$ alkyl), $NHCO_2$($C_{1-4}$alkyl), S($C_{1-4}$alkyl), $NH_2$, NH($C_{1-4}$ alkyl), N($C_{1-4}$alkyl)$_2$, N($C_{1-4}$alkyl)$_3^+$, $SO_2$($C_{1-4}$alkyl), C(=O)($C_{1-4}$alkylene)$NH_2$, C(=O)($C_{1-4}$alkylene)NH (alkyl), and/or C(=O)($C_{1-4}$alkylene)N($C_{1-4}$alkyl)$_2$. The term "cycloalkyl" also includes such rings having a second ring fused thereto (e.g., including benzo, heterocyclo, or heteroaryl rings) or having a carbon-carbon bridge of 3 to 4 carbon atoms.

The term "halo" or "halogen" refers to chloro, bromo, fluoro and iodo.

The term "haloalkyl" means a substituted alkyl having one or more halo substituents. For example, "haloalkyl" includes mono, bi, and trifluoromethyl.

The term "haloalkoxy" means an alkoxy group having one or more halo substituents. For example, "haloalkoxy" includes $OCF_3$.

The term "heteroatoms" shall include oxygen, sulfur and nitrogen.

The term "aryl" refers to phenyl, biphenyl, fluorenyl, 1-naphthyl and 2-naphthyl. The term "aryl" includes such rings having zero, one, two or three substituents selected from $(C_{1-4})$alkyl, $(C_{2-4})$alkenyl, halogen, hydroxy, cyano, nitro, $CF_3$, $O(C_{1-4}alkyl)$, $OCF_3$, $C(\!=\!O)H$, $C(\!=\!O)(C_{1-4}alkyl)$, $CO_2H$, $CO_2(C_{1-4}alkyl)$, $NHCO_2(C_{1-4}alkyl)$, $S(C_{1-4}alkyl)$, $NH_2$, $NH(C_{1-4}alkyl)$, $N(C_{1-4}alkyl)_2$, $N(C_{1-4}alkyl)_3^+$, $SO_2(C_{1-4}\ alkyl)$, $C(\!=\!O)(C_{1-4}alkylene)NH_2$, $C(\!=\!O)(C_{1-4}alkylene)NH(alkyl)$, and/or $C(\!=\!O)(C_{1-4}alkylene)N(C_{1-4}alkyl)_2$.

The terms "heterocyclo" or "heterocyclic" refers to substituted and unsubstituted non-aromatic (which may be partially or fully saturated) 3- to 15-membered rings having one to four heteroatoms. Such rings can be 3- to 7-membered monocyclic groups, 7- to 11-membered bicyclic groups, and 10- to 15-membered tricyclic groups. Each ring of the heterocyclo group containing a heteroatom can contain one or two oxygen or sulfur atoms and/or from one to four nitrogen atoms provided that the total number of heteroatoms in each ring is four or less, and further provided that the ring contains at least one carbon atom. The fused rings completing bicyclic and tricyclic groups may contain only carbon atoms and may be saturated, partially saturated, or unsaturated. The nitrogen and sulfur atoms may optionally be oxidized and the nitrogen atoms may optionally be quaternized. The heterocyclo group may be attached at any available nitrogen or carbon atom. The heterocyclo ring may contain zero, one, two or three substituents selected from $(C_{1-4})$alkyl, $(C_{2-4})$alkenyl, halogen, hydroxy, cyano, nitro, $CF_3$, $O(C_{1-4}alkyl)$, $OCF_3$, $C(\!=\!O)H$, $C(\!=\!O)(C_{1-4}alkyl)$, $CO_2H$, $CO_2(C_{1-4}alkyl)$, $NHCO_2(C_{1-4}alkyl)$, $S(C_{1-4}alkyl)$, $NH_2$, $NH(C_{1-4}alkyl)$, $N(C_{1-4}alkyl)_2$, $N(C_{1-4}alkyl)_3^+$, $SO_2(C_{1-4}alkyl)$, $C(\!=\!O)(C_{1-4}alkylene)NH_2$, $C(\!=\!O)(C_{1-4}alkylene)NH(alkyl)$, and/or $C(\!=\!O)(C_{1-4}alkylene)N(C_{1-4}alkyl)_2$. Exemplary heterocyclic groups include azetidinyl, pyrrolidinyl, oxetanyl, imidazolinyl, oxazolidinyl, isoxazolinyl, thiazolidinyl, isothiazolidinyl, tetrahydrofuranyl, piperidyl, piperazinyl, 2-oxopiperazinyl, 2-oxopiperidyl, 2-oxopyrrolodinyl, 2-oxoazepinyl, azepinyl, 4-piperidonyl, tetrahydropyranyl, morpholinyl, thiamorpholinyl, thiamorpholinyl sulfoxide, thiamorpholinyl sulfone, 1,3-dioxolane, quinuclidinyl, and tetrahydro-1,1-dioxothienyl and the like.

The term "heteroaryl" refers to substituted and unsubstituted aromatic 3- to 14-membered rings having one to four heteroatoms selected from O, S, or N in at least one of the rings. Said rings can be 5- or 6-membered monocyclic groups, 9- or 10-membered bicyclic groups, and 11- to 14-membered tricyclic groups. Each ring of the heteroaryl group containing a heteroatom can contain one or two oxygen or sulfur atoms and/or from one to four nitrogen atoms provided that the total number of heteroatoms in each ring is four or less and each ring has at least one carbon atom. The fused rings completing the bicyclic and tricyclic groups may contain only carbon atoms and may be saturated, partially saturated, or unsaturated. The nitrogen and sulfur atoms may optionally be oxidized and the nitrogen atoms may optionally be quaternized. Heteroaryl groups which are bicyclic or tricyclic must include at least one fully aromatic ring but the other fused ring or rings may be aromatic or non-aromatic. The heteroaryl group may be attached at any available nitrogen or carbon atom of any ring. The heteroaryl ring system may contain zero, one, two or three substituents selected from $(C_{1-4})$alkyl, $(C_{2-4})$alkenyl, halogen, hydroxy, cyano, nitro, $CF_3$, $O(C_{1-4}alkyl)$, $OCF_3$, $C(\!=\!O)H$, $C(\!=\!O)(C_{1-4}alkyl)$, $CO_2H$, $CO_2(C_{1-4}alkyl)$, $NHCO_2(C_{1-4}alkyl)$, $S(C_{1-4}alkyl)$, $NH_2$, $NH(C_{1-4}alkyl)$, $N(C_{1-4}alkyl)_2$, $N(C_{1-4}alkyl)_3^+$, $SO_2(C_{1-4}\ alkyl)$, $C(\!=\!O)(C_{1-4}alkylene)NH_2$, $C(\!=\!O)(C_{1-4}alkylene)NH(alkyl)$, and/or $C(\!=\!O)(C_{1-4}alkylene)N(C_{1-4}alkyl)_2$.

Exemplary heteroaryl groups include pyrrolyl, pyrazolyl, pyrazolinyl, imidazolyl, oxazolyl, isoxazolyl, thiazolyl, thiadiazolyl, isothiazolyl, furanyl, thienyl, oxadiazolyl, pyridyl, pyrazinyl, pyrimidinyl, pyridazinyl, triazinyl, indolyl, benzothiazolyl, benzodioxolyl, benzoxazolyl, benzothienyl, quinolinyl, tetrahydroisoquinolinyl, isoquinolinyl, benzimidazolyl, benzopyranyl, indolizinyl, benzofuranyl, chromonyl, coumarinyl, benzopyranyl, cinnolinyl, quinoxalinyl, indazolyl, pyrrolopyridyl, furopyridyl, dihydroisoindolyl, tetrahydroquinolinyl and the like. Particular heteroaryl groups include, for example, 6-substituted quinazolin-4-yl and 6-trifluoromethyl-quinazolin-4-yl.

Where a group is optionally substituted, it shall include substituted and unsubstituted groups.

The compounds herein described may have asymmetric centers. Compounds of the present invention containing an asymmetrically substituted atom may be isolated in optically active or racemic forms. It is well known in the art how to prepare optically active forms, such as by resolution of racemic forms or by synthesis from optically active starting materials. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomeric form is specifically indicated.

One enantiomer of compounds disclosed herein may display superior activity compared with the other. Thus, all of the stereochemistries are considered to be a part of the present invention. When required, separation of the racemic material can be achieved by HPLC using a chiral column or by a resolution using a resolving agent such as camphonic chloride as in Steven D. Young et al., *Antimicrobial Agents and Chemotherapy*, 1995, 2602-2605.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, benzene sulfonic, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in *Remington's Pharmaceutical Sciences*, 17th ed., Mack Publishing Company, Easton, Pa., 1985, p. 1418, the disclosure of which is hereby incorporated by reference.

Since prodrugs are known to enhance numerous desirable qualities of pharmaceuticals (e.g., solubility, bioavailability, manufacturing, etc . . . ) the compounds of the present invention may be delivered in prodrug form. Thus, the present invention is intended to cover prodrugs of the presently claimed compounds, methods of delivering the same and compositions containing the same. "Prodrugs" are intended to include any covalently bonded carriers which release an active parent drug of the present invention in vivo when such prodrug is administered to a mammalian subject. Prodrugs in the present invention are prepared by modifying functional groups present in the compound in such a way that the modifications are cleaved, either in routine manipulation or in vivo, to the parent compound. Prodrugs include compounds of the present invention wherein a hydroxy, amino, or sulfhydryl group is bonded to any group that, when the prodrug of the present invention is administered to a mammalian subject, it cleaves to form a free hydroxyl, free amino, or free sulfhydryl group, respectively. Examples of prodrugs include, but are not limited to, acetate, formate and benzoate derivatives of alcohol and amine functional groups in the compounds of the present invention.

"Stable compound" and "stable structure" are meant to indicate a compound that is sufficiently robust to survive isolation to a useful degree of purity from a reaction mixture, and formulation into an efficacious therapeutic agent. The present invention is intended to embody stable compounds.

"Therapeutically effective amount" is intended to include an amount of a compound of the present invention alone or an amount of the combination of compounds claimed or an amount of a compound of the present invention in combination with other active ingredients effective to inhibit MCP-1 or effective to treat or prevent disorders as discussed herein.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting it development; and/or (c) relieving the disease-state, i.e., causing regression of the disease state.

The names used herein to designate a specific form, e.g., "N-2", should not be considered limiting with respect to any other substance possessing similar or identical physical and chemical characteristics, but rather it should be understood that these designations are mere identifiers that should be interpreted according to the characterization information also presented herein.

The present invention provides crystalline forms of the free base of N-((1R,2S,5R)-5-(isopropyl(methyl)amino)-2-((S)-2-oxo-3-(6-(trifluoromethyl)quinazolin-4-ylamino)pyrrolidin-1-yl)cyclohexyl)acetamide as a novel material, in particular, in a pharmaceutically acceptable form. In certain preferred embodiments, crystalline forms of the free base are in substantially pure form. Preferred embodiments of the free base are disclosed in the Examples as the N-2, DC-1, THOO-1, E-1, A-1, and AN-3.

The present invention also provides crystalline forms of salts of N-((1R,2S,5R)-5-(isopropyl(methyl)amino)-2-((S)-2-oxo-3-(6-(trifluoromethyl)quinazolin-4-ylamino)pyrrolidin-1-yl)cyclohexyl)acetamide as a novel material, in particular, in a pharmaceutically acceptable form. In certain preferred embodiments, crystalline forms of the salts are in substantially pure form. Preferred embodiments of the salts are disclosed in the Examples as the N-1 form of the dibenzene sulfonic acid salt and the H4-1 form of the HCl salt.

As used herein "polymorph" refers to crystalline forms having the same chemical composition but different spatial arrangements of the molecules, atoms, and/or ions forming the crystal.

As used herein "solvate" refers to a crystalline form of a molecule, atom, and/or ions that further contains molecules of a solvent or solvents incorporated into the crystalline structure. The solvent molecules in the solvate may be present in a regular arrangement and/or a non-ordered arrangement. The solvate may comprise either a stoichiometric or nonstoichiometric amount of the solvent molecules. For example, a solvate with a nonstoichiometric amount of solvent molecules may result from partial loss of solvent from the solvate.

As used herein "amorphous" refers to a solid form of a molecule, atom, and/or ions that is not crystalline. An amorphous solid does not display a definitive X-ray diffraction pattern.

As used herein, "substantially pure," when used in reference to a crystalline form, means a compound having a purity greater than 90 weight %, including greater than 90, 91, 92, 93, 94, 95, 96, 97, 98 and 99 weight %, and also including equal to about 100 weight % of Compound I, based on the weight of the compound. The remaining material comprises other form(s) of the compound, and/or reaction impurities and/or processing impurities arising from its preparation. For example, a crystalline form of N-((1R,2S,5R)-5-(isopropyl (methyl)amino)-2-((S)-2-oxo-3-(6-(trifluoromethyl) quinazolin-4-ylamino)pyrrolidin-1-yl)cyclohexyl)acetamide, free base or salt, may be deemed substantially pure in that it has a purity greater than 90 weight %, as measured by means that are at this time known and generally accepted in the art, where the remaining less than 10 weight % of material comprises other form(s) of N-((1R,2S,5R)-5-(isopropyl(methyl)amino)-2-((S)-2-oxo-3-(6-(trifluoromethyl)quinazolin-4-ylamino)pyrrolidin-1-yl)cyclohexyl)acetamide, free base or salt, and/or reaction impurities and/or processing impurities.

Samples of the crystalline forms may be provided with substantially pure phase homogeneity, indicating the presence of a dominant amount of a single crystalline form and optionally minor amounts of one or more other crystalline forms. The presence of more than one crystalline form in a sample may be determined by techniques such as powder X-ray diffraction (PXRD) or solid state nuclear magnetic resonance spectroscopy (SSNMR). For example, the presence of extra peaks in the comparison of an experimentally measured PXRD pattern with a simulated PXRD pattern may indicate more than one crystalline form in the sample. The simulated PXRD may be calculated from single crystal X-ray data. See Smith, D. K., "A FORTRAN Program for Calculating X-Ray Powder Diffraction Patterns," Lawrence Radiation Laboratory, Livermore, Calif., UCRL-7196 (April 1963).

Preferably, the crystalline form has substantially pure phase homogeneity as indicated by less than 10%, preferably less than 5%, and more preferably less than 2% of the total peak area in the experimentally measured PXRD pattern arising from the extra peaks that are absent from the simulated PXRD pattern. Most preferred is a crystalline form having substantially pure phase homogeneity with less than 1% of the total peak area in the experimentally measured PXRD pattern arising from the extra peaks that are absent from the simulated PXRD pattern.

Procedures for the preparation of crystalline forms are known in the art. The crystalline forms may be prepared by a variety of methods, including for example, crystallization or recrystallization from a suitable solvent, sublimation, growth from a melt, solid state transformation from another phase, crystallization from a supercritical fluid, and jet spraying. Techniques for crystallization or recrystallization of crystalline forms from a solvent mixture include, for example, evaporation of the solvent, decreasing the temperature of the solvent mixture, crystal seeding a supersaturated solvent mixture of the molecule and/or salt, freeze drying the solvent mixture, and addition of antisolvents (countersolvents) to the solvent mixture.

The forms may be characterized and distinguished using single crystal X-ray diffraction, which is based on unit cell measurements of a single crystal of a form at a fixed analytical temperature. A detailed description of unit cells is provided in Stout & Jensen, X-Ray Structure Determination: A Practical Guide, Macmillan Co., New York (1968), Chapter 3, which is herein incorporated by reference. Alternatively, the unique arrangement of atoms in spatial relation within the crystalline lattice may be characterized according to the observed fractional atomic coordinates. Another means of characterizing the crystalline structure is by powder X-ray diffraction analysis in which the experimental or observed diffraction profile is compared to a simulated profile representing pure powder material, both run at the same analytical temperature, and measurements for the subject form characterized as a series of 2θ values.

Other means of characterizing the form may be used, such as solid state nuclear magnetic resonance (SSNMR), differential scanning calorimetry and thermogravimetric analysis. These parameters may also be used in combination to characterize the subject form.

The term "negligible weight loss," as employed herein, as characterized by TGA indicates the presence of a neat (non-solvated) crystal form.

The term "negligible % water uptake," as employed herein, as characterized by moisture-sorption isotherm indicates that the form tested is non-hygroscopic.

In one embodiment of the invention, a crystalline form of N-((1R,2S,5R)-5-(isopropyl(methyl)amino)-2-((S)-2-oxo-3-(6-(trifluoromethyl)quinazolin-4-ylamino)pyrrolidin-1-yl)cyclohexyl)acetamide, free base or salt, is provided in substantially pure form. This crystalline form may be employed in pharmaceutical compositions which may optionally include one or more other components selected, for example, from the group consisting of excipients, carriers, and one of other active pharmaceutical ingredients or active chemical entities of different molecular structures.

Preferably, the crystalline form has substantially pure phase homogeneity as indicated by less than 10%, preferably less than 5%, and more preferably less than 2% of the total peak area in the experimentally measured PXRD pattern arising from the extra peaks that are absent from the simulated PXRD pattern. Most preferred is a crystalline form having substantially pure phase homogeneity with less than 1% of the total peak area in the experimentally measured PXRD pattern arising from the extra peaks that are absent from the simulated PXRD pattern.

In another embodiment, a composition is provided consisting essentially of the crystalline forms of N-((1R,2S,5R)-5-(isopropyl(methyl)amino)-2-((S)-2-oxo-3-(6-(trifluoromethyl)quinazolin-4-ylamino)pyrrolidin-1-yl)cyclohexyl) acetamide, free base or salt. The composition of this embodiment may comprise at least 90 weight % of the form, based on its weight in the composition.

The presence of reaction impurities and/or processing impurities may be determined by analytical techniques known in the art, such as, for example, chromatography, nuclear magnetic resonance spectroscopy, mass spectrometry or infrared spectroscopy.

Crystalline forms may be prepared by a variety of methods, including for example, crystallization or recrystallization from a suitable solvent, sublimation, growth from a melt, solid state transformation from another phase, crystallization from a supercritical fluid, and jet spraying. Techniques for crystallization or recrystallization of crystalline forms from a solvent mixture include, for example, evaporation of the solvent, decreasing the temperature of the solvent mixture, crystal seeding a supersaturated solvent mixture of the molecule and/or salt, freeze drying the solvent mixture, and addition of antisolvents (countersolvents) to the solvent mixture. High throughput crystallization techniques may be employed to prepare crystalline forms including polymorphs.

Crystals of drugs, including polymorphs, methods of preparation, and characterization of drug crystals are discussed in Solid-State Chemistry of Drugs, S. R. Byrn, R. R. Pfeiffer, and J. G. Stowell, 2nd Edition, SSCI, West Lafayette, Ind. (1999).

For crystallization techniques that employ solvent, the choice of solvent or solvents is typically dependent upon one or more factors, such as solubility of the compound, crystallization technique, and vapor pressure of the solvent. Combinations of solvents may be employed; for example, the compound may be solubilized into a first solvent to afford a solution, followed by the addition of an antisolvent to decrease the solubility of the compound in the solution and to afford the formation of crystals. An "antisolvent" is a solvent in which the compound has low solubility. Suitable solvents for preparing crystals include polar and nonpolar solvents.

In one method to prepare crystals, N-((1R,2S,5R)-5-(isopropyl(methyl)amino)-2-((S)-2-oxo-3-(6-(trifluoromethyl)quinazolin-4-ylamino)pyrrolidin-1-yl)cyclohexyl)acetamide, free base or salt, is suspended and/or stirred in a suitable solvent to afford a slurry, which may be heated to promote dissolution. The term "slurry," as used herein, means a saturated solution, which may also contain an additional amount of the solid to afford a heterogeneous mixture at a given temperature. Suitable solvents in this regard include, for example, polar aprotic solvents and polar protic solvents, and mixtures of two or more of these, as disclosed herein.

Seed crystals may be added to any crystallization mixture to promote crystallization. As will be clear to the skilled artisan, seeding is used as a means of controlling growth of a particular crystalline form or as a means of controlling the particle size distribution of the crystalline product. Accordingly, calculation of the amount of seeds needed depends on the size of the seed available and the desired size of an average product particle as described, for example, in "Programmed cooling of batch crystallizers," J. W. Mullin and J. Nyvlt, Chemical Engineering Science (1971) 26:369-377. In general, seeds of small size are needed to effectively control the growth of crystals in the batch. Seeds of small size may be generated by sieving, milling, or micronizing of larger crystals, or by micro-crystallization of solutions. Care should be taken that milling or micronizing of crystals does not result in any change in crystallinity from the desired crystal form (i.e., change to amorphous or to another polymorph).

A cooled mixture may be filtered under vacuum, and the isolated solids may be washed with a suitable solvent, such as cold recrystallization solvent, and dried under a nitrogen purge to afford the desired crystalline form. The isolated solids may be analyzed by a suitable spectroscopic or analytical technique, such as SSNMR, DSC, PXRD, or the like, to assure formation of the preferred crystalline form of the product. The resulting crystalline form is typically produced in an amount of greater than about 70 weight % isolated yield, but preferably greater than 90 weight % based on the weight of N-((1R,2S,5R)-5-(isopropyl(methyl)amino)-2-((S)-2-oxo-3-(6-(trifluoromethyl)quinazolin-4-ylamino)pyrrolidin-1-yl)cyclohexyl)acetamide, free base or salt, originally employed in the crystallization procedure. The product may be co-milled or passed through a mesh screen to de-lump the product, if necessary.

Crystalline forms may be prepared directly from the reaction medium of the final process step for preparing N-((1R,2S,5R)-5-(isopropyl(methyl)amino)-2-((S)-2-oxo-3-(6-(trifluoromethyl)quinazolin-4-ylamino)pyrrolidin-1-yl)cyclohexyl)acetamide, free base or salt. This may be achieved, for example, by employing in the final process step a solvent or mixture of solvents from which the compound may be crystallized. Alternatively, crystalline forms may be obtained by distillation or solvent addition techniques. Suitable solvents for this purpose include any of those solvents described herein, including protic polar solvents, such as alcohols, and aprotic polar solvents, such as ketones.

By way of general guidance, the reaction mixture may be filtered to remove any undesired impurities, inorganic salts, and the like, followed by washing with reaction or crystallization solvent. The resulting solution may be concentrated to remove excess solvent or gaseous constituents. If distillation is employed, the ultimate amount of distillate collected may vary, depending on process factors including, for example, vessel size, stirring capability, and the like. By way of general guidance, the reaction solution may be distilled to about 1/10 the original volume before solvent replacement is carried out. The reaction may be sampled and assayed to determine the extent of the reaction and the wt % product in accordance with standard process techniques. If desired, additional reaction solvent may be added or removed to optimize reaction concentration. Preferably, the final concentration is adjusted to about 50 wt % at which point a slurry typically results.

It may be preferable to add solvents directly to the reaction vessel without distilling the reaction mixture. Preferred solvents for this purpose are those which may ultimately participate in the crystalline lattice, as discussed above in connection with solvent exchange. Although the final concentration may vary depending on desired purity, recovery and the like, the final concentration of the free base in solution is preferably about 4% to about 7%. The reaction mixture may be stirred following solvent addition and simultaneously warmed. By way of illustration, the reaction mixture may be stirred for about 1 hour while warming to about 70° C. The reaction is preferably filtered hot and washed with either the reaction solvent, the solvent added or a combination thereof. Seed crystals may be added to any crystallization solution to initiate crystallization.

The various forms described herein may be distinguishable from one another through the use of various analytical techniques known to one of ordinary skill in the art. Such techniques include, but are not limited to, powder X-ray diffraction (PXRD), differential scanning calorimetry (DSC) and/or thermogravimetric analysis (TGA). Alternatively, the forms may be characterized and distinguished using single crystal x-ray diffraction, which is based on unit cell measurements of a single crystal of a given form at a fixed analytical temperature. A detailed description of unit cells is provided in Stout & Jensen, X-Ray Structure Determination: A Practical Guide, Macmillan Co., New York (1968), Chapter 3, which is herein incorporated by reference. Specifically, the unique arrangement of atoms in spatial relation within the crystalline lattice may be characterized according to the observed fractional atomic coordinates. Another means of characterizing the crystalline structure is by powder x-ray diffraction analysis in which the observed diffraction profile is compared to a simulated profile generated from single crystal structure data. Powder x-ray diffraction measurements for the subject form are characterized as a series of 2θ values (usually four or more).

Other means of characterizing the form may be used, such as solid state nuclear magnetic resonance (SSNMR) spectroscopy, differential scanning calorimetry (DSC), thermography and gross examination of the crystalline or amorphous morphology. These parameters may also be used in combination to characterize the subject form.

One of ordinary skill in the art will appreciate that an X-ray diffraction pattern may be obtained with a measurement error that is dependent upon the measurement conditions employed. In particular, it is generally known that intensities in a X-ray diffraction pattern may fluctuate depending upon measurement conditions employed and the shape or morphology of the crystal. It should be further understood that relative intensities may also vary depending upon experimental conditions and, accordingly, the exact order of intensity should not be taken into account. Additionally, a measurement error of diffraction angle for a conventional X-ray diffraction pattern is typically about 0.2° 2θ values or less, preferably about 0.1° 2θ values (as discussed hereinafter), and such degree of measurement error should be taken into account as pertaining to the aforementioned diffraction angles. Consequently, it is to be understood that the crystal forms of the instant invention are not limited to the crystal forms that provide X-ray diffraction patterns completely identical to the X-ray diffraction patterns depicted in the accompanying Figures disclosed herein. Any crystal forms that provide X-ray diffraction patterns substantially identical to those disclosed in the accompanying Figures fall within the scope of the present invention. The ability to ascertain substantial identities of X-ray diffraction patterns is within the purview of one of ordinary skill in the art.

SYNTHESIS

Scheme 1: Preparation of amide IV.

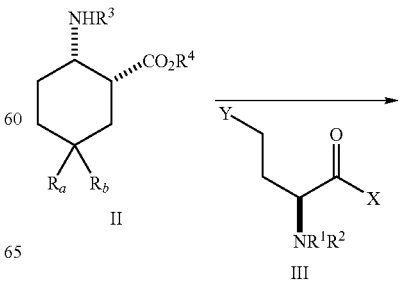

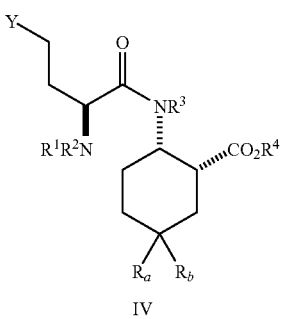

IV

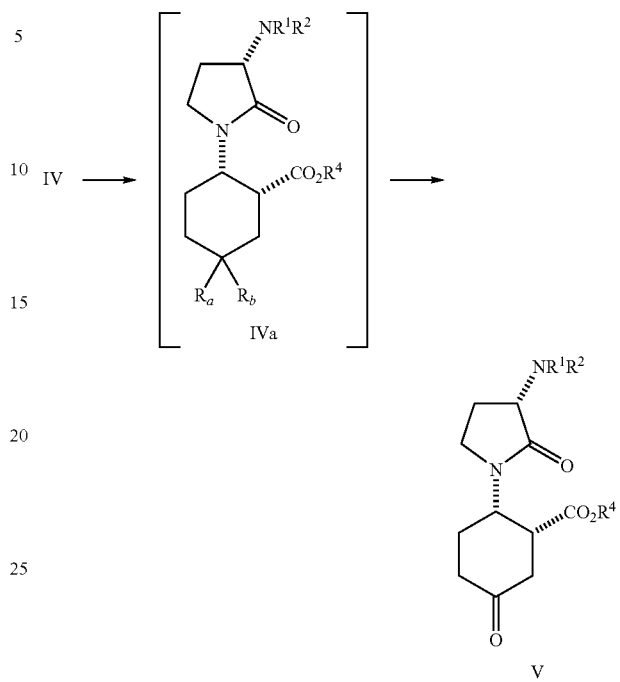

The β-aminoester of formula II, or a salt thereof, including a toluenesulfonate or a hydrobromide salt, is coupled with a suitably protected chiral α-aminoacid of formula III, to give amide IV using methods known in the art. See e.g. the preparation in WO2005021500. The coupling reaction may be performed with a diimide reagent in the presence of an activator, and a tertiary amine base under an inert atmosphere, such as nitrogen or argon (preferably nitrogen) in an aprotic solvent such as proprionitrile, isopropyl acetate, n-butyl acetate, tert-butyl acetate or acetonitrile (especially acetonitrile and/or ethyl acetate). The diimide coupling reagent includes, for example, reagents such as EDAC. Examples of activators include 1-hydroxybenzotriazole (HOBt; said term includes hydrates thereof) and N',N'-4-dimethylamino-pyridine. A tertiary amine base, includes for example, triethylamine, N-N-diisopropyl-N-ethyl amine and tri-n-propylamine. The molar ratios of the aminoester of formula II to the diimide coupling reagent to the activator to the tertiary amine is one to about 0.90-1.50 to about 0.95-1.50 to about 2.00 to 3.00, respectively. Said mole ratios are preferably one to about 0.95-1.05 to about 0.95-1.10 and to about 2.10 to 2.30, respectively.

The β-aminoester is chosen so that $R_a$ and $R_b$ are alkoxy or alkylthiolate groups, or together with the carbon atom to which they are attached form a carbonyl, or form a cyclic or acyclic acetal or thioacetal, preferably a 1,3-dioxolane group. $R_4$ is $C_{1-6}$alkyl, preferably an ethyl group.

The chiral α-aminoacid of formula III incorporates a functionalizable terminal residue Y that either represents or can be elaborated into an alkylating group suitable for later cyclization of the side chain's distal carbon, to which Y is attached, onto the amide nitrogen. Accordingly, Y can be chosen from groups such as halogen, SMe, or $OSO_2R_{12}$, wherein $R_{12}$ is $C_{1-6}$alkyl, —($CH_2$)C(O)$OR_{13}$, or —($CH_2$)C(O)$R_{13}$; and $R_{13}$ at each occurrence is $C_{1-6}$alkyl. X is OH, halogen or $OCOR_{14}$, wherein $R_{14}$ is $C_{1-6}$alkyl. Appropriate protecting groups $R_1$ and $R_2$ for the chiral α-aminoacid, of formula III are independently selected from hydrogen or amine-protecting groups that can be removed by hydrolysis or hydrogenolysis under standard conditions. Such groups include without limitation, a carbobenzyloxy (Cbz) group, a tert-butyloxycarbonyl (BOC), a fluorenylmethyloxycarbonyl (FMOC) group, a benzyl (Bn) group or a p-methoxybenzyl (PMB) group. Preferred groups are Cbz, BOC, or Bn groups. Cbz is most preferred.

Scheme 2: Preparation of an amide of Formula IV

A compound of formula V is prepared by cyclization of alkylating moiety Y onto the amide nitrogen to form a pyrrolidinone ring, during which transformation Y acts as a leaving group. In a preferrred embodiment, the alkylating moiety represents a sulfonium salt (Y=$S^{\oplus}$(Me)$R_{13}$, wherein $R_{13}$ is $C_{1-6}$alkyl, benzyl or substituted benzyl, methyl is most preferred) generated by activation of a methionine-derived amide IV (Y=SMe) using sulfur-alkylating agents well known in the art, for example a $C_{1-6}$alkyl or benzyl halide, preferably methyl iodide. See e.g. Freidinger et al., J. Org. Chem. 1982, 47, 10.

Cyclization is conducted under an inert atmosphere, such as nitrogen or argon (preferably nitrogen) in a solvent by contacting compound IV, or a salt thereof, with a base in the presence of an aprotic solvent. Such bases may be, for example without limitation, cesium carbonate, cesium bicarbonate, potassium carbonate, sodium tert-butylate, or sodium hexamethyldisilazide, especially cesium carbonate. Aprotic solvents include, for example without limitation, DMSO, DMF, DMA, N-methylpyrrolidinone (NMP), and sulfolane, preferably DMSO and/or DMF.

Where $R_a$ and $R_b$ are independently $C_{1-6}$alkoxy, or together with the atom to which they are attached $R_a$ and $R_b$ combine to form a cyclic or acyclic acetal or thioacetal, the acetal groups are removed by deprotection according to methods well known in the art to form a carbonyl. For acetals, deprotection may be performed by hydrolysis, preferably conducted in a solvent such as acetone, butanone, acetonitrile and isopropanol, or aqueous solutions thereof, and is preferably conducted in aqueous acetone. Where said acetal deprotection requires proton acids, for example sulfuric acid, toluenesulfonic acid, nitric acid, methanesulfonic acid, hydrobromic acid or hydrochloric acid, hydrodrochloric acid is most preferred.

Scheme 3: Reductive Amination of Compound V

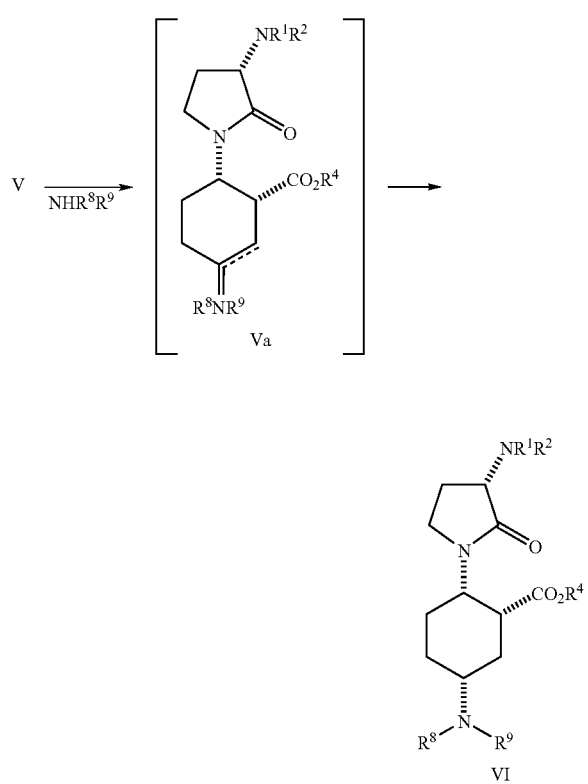

Scheme 4: Preparation of γ-aminoacid of formula VII, or a salt thereof

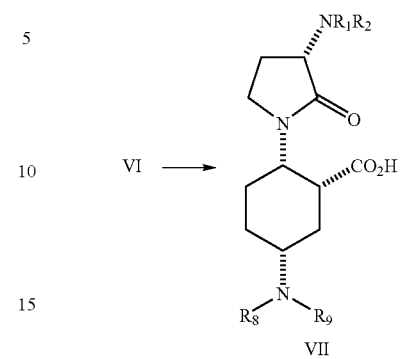

The ester of a compound of formula VI is hydrolyzed to afford the corresponding acid of formula VII, or a salt thereof. Hydrolysis may be performed by base hydrolysis using methods commonly known in art, or, alternatively, with aqueous acids at elevated temperatures, to obtain the corresponding γ-aminoacid of formula VII. Acid hydrolysis is most preferred. The temperature ranges from about 40° C. to about 100° C. (a temperature range of from about 50° C. to about 70° C. is most preferred). Acids are selected, without limitation, from sulfuric acid, toluenesulfonic acid, nitric acid, methanesulfonic acid, hydrobromic acid or hydrochloric acid. Hydrodrochloric acid is most preferred. Optionally, compounds of formula VII may be converted to their carboxylate salts. Preferably, VII is converted to its sodium salt.

Compound VI is prepared by reductively aminating a compound of formula V in two steps by (a) adding an amine, $NH(R_8)(R_9)$, and a dehydrating agent, to a solution of formula V in an aprotic solvent, and mixing at a temperature of from −20° to +50° C. to form the imine/enamine of formula Va; and (b) treating a solution of the imine/enamine of formula Va with a platinum catalyst, preferably containing a deactivator such as sulfur, preferably 5% Pt/C/S, under a pressure of hydrogen gas. Amine substituents, $R_8$ and $R_9$, are independently selected from hydrogen and $C_{1-6}$alkyl. The amine of formula $NH(R_8)(R_9)$ is preferably N-methyl-N-isopropylamine. The dehydrating agent is a Lewis acid/Bronsted acid dehydration promoter which includes, without limitation, titanium reagents, preferably titanium tetrachloride or titanium tetraisopropoxide or a mixture thereof (especially titanium tetraisopropoxide). See e.g. R. Mattson et al., *J. Org. Chem.* 1990, 55, 2552-2554. The aprotic solvent may be selected, without limitation, from solvents such as dichloroethane, dichloromethane, acetonitrile, DMSO, DMF, and N-methyl-pyrrolidinone (preferably dichloromethane). Preferably the solution of the intermediate imine/enamine Va in dichloromethane is treated with hydrogen gas at a pressure of 15-35 psig. and 5% Pt/S/C at approximately 0.5 to 50% (wt/wt) relative to compound V. A most preferred range is 5-10% (wt/wt).

Scheme 5: Preparation of carbamate VIII

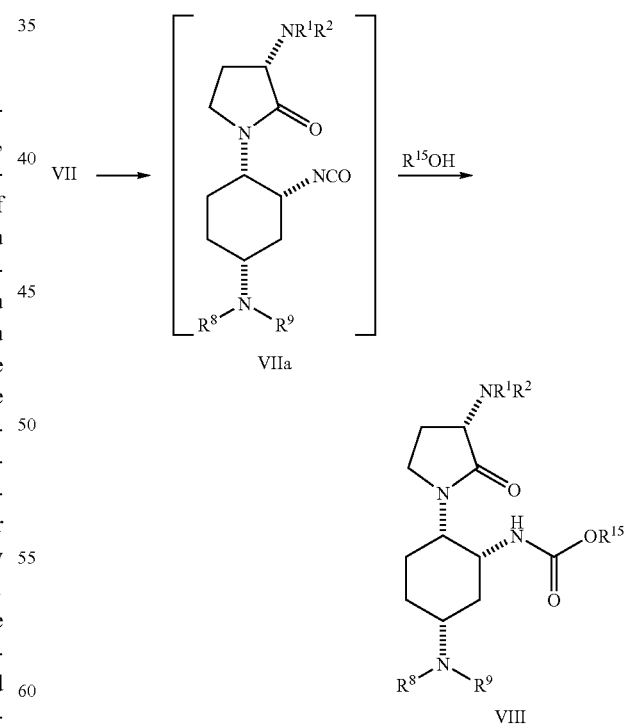

Carbamates of formula VIII are prepared by converting a γ-aminoacid of formula VII to an isocyanate having formula VJIa; and reacting the isocyanate with an alcohol of formula $R^{15}OH$ to afford a carbamate of formula VIII. The variable $R^{15}$ is chosen so that the carbamate forms an amine-protecting group that is removable under standard hydrolysis or hydrogenolysis conditions. Such amine-protecting groups are preferably N—CO$_2$-tert.-butyl (from R$^{15}$=tert.-butyl), or N—CO$_2$— benzyl (from R$^{15}$=benzyl), or N—CO$_2$-substituted benzyl (from R$^{15}$=substituted benzyl). A preferred alcohol is tert-butyl alcohol.

Conversion of VII to the isocyanate VIIa may be conducted via one of several methods, i.e., Curtius-, Hofmann-, or Schmidt-Lossen rearrangement. Preferably, a Curtius rearrangement is performed by contacting γ-aminoacid VII (or a salt thereof) with diphenylphosphoryl azide in an alcohol solvent (preferably tert.-butyl alcohol), preferably, but not limited to, containing toluene or other suitable non-protic co-solvents, at a temperature above the trigger point of thermal rearrangement to the isocyanate (preferably at or above 50° C.).

Scheme 6: Preparation of a compound of formula IX

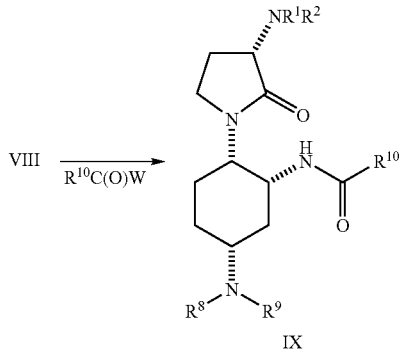

Compounds of formula IX are prepared by deprotecting the carbamate moiety in compound of formula VIII, followed by acylating of the free amine a with reagent of formula R$^{10}$C(O)W, wherein W is halogen or R$^{10}$C(O) to give a compound of formula IX. Carbamate deprotection is performed by methods commonly known in the art (e.g., for R$^{10}$=tert.-butyl, acid deprotection can be performed with sulfuric acid, toluenesulfonic acid, nitric acid, methanesulfonic acid, hydrobromic acid or hydrochloric acid—methanesulfonic acid is most preferred). A base (preferably triethylamine) is then added and the free amine is contacted with a compound of formula R$_{10}$C(O)W, wherein W is halogen or R$^{10}$C(O), to afford a compound of structure IX.

Scheme 7: Alternate prepartion of a compound of formula IX

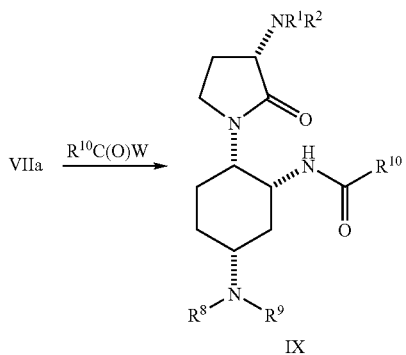

An alternative preparation of compounds of formula IX consists of directly acylating the intermediate isocyanate VIIa (see above Scheme 5) by optional in situ addition to an acylating agent agent R$^{10a}$C(O)W, wherein W is R$^{10a}$C(O), in the presence of its corresponding acid (W=hydrogen). Preferably, the acylation is conducted by introducing the isocyanate into a mixture of acetic acid and acetic anhydride (where R$^{10a}$ is methyl and W is hydrogen) to the isocyanate of formula VIIa to afford a compound of formula IX.

Scheme 7: Preparation of compounds of formula X

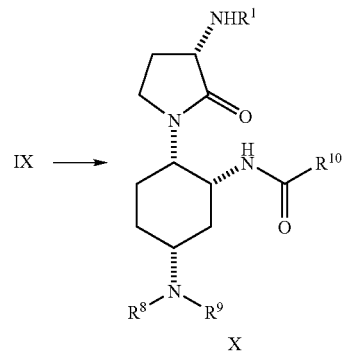

The R$^2$ group in the compound of formula IX is removed by deprotection to provide a compound of formula X. Preferably, if R$^2$ is Cbz, deprotection is effected by hydrogenation in the presence of a palladium catalyst, preferably 10% Pd/C.

Scheme 8: Preparation of compounds of formula I

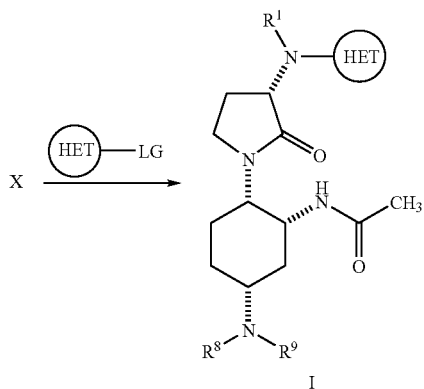

Compounds of formula I are prepared by coupling the deprotected amine of formula X with a compound of formula:

to give a compound of formula I. Such coupling reactions and conditions under which they are conducted are known to one of skill in the art. HET is an optionally substituted 3-14 membered heterocyclo or heteroaryl ring having one or more heteroatoms selected from N, O or S (preferably one to three heteroatoms, especially one to two nitrogen atoms). Preferable heteroaryl groups include, without limitation, a 6-substituted quinazolin-4-yl, more preferably 6-trifluoromethyl-quinazolin-4-yl. A leaving group (LG) as used herein includes, without limitation, groups such as halogen, $C_{1-6}$alkoxy, mesylate, nonaflates, sulfonates, tosylates and triflates. Preferably LG is a leaving group selected from halogen or $OSO_2R_{16}$, wherein $R_{16}$ is phenyl, a 5- to 7-membered heteroaryl having one or more atoms selected from N, S, or O, $C_{1-6}$alkyl, or a 3- to 7-membered cycloalkyl, all of which are optionally substituted by one to three groups selected from halogen, $CF_3$ and $C_{1-6}$alkyl. A preferred leaving group is a halogen, especially chloride.

For the process of this invention, starting materials are commercially available or can be readily prepared by one or ordinary skill in the art. Solvents, temperatures, pressures, starting materials having the desired groups, and other reaction conditions, may be readily selected as appropriate by one of ordinary skill in the art. The process can be scaled up in order to prepare larger quantities of the compound of formula I, such as in a commercial production facility.

EXAMPLES

The following Examples illustrate embodiments of the inventive compounds and starting materials, and are not intended to limit the scope of the claims.

As appropriate, reactions were conducted under an atmosphere of dry nitrogen (or argon). For anhydrous reactions, Dri-Solv solvents from EM were employed. For other reactions, reagent grade or HPLC grade solvents were utilized. Unless otherwise stated, all commercially obtained reagents were used as received.

LC/MS measurements were obtained using a Shimadzu HPLC/Waters ZQ single quadropole mass spectrometer hybrid system. Data for the peak of interest are reported from positive-mode electrospray ionization. NMR (nuclear magnetic resonance) spectra were typically obtained on Bruker or JEOL 400 MHz and 500 MHz instruments in the indicated solvents. All chemical shifts are reported in ppm from tetramethylsilane with the solvent resonance as the internal standard. $^1$H-NMR spectral data are typically reported as follows: chemical shift, multiplicity (s=singlet, br s=broad singlet, d=doublet, dd=doublet of doublets, t=triplet, q=quartet, sep=septet, m=multiplet, app=apparent), coupling constants (Hz), and integration.

One of skill in the art will recognize the standard abbreviations utilized herein. For ease of reference, the abbreviations include, but are not necessarily limited to: sat.=saturated, HPLC=high-performance liquid chromatography, AP=area percent, KF=Karl-Fischer, RT=room temperature (unless specified otherwise RT is a temperature of about 22° C.), mmol=millimoles, HRMS=high-resolution mass spectroscopy, TBTU=O-benzotriazol-2-yl-N,N,N',N'-tetramethyluronium tetrafluoroborate, MTBE=TBME=tert-butyl methyl ether, EDAC=N-(3-dimethylaminopropyl)-N'-ethylcarbodiimide hydrochloride, EDC=N-(3-dimethylaminopropyl)-N'-ethylcarbodiimide, TEA=triethylamine, DPPA=diphenyl phosphoryl azide, IPA=isopropyl alcohol, TFA=trifluoroacetic acid, DCM=dichloromethane, THF=tetrahydrofuran, DMF=N,N-dimethylformamide, BOP=(benzotriazol-1-yloxy)tris(dimethylamino)phosphonium hexafluorophosphate, EtOAc=Ethyl acetate, DMSO=dimethylsulfoxide, ° C.=degrees Celsius, eq=equivalent or equivalents, g=gram or grams, mg=milligram or milligrams, mL (or ml)=milliliter or milliliters, h=hour or hours, M=molar, N=normal, min=minute or minutes, MHz=megahertz, tlc=thin layer chromatography, v/v=volume to volume ratio.

"α", "β", "R" and "S" are stereochemical designations familiar to those skilled in the art.

Example 1

N-((1R,2S,5R)-5-(isopropyl(methyl)amino)-2-((S)-2-oxo-3-(6-(trifluoromethyl)quinazolin-4-ylamino)pyrrolidin-1-yl)cyclohexyl)acetamide

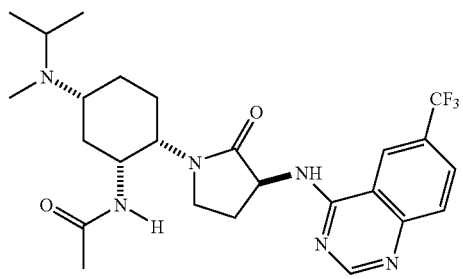

Example 1, Step 1: (1R,2S,5R)-tert-Butyl 2-benzyloxycarbonylamino-7-oxo-6-aza-bicyclo[3.2.1]octane-6-carboxylate (89.6 g, 0.24 mol, see: P. H. Carter, et al. PCT application WO 2005/021500) was dissolved in ethyl acetate (1.5 L) and the resulting solution was washed with sat. NaHCO$_3$ (2×0.45 L) and sat. NaCl (1×0.45 L). The solution was dried (Na$_2$SO$_4$) and then filtered directly into a 3-necked 3 L round-bottom flask. The solution was purged with direct nitrogen injection before being charged with 10% Pd/C (13.65 g) under nitrogen atmosphere. The flask was evacuated and back-filled with hydrogen; this was repeated twice more. Hydrogen was bubbled through the solution for 30 min and then the reaction was stirred under 1 atm H$_2$ for 18 h. The flask was evacuated, back-filled with nitrogen, and charged with fresh catalyst (6 g of 10% Pd/C). Hydrogen was bubbled through the solution for 30 min and then the reaction was stirred under 1 atm H$_2$ for 18 h. The flask was evacuated and back-filled with nitrogen. The mixture was filtered through Celite; the filter pad was then washed with ethyl acetate. The filtrate (~1.6 L EtOAc volume) was diluted with acetonitrile (0.3 L) and charged sequentially with L-N-Cbz-methionine (68 g, 0.24 mol), TBTU (77 g, 0.24 mol), and N,N-diisopropylethylamine (42 mL, 0.24 mol). The reaction was stirred at room temperature for 4 h, during which time it changed from a suspension to a clear solution. The reaction was quenched with the addition of sat. NH$_4$Cl (0.75 L) and water (0.15 L); the mixture was diluted further with EtOAc (0.75 L). The phases were mixed and separated and the organic phase was washed with sat. Na$_2$CO$_3$ (2×0.9 L) and sat. NaCl (1×0.75 L). The solution was dried (Na$_2$SO$_4$), filtered, and concentrated in vacuo to give (1R,2S,5R)-tert-butyl 2-((S)-2-(benzyloxycarbonylamino)-4-(methylthio)butanamido)-7-oxo-6-aza-bicyclo[3.2.1]octane-6-carboxylate as an oil, which was taken into the next step without further purification. LC/MS for primary peak: [M-Boc+H]$^+$=406.3; [M+Na]$^+$=528.3. $^1$H-NMR (400 MHz, d$_4$-MeOH): δ 7.36 (m, 5H), 5.11 (s, 2H), 4.32 (m, 1H), 4.2 (m, 1H), 4.0 (m, 1H), 2.5-2.7 (m, 3H), 2.25 (m, 1H), 2.11 (s, 3H), 2.05 (m, 4H), 1.9 (m, 1H), 1.7 (m, 2H), 1.54 (s, 9H). Also present are EtOAc [1.26 (t), 2.03 (s), 4.12 (q)] and N,N,N,N-tetramethylurea [2.83 (s)].

Example 1, Step 2: A sample of (1R,2S,5R)-tert-butyl 2-((S)-2-(benzyloxycarbonylamino)-4-(methylthio)butanamido)-7-oxo-6-aza-bicyclo[3.2.1]octane-6-carboxylate (0.24 mol assumed; see previous procedure) was dissolved in iodomethane (1,250 g) and stirred for 48 h at room temperature. The reaction was concentrated in vacuo. The residue was dissolved in dichloromethane and concentrated in vacuo. This was repeated twice more. The resultant sludge was dissolved in dichloromethane (0.4 L) and poured into a rapidly stirring solution of MTBE (4.0 L). The resultant yellow solids were collected via suction filtration and dried under high vacuum to afford the sulfonium salt (179 g). This material was taken into the next step without further purification. LC/MS for primary peak: [M-Me$_2$S+H]$^+$=458.4; [M]$^+$=520.4. $^1$H-NMR (400 MHz, d$_4$-MeOH): δ 7.35 (m, 5H), 5.09 (s, 2H), 4.33 (m, 1H), 4.28 (m, 1H), 3.98 (m, 1H), 3.3-3.45 (m, 2H), 2.97 (s, 3H), 2.94 (s, 3H), 2.78 (m, 1H), 2.0-2.3 (m, 4H), 1.7 (m, 2H), 1.52 (s, 9H). Also present are MTBE [1.18 (s), 3.2 (s)] and traces of N,N,N,N-tetramethylurea [2.81 (s)].

Example 1, Step 3: All of the sulfonium salt from the previous step (0.24 mol assumed) was dissolved in DMSO (2.0 L). The resultant solution was stirred under nitrogen at room temperature and charged with cesium carbonate (216 g) portionwise. The suspension was stirred at room temperature for 3 h and then filtered to remove the solids. The solution was divided into ~0.22 L portions and worked up as follows: the reaction mixture (~0.22 L) was diluted with ethyl acetate (1.5 L) and washed successively with water (3×0.5 L) and brine (1×0.3 L). The organic phase was dried (Na$_2$SO$_4$), filtered, and concentrated in vacuo. The desired (1R,2S,5R)-tert-butyl 2-((S)-3-(benzyloxycarbonylamino)-2-oxopyrrolidin-1-yl)-7-oxo-6-azabicyclo[3.2.1]octane-6-carboxylate (90.8 g, 83%) was obtained as a microcrystalline foam, free from tetramethyl urea impurity. LC/MS for primary peak: [M-Boc+H]$^+$=358.4; [M+Na]$^+$=480.4. $^1$H-NMR (400 MHz, d$_4$-MeOH): δ 7.35 (m, 5H), 5.12 (s, 2H), 4.35 (m, 2H), 4.2 (m, 1H), 3.6 (m, 1H), 3.3 (m, 1H), 2.64 (m, 1H), 2.28-2.42 (m, 2H), 2.15 (m, 1H), 1.7-2.0 (m, 5H), 1.55 (s, 9H). If desired, this material can be isolated as a solid by dissolving in MTBE (1 volume), adding to heptane (3.3 volumes), and collecting the resultant precipitate.

Example 1, Step 4: A stirring solution of (1R,2S,5R)-tert-butyl 2-((S)-3-(benzyloxycarbonylamino)-2-oxopyrrolidin-1-yl)-7-oxo-6-azabicyclo[3.2.1]octane-6-carboxylate (108 g, 0.236 mol) in THF (1 L) was charged with lithium hydroxide monohydrate (21.74 g, 0.519 mol). Water (0.3 L) was added slowly, such that the temperature did not exceed 20° C. The reaction was stirred at room temperature overnight and the volatiles were removed in vacuo. The pH was adjusted to ~4 through the addition of 1N HCl (450 mL) and NaH$_2$PO$_4$. The resultant white precipitates were collected by filtration and washed with water (2×1 L). The solid was dissolved in dichloromethane (1.5 L) and water (~1 L). The organic layer was dried (Na$_2$SO$_4$), filtered, and concentrated in vacuo. The residue was dissolved in EtOAc (0.7 L) and the resultant solution was heated at reflux for 1 h. Solids separated after cooling to RT, and were collected via filtration. These solids were purified by recrystallization in isopropanol to afford the desired (1R,2S,5R)-2-((S)-3-(benzyloxycarbonylamino)-2-oxopyrrolidin-1-yl)-5-(tert-butoxycarbonylamino)cyclohexanecarboxylic acid as a white solid (104.5 g, 93% yield). LC/MS for primary peak: [M-tBu+H]$^+$=420.2; [M-Boc+H]$^+$=376.2; [M+H]$^+$=476.2. $^1$H-NMR (400 MHz, d$_4$-MeOH): δ 7.35 (m, 5H), 5.11 (s, 2H), 4.35 (m, 2H), 3.71 (m, 1H), 3.45-3.6 (m, 2H), 2.99 (m, 1H), 2.41 (m, 1H), 2.15 (m, 1H), 2.0 (m, 2H), 1.6-1.9 (m, 4H), 1.46 (s, 9H).

Example 1, Step 5: A 3 L round bottom flask was charged with (1R,2S,5R)-2-((S)-3-(benzyloxycarbonylamino)-2-oxopyrrolidin-1-yl)-5-(tert-butoxycarbonylamino)cyclohexanecarboxylic acid (75.5 g, 0.158 mol), EDC.HCl (33.5 g, 0.175 mol), 1-hydroxybenzotriazole (23.6 g, 0.175 mol), and dichloromethane (1 L). The reaction was stirred at room temperature for 2 h, during which time it changed from a white suspension to a clear solution. Ammonia (gas) was bubbled into the solution until the pH was strongly basic (paper) and the reaction was stirred for 10 min; this ammonia addition was repeated and the reaction was stirred for an additional 10 min. Water was added. The organic phase was washed with sat. NaHCO$_3$, NaH$_2$PO$_4$, and brine before being concentrated in vacuo. The residue was slurried with acetonitrile (0.5 L) and then concentrated in to give (1R,2S,5R)-2-((S)-3-(benzyloxycarbonylamino)-2-oxopyrrolidin-1-yl)-5-(tert-butoxycarbonylamino)cyclohexanecarboxamide as a white solid (75.9 g, ~100%), which was used in the next step without further purification. LC/MS for primary peak: [M-Boc+H]$^+$=375.3; [M+H]$^+$=475.4; [M-tBu+H]$^+$=419.3. $^1$H-NMR (400 MHz, d$_4$-MeOH): δ 7.35 (m, 5H), 5.11 (s, 2H), 4.25 (m, 2H), 3.70 (m, 1H), 3.6 (m, 1H), 3.45 (m, 1H), 2.91 (m, 1H), 2.38 (m, 1H), 2.12 (m, 1H), 1.9-2.05 (m, 2H), 1.65-1.9 (m, 4H), 1.46 (s, 9H).

Example 1, Step 6: The reaction was run in three equal portions and combined for aqueous workup. A 5 L, 3-necked round bottom flask was charged with (1R,2S,5R)-2-((S)-3-(benzyloxycarbonylamino)-2-oxopyrrolidin-1-yl)-5-(tert-butoxycarbonylamino)cyclohexanecarboxamide (25.3 g, 53 mmol), acetonitrile (1.9 L), and 2.6 L of water/ice. The mixture was stirred and cooled to 0° C. Iodobenzene diacetate (25.77 g, 80 mmol) was added and the reaction was stirred for 2 h; another 0.5 eq of iodobenzene diacetate was added. The reaction was stirred for 9 h (reaction temp<10° C.). The mixture was charged with 8 eq N,N-diisopropylethylamine and 2 eq acetic anhydride. Over the next thirty minutes, 4 eq N,N-diisopropylethylamine and 2 eq acetic anhydride were added every ten minutes, until the reaction had proceeded to completion (HPLC). The acetonitrile was removed in vacuo; some solid separated from the residue, and this was collected by filtration. The remaining residue was extracted with dichloromethane (3 L, then 1 L). The organic phase was washed sequentially with water, sat. NaHCO$_3$, and brine. The collected solids were added to the organic phase, along with activated carbon (15 g). The mixture was stirred for 30 minutes at 40° C. before being filtered and concentrated in vacuo. The residue was dissolved in EtOAc (1 L), and the resultant solution was stirred at 75° C. for 1 h before being allowed to cool to room temperature. A solid separated and was collected by filtration. This solid was purified further by recrystallization: it was first dissolved in 0.5 L CH$_2$Cl$_2$, then concentrated in vacuo, then re-crystallized from 1 L EtOAc; this was repeated three times. The solids obtained from the mother liquors of the above were recrystallized three times using the same method. The combined solids were recrystallized twice more from acetonitrile (0.7 L) to provide 66 g (84%) of tert-butyl (1R,3R,4S)-3-acetamido-4-((S)-3-(benzyloxycarbonylamino)-2-oxopyrrolidin-1-yl)cyclohexylcarbamate (purity>99.5% by HPLC). LC/MS for primary peak: [M+H]$^+$=489.4; [M-tBu+H]$^+$=433.3. $^1$H-NMR (400 MHz, d$_4$-MeOH): δ 7.3-7.4 (m, 5H), 5.11 (s, 2H), 4.35 (m, 1H), 4.15 (m, 1H), 4.04 (m, 1H), 3.8 (m, 1H), 3.6 (m, 2H), 2.44 (m, 1H), 2.12 (m, 1H), 1.87-2.05 (m, 4H), 1.87 (s, 3H), 1.55-1.7 (m, 2H), 1.46 (s, 9H). The stereochemical fidelity of the Hofmann rearrangement was confirmed through X-ray crystal structure analysis of this compound, as shown in FIG. 1.

Example 1, Step 7: A stirring solution of tert-butyl (1R,3R,4S)-3-acetamido-4-((S)-3-(benzyloxycarbonylamino)-2-oxopyrrolidin-1-yl)cyclohexylcarbamate (66 g, 0.135 mol) in dichloromethane (216 mL) was charged with trifluoroacetic acid (216 mL). The reaction was stirred for 2 h at room temperature and concentrated in vacuo. The residue was dissolved in methanol and the resultant solution was concentrated in vacuo; this was repeated once. Benzyl (S)-1-((1S,2R,4R)-2-acetamido-4-aminocyclohexyl)-2-oxopyrrolidin-3-ylcarbamate was obtained as an oil and used directly in Step 8 below. LC/MS found [M+H]$^+$=389.4. $^1$H-NMR (400 MHz, d$_4$-MeOH): δ 7.3-7.4 (m, 5H), 5.12 (s, 2H), 4.41 (br. s, 1H), 4.15 (m, 1H), 4.00 (t, J=9.3 Hz, 1H), 3.81 (t, J=9.1 Hz, 1H), 3.65 (q, J=8.4 Hz, 1H), 3.3-3.4 (m, 1H), 2.45 (m, 1H), 1.95-2.24 (m, 5H), 2.00 (s, 3H), 1.6-1.8 (m, 2H).

Example 1, Step 8: A stirring solution of benzyl (S)-1-((1S,2R,4R)-2-acetamido-4-aminocyclohexyl)-2-oxopyrrolidin-3-ylcarbamate (~0.135 mol) in methanol (675 mL) was charged sequentially with acetone (37.8 g, 4 eq), sodium acetate (33.2 g, 3 eq), and sodium cyanoborohydride (16.9 g, 2 eq). The mixture was stirred at room temperature for 6 h and filtered. The filtrate was dissolved in dichloromethane (1 L); this solution was washed with 1N NaOH (1 L). The solids collected in the filtration were dissolved in 1N NaOH (1 L) at 0° C. and then extracted with dichloromethane (1 L). The organic extracts were combined and extracted with aqueous HCl (200 mL 1N HCl+800 mL water). The aqueous phase was basified with sat. NaHCO$_3$ (500 mL) and then 1N NaOH (100 mL) until pH 11. The aqueous phase was extracted with dichloromethane (2 L). The organic extracts were combined, dried (Na$_2$SO$_4$), filtered, and concentrated in vacuo to give benzyl (S)-1-((1S,2R,4R)-2-acetamido-4-(isopropylamino)cyclohexyl)-2-oxopyrrolidin-3-ylcarbamate as an oil. LC/MS found [M+H]$^+$=431.45. $^1$H-NMR (400 MHz, d$_4$-MeOH): δ 7.3-7.4 (m, 5H), 5.12 (s, 2H), 4.31 (m, 1H), 4.24 (t, J=9.4 Hz, 1H), 4.11 (m, 1H), 3.61 (t, J=9.1 Hz, 1H), 3.52 (q, J=8.6 Hz, 1H), 3.04 (br. s, 1H), 2.96 (sep, J=6.3 Hz, 1H), 2.40 (m, 1H), 2.15 (m, 1H), 1.92 (s, 3H), 1.7-1.9 (m, 5H), 1.65 (m, 1H), 1.12 (app. dd, J=6.3, 1.1 Hz, 6H).

Example 1, Step 9 (See Alternative Step 9, below): A stirring solution of benzyl (S)-1-((1S,2R,4R)-2-acetamido-4-(isopropylamino)cyclohexyl)-2-oxopyrrolidin-3-ylcarbamate (~115 mmol) in dichloromethane (600 mL) was cooled to 0° C. and charged sequentially with formaldehyde (18.6 g, 37 wt % solution), triethylamine (23 mL), and sodium triacetoxyborohydride (28.7 g). The mixture was stirred at room temperature for 30 minutes and diluted with dichloromethane (up to 1.2 L). This solution was washed thrice with 500 mL sat. NaHCO$_3$+NaOH (sat. NaHCO$_3$, pH to 11 w/1N NaOH). The organic layer was extracted with aq. HCl (200 mL 1N HCl+600 mL water). The aqueous phase was basified with sat. NaHCO$_3$ (500 mL) and then 1N NaOH (100 mL) until pH 11. The aqueous phase was extracted with dichloromethane (1.2 L). The organic extracts were combined, dried (Na$_2$SO$_4$), filtered, and concentrated in vacuo to give benzyl (S)-1-((1S,2R,4R)-2-acetamido-4-(isopropyl(methyl)amino)cyclohexyl)-2-oxopyrrolidin-3-ylcarbamate as an oil, which was used directly in Step 10 below. LC/MS found [M+H]$^+$=445.4. $^1$H-NMR (400 MHz, d$_4$-MeOH): δ 7.3-7.4 (m, 5H), 5.12 (s, 2H), 4.33 (br s, 1H), 4.25 (t, J=9.2 Hz, 1H), 4.11 (br s, 1H), 3.5-3.6 (m, 2H), 2.77 (v br s, 2H), 2.41 (m, 1H), 2.26 (s, 3H), 2.0-2.1 (m, 2H), 1.92 (s, 3H), 1.7-1.9 (m, 5H), 1.10 (app. dd, J=17, 6.4 Hz, 6H).

Example 1, Step 10: To a solution of benzyl (S)-1-((1S,2R,4R)-2-acetamido-4-(isopropyl(methyl)amino)-cyclohexyl)-2-oxopyrrolidin-3-ylcarbamate (0.115 mol) in methanol (600 mL) was added 10% Pd/C (6 g of 50% wet catalyst). The flask was evacuated and back-filled with hydrogen. The mixture was stirred under 1 atm H$_2$ for 2 h and the catalyst was removed by filtration through Celite. The filtrate was concentrated in vacuo to provide N-((1R,2S,5R)-2-((S)-3-amino-2-oxopyrrolidin-1-yl)-5-(isopropyl(methyl)amino)cyclohexyl) acetamide as an oil, which was taken on to the next step without further purification. LC/MS found [M+H]$^+$=311.47. $^1$H-NMR (400 MHz, d$_4$-MeOH): δ 4.39 (br s, 1H), 4.00 (m, 1H), 3.3-3.5 (m, 4H), 2.73 (m, 1H), 2.38 (m, 1H), 2.25 (s, 3H), 2.0-2.2 (m, 3H), 1.94 (s, 3H), 1.6-1.75 (m, 4H), 1.07 (app. dd, J=21, 6.4 Hz, 6H).

Example 1, Step 11: To a solution of N-((1R,2S,5R)-2-((S)-3-amino-2-oxopyrrolidin-1-yl)-5-(isopropyl(methyl)amino)cyclohexyl)acetamide (~35 g, 0.115 mol) in isopropanol (600 mL) was added 4-chloro-6-(trifluoromethyl)quinazoline (32 g, 0.138 mol, 1.2 eq, see: P. H. Carter et al., PCT application WO 2005/021500). The mixture was stirred at room temperature overnight before being charged with triethylamine (46 g, 0.46 mol, 4 eq). The mixture was stirred at 60° C. for 10 h. The solvent was removed under reduced pressure to give an oil. Azeotropic distillation with isopropanol was performed twice. The residue was dissolved in dichloromethane (600 mL) and extracted with water (250 mL, containing 4 eq acetic acid). Dichloromethane (600 mL) was added to the combined aqueous washes, and the mixture was cooled to 0° C. Aqueous NaOH (50% by weight) was added with stirring until the pH reached 11. The water layer was extracted with dichloromethane twice (2×600 mL). The combined organic extracts were dried (Na$_2$SO$_4$), filtered, and concentrated in vacuo to give the amorphous free base of the title compound (99% purity by HPLC). LC/MS found [M+H]$^+$=507.3. $^1$H-NMR (400 MHz, d$_4$-MeOH): δ 8.82 (s, 1H), 8.59 (s, 1H), 8.05 (dd, J=8.8, 1.8 Hz, 1H), 7.9 (d, J=8.7 Hz, 1H), 5.28 (t, J=8.6 Hz, 1H), 4.58 (br s, 1H), 4.06 (m, 1H), 3.52-3.68 (m, 2H), 3.43 (m, 1H), 2.76 (br s, 1H), 2.55 (m, 1H), 2.28 (s, 3H), 2.1-2.3 (m, 3H), 2.0 (s, 3H), 2.0 (m, 1H), 1.65-1.8 (m, 3H), 1.09 (app. dd, J=24, 6.4 Hz, 6 H).

Example 1

Alternative Step 9

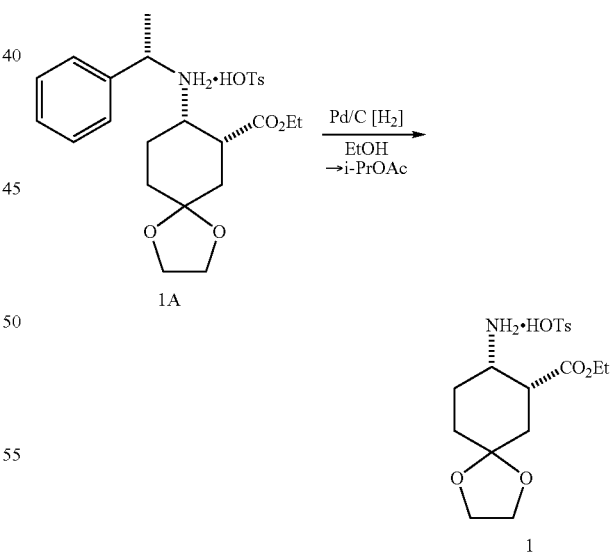

Example 1, Alternative step 9a$^i$: To a hydrogenator were charged ethyl (7R,8S)-8-((S)-1-phenyl-ethylamino)-1,4-dioxa-spiro[4.5]decane-7-carboxylate 4-toluenesulfonate salt 1A (1417 g, 2.8 moles, c.f.: WO2004098516, prepared analogous to U.S. Pat. No. 6,835,841), ethanol (200 proof, 11.4 L), and 10% Pd/C catalyst (50% wet, 284 g). The mixture was inerted with nitrogen, then pressurized with hydrogen gas (45 psig) and agitated vigorously at approx. 40° C. until starting material was consumed (HPLC). The suspension was cooled, purged with nitrogen gas and the catalyst was removed by filtration while inerted. The spent catalyst was washed with ethanol (4.3 L). The filtrate and washings were combined and concentrated under vacuum to a volume of 2-3 L while maintaining the batch between 40°-60° C. Isopropyl acetate (5 L) was charged and the mixture was concentrated to a volume of ~2 L until most ethanol was removed (<0.5%) and residual moisture content was <1,000 ppm. Batch volume was adjusted to ~7.5 L by the addition of isopropyl acetate. The mixture was heated to 80° C. until clear, then cooled 65°-70° C. Seed crystals of 1 (5 g) were added and the batch was cooled to 50° C. over 2 hours, then further cooled to 20° C. over 4 hours and held for ~10 hours. The resulting slurry was filtered and the cake was washed with isopropyl acetate (2 L). The product was dried under vaccum at ~35° C. until volatiles were reduced below ~1% (LOD). Ethyl (7R,8S)-8-amino-1,4-dioxa-spiro[4.5]decane-7-carboxylate 4-toluenesulfonate salt 1 was obtained as a white, crystalline solid (936 g, 83% yield; HPLC purity: 99.8%). $^1$H-NMR: (300 MHz, CDCl$_3$) 8.14-7.89 (brs, 3H), 7.75 (d, J 9.0 Hz, 2H), 7.15 (d, J 8.0 Hz, 2H), 4.22-4.04 (m, 2H), 4.01-3.77 (m, 4H), 3.55-3.43 (m, 1H,), 3.20-3.13 (m, 1H), 2.40-2.27 (m, 4H), 2.21-1.94 (m, 2H), 1.81-1.51 (m, 3H), 1.23 (t, J 7.0 Hz, 3H); HPLC: Waters Xterra MS C18 4.6 mm×150 mm i.d., 3.5 μm particle size, 0.05% NH4OH (5% ACN, 95% H$_2$O, solvent A), to 0.05% NH$_4$OH (95% ACN, 5% H$_2$O, solvent B), 5% B to 20% B in 10 minutes, changed to 95% B in 25 minutes, and then changed to 5% B in 1 minute; 11.1 minutes (aminoester 1).

was left to stir at RT. After 30 mins, HPLC indicated complete conversion. The reaction mass was diluted with EtOAc (2.5 L) and washed with KHCO$_3$ (4×500 mL, 20 wt % aq. solution) and brine (500 mL). The organic phase was separated, dried over MgSO$_4$ and concentrated. The residue was dissolved in TBME and reconcentrated to give ethyl (7R,8S)-8-{(2S)-2-benzyloxycarbonylamino-4-methylsulfanyl-butyryl-amino}-1,4-dioxa-spiro[4.5]decane-7-carboxylate 2 as a sticky semi-solid (76.2 g, 98% yield, 93 AP purity). $^1$H-NMR: (300 MHz, CDCl$_3$) δ 7.36-7.30 (m, 5H), 7.03 (d, J 9.0 Hz, 1H), 5.66 (d, J 8.0 Hz, 1H), 5.10 (s, 2H), 4.35-4.25 (m, 2H), 4.19-4.04 (m, 2H,), 3.98-3.86 (m, 4H), 2.87-2.80 (m, 1H), 2.55-2.45 (m, 2H), 2.18 (dd, J 14.0 Hz, 7.0 Hz, 1H), 2.08 (s, 3H), 2.05-1.67 (m, 6H), 1.26 (t, J 7.0 Hz, 3H). HPLC: YMC-Pack Pro C18 5 μm 4.6×150 mm, 0.05% TFA (20% MeOH, 80% H$_2$O), to 0.05% TFA (20% MeOH, 80% MeCN), 0-100% 10 min gradient. 10.01 min (Compound 2, 93.1 AP). HRMS: m/z 495.2166 [Calc: C$_{24}$H$_{35}$N$_2$O$_7$S 495.2165].

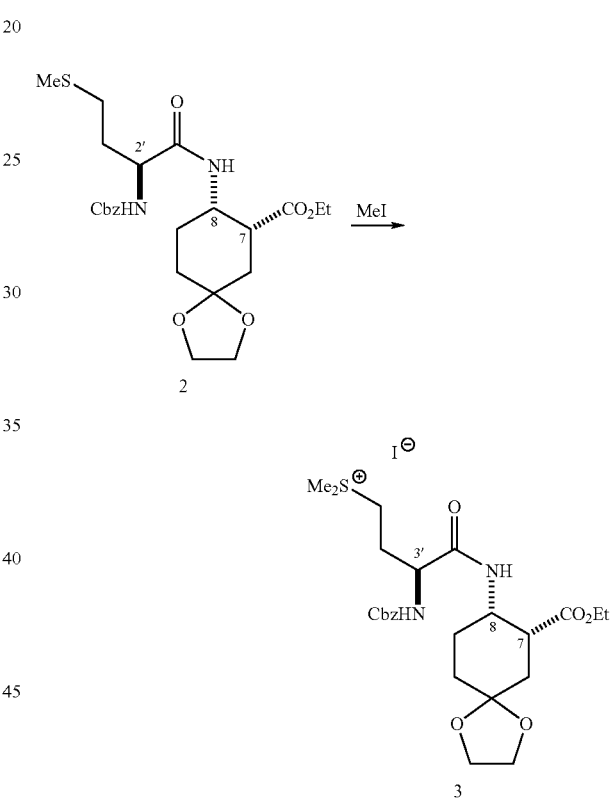

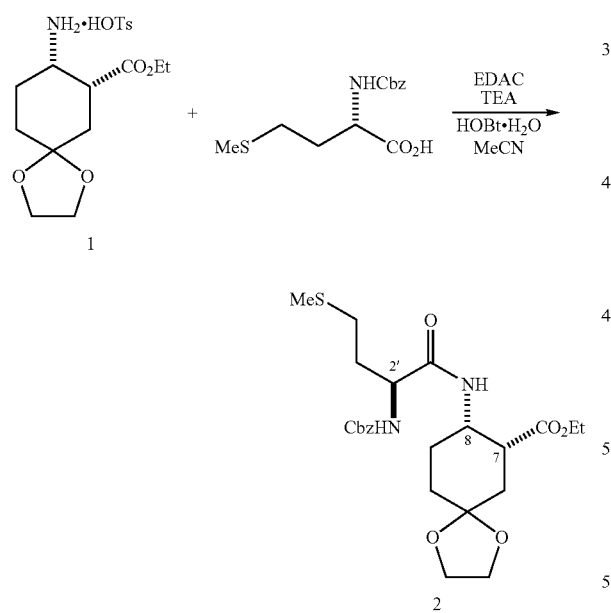

Example 1, Alternative Step 9a$^{ii}$: Aminoester 1 (63 g, 0.16M, 1 eq.; the product of reductive deprotection of a known compound—(See e.g. R. J. Cherney, WO 2004/098516 and G. V. Delucca & S. S. Ko, WO 2004/110993) was placed in a round bottom flask and MeCN (500 mL) was added. EDAC (33.1 g, 0.17M, 1.1 eq), HOBt.H$_2$O (21.2 g, 0.16M, 1.0 eq) and N-Cbz-L-methionine (46.7 g, 0.17M, 1.05 eq) were then added followed by TEA (48.0 mL, 0.35M, 2.2 eq). An exotherm to 38° C. was observed. The reaction mass Example 1, Alternative Step 9b: Methionine amide 2 (75.0 g, 0.15M) was dissolved in MeI (225 mL, 3 mL/g)—some off gassing was noted but no exotherm. The reaction mass was left to stir in the dark for 16.5 h. After this time a thick light yellow precipitate had formed. The flask was then evacuated to 200 mmHg and some of the MeI removed. The remaining material was slurried in TBMF (500 mL), after a 30 min stir-out the slurry was filtered, the cake washed with TBMF (500 mL). NMR analysis of this material indicated a small amount of MeI remaining. The cake was re-slurried in TBMF (500 mL), filtered, washed with TBMF (500 mL) and dried under vacuum to give [(3S)-3-benzyloxycarbonylamino-3-{(7R,8S)-7-ethoxycarbonyl-1,4-di-oxa-spiro[4.5]dec-8-yl-carbamoyl}-propyl]-dimethylsulfonium iodide 3 as a free flowing off-white solid (93.5 g, 97%, 99 area % purity). $^1$H-NMR: (300 MHz, CDCl$_3$) δ 7.75 (d, J 9.0 Hz, 1H), 7.38-

7.27 (m, 5H), 6.40 (d, J 7.0 Hz, 1H), 5.10 (s, 2H), 4.76-4.65 (m, 1H), 4.48-4.39 (m, 1H), 4.14-3.85 (m, 6H), 3.84-7.73 (m, 1H), 3.68-3.55 (m, 1H), 3.21 (s, 3H), 3.12 (s, 3H), 2.90-2.83 (s, 1H), 2.52-1.55 (m, 8H), 1.24 (t, J 7.0 Hz, 3H). HPLC: YMC-Pack Pro C18 5 μm 4.6×150 mm, 0.05% TFA (20% MeOH, 80% H$_2$O), to 0.05% TFA (20% MeOH, 80% MeCN), 0-100% 10 min gradient. 2.45 min (I−), 8.14 min (Compound 3, 43.6 AP, I−54.6 AP). HRMS: m/z 509.2341 [Calc: C$_{25}$H$_{37}$N$_2$O$_7$S 509.2321].

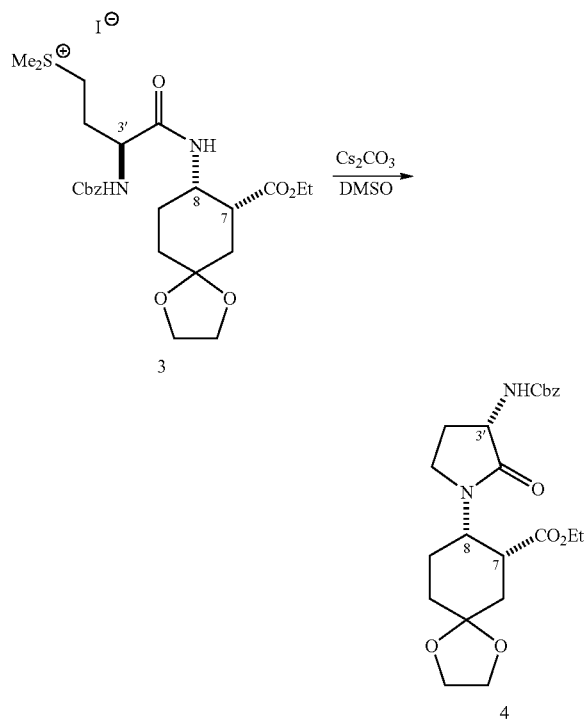

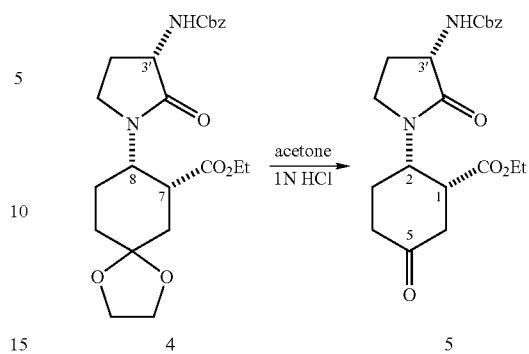

Example 1, Alternative Step 9d: Pyrrolidinone 4 (50.0 g, 0.11M) was dissolved in acetone (500 mL) and 1N HCl (500 mL) was added. The reaction mass was then heated to 65° C. After 20 mins HPLC indicated complete reaction. The reaction mass was allowed to cool to RT and the acetone was removed on a rotary evaporator. During this distillation the product precipitated from solution as a white solid. This was isolated by filtration and the cake washed with water. The cake was then dried azeotropically with toluene (3×300 mL) to give ethyl (1R,2S)-2-((3S)-3-Benzyloxycarbonylamino-2-oxo-pyrrolidin-1-yl)-5-oxo-cyclohexanecarboxylate 5 as a white solid (39.8 g, 88%, 97 area-% purity). $^1$H-NMR: (300 MHz, CDCl$_3$) δ 7.37-7.32 (m, 5H), 6.65 (br d, J 4.0 Hz, 1H), 5.12 (s, 2H), 4.54-4.47 (m, 1H), 4.34-4.26 (m, 1H), 4.18 (dq, J 11.0 Hz, 7.0 Hz, 1H), 4.09 (dq, J 11.0 Hz, 7.0 Hz, 1H), 3.36-3.20 (m, 3H), 2.70-2.35 (m, 6H), 2.05-1.96 (m, 1H), 1.81 (quin., J 11.0 Hz, 1H), 1.24 (t, J 7.0 Hz, 3H). HPLC: YMC-Pack Pro C18 5 μm 4.6×150 mm, 0.05% TFA (20% MeOH, 80% H$_2$O), to 0.05% TFA (20% MeOH, 80% MeCN), 0-100% 10 min gradient. 8.95 min (Compound 5). HRMS: m/z 403.1864 [Calc: C$_{21}$H$_{27}$N$_2$O$_6$ 403.1869].

Example 1, Alternative Step 9c: Cs$_2$CO$_3$ (61.5 g, 0.19M, 1.5 eq) was placed in an round bottom flask and anhydrous DMSO (2.4 L) was added. Sulfonium salt 3 (80.0 g, 0.13M, 1.0 eq) was then added portionwise. Once the addition was complete the reaction mass was left to stir in the dark for 20 h. The reaction mass was then split in half and each half worked up separately: the reaction mass was diluted with EtOAc (2.0 L) and washed with brine (2 L), the organic phase was washed with brine (500 mL). The combined aq. layers were then washed EtOAc (500 mL). The combined organic phases were then washed with brine (3×750 mL). The second half of the reaction mass was treated in an identical manner and the combined organics dried over MgSO$_4$ and concentrated to give ethyl (7R,8S)-8-{(3S)-3-Benzyloxycarbonylamino-2-oxo-pyrrolidin-1-yl}-1,4-dioxa-spiro[4.5]decane-7-carboxylate 4 as a light colored oil (56.5 g, 0.13M, ~100 area-% purity) pure by NMR analysis. $^1$H-NMR: (300 MHz, CDCl$_3$) δ 7.38-7.30 (m, 5H), 5.37 (br d, J 4.0 Hz, 1H), 5.11 (s, 2H), 4.27-4.18 (m, 1H), 4.17-3.82 (m, 8H), 3.32 (td, J 10.0Hz, 60.0 Hz, 1H), 3.23 (q, J 5.0 Hz, 1H), 2.63-2.57 (m, 1H), 2.42-2.25 (m, 2H), 1.94-1.68 (m, 5H), 1.25 (t, J 7.0 Hz, 3H). HPLC: YMC-Pack Pro C18 5 μm 4.6×150 mm, 0.05% TFA (20% MeOH, 80% H$_2$O), to 0.05% TFA (20% MeOH, 80% MeCN), 0-100% 10 min gradient. 8.99 min (Compound 5, produced on column, 4.2 AP), 9.48 (Compound 4, 74.3 AP). HRMS: m/z 447.2127 [Calc: C$_{23}$H$_{31}$N$_2$O$_7$ 447.2131].

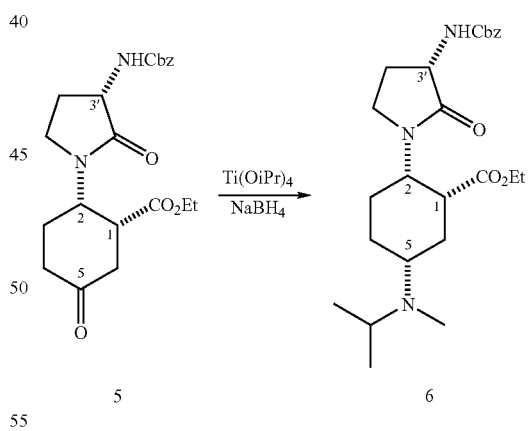

Example 1, Alternative Step 9e: Cyclohexanone 5 (22.5 g, 0.06M, 1 eq), DMSO (30 mL) and Ti(O-iPr)$_4$ (33.7 mL, 0.11M, 2.04 eq) were placed in a round bottom flask. N-isopropyl-N-methylamine (11.6 mL, 0.11M, 2.0 eq) was then added in one portion. The mixture was left to stir for 30 mins at room temperature before being cooled to <3° C. in ice/water. MeOH (30 mL) was then added followed by the portionwise addition of NaBH$_4$ (4.33 g, 0.11M, 2.04 eq)—temperature kept <8° C. 30 mins after the addition was completed the reaction mass was diluted with methylene chloride (300 mL) and then NaOH (1N, 40 mL). The resulting slurry was filtered through Celite, and the cake washed with methylene chloride (100 mL). The resulting liquor was concentrated under reduced pressure and the residue dissolved in EtOAc (500 mL). This solution was extracted with 1N HCl (2×400 mL), the combined aqueous layers were then basified with Na$_2$CO$_3$. Extraction with EtOAc (4×250 mL) provided a clear and colorless organic phase which was dried over Na$_2$SO$_4$ and concentrated to give a white powder (24.6 g, 96%, 7:1 d.r.). This material was then slurried overnight in hexane (670 mL). The solid was isolated by filtration and dried under reduced pressure to give ethyl (1R,2S,5R)-2-((3S)-3-benzyloxycarbonylamino-2-oxo-pyrrolidin-1-yl)-5-(isopropylmethyl-amino)-cyclohexanecarboxylate 6 as a while solid (20.9 g, 81%, 24:1 d.r.). $^1$H-NMR: (300 MHz, CDCl$_3$) δ 7.37-7.28 (m, 5H), 5.55 (d, J 4.5, 1H), 5.10 (s, 2H), 4.42 (q, J 4.5, 1H), 4.23-4.12 (m, 1H), 4.08 (dq, J 10.5, 7.0, 1H), 4.02 (dq, J 10.5, 7.0, 1H), 3.84 (t, J 9.0, 1H), 3.46-3.36 (m, 1H), 3.04 (septet, J 6.5, 1H), 2.86-2.80 (m, 1H), 2.63-2.48 (m, 2H), 2.17 (s, 3H, Me), 2.10-1.63 (m, 7H), 1.22 (t, J 7.0, 3H), 1.00 (d, J 6.5, 3H), 0.97 (d, J 6.5, 3H). HPLC: YMC-Pack Pro C18 5 μm 4.6×150 mm, 0.01M NH$_4$OAc (MeOH:water 20:80) to 0.01M NH$_4$OAc (MeOH:water:MeCN 20:5:75) 10 to 100% 15 min gradient. 8.23 (Compound 6), 8.88 (5-epi-Compound 6). HRMS: 460.2798 [Calc: C$_{25}$H$_{38}$N$_3$O$_5$ 460.2811].

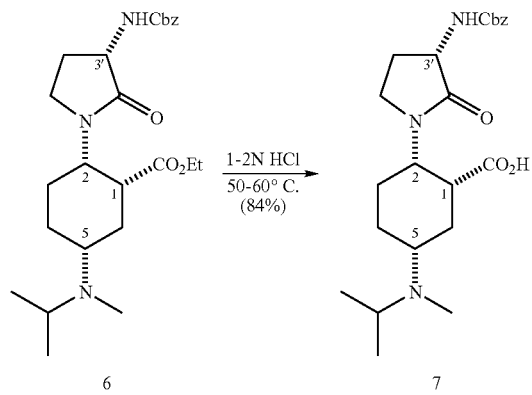

Example 1, Alternative Step 9f: The aminoester 6 (9.76 g, 2.12 mmol) was dissolved in 2N HCl (80 mL), then heated to ~55° C. under inert atmosphere. The reaction was stirred for 20 h, then cooled to room temperature. The reaction solution was washed twice with toluene (25 mL portions), neutralized to pH 6-7 by the addition of KOH pellets, then extracted eight times with methylene chloride (100 mL portions). The combined extracts were dried (Na$_2$SO$_4$), filtered, and concentrated under reduced pressure to 50 mL total volume. The concentrated solution was then slowly added to methyl tert-butyl ether (300 mL) over 15 min in an addition funnel with vigorous stirring. The resulting white slurry was stirred at ambient temperature for 1h, then cooled to 0° C. and stirred for 1 h. The product was filtered, and washed twice with methyl tert-butyl ether (25 mL portions). Water from the wet cake was removed by azeotropic distillation with acetonitrile (300 mL). The product was dried under reduced pressure to provide (1R,2S,5R)-2-((3S)-3-Benzyloxycarbonylamino-2-oxo-pyrrolidin-1-yl)-5-(isopropyl-methyl-amino)-cyclohexanecarboxylic acid 7, (7.69 g, 84% yield) as a white foam. $^1$H-NMR: (400 MHz, 50° C., CDCl$_3$) δ 7.44-7.32 (m, 5H), 6.10 (broad s, 1H), 5.19 (app s, 2H), 4.42 (dd, J=15.6, 7.8 Hz, 1H), 4.29-4.23 (m, 1H), 3.68-3.60 (m, 2H), 3.33-3.27 (m, 2H), 3.20 (broad s, 1H), 2.99 (broad s, 1H), 2.51 (s, 3H), 2.49-2.45 (m, 3H), 2.33-2.31 (m, 3H), 2.00 (ddd, J=9.0, 8.6, 3.9 1H), 1.95-1.78 (m, 2H), 1.36-1.21 (m, 6H). LCMS: m/z 432.20 [Calc: C$_{23}$H$_{34}$N$_3$O$_5$ 432.25].

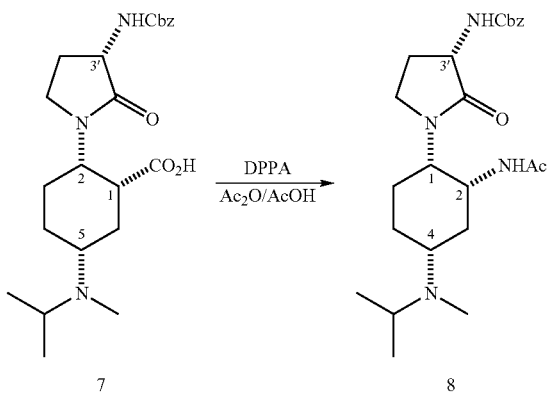

Example 1, Alternative Step 9g: Amino acid 7 (6.3 g, 14.7 mmol, 1.0 eq) was dissolved in THF (80 mL) under N$_2$ and NaH (584 mg, 14.7 mmol, 1.0 eq, 60 wt % dispersion in mineral oil) was added portionwise. When the addition was complete, and the evolution of gas had ceased, the reaction mass was concentrated under reduced pressure and the resulting solid azeotroped with toluene (50 mL) to give a white solid (KF 0.59 wt %). This solid was slurried in toluene (100 mL) under N$_2$ and heated to 90° C. DPPA (3.32 mL, 15.3 mmol, 1.05 eq) was added dropwise over ~2 min. After ~5 min all the solids had dissolved, after 10 mins precipitation of a white solid was observed. After 30 mins HPLC analysis indicated complete reaction. The reaction mass was allowed to cool to RT before being filtered, the cake was washed with toluene. The liquors where then slowly added into AcOH/Ac$_2$O (80/20, 168 mL) solution at 90° C. After 45 mins HPLC still indicated some isocyanate. At 1.15 h, the reaction mass was cooled to RT and diluted with toluene (100 mL) and water (100 mL). The organic layer was removed and the toluene washed with 1N HCl (100 mL). The combined aq. phases were then basified with K$_2$CO$_3$(s) and brought to pH 12 with NaOH (10N), keeping the temperature below 20° C. The aq layer was then extracted with methylene chloride (4×150 mL), the combined organic layers dried over K$_2$CO$_3$ and concentrated to give benzyl (S)-1-((1S,2R,4R)-2-acetamido-4-(isopropyl(methyl)amino)cyclohexyl)-2-oxopyrrolidin-3-ylcarbamate 8 as a white foam (4.5 g, 70%, 94AP purity). The $^1$H-NMR was identical to material obtained from the route described above (Example 1, Step 9). HPLC: YMC-Pack Pro C18 5 μm 4.6×150 mm, 0.05% TFA (20% MeOH, 80% H$_2$O), to 0.05% TFA (20% MeOH, 80% MeCN), 0-100% 10 min gradient. 7.20 min (Compound 8), 7.85 min (urea dimer). HRMS: 445.2809 [Calc: C$_{24}$H$_{37}$N$_4$O$_4$ 445.2815].

Alternative Preparation of Example 1

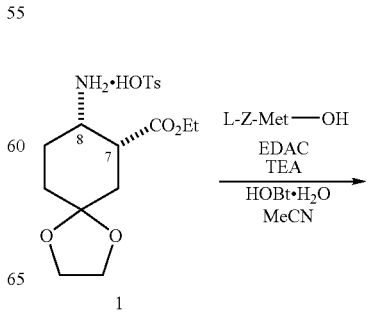

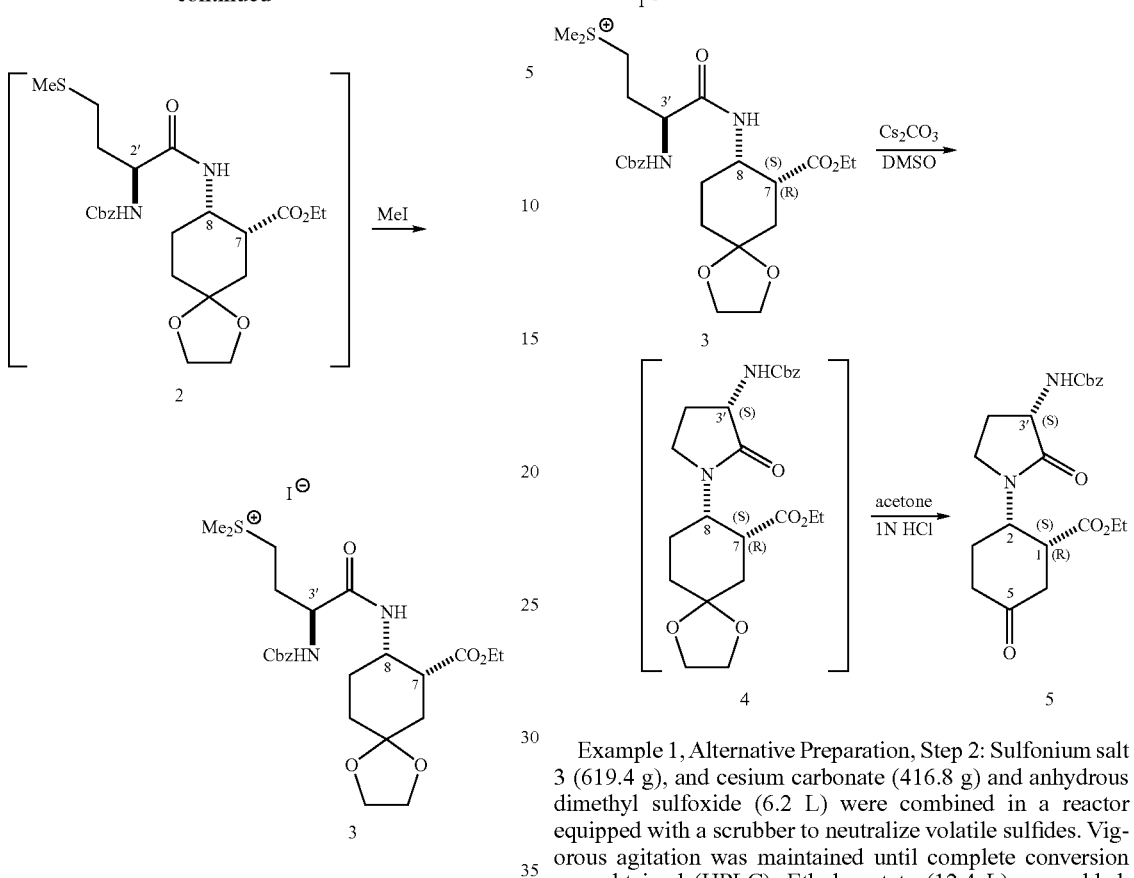

Example 1, Alternative Preparation, Step 1: Ethyl (7R,8S)-8-amino-1,4-dioxa-spiro[4.5]decane-7-carboxylate 4-toluenesulfonate salt 1 (450.1 g), was combined with 1-ethyl-3-(3-dimethyl-amino-propyl)carbo-diimide hydrochloride (236.3 g), 1-hydroxy benzotriazole hydrate (171.9 g), N-carbobenzyloxy-L-methionine (333.4 g) and acetonitrile (3.1 L). To the stirred mixture was added triethylamine (249.5 g) below 30° C. Upon reaction completion (HPLC), the mixture was diluted with ethyl acetate (8.2 L) and washed with aqueous 25% potassium bicarbonate solution (2×4.5 L) followed by water (4.5 L). The organic phase was separated and concentrated under reduced pressure to obtain a solution of ethyl (7R,8S)-8-((S)-2-benzyloxycarbonylamino-4-methylsulfanyl-butyrylamino)-1,4-dioxa-spiro[4.5]decane-7-carboxylate 2 (1.4 L). Methyl iodide (2.39 kg) was added, the vessel was shielded from light and the mixture was held under slow agitation for approx. 24 h. To the thick yellow precipitate was added methyl tert-butyl ether (2.7 L) and the mixture was held for approx. 1 h. The product was isolated by filtration and the cake was washed with methyl tert-butyl ether (2×1.4 L), then dried under vacuum, yielding [(S)-3-benzyloxy-carbonylamino-3-((7R,8S)-7-ethoxycarbonyl-1,4-dioxa-spiro[4.5]dec-8-ylcarbamoyl)-propyl]-dimethylsulfonium iodide 3 (671.4 g, ~94% yield) as an off-white solid (HPLC purity 99.9%).

Example 1, Alternative Preparation, Step 2: Sulfonium salt 3 (619.4 g), and cesium carbonate (416.8 g) and anhydrous dimethyl sulfoxide (6.2 L) were combined in a reactor equipped with a scrubber to neutralize volatile sulfides. Vigorous agitation was maintained until complete conversion was obtained (HPLC). Ethyl acetate (12.4 L) was added, followed by 20% brine (3 L). The organic phase was separated, washed twice with brine (2×3 L) and evaporated to obtain a solution of ethyl (7R,8S)-8-((S)-3-benzyloxycarbonylamino-2-oxo-pyrrolidin-1-yl)-1,4-dioxa-spiro[4.5]decane-7-carboxylate 4 in ethyl acetate (~0.8 L). Acetone (2.55 L) was added, followed by aqueous 0.5 M hydrochloric acid solution (2.3 L). With good mixing, the solution was heated to 50 to 60° C. until conversion of 4 to ethyl (1R,2S)-2-((S)-3-benzyloxycarbonylamino-2-oxo-pyrrolidin-1-yl)-5-oxo-cyclohexanecarboxylate 5 was complete (HPLC). The mixture was concentrated under reduced pressure while below 40° C., cooled to ~30° C., and water (4.1 L) was added. The resulting slurry was cooled to 5 to 10° C. and agitated for ~1 hour. The product was filtered and the cake was washed with water (2×2.5 L). Upon deliquoring, the cake was dried to a constant weight below 40° C. in a vacuum oven. Cyclohexanone 5 (272 g, 70% yield) was obtained (HPLC purity 98.7%).

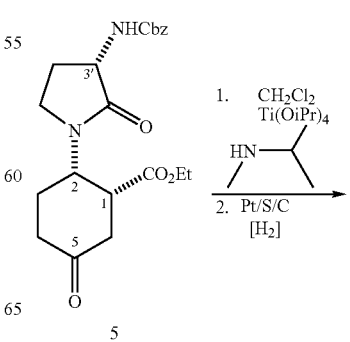

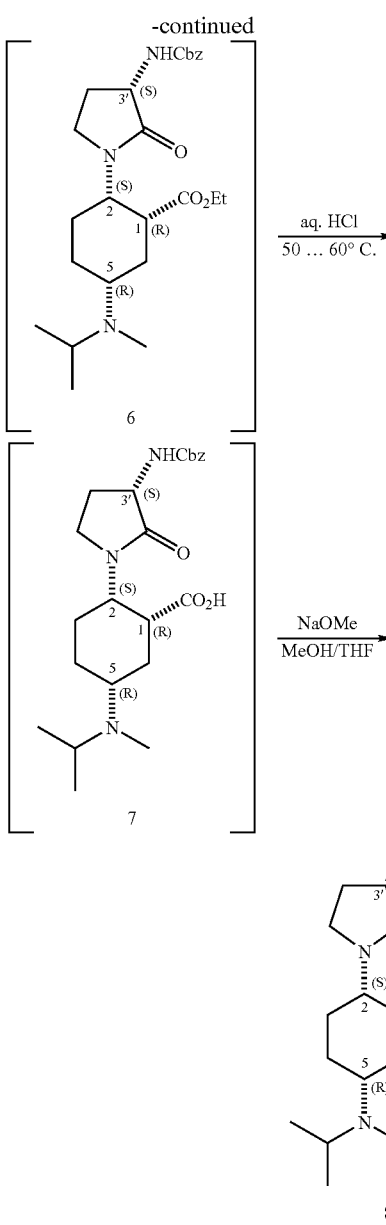

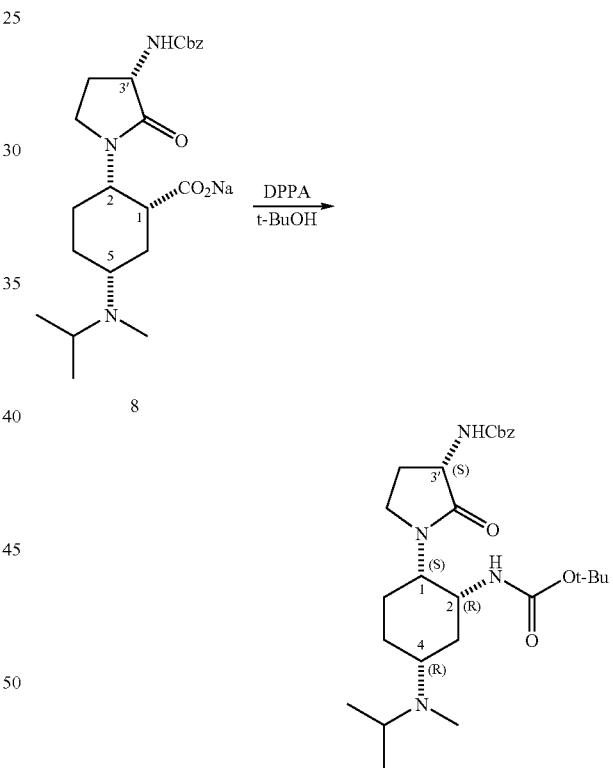

added and the solution was washed with 2M aqueous hydrochloric acid (2×400 mL). The aqueous layer was warmed to 50° to 60° C. for approx. 20 h or hydrolysis of 6 was deemed complete (HPLC). Aqueous sodium hydroxide solution was added to adjust to pH ~10, and mixture was extracted with toluene (3×600 mL). The organic phase was discarded and pH was readjusted to ~6 by addition of aqueous hydrochloric acid. The aqueous phase was concentrated to ~600 mL under reduced pressure and extracted with methylene chloride (at least 3×2.0 L). The combined methylene chloride layers were evaporated under reduced pressure and continuously replaced with THF to obtain a solution of (1R,2S,5R)-2-((S)-3-benzyloxycarbonylamino-2-oxo-pyrrolidin-1-yl)-5-(isopropyl-methyl-amino)-cyclohexane carboxylic acid 7 (~148 g) in THF (~4 L). Seed crystals of 8 were added, followed by 25% solution of sodium methoxide in methanol (81.24 g) below 25° C. The slurry was held for at least additional 16 h with agitation. The product was isolated by filtration and the cake was washed with THF (4×200 mL) and dried to a constant weight in vacuo below 30° C. Dry (1R,2S,5R)-2-((S)-3-benzyloxycarbonyl-amino-2-oxo-pyrrolidin-1-yl)-5-(isopropyl-methyl-amino)-cyclohexane-carboxylate sodium salt 8 was obtained (139 g, ~60% yield from 5).

Example 1, Alternative Preparation, Step 3: Cyclohexanone 5 (206 g) was dissolved in dichloromethane (1.1 L) and charged to a hydrogenator. Titanium tetraisopropoxide (218.2 g) and N-isopropyl N-methylamine (63.64 g) were added and the mixture was stirred at ambient temperature (23 to 25° C.) for at least 5 h. Platinum catalyst (5% Pt/S/C, 15 g, approx. 7.5% relative to 5) was added and hydrogenation was performed at ~30 psig for at least 6 h, yielding a mixture of ethyl (1R,2S,5R)-2-((S)-3-benzyloxycarbonylamino-2-oxo-pyrrolidin-1-yl)-5-(isopropyl-methyl-amino)-cyclohexanecarboxylate 6 and its 5-epi-isomer (~7%). The catalyst was removed by filtration and the filtrate was concentrated under reduced pressure to approx. ~600 mL. Wet ethyl acetate (~3% water, 2.0 L) was added with vigorous agitation over a period of at least 1.5 h. Stirring was continued for at least an additional 6 h. The slurry was filtered. Filter cake was washed with ethyl acetate (1.0 L) and discarded. The combined filtrate and washings were concentrated to ~400 mL. Toluene (2.0 L) was Example 1, Alternative Preparation, Step 4: Aminoester sodium salt 8 (100 g), diphenyl phosphate (3.86 g), tert-BuOH (1275 mL) and toluene (225 mL) were combined and heated to reflux under reduced pressure. Approx. 500 mL of distillate were collected and discarded while being continuously replaced with a solution of toluene in tert-BuOH. Vacuum was removed and distillate was switched to percolate through a column filled with molecular sieves and allowed to return to the vessel. After drying was complete, DPPA (52.4 mL; dissolved in 60 mL toluene) was added slowly to the slurry at 80° C. Upon complete conversion (HPLC), tert- BuOH was removed by vacuum distillation and continuously replaced with toluene. The mixture was cooled to room temperature and washed twice with 10% aqueous K₂HPO₄ (1×800 mL, 1×400 mL) and water (400 mL). The organic phase was heated and concentrated in vacuo to approx. 270 mL. Vacuum was removed and heptane (1.1 L) was added slowly at approx. 80° C., followed by seeds of 9 (~1 g). The slurry was slowly cooled to room temperature and benzyl {(S)-1-[(1S,2R,4R)-2-tert-butoxycarbonylamino-4-(isopropyl-methyl-amino)-cyclo-hexyl]-2-oxo-pyrrolidin-3-yl}-carbamate 9 was isolated by filtration as a white solid (86.76 g, 78% yield).

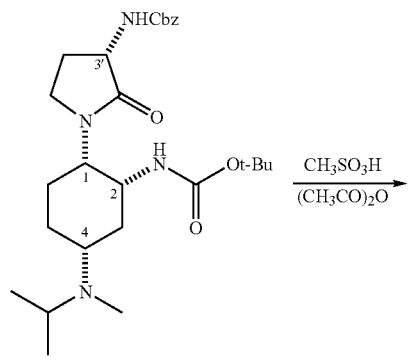

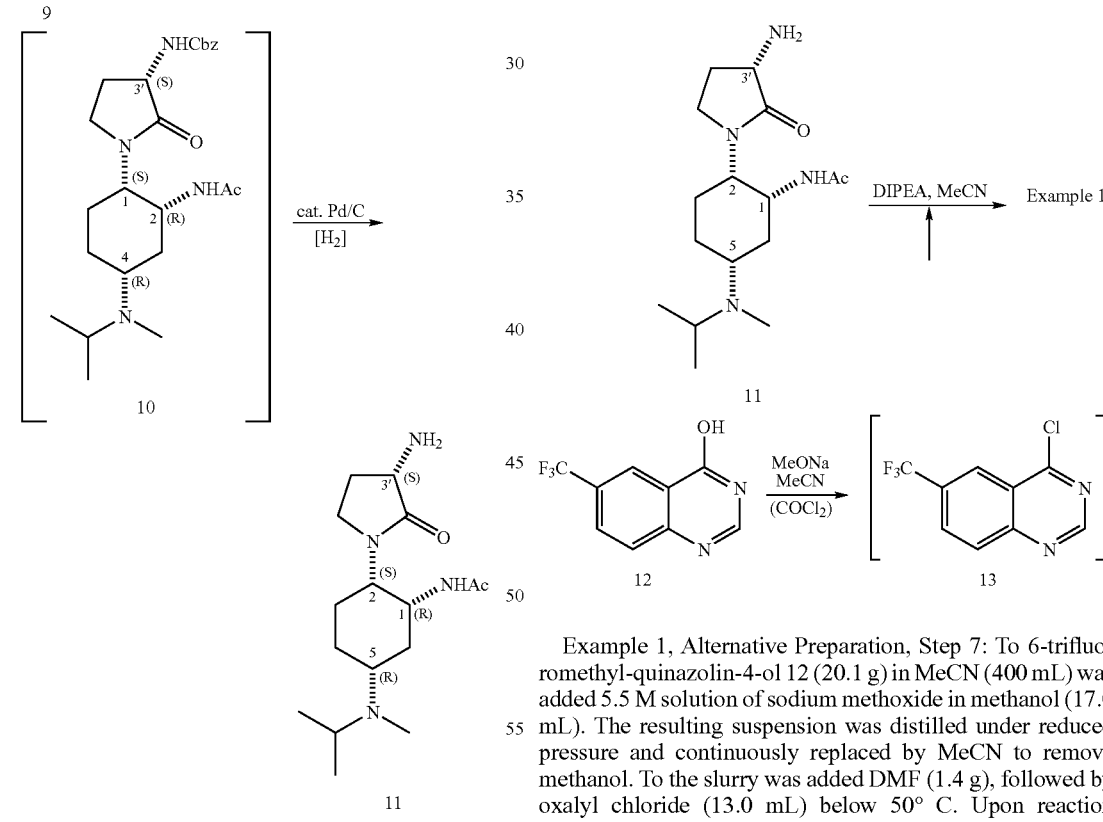

Example 1, Alternative Preparation, Step 5: The tert-Butyl carbamate 9 (50 g) was dissolved in Toluene (500 mL) and i-PrOH (150 mL). The resulting solution was then heated to 60° C. Methanesulfonic acid (19.6 mL) was added below 65° C. Upon reaction completion (HPLC), the mixture was cooled to RT and triethylamine (69.4 mL) added slowly below 25° C. Acetic anhydride was then added below 25° C. After 1 h acetic acid (250 mL) was added below 25° C. The toluene phase was discarded and 2-methyl-THF (500 mL) was added to the aqueous phase. The mixture was stirred vigorously and basified with NaOH (25% aqueous solution) to pH 12. The aqueous phase was discarded and the organic layer was washed with brine (250 mL). The organic layer was concentrated under reduced pressure and continuously replaced with i-PrOH. The solution was cooled and filtered to provide benzyl {(S)-1-[(1S,2R,4R)-2-acetylamino-4-(isopropyl-methyl-amino)-cyclohexyl]-2-oxo-pyrrolidin-3-yl}-carbamate 10 in i-PrOH solution which was used directly in the hydrogenation.

Example 1, Alternative Preparation, Step 6: To a solution containing acetamide 10 (~61 g) in i-PrOH (~625 mL) was added 10% Pd/C wet catalyst (2.5 g) and the suspension was hydrogenated at 30 psig and approx. 25° C. for at least 2 h. Upon completion (HPLC), the catalyst was removed by filtration and the filtrate was concentrated to approx. 550 mL. Water (8.8 mL) was added, followed by 5.6 N hydrochloric acid in i-PrOH solution (69.5 mL). The resulting slurry was held at room temperature overnight. The product was isolated by filtration and the cake was rinsed with i-PrOH (2×100 mL) and dried in vacuo to constant weight at ~50° C. to give N-[(1R,2S,5R)-2-((S)-3-amino-2-oxo-pyrrolidin-1-yl)-5-(isopropyl-methyl-amino)-cyclohexyl]-acetamide 11 (55.6 g, 97% yield) as its hydrochloric acid salt (73.6% free base assay, HPLC).

Example 1, Alternative Preparation, Step 7: To 6-trifluoromethyl-quinazolin-4-ol 12 (20.1 g) in MeCN (400 mL) was added 5.5 M solution of sodium methoxide in methanol (17.0 mL). The resulting suspension was distilled under reduced pressure and continuously replaced by MeCN to remove methanol. To the slurry was added DMF (1.4 g), followed by oxalyl chloride (13.0 mL) below 50° C. Upon reaction completion (HPLC), excess reagent was removed under reduced pressure to give ~400 mL of slurry. The mixture was cooled to room temperature and washed with 10% aqueous K₂HPO₄ (1×1.0 L, 1×0.5 L) to afford 4-chloro-6-trifluoromethyl-quinazoline 13 (~21.2 g) in approx. 450 mL of wet MeCN solution, which was used directly in the subsequent coupling reaction (HPLC purity 99.8%).

Example 1, Alternative Preparation, Step 8: To a mixture of acetamide 11 (28.5 g, HCl salt, 73.6% free base assay), acetonitrile (100 mL), N,N,-di-isopropyl-N-ethylamine (61 mL) at room temperature was added a solution of 13 (~21.2 g) in MeCN (~450 mL). The homogeneous mixture was held overnight. Upon reaction completion (HPLC), the mixture was concentrated in vacuo to approx. 125 mL. A 9.5% aqueous solution of acetic acid (240 mL) was added and the aqueous phase was extracted with methylene chloride. The aqueous phase was separated and methyl tert-butyl ether (450 mL) was added, followed by 2N aqueous lithium hydroxide solution to adjust to pH>11.5. The organic layer was separated, washed with water and filtered. Approx. half of the ether phase was diluted with methyl tert-butyl ether (~250 mL) and concentrated in vacuo. Heptane (45 mL) was added slowly below 60° C., followed by seed crystals of Example 1 (0.4 g). Additional heptane (125 mL) was added and the mixture was slowly cooled to room temperature and the resulting slurry was held overnight. The product was isolated by filtration, the cake was washed with heptane and dried in vacuo to constant weight to give N-((1R,2S,5R)-5-(isopropylamino)-2-((S)-2-oxo-3-(6-(trifluoromethyl)-quin-azolin-4-ylamino)pyrrolidin-1-yl)cyclohexyl)acetamide 14 (15.0 g, 85% yield).

Crystallization Procedures for Example 1

Example 1, Production of bis-BSA salt and purification: The entirety of the amorphous free base from Example 1, Step 11 was dissolved in methanol (600 mL). The resultant solution was heated at 60° C. and charged with benzenesulfonic acid (2.5 eq). The mixture was cooled to room temperature and the resultant white solid was collected by filtration to yield the bis-benzene sulfonic acid salt of the title compound (95 g, 86%). This material was >99% pure by HPLC. This material was further purified by re-crystallization from 80/20 EtOH/$H_2O$, which provided the salt free from any residual methanol. HPLC purity=99.8%. $^1$H NMR (500 MHz, $D_2O$) δ ppm 8.75 (1H, s), 8.66 (1H, s), 8.25 (1H, d, J=8.80 Hz), 7.90 (1H, d, J=8.80 Hz), 7.75 (4H, d, J=8.25 Hz), 7.43-7.57 (6H, m), 5.42 (1H, t), 4.33-4.44 (1H, m), 4.09-4.19 (1H, m), 3.83-3.91 (1H, m), 3.74-3.83 (2H, m), 3.61 (1H, t, J=11.55 Hz), 2.75 (3H, d, J=6.60 Hz), 2.61-2.70 (1H, m), 2.31-2.44 (1H, m), 2.20-2.27 (1H, m), 2.17 (2H, d, J=12.10 Hz), 1.94-2.04 (1H, m, J=12.65 Hz), 1.90-1.95 (3H, m), 1.72-1.91 (2H, m), 1.37 (3H, d, J=6.05 Hz), 1.29 (3H, d, J=6.60 Hz). Differential scanning calorimetry utilized a heating rate of 10° C./min and revealed a melting/decomposition endotherm with an onset temperature of 297.6° C. and a peak temperature at 299.1° C.

Example 1, Crystallization of the Free Base: A sample of the amorphous free base of N-((1R,2S,5R)-5-(isopropyl(methyl)amino)-2-((S)-2-oxo-3-(6-(trifluoromethyl)quinazolin-4-ylamino)pyrrolidin-1-yl)cyclohexyl)acetamide (1 g) was dissolved in dichloromethane (5 mL). The solution was charged with heptane (30 mL) and then warmed to distill the dichloromethane. The solution was cooled to 40° C.; a white solid precipitated. The suspension was heated to 90° C. and stirred for 2 h. The suspension was cooled to room temperature and filtered to provide the pure free base of the title compound. No residual solvent was apparent by $^1$H-NMR.

Example 2

Crystal Forms of N-((1R,2S,5R)-5-(isopropyl(methyl)amino)-2-((S)-2-oxo-3-(6-(trifluoromethyl) quinazolin-4-ylamino)pyrrolidin-1-yl)cyclohexyl) acetamide Various crystal forms of N-((1R,2S,5R)-5-(isopropyl(methyl)amino)-2-((S)-2-oxo-3-(6-(trifluoromethyl)quinazolin-4-ylamino)pyrrolidin-1-yl)cyclohexyl)acetamide, including the free base and salt forms, and solvates thereof, were prepared and characterized as described below.

Procedures for Characterizing the Forms

Single Crystal Data

Data were collected on a Bruker-Nonius (BRUKER AXS, Inc., 5465 East Cheryl Parkway Madison, Wis. 53711 USA) CAD4 serial diffractometer. Unit cell parameters were obtained through least-squares analysis of the experimental diffractometer settings of 25 high-angle reflections. Intensities were measured using Cu Kα radiation (λ=1.5418 Å) at a constant temperature with the θ-2θ variable scan technique and were corrected only for Lorentz-polarization factors. Background counts were collected at the extremes of the scan for half of the time of the scan. Alternately, single crystal data were collected on a Bruker-Nonius Kappa CCD 2000 system using Cu Kα radiation (λ=1.5418 Å). Indexing and processing of the measured intensity data were carried out with the HKL2000 software package (Otwinowski, Z. & Minor, W. (1997) in *Macromolecular Crystallography*, eds. Carter, W. C. Jr & Sweet, R. M. (Academic, NY), Vol. 276, pp. 307-326) in the Collect program suite. (Collect Data collection and processing user interface: Collect: Data collection software, R. Hooft, Nonius B. V., 1998.) Alternately, single crystal data were collected on a Bruker-AXS APEX2 CCD system using Cu Kα radiation (λ=1.5418 Å). Indexing and processing of the measured intensity data were carried out with the APEX2 software package/program suite (APEX2 Data collection and processing user interface: APEX2 User Manual, v1.27; BRUKER AXS, Inc., 5465 East Cheryl Parkway Madison, Wis. 53711 USA).

When indicated, crystals were cooled in the cold stream of an Oxford cryo system (Oxford Cryosystems Cryostream cooler: J. Cosier and A. M. Glazer, J. Appl. Cryst., 1986, 19, 105) during data collection.

The structures were solved by direct methods and refined on the basis of observed reflections using either the SDP (SDP, Structure Determination Package, Enraf-Nonius, Bohemia N.Y. 11716. Scattering factors, including f' and f", in the SDP software were taken from the "International Tables for Crystallography", Kynoch Press, Birmingham, England, 1974; Vol. IV, Tables 2.2A and 2.3.1) software package with minor local modifications or the crystallographic packages MAXUS (maXus solution and refinement software suite: S. Mackay, C. J. Gilmore, C. Edwards, M. Tremayne, N. Stewart, K. Shankland. maXus: a computer program for the solution and refinement of crystal structures from diffraction data or SHELXTL[4]. The derived atomic parameters (coordinates and temperature factors) were refined through full matrix least-squares. The function minimized in the refinements was $\Sigma_w(|F_o|-|F_c|)^2$. R is defined as $\Sigma||F_o|-|F_c||/\Sigma|F_o|$ while $R_w=[\Sigma_w(|F_o|-|F_c|)^2/\Sigma_w|F_o|^2]^{1/2}$ where w is an appropriate weighting function based on errors in the observed intensities. Difference maps were examined at all stages of refinement. Hydrogens were introduced in idealized positions with isotropic temperature factors, but no hydrogen parameters were varied.

X-ray Powder Diffraction Data (PXRD)

PXRD data were obtained using a Bruker C2 GADDS. The radiation was Cu Kα (40 KV, 50 mA). The sample-detector distance was 15 cm. Powder samples were placed in sealed glass capillaries of 1 mm or less in diameter; the capillary was rotated during data collection. Data were collected for $3 \leq 2\theta \leq 35°$ with a sample exposure time of at least 2000 seconds. The resulting two-dimensional diffraction arcs were integrated to create a traditional 1-dimensional PXRD pattern with a step size of 0.02 degrees 2θ in the range of 3 to 35 degrees 2θ. About 200 mg were packed into a Philips powder X-ray diffraction (PXRD) sample holder. The sample was transferred to a Philips MPD unit (45 KV, 40 mA, Cu Kα). Data were collected at room temperature in the 2 to 32 2-theta range (continuous scanning mode, scanning rate 0.03 degrees/sec., auto divergence and anti scatter slits, receiving slit: 0.2 mm, sample spinner: ON)

Differential Scanning Calorimetry (DSC)

DSC experiments were performed in a TA Instruments™ model Q1000 or 2920. The sample (about 2-6 mg) was weighed in an aluminum pan and recorded accurately recorded to a hundredth of a milligram, and transferred to the DSC. The instrument was purged with nitrogen gas at 50 mL/min. Data were collected between room temperature and 300° C. at 10° C./min heating rate. The plot was made with the endothermic peaks pointing down.

Thermal Gravimetric Analysis (TGA)

TGA experiments were performed in a TA Instruments™ model Q500 or 2950. The sample (about 10-30 mg) was placed in a previously tared platinum pan previously tared. The weight of the sample was measured accurately and recorded to a thousandth of a milligram by the instrument. The furnace was purged with nitrogen gas at 100 mL/min. Data were collected between room temperature and 300° C. at 10° C./min heating rate.

Preparation and Analysis of the Forms

The unit cell data and other properties for these examples are presented in Table 1. The unit cell parameters were obtained from single crystal X-ray crystallographic analysis. A detailed account of unit cells can be found in Chapter 3 of Stout & Jensen, *X-Ray Structure Determination: a Practical Guide*, (MacMillian, 1968).

Fractional atomic coordinates for Examples 2a, b, c, d, e, f, g, and h, are presented in Tables 2, 3, 4, 5, 6, 7, 8 and 9, respectively.

Additionally, characteristic powder x-ray diffraction peak positions (degrees 2θ±0.1)@RT for Examples 2a, b, d, e, f, g, and h, are presented in Table 10, all of which are based on high quality patterns collected with a diffractometer (CuKα) with a spinning capillary with 2θ calibrated with a NIST other suitable standard.

Figure 8:
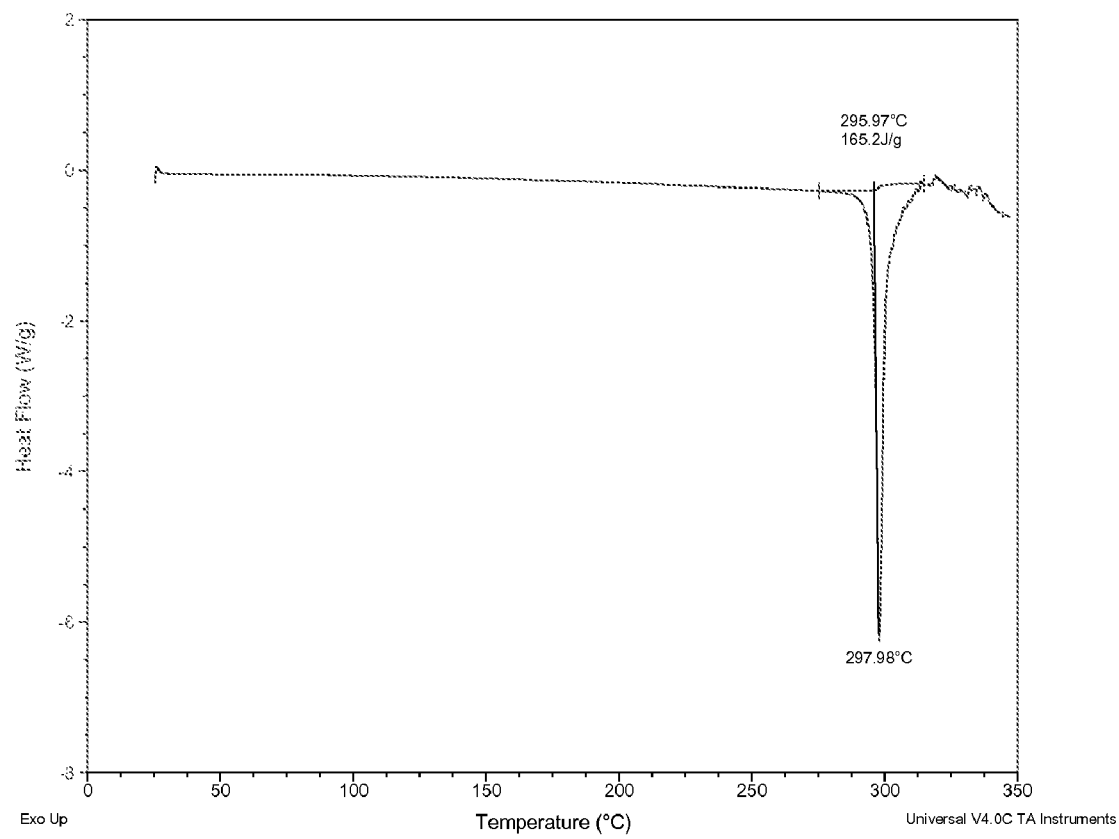
FIG. 8 discloses the differential scanning calorimetry analysis of the N-((1R,2S,5R)-5-(isopropyl(methyl)amino)-2-((S)-2-oxo-3-(6-(trifluoromethyl)quinazolin-4-ylamino)pyrrolidin-1-yl)cyclohexyl)acetamide, di-besylate salt Form N-1.
Figure 9:
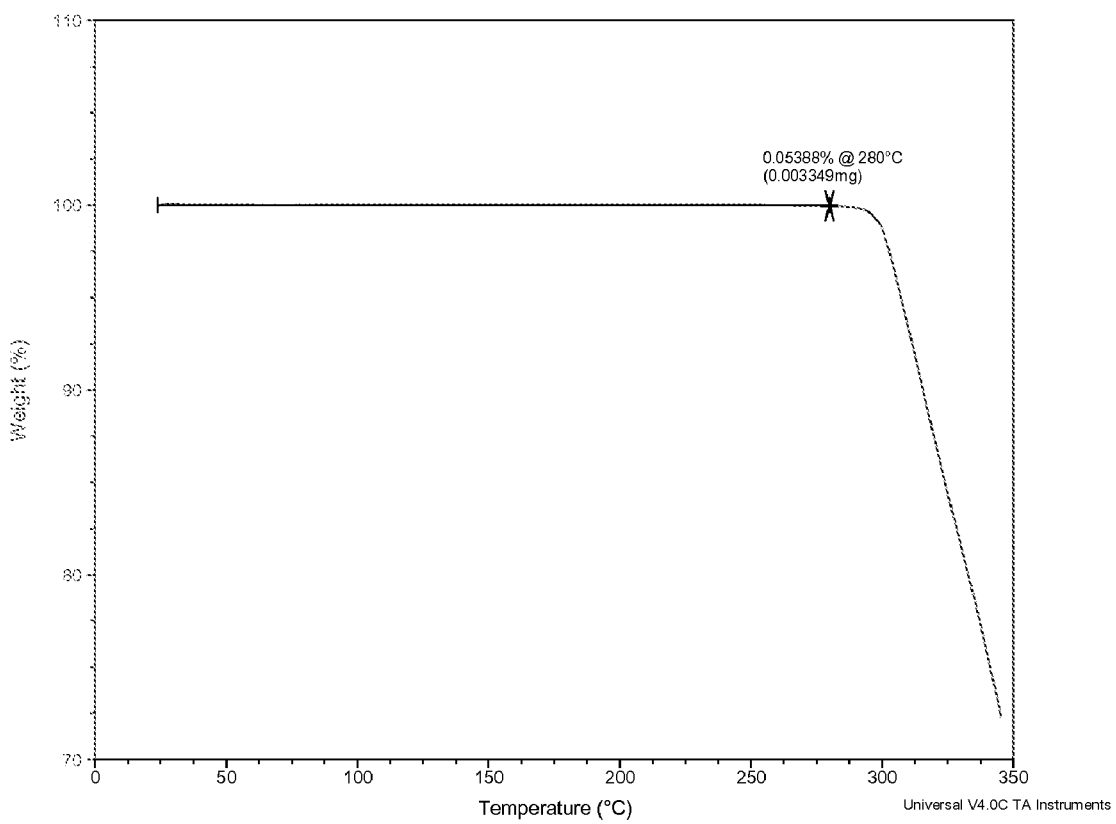
FIG. 9 discloses the thermogravimetric analysis of N-((1R,2S,5R)-5-(isopropyl(methyl)amino)-2-((S)-2-oxo-3-(6-(trifluoromethyl)quinazolin-4-ylamino)pyrrolidin-1-yl)cyclohexyl)acetamide, di-besylate salt Form N-1.
Figure 10:
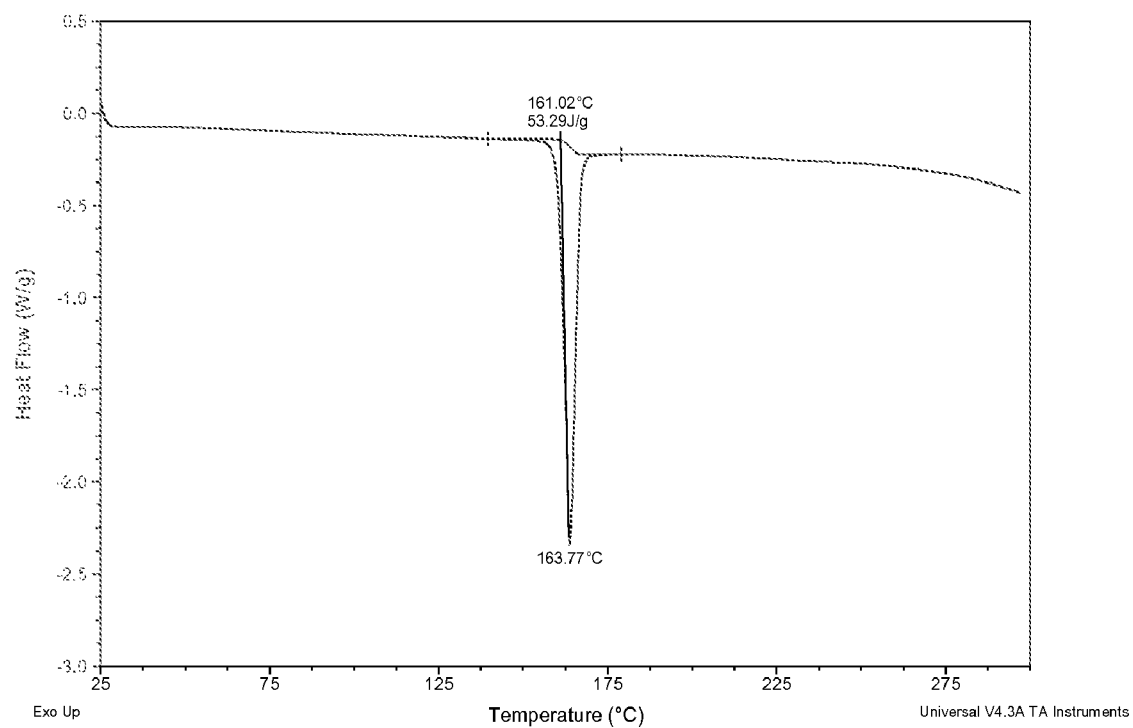
FIG. 10 discloses the differential scanning calorimetry analysis of N-((1R,2S,5R)-5-(isopropyl(methyl)amino)-2-((S)-2-oxo-3-(6-(trifluoromethyl)quinazolin-4-ylamino)pyrrolidin-1-yl)cyclohexyl)acetamide, free base, Form N-2.
Figure 11:
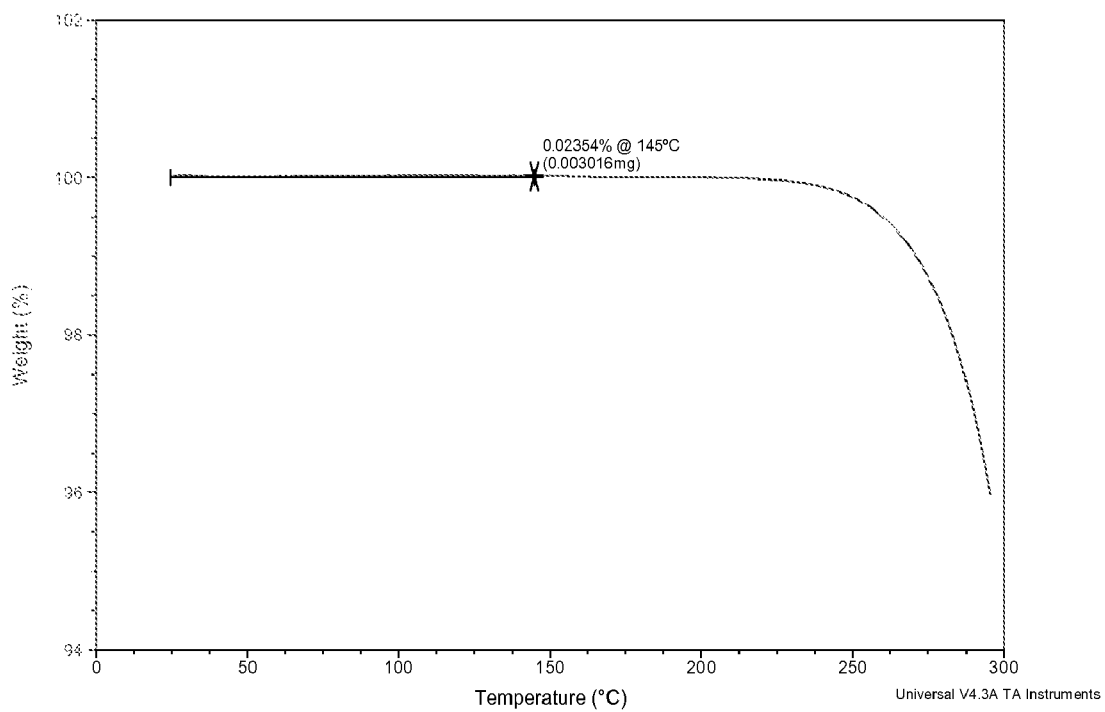
FIG. 11 discloses the thermogravimetric analysis of N-((1R,2S,5R)-5-(isopropyl(methyl)amino)-2-((S)-2-oxo-3-(6-(trifluoromethyl)quinazolin-4-ylamino)pyrrolidin-1-yl)cyclohexyl)acetamide, free base, Form N-2.
Figure 12:
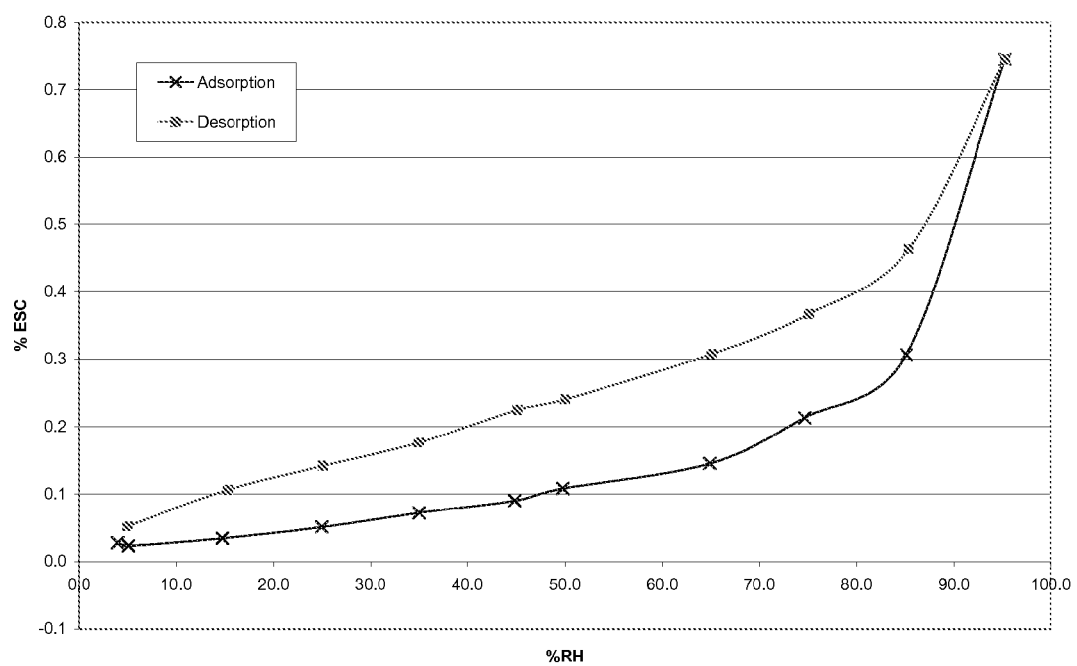
FIG. 12 discloses the Moisture Sorption Isotherm of N-((1R,2S,5R)-5-(isopropyl(methyl)amino)-2-((S)-2-oxo-3-(6-(trifluoromethyl)quinazolin-4-ylamino)pyrrolidin-1-yl)cyclohexyl)acetamide, free base, Form N-2.
Figure 13:
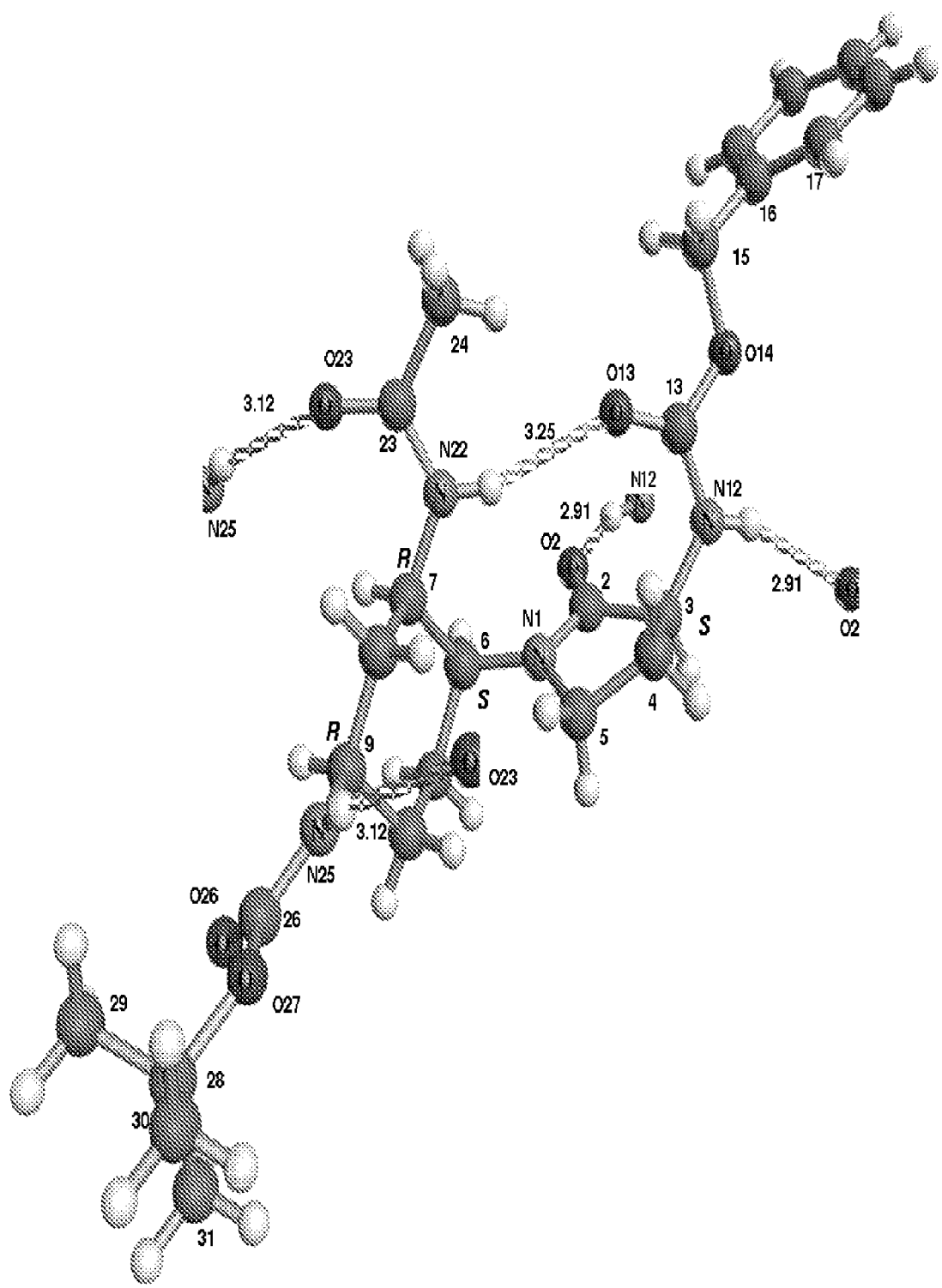
FIG. 13 discloses an X-ray crystal structure of tert-butyl (1R,3R,4-3-acetamido-4-((S)-3-(benzyloxycarbonylamino)-2-oxopyrrolidin-1-yl)cyclohexylcarbamate.
Figure 14:
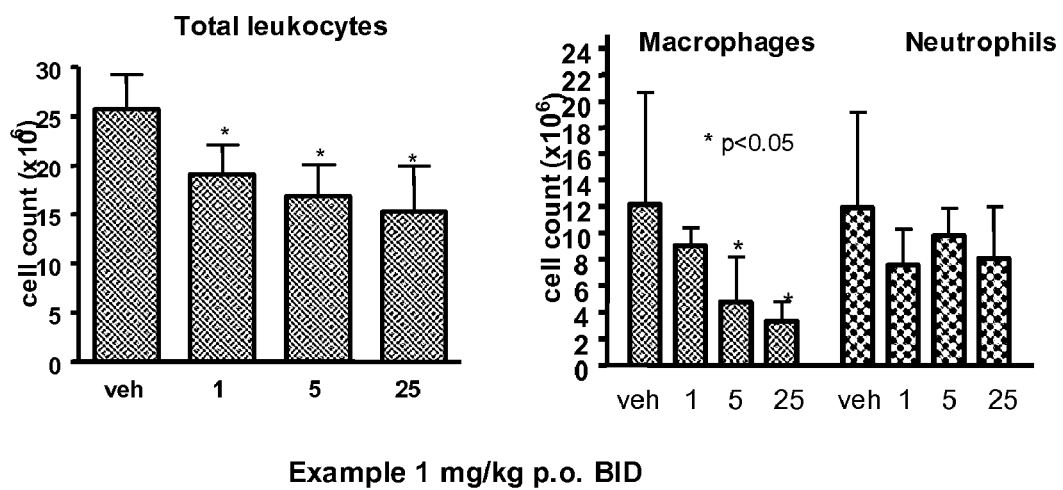
FIG. 14. 48-hour TG peritonitis model in hCCR2 KI mice: Example 1 inhibition of monocyte/macrophage infiltration into peritoneal cavity (differential cell count).

Finally, FIGS. 1, 2, 3, 4, 5, 6, and 7 present XRPD patterns for Examples 2a, b, d, e, f, g and h, respectively. FIGS. 8 and 9 disclose the DSC and TGA analysis, respectively, of Example 2a and FIGS. 10, 11, and 12 disclose the DSC, TGA, and Moisture Sorption Isotherm spectra of Example 2f, respectively.

Form Preparation, XRD, DSC and TGA Characterization

Example 2a

N-1 Form, Dibesylate

N-((1R,2 S,5R)-5-(isopropyl(methyl)amino)-2-((S)-2-oxo-3-(6-(trifluoromethyl)quinazolin-4-ylamino)pyrrolidin-1-yl)cyclohexyl)acetamide, di-benzene sulfonic acid salt, was crystallized from ethyl acetate, ethanol, methanol and acetone. Form N-1, dibesylate salt, is the neat (no molecules of water or solvent) form of N-((1R,2S,5R)-5-(isopropyl(methyl)amino)-2-((S)-2-oxo-3-(6-(trifluoromethyl)quinazolin-4-ylamino)pyrrolidin-1-yl)cyclohexyl)acetamide, di-benzene sulfonic acid salt. Form N-1 dibesylate was characterized by a XRD pattern which matches the simulated pattern generated from the single crystal structure data. Form N-1 dibesylate was characterized by a DSC thermogram having a melt/decomposition endotherm with an onset typically at ca. 296° C. Form N-1, dibesylate, was characterized by a TGA thermal curve having negligible weight loss (consistent with non-solvated form) at up to ca. 280° C.

Example 2b

DC-1 Form

A sample of the oily, gel-like (amorphous) free base of N-((1R,2S,5R)-5-(isopropyl(methyl)amino)-2-((S)-2-oxo-3-(6-(trifluoromethyl)quinazolin-4-ylamino)pyrrolidin-1-yl)cyclohexyl)acetamide (approx 0.5 g), after extracted from a sample of the BSA salt, was dissolved in dichloromethane (approx 3 mL). To the solution was added approx 5 ml of heptane and the resulting oily mixture was agitated vigorously by a magnetic stir bar in an open beaker at 20-25° C. A white solid was obtained after the solvents evaporated. The solid was re-suspended in the mixture of approx 5 ml of heptane and 0.2 ml of dichloromethane and stirred at 25° C. for 7 days. The resulting slurry was filtered and air-dried to provide N-((1R,2S,5R)-5-(isopropyl(methyl)amino)-2-((S)-2-oxo-3-(6-(trifluoromethyl)quinazolin-4-ylamino)pyrrolidin-1-yl)cyclohexyl)acetamide, free base, Form DC-1. Form DC-1 is characterized by one mole of dichloromethane per mole of N-((1R,2S,5R)-5-(isopropyl(methyl)amino)-2-((S)-2-oxo-3-(6-(trifluoromethyl)quinazolin-4-ylamino)pyrrolidin-1-yl)cyclohexyl)acetamide, free base. Form DC-1, was characterized by an XRD pattern which matches the simulated pattern generated from the single crystal structure data.

Example 2c

THOO-1 Form

N-((1R,2 S,5R)-5-(isopropyl(methyl)amino)-2-((S)-2-oxo-3-(6-(trifluoromethyl)quinazolin-4-ylamino)pyrrolidin-1-yl)cyclohexyl)acetamide, free base, 1 mg, was dissolved in 80 uL of THF. The solvent was removed by Speed-vac (SpeedVac Plus, SC250DDA, Savant/ThermoElectron Corp) under high vacuum at 22° C. for 16 hours. A total of 100 uL of MIBK/Heptane (½ by volume) was charged to this well. After holding for 2 weeks at ambient temperature (20-25° C.), crystals were observed in this well. Form THOO is characterized by one mole of THF per one mole of N-((1R,2S,5R)-5-(isopropyl(methyl)amino)-2-((S)-2-oxo-3-(6-(trifluoromethyl)quinazolin-4-ylamino)pyrrolidin-1-yl)cyclohexyl) acetamide, free base.

Example 2d

E-1 Form

N-((1R,2 S,5R)-5-(isopropyl(methyl)amino)-2-((S)-2-oxo-3-(6-(trifluoromethyl)quinazolin-4-ylamino)pyrrolidin-1-yl)cyclohexyl)acetamide, free base was crystallized from a solution of ethanol and heptane. Form E-1 is characterized by a mole of ethanol per one mole of N-((1R,2S,5R)-5-(isopropyl(methyl)amino)-2-((S)-2-oxo-3-(6-(trifluoromethyl) quinazolin-4-ylamino)pyrrolidin-1-yl)cyclohexyl)acetamide, free base. Form E-1 was characterized by an XRD pattern which matches the simulated pattern generated from the single crystal structure data.

Example 2e

A-1 Form

N-((1R,2 S,5R)-5-(isopropyl(methyl)amino)-2-((S)-2-oxo-3-(6-(trifluoromethyl)quinazolin-4-ylamino)pyrrolidin-1-yl)cyclohexyl)acetamide, free base, was suspended at concentration in excess of 150 mg/mL in acetone. The suspension was allowed to equilibrate at room temperature to provide a somewhat thin suspension. Part of the suspension was filtered and both the filtrate and the suspension were refrigerated at 5° C. to provide crystals of the mono acetone solvate (A-1). Form A-1 is characterized by one mole of acetone per one mole of N-((1R,2S,5R)-5-(isopropyl(methyl)amino)-2-((S)-2-oxo-3-(6-(trifluoromethyl)quinazolin-4-ylamino)pyrrolidin-1-yl)cyclohexyl)acetamide, free base. Form A-1 free base was characterized by an XRD pattern which matches the simulated pattern generated from the single crystal structure data.

Example 2f

N-2 Form

A sample of the oily, gel-like (amorphous) free base of N-((1R,2S,5R)-5-(isopropyl(methyl)amino)-2-((S)-2-oxo-3-(6-(trifluoromethyl)quinazolin-4-ylamino)pyrrolidin-1-yl)cyclohexyl)acetamide (approx 0.5 g), extracted from a sample of the BSA salt, was suspended in heptane (approx 5 mL). The flask was scratched with a metal spatula, and the suspension was stirred vigorously by a magnetic stir bar at 25° C. A white slurry of crystalline particles was obtained after 24 hours of stirring. The slurry was filtered and the wet cake dried in vacuo (40° C.) to provide the pure N-2 form (confirmed by PXRD) of the free base. Form N-2 was characterized by an XRD pattern which matches the simulated pattern generated from the single crystal structure data. Form N-2 is the neat (no solvate molecules or no molecules of water or solvent) form of N-((1R,2S,5R)-5-(isopropyl(methyl)amino)-2-((S)-2-oxo-3-(6-(trifluoromethyl)quinazolin-4-ylamino)pyrrolidin-1-yl)cyclohexyl)acetamide, free base. Form N-2, was characterized by a DSC thermogram having a melt endotherm onset typically at ca. 158° C. to ca. 162° C. Form N-2 was characterized by a TGA thermal curve having a negligible weight loss at up to ca. 145° C. which agreed with the single crystal structure data. The weight loss corresponded to adventitious solvent. The moisture-sorption isotherm was characterized by 0.15% weight gain in the range of ca. 25% to ca. 75% RH at 25° C. indicating that the N-2 form was slightly hygroscopic (I would say very slightly or non-hygroscopic).

Example 2g

Form AN-3

A suspension of N-((1 R,2 S,5R)-5-(isopropyl(methyl)amino)-2-((S)-2-oxo-3-(6-(trifluoromethyl)quinazolin-4-ylamino)pyrrolidin-1-yl)cyclohexyl)acetamide, free base, at ~200 mg/mL was prepared in acetonitrile and allowed to equilibrate at room temperature to provide a somewhat thin suspension. Part of the suspension was filtered and both the filtrate and the suspension were refrigerated at 5° C. to provide crystals of the acetornitrile solvate (AN-3). Form AN-3 is characterized by one mole of acetonitrile per one mole of N-((1R,2S,5R)-5-(isopropyl(methyl)amino)-2-((S)-2-oxo-3-(6-(trifluoromethyl)quinazolin-4-ylamino)pyrrolidin-1-yl)cyclohexyl)acetamide, free base. Form AN-3 was characterized by an XRD pattern which matches the simulated pattern generated from the single crystal structure data.

Example 2h

Form H4-1, HCl

A sample of the free base of N-((1R,2S,5R)-5-(isopropyl(methyl)amino)-2-((S)-2-oxo-3-(6-(trifluoromethyl)quinazolin-4-ylamino)pyrrolidin-1-yl)cyclohexyl)acetamide (approx 0.2 g) was dissolved in ethanol (approx 1 mL). To the free base solution was added approx 310 µl of HCl solution in ethanol (approx 1.25M concentration). The solution was seeded with a small amount of crystal slurry of the HCl salt. To the resulting hazy solution was added 3 ml of heptane. A white slurry developed gradually over 1-2 hours while stirred at 20-25° C. The slurry was stirred at 20° C. for additional 12 hours, filtered and washed with heptane. The wet cake was dried in vacuo (40° C.) to provide the HCl salt tetrahydrate, form H4-1, HCl. Form H4-1, HCl is characterized by having 4 moles of water per a mole of N-((1R,2S,5R)-5-(isopropyl(methyl)amino)-2-((S)-2-oxo-3-(6-(trifluoromethyl)quinazolin-4-ylamino)pyrrolidin-1-yl)cyclohexyl)acetamide, hydrochloride salt. Form H4-1 HCl salt tetrahydrate was characterized by an SRD pattern which matches the the simulated pattern generated from the single crystal structure data.

TABLE 1

Unit Cell Parameters

| Compound | Salt | Form | T | a(Å) | b(Å) | c(Å) | α° | β° | γ° | V(Å³) | Z' | Vm | sg | dcalc |
|---|---|---|---|---|---|---|---|---|---|---|---|---|---|---|
| Exp 2a | di-BSA | N-1 | RT | 15.1737(8) | 7.6544(4) | 16.7722(9) | 90 | 93.758(2) | 90 | 1943.8(2) | 1 | 972 | P2$_1$ | 1.406 |
| Exp 2b | Base | DC-1 | RT | 8.7496(5) | 10.729(2) | 31.029(3) | 90 | 90 | 90 | 2912.8(6) | 1 | 728 | P2$_1$2$_1$2$_1$ | 1.349 |
| Exp 2c | Base | THOO-1 | −50 | 8.7909(6) | 11.1527(5) | 30.862(2) | 90 | 90 | 90 | 3025.8(3) | 1 | 756 | P2$_1$2$_1$2$_1$ | 1.340 |
| Exp 2d | Base | E-1 | RT | 8.2050(5) | 11.2186(5) | 32.041(2) | 90 | 90 | 90 | 2949.3(3) | 1 | 737 | P2$_1$2$_1$2$_1$ | 1.245 |
| Exp 2e | Base | A-1 | RT | 8.8773(7) | 10.5735(8) | 31.319(2) | 90 | 90 | 90 | 2939.8(4) | 1 | 735 | P2$_1$2$_1$2$_1$ | 1.276 |
| Exp 2f | Base | N-2 | RT | 11.8427(3) | 18.1503(7) | 12.7923(4) | 90 | 105.362(2) | 90 | 2651.4(2) | 2 | 663 | P2$_1$ | 1.269 |
| Exp 2g | Base | AN-3 | RT | 7.5341(9) | 13.514(2) | 14.342(2) | 90 | 91.671(8) | 90 | 1459.6(4) | 1 | 730 | P2$_1$ | 1.246 |
| Exp 2h | HCl | H4-1 | RT | 11.8391(2) | 11.8391(2) | 78.158(2) | 90 | 90 | 90 | 9487.2(4) | 1 | 791 | P6$_1$22 | 1.292 |

The variables used in Table 1 are defined below:
T=temperature in Centigrade for the crystallographic data
  (RT is room temperature which is about +22° C.)
V=volume of unit cell
Z'=number of drug molecules per asymmetric unit
Vm=V(unit cell)/(Z drug molecules per cell)
sg=space group
dcalc=calculated crystal density

TABLE 2

Atomic Coordinates for Example 2a, Form N-1, dibesylate

| Atom | X | Y | Z |
|---|---|---|---|
| S1 | 0.4296 | 0.3405 | 0.1278 |
| O2 | 0.3848 | 0.2640 | 0.1944 |
| O3 | 0.5075 | 0.2480 | 0.1097 |
| O4 | 0.3692 | 0.3687 | 0.0581 |
| C5 | 0.4631 | 0.5514 | 0.1598 |
| C6 | 0.5031 | 0.6610 | 0.1068 |
| C7 | 0.4500 | 0.6066 | 0.2360 |
| C8 | 0.5279 | 0.8279 | 0.1298 |
| C9 | 0.5113 | 0.8867 | 0.2054 |
| C10 | 0.4744 | 0.7756 | 0.2590 |
| S11 | 0.0304 | 0.2103 | 0.6431 |
| O12 | 0.0580 | 0.0675 | 0.5918 |
| O13 | 0.0507 | 0.1758 | 0.7265 |
| O14 | 0.0615 | 0.3788 | 0.6162 |
| C15 | −0.0863 | 0.2166 | 0.6296 |
| C16 | −0.1295 | 0.1458 | 0.5613 |
| C17 | −0.1335 | 0.2944 | 0.6877 |
| C18 | −0.2249 | 0.3021 | 0.6795 |
| C19 | −0.2234 | 0.1541 | 0.5537 |
| C20 | −0.2690 | 0.2305 | 0.6124 |
| N21 | 0.1351 | 0.3402 | 0.0394 |
| N22 | 0.2122 | 0.3075 | 0.2421 |
| N23 | 0.2612 | 0.1387 | −0.0417 |
| N24 | 0.0979 | 0.2591 | 0.3211 |
| O25 | 0.1429 | 0.0840 | 0.1114 |
| N26 | 0.1222 | 0.1701 | 0.4545 |
| O27 | 0.2029 | −0.1265 | −0.0688 |
| N28 | 0.1897 | 0.6703 | −0.2034 |
| C29 | 0.1114 | 0.2601 | −0.0390 |
| C30 | 0.2281 | 0.4006 | −0.1212 |
| C31 | 0.3926 | 0.1870 | 0.4435 |
| C32 | 0.2482 | 0.2192 | 0.3790 |
| C33 | 0.1850 | 0.2609 | 0.3119 |
| C34 | 0.3395 | 0.2220 | 0.3762 |
| C35 | 0.1915 | 0.2339 | −0.0878 |
| C36 | 0.2131 | 0.1749 | 0.4516 |
| C37 | 0.1374 | 0.5280 | 0.0550 |
| C38 | 0.1447 | 0.2421 | 0.1065 |
| C39 | 0.2678 | 0.1409 | 0.5195 |
| C40 | 0.0410 | 0.3593 | −0.0898 |
| C41 | 0.2593 | −0.0327 | −0.0318 |
| C42 | 0.1523 | 0.3701 | 0.1769 |
| C43 | 0.1572 | 0.4920 | −0.1737 |
| C44 | 0.1203 | 0.7566 | −0.2584 |
| C45 | 0.3559 | 0.1483 | 0.5161 |
| C46 | 0.0730 | 0.5239 | −0.1311 |
| C47 | 0.0706 | 0.2135 | 0.3909 |
| C48 | 0.1814 | 0.5399 | 0.1402 |
| C49 | 0.2788 | 0.6660 | −0.2381 |
| C50 | 0.4909 | 0.1922 | 0.4387 |
| C51 | 0.3294 | −0.1139 | 0.0239 |
| F52 | 0.5219 | 0.0514 | 0.4093 |
| F53 | 0.5340 | 0.2113 | 0.5073 |
| F54 | 0.5176 | 0.3178 | 0.3953 |
| C55 | 0.3112 | 0.8512 | −0.2507 |
| C56 | 0.2765 | 0.5513 | −0.3130 |
| H57 | 0.5146 | 0.6132 | 0.0473 |
| H58 | 0.4218 | 0.5168 | 0.2790 |
| H59 | 0.5591 | 0.9137 | 0.0886 |
| H60 | 0.5305 | 1.0179 | 0.2235 |
| H61 | 0.4602 | 0.8229 | 0.3179 |
| H62 | −0.0921 | 0.0872 | 0.5134 |
| H63 | −0.0975 | 0.3507 | 0.7393 |
| H64 | −0.2621 | 0.3609 | 0.7274 |
| H65 | −0.2589 | 0.0940 | 0.5014 |

TABLE 2-continued

Atomic Coordinates for Example 2a, Form N-1, dibesylate

| Atom | X | Y | Z |
|---|---|---|---|
| H66 | −0.3412 | 0.2321 | 0.6040 |
| H67 | 0.2813 | 0.2966 | 0.2330 |
| H68 | 0.3163 | 0.2103 | −0.0149 |
| H69 | 0.0931 | 0.1273 | 0.5084 |
| H70 | 0.0812 | 0.1334 | −0.0296 |
| H71 | 0.2494 | 0.4855 | −0.0720 |
| H72 | 0.2837 | 0.3700 | −0.1556 |
| H73 | 0.3692 | 0.2507 | 0.3208 |
| H74 | 0.1718 | 0.1588 | −0.1410 |
| H75 | 0.1760 | 0.5937 | 0.0122 |
| H76 | 0.0713 | 0.5818 | 0.0518 |
| H77 | 0.2388 | 0.1059 | 0.5751 |
| H78 | 0.0144 | 0.2704 | −0.1359 |
| H79 | −0.0107 | 0.3948 | −0.0519 |
| H80 | 0.0877 | 0.3884 | 0.1993 |
| H81 | 0.1400 | 0.4103 | −0.2251 |
| H82 | 0.1443 | 0.8789 | −0.2785 |
| H83 | 0.1063 | 0.6705 | −0.3097 |
| H84 | 0.0611 | 0.7736 | −0.2276 |
| H85 | 0.3994 | 0.1229 | 0.5687 |
| H86 | 0.0212 | 0.5681 | −0.1742 |
| H87 | 0.0851 | 0.6247 | −0.0863 |
| H88 | −0.0003 | 0.2113 | 0.3972 |
| H89 | 0.2528 | 0.5466 | 0.1402 |
| H90 | 0.1580 | 0.6514 | 0.1725 |
| H91 | 0.3253 | 0.5947 | −0.1972 |
| H92 | 0.3197 | −0.2538 | 0.0275 |
| H93 | 0.3937 | −0.0865 | 0.0040 |
| H94 | 0.3249 | −0.0591 | 0.0839 |
| H95 | 0.3767 | 0.8481 | −0.2754 |
| H96 | 0.2667 | 0.9209 | −0.2913 |
| H97 | 0.3183 | 0.9202 | −0.1940 |
| H98 | 0.3388 | 0.5477 | −0.3381 |
| H99 | 0.2541 | 0.4208 | −0.3000 |
| H100 | 0.2273 | 0.6084 | −0.3576 |
| H101 | 0.2047 | 0.7544 | −0.1523 |

TABLE 3

Atomic Coordinates for Example 2b, Form DC-1

| Atom | X | Y | Z |
|---|---|---|---|
| O1 | 0.3874 | 0.5713 | 0.1042 |
| N2 | 0.6277 | 0.6481 | 0.1041 |
| C3 | 0.3731 | 0.6931 | 0.1987 |
| O4 | 0.3088 | 0.7902 | 0.1889 |
| N5 | 0.5234 | 0.6709 | 0.1945 |
| C6 | 0.0370 | 0.3707 | 0.1487 |
| N7 | 0.9171 | 0.7535 | 0.0862 |
| C8 | 0.5884 | 0.7673 | 0.1246 |
| N9 | 0.2197 | 0.5147 | 0.1799 |
| C10 | 0.6819 | 0.8733 | 0.1041 |
| C11 | 0.0994 | 0.4380 | 0.1852 |
| C12 | 0.5232 | 0.5593 | 0.0958 |
| C13 | 0.0339 | 0.3042 | 0.0748 |
| C14 | 0.0966 | 0.3752 | 0.1068 |
| N15 | 0.0413 | 0.4260 | 0.2242 |
| C16 | −0.0879 | 0.2935 | 0.1577 |
| N17 | −0.1495 | 0.2843 | 0.1988 |
| C18 | 0.6213 | 0.7635 | 0.1729 |
| C19 | 0.2969 | 0.5749 | 0.2162 |
| C20 | 0.8547 | 0.8596 | 0.1114 |
| C21 | −0.0807 | 0.3504 | 0.2284 |
| C22 | 0.8829 | 0.8492 | 0.1601 |
| C23 | 0.0961 | 0.3041 | 0.0303 |
| C24 | 0.7904 | 0.7443 | 0.1815 |
| C25 | −0.1519 | 0.2227 | 0.1243 |
| C26 | 0.5854 | 0.4415 | 0.0762 |
| C27 | 0.4325 | 0.5005 | 0.2333 |
| F28 | 0.2100 | 0.3820 | 0.0251 |
| C29 | 0.5694 | 0.5442 | 0.2072 |

TABLE 3-continued

Atomic Coordinates for Example 2b, Form DC-1

| Atom | X | Y | Z |
|---|---|---|---|
| C30 | 0.8956 | 0.7650 | 0.0399 |
| F31 | −0.0040 | 0.3354 | 0.0005 |
| C32 | −0.0935 | 0.2269 | 0.0831 |
| F33 | 0.1425 | 0.1946 | 0.0181 |
| C34 | 1.0774 | 0.7297 | 0.0973 |
| C35 | 0.9360 | 0.6480 | 0.0149 |
| C36 | 0.9736 | 0.8757 | 0.0185 |
| CL37 | −0.6723 | 0.0636 | 0.0976 |
| CL38 | −0.6200 | 0.1776 | 0.1776 |
| C39 | −0.7292 | 0.0689 | 0.1511 |
| CL40 | −0.8261 | 0.1021 | 0.1984 |
| CL41 | −0.5719 | 0.1649 | 0.1533 |
| H41 | −0.1294 | 0.3465 | 0.2606 |
| H42 | −0.2461 | 0.1574 | 0.1324 |
| H43 | −0.1481 | 0.1749 | 0.0586 |
| H44 | 0.1951 | 0.4379 | 0.0994 |
| H45 | 0.2635 | 0.5336 | 0.1473 |
| H46 | 0.4541 | 0.5194 | 0.2668 |
| H47 | 0.4188 | 0.4033 | 0.2278 |
| H48 | 0.5887 | 0.4873 | 0.1799 |
| H49 | 0.6714 | 0.5483 | 0.2272 |
| H50 | 0.5969 | 0.8538 | 0.1868 |
| H51 | 0.8120 | 0.7421 | 0.2149 |
| H52 | 0.8245 | 0.6564 | 0.1665 |
| H53 | 0.4689 | 0.7873 | 0.1195 |
| H54 | 0.7443 | 0.6307 | 0.0952 |
| H55 | 0.6606 | 0.8737 | 0.0699 |
| H56 | 0.6450 | 0.9598 | 0.1181 |
| H57 | 0.9128 | 0.9427 | 0.1024 |
| H58 | 0.9994 | 0.8349 | 0.1664 |
| H59 | 0.8434 | 0.9363 | 0.1746 |
| H60 | 1.1241 | 0.6556 | 0.0774 |
| H61 | 1.1465 | 0.8155 | 0.0889 |
| H62 | 1.0949 | 0.7111 | 0.1303 |
| H63 | 0.9541 | 0.8697 | −0.0162 |
| H64 | 0.9409 | 0.9581 | 0.0316 |
| H65 | 1.0997 | 0.8600 | 0.0230 |
| H66 | 0.9136 | 0.6679 | −0.0189 |
| H67 | 1.0529 | 0.6293 | 0.0199 |
| H68 | 0.8640 | 0.5745 | 0.0257 |
| H69 | 0.7752 | 0.7851 | 0.0338 |
| H70 | 0.7087 | 0.4513 | 0.0715 |
| H71 | 0.5635 | 0.3648 | 0.0972 |
| H72 | 0.5326 | 0.4265 | 0.0453 |
| H73 | 0.2091 | 0.6032 | 0.2400 |
| H75 | −0.7132 | −0.0216 | 0.1657 |

TABLE 4

Atomic Coordinates for Example 2c, Form THOO-1

| Atom | X | Y | Z |
|---|---|---|---|
| N1 | 0.6241 | 0.6511 | 0.1036 |
| N2 | 0.5165 | 0.6586 | 0.1938 |
| N3 | 0.0409 | 0.4138 | 0.2209 |
| N4 | 0.9119 | 0.7577 | 0.0893 |
| N5 | 0.2188 | 0.5080 | 0.1767 |
| N6 | −0.1428 | 0.2821 | 0.1910 |
| F7 | 0.2088 | 0.4068 | 0.0184 |
| F8 | 0.1464 | 0.2269 | 0.0085 |
| F9 | −0.0051 | 0.3616 | −0.0061 |
| O10 | 0.3873 | 0.5694 | 0.1019 |
| O11 | 0.2971 | 0.7711 | 0.1928 |
| C12 | −0.0831 | 0.2960 | 0.1506 |
| C13 | 0.0371 | 0.3738 | 0.1430 |
| C14 | 0.5812 | 0.7621 | 0.1256 |
| C15 | 0.0986 | 0.4345 | 0.1815 |
| C16 | −0.0886 | 0.2415 | 0.0746 |
| C17 | 0.6739 | 0.8655 | 0.1071 |
| C18 | 0.0331 | 0.3225 | 0.0673 |
| C19 | 0.6111 | 0.7539 | 0.1748 |

TABLE 4-continued

Atomic Coordinates for Example 2c, Form THOO-1

| Atom | X | Y | Z |
|---|---|---|---|
| C20 | 0.7789 | 0.7380 | 0.1846 |
| C21 | 0.0953 | 0.3862 | 0.1014 |
| C22 | −0.1446 | 0.2303 | 0.1158 |
| C23 | 0.8438 | 0.8556 | 0.1148 |
| C24 | 0.3673 | 0.6754 | 0.2001 |
| C25 | −0.0810 | 0.3420 | 0.2233 |
| C26 | 0.8681 | 0.8418 | 0.1645 |
| C27 | 0.5709 | 0.5348 | 0.2038 |
| C28 | 0.8975 | 0.7762 | 0.0422 |
| C29 | 0.2923 | 0.5573 | 0.2150 |
| C30 | 0.4345 | 0.4867 | 0.2295 |
| C31 | 0.0958 | 0.3306 | 0.0236 |
| C32 | 0.9346 | 0.6664 | 0.0161 |
| C33 | 0.9942 | 0.8828 | 0.0245 |
| C34 | 1.0667 | 0.7324 | 0.1019 |
| C35 | 0.5239 | 0.5633 | 0.0937 |
| C36 | 0.5916 | 0.4548 | 0.0733 |
| O37 | −0.4684 | 0.1388 | 0.1701 |
| O38 | −0.4289 | 0.2122 | 0.2075 |
| O39 | −0.7214 | 0.1782 | 0.1852 |
| C40 | −0.6079 | 0.2004 | 0.1513 |
| C41 | −0.7805 | 0.0664 | 0.1760 |
| C42 | −0.6561 | 0.1265 | 0.1151 |
| C43 | −0.7758 | 0.0381 | 0.1281 |
| H44 | 0.8469 | 0.6491 | −0.0084 |
| H45 | 1.0426 | 0.6769 | −0.0009 |
| H46 | 0.9420 | 0.5884 | 0.0369 |
| H47 | 0.9710 | 0.8879 | −0.0108 |
| H48 | 0.9644 | 0.9636 | 0.0393 |
| H49 | 1.1113 | 0.8600 | 0.0288 |
| H50 | 1.1138 | 0.6612 | 0.0823 |
| H51 | 1.1368 | 0.8124 | 0.0977 |
| H52 | 1.0715 | 0.7062 | 0.1357 |
| H53 | 0.8967 | 0.9395 | 0.1069 |
| H54 | 0.8364 | 0.9249 | 0.1799 |
| H55 | 0.9892 | 0.8264 | 0.1696 |
| H56 | 0.6557 | 0.8698 | 0.0727 |
| H57 | 0.6337 | 0.9476 | 0.1221 |
| H58 | 0.7936 | 0.7360 | 0.2193 |
| H59 | 0.8150 | 0.6527 | 0.1711 |
| H60 | 0.5860 | 0.8385 | 0.1901 |
| H61 | 0.4619 | 0.7796 | 0.1196 |
| H62 | 0.7430 | 0.6376 | 0.0952 |
| H63 | 0.5034 | 0.3895 | 0.0665 |
| H64 | 0.6466 | 0.4797 | 0.0433 |
| H65 | 0.6742 | 0.4155 | 0.0950 |
| H66 | 0.5931 | 0.4838 | 0.1746 |
| H67 | 0.6760 | 0.5373 | 0.2229 |
| H68 | 0.4199 | 0.3911 | 0.2235 |
| H69 | 0.4543 | 0.4982 | 0.2644 |
| H70 | 0.2110 | 0.5756 | 0.2404 |
| H71 | 0.2578 | 0.5312 | 0.1447 |
| H72 | −0.1392 | 0.3344 | 0.2555 |
| H73 | 0.1922 | 0.4468 | 0.0960 |
| H74 | −0.2394 | 0.1689 | 0.1216 |
| H75 | −0.1341 | 0.1904 | 0.0479 |
| H76 | 0.7798 | 0.8064 | 0.0354 |
| H77 | −0.5859 | 0.2979 | 0.1468 |
| H78 | −0.6934 | 0.1865 | 0.0883 |
| H79 | −0.5532 | 0.0802 | 0.1023 |
| H80 | −0.7442 | −0.0491 | 0.1228 |
| H81 | −0.8828 | 0.0626 | 0.1139 |
| H82 | −0.7168 | 0.0010 | 0.1956 |
| H83 | −0.8983 | 0.0662 | 0.1893 |
| H84 | −0.3123 | 0.2450 | 0.2037 |

TABLE 5

Atomic Coordinates for Example 2d, Form E-1

| Atom | X | Y | Z |
|---|---|---|---|
| N1 | 0.5556 | 0.6575 | 0.1971 |
| N2 | 0.9580 | 0.7945 | 0.0952 |
| N3 | 0.0504 | 0.4000 | 0.2167 |
| N4 | 0.2466 | 0.4969 | 0.1788 |
| N5 | 0.6640 | 0.6706 | 0.1083 |
| O6 | 0.4235 | 0.5727 | 0.1071 |
| O7 | 0.3141 | 0.7585 | 0.2020 |
| C8 | 0.0563 | 0.3683 | 0.1425 |
| C9 | 0.3945 | 0.6665 | 0.2051 |
| N10 | −0.1464 | 0.2693 | 0.1855 |
| C11 | 0.1179 | 0.4244 | 0.1805 |
| C12 | −0.0757 | 0.2900 | 0.1475 |
| C13 | 0.5699 | 0.5796 | 0.0976 |
| C14 | 0.6460 | 0.7574 | 0.1795 |
| C15 | 0.6096 | 0.7741 | 0.1332 |
| C16 | −0.0804 | 0.3256 | 0.2169 |
| C17 | 0.1256 | 0.3867 | 0.1021 |
| C18 | 0.8278 | 0.7497 | 0.1874 |
| C19 | −0.1350 | 0.2278 | 0.1118 |
| C20 | 0.3307 | 0.5423 | 0.2161 |
| C21 | −0.0669 | 0.2438 | 0.0739 |
| C22 | 0.8827 | 0.8818 | 0.1241 |
| C23 | 0.6945 | 0.8866 | 0.1168 |
| C24 | 0.4824 | 0.4737 | 0.2271 |
| C25 | 0.0642 | 0.3239 | 0.0689 |
| C26 | 0.9139 | 0.8598 | 0.1701 |
| C27 | 0.6193 | 0.5376 | 0.2034 |
| C28 | 0.1332 | 0.3426 | 0.0264 |
| C29 | 0.6490 | 0.4838 | 0.0720 |
| F30 | 0.1426 | 0.2490 | 0.0048 |
| F31 | 0.2603 | 0.4035 | 0.0246 |
| C32 | 1.1203 | 0.7545 | 0.1087 |
| C33 | 0.9653 | 0.8421 | 0.0525 |
| C34 | 0.9802 | 0.7362 | 0.0215 |
| C35 | 1.1042 | 0.9365 | 0.0471 |
| F36 | 0.0282 | 0.4017 | 0.0020 |
| O37 | −0.4308 | 0.1231 | 0.1846 |
| C38 | −0.5696 | 0.1669 | 0.1671 |
| C39 | −0.7016 | 0.0870 | 0.1643 |
| H40 | 0.2903 | 0.5250 | 0.1486 |
| H41 | 0.7902 | 0.6695 | 0.0980 |
| H42 | 0.6121 | 0.8376 | 0.1960 |
| H43 | 0.4802 | 0.7853 | 0.1289 |
| H44 | −0.1345 | 0.3091 | 0.2471 |
| H45 | 0.2219 | 0.4518 | 0.0971 |
| H46 | 0.8518 | 0.7434 | 0.2205 |
| H47 | 0.8769 | 0.6703 | 0.1722 |
| H48 | −0.2356 | 0.1657 | 0.1154 |
| H49 | 0.2468 | 0.5491 | 0.2421 |
| H50 | −0.1137 | 0.1969 | 0.0471 |
| H51 | 0.9339 | 0.9678 | 0.1186 |
| H52 | 0.6715 | 0.8931 | 0.0836 |
| H53 | 0.6450 | 0.9623 | 0.1326 |
| H54 | 0.5054 | 0.4773 | 0.2603 |
| H55 | 0.4724 | 0.3825 | 0.2172 |
| H56 | 0.8706 | 0.9373 | 0.1867 |
| H57 | 1.0434 | 0.8510 | 0.1741 |
| H58 | 0.6429 | 0.4941 | 0.1737 |
| H59 | 0.7309 | 0.5392 | 0.2214 |
| H60 | 0.5606 | 0.4154 | 0.0654 |
| H61 | 0.6932 | 0.5215 | 0.0431 |
| H62 | 0.7497 | 0.4462 | 0.0892 |
| H63 | 1.1678 | 0.6903 | 0.0868 |
| H64 | 1.2002 | 0.8299 | 0.1107 |
| H65 | 1.1111 | 0.7125 | 0.1393 |
| H66 | 0.8527 | 0.8919 | 0.0459 |
| H67 | 0.9828 | 0.7726 | −0.0103 |
| H68 | 1.0893 | 0.6894 | 0.0276 |
| H69 | 0.8751 | 0.6798 | 0.0245 |
| H70 | 1.1045 | 0.9693 | 0.0155 |
| H71 | 1.0868 | 1.0079 | 0.0687 |
| H72 | 1.2197 | 0.8923 | 0.0534 |
| H73 | −0.3356 | 0.1901 | 0.1827 |
| H74 | −0.6100 | 0.2427 | 0.1853 |
| H75 | −0.5435 | 0.1919 | 0.1361 |
| H76 | −0.8101 | 0.1237 | 0.1519 |
| H77 | −0.6709 | 0.0043 | 0.1485 |
| H78 | −0.7374 | 0.0551 | 0.1977 |

TABLE 6

Atomic Coordinates for Example 2e, Form A-1

| Atom | X | Y | Z |
|---|---|---|---|
| O1 | 0.3737 | 0.5677 | 0.1038 |
| N2 | 0.6127 | 0.6388 | 0.1027 |
| O3 | 0.3132 | 0.7830 | 0.1897 |
| C4 | 0.5064 | 0.5520 | 0.0949 |
| N5 | 0.2190 | 0.5059 | 0.1814 |
| C6 | 0.1016 | 0.4290 | 0.1870 |
| N7 | 0.9018 | 0.7409 | 0.0835 |
| N8 | 0.5246 | 0.6588 | 0.1932 |
| C9 | 0.3746 | 0.6827 | 0.1988 |
| N10 | 0.0495 | 0.4145 | 0.2272 |
| C11 | 0.5829 | 0.7591 | 0.1239 |
| C12 | 0.0312 | 0.3644 | 0.1517 |
| C13 | −0.0936 | 0.2901 | 0.1617 |
| N14 | −0.1492 | 0.2774 | 0.2023 |
| C15 | 0.3004 | 0.5650 | 0.2162 |
| C16 | 0.0858 | 0.3691 | 0.1092 |
| C17 | 0.6197 | 0.7499 | 0.1719 |
| C18 | 0.5600 | 0.4313 | 0.0739 |
| C19 | 0.6747 | 0.8657 | 0.1038 |
| F20 | 0.1808 | 0.3831 | 0.0261 |
| C21 | 0.0143 | 0.3015 | 0.0775 |
| C22 | 0.7871 | 0.7290 | 0.1785 |
| C23 | 0.8454 | 0.8483 | 0.1091 |
| C24 | −0.0739 | 0.3401 | 0.2315 |
| F25 | 0.1345 | 0.1856 | 0.0238 |
| C26 | 0.0743 | 0.2971 | 0.0335 |
| C27 | 0.8780 | 0.8348 | 0.1570 |
| C28 | 0.4326 | 0.4864 | 0.2320 |
| F29 | −0.0287 | 0.3175 | 0.0040 |
| C30 | 0.5653 | 0.5283 | 0.2038 |
| C31 | 0.8750 | 0.7554 | 0.0374 |
| C32 | −0.1674 | 0.2229 | 0.1280 |
| C33 | 1.0612 | 0.7135 | 0.0915 |
| C34 | −0.1156 | 0.2277 | 0.0877 |
| C35 | −0.6607 | 0.1145 | 0.1509 |
| C36 | 0.9067 | 0.6372 | 0.0125 |
| C37 | 0.9468 | 0.8688 | 0.0169 |
| C38 | −0.7123 | 0.0511 | 0.1141 |
| O39 | −0.5629 | 0.1869 | 0.1523 |
| C40 | −0.7542 | 0.0996 | 0.1900 |
| H34 | −0.1640 | 0.1792 | 0.0657 |
| H16 | 0.1740 | 0.4180 | 0.1027 |
| H32 | −0.2563 | 0.1746 | 0.1343 |
| H24 | −0.1168 | 0.3282 | 0.2594 |
| H5 | 0.2557 | 0.5241 | 0.1532 |
| H28A | 0.4510 | 0.5073 | 0.2614 |
| H28B | 0.4099 | 0.3978 | 0.2297 |
| H30A | 0.5706 | 0.4800 | 0.1779 |
| H30B | 0.6614 | 0.5265 | 0.2179 |
| H15 | 0.2312 | 0.5873 | 0.2385 |
| H17 | 0.5966 | 0.8294 | 0.1852 |
| H2 | 0.7132 | 0.6191 | 0.0935 |
| H18A | 0.6668 | 0.4348 | 0.0693 |
| H18B | 0.5096 | 0.4227 | 0.0469 |
| H18C | 0.5363 | 0.3599 | 0.0916 |
| H22A | 0.8097 | 0.7261 | 0.2084 |
| H22B | 0.8144 | 0.6500 | 0.1655 |
| H11 | 0.4780 | 0.7781 | 0.1200 |
| H19A | 0.6550 | 0.8673 | 0.0737 |
| H19B | 0.6472 | 0.9456 | 0.1161 |
| H27A | 0.8511 | 0.9136 | 0.1702 |
| H27B | 0.9840 | 0.8202 | 0.1605 |

TABLE 6-continued

Atomic Coordinates for Example 2e, Form A-1

| Atom | X | Y | Z |
|---|---|---|---|
| H23 | 0.8972 | 0.9223 | 0.0991 |
| H33A | 1.0920 | 0.6435 | 0.0741 |
| H33B | 1.0747 | 0.6924 | 0.1211 |
| H33C | 1.1211 | 0.7863 | 0.0846 |
| H31 | 0.7694 | 0.7749 | 0.0364 |
| H37A | 0.9230 | 0.8700 | −0.0130 |
| H37B | 1.0541 | 0.8649 | 0.0205 |
| H37C | 0.9089 | 0.9442 | 0.0302 |
| H36A | 0.8874 | 0.6527 | −0.0172 |
| H36B | 0.8419 | 0.5709 | 0.0225 |
| H36C | 1.0100 | 0.6124 | 0.0161 |
| H40A | −0.7132 | 0.1528 | 0.2120 |
| H40B | −0.7533 | 0.0132 | 0.1994 |
| H40C | −0.8560 | 0.1249 | 0.1840 |
| H38A | −0.7948 | 0.0004 | 0.1242 |
| H38B | −0.6331 | −0.0032 | 0.1041 |
| H38C | −0.7461 | 0.1041 | 0.0912 |

TABLE 7

Atomic Coordinates for Example 2f, Form N-2

| Atom | X | Y | Z |
|---|---|---|---|
| C1 | −0.1614 | 0.2577 | 0.0383 |
| C2 | 0.0133 | 0.3873 | 0.0895 |
| C3 | −0.0055 | 0.3310 | −0.0010 |
| C4 | −0.0893 | 0.3603 | −0.1048 |
| C5 | −0.0096 | 0.1977 | −0.0307 |
| C6 | 0.1226 | 0.1850 | −0.0004 |
| C7 | −0.0693 | 0.1244 | −0.0205 |
| C8 | 0.1708 | 0.1498 | 0.1106 |
| C9 | 0.1075 | 0.0771 | 0.1147 |
| C10 | −0.0234 | 0.0881 | 0.0905 |
| C11 | 0.2617 | 0.0045 | 0.2339 |
| C12 | 0.2925 | −0.0262 | 0.3476 |
| C13 | 0.1771 | −0.0254 | 0.3775 |
| C14 | 0.1062 | 0.0350 | 0.3075 |
| C15 | 0.2367 | 0.2052 | 0.2942 |
| C16 | 0.2078 | 0.2604 | 0.3702 |
| C17 | 0.5499 | −0.0989 | 0.6085 |
| C18 | 0.4630 | −0.0041 | 0.5011 |
| C19 | 0.5492 | 0.0453 | 0.5666 |
| C20 | 0.6362 | 0.0119 | 0.6505 |
| C21 | 0.5475 | 0.1213 | 0.5540 |
| C22 | 0.7226 | 0.0568 | 0.7150 |
| C23 | 0.7201 | 0.1309 | 0.7026 |
| C24 | 0.6306 | 0.1640 | 0.6225 |
| C25 | 0.6233 | 0.2457 | 0.6114 |
| C26 | 0.3178 | 0.0508 | −0.3076 |
| C27 | 0.3677 | 0.1429 | −0.1554 |
| C28 | 0.2847 | −0.0135 | −0.1112 |
| C29 | 0.3985 | 0.0680 | −0.1941 |
| C30 | 0.4839 | −0.0499 | −0.1192 |
| C31 | 0.4689 | −0.1207 | −0.0596 |
| C32 | 0.6120 | −0.0241 | −0.0769 |
| C33 | 0.6492 | −0.0164 | 0.0464 |
| C34 | 0.6335 | −0.0892 | 0.1001 |
| C35 | 0.5063 | −0.1148 | 0.0626 |
| C36 | 0.6313 | 0.0922 | 0.1569 |
| C37 | 0.5494 | 0.1489 | 0.1804 |
| C38 | 0.7946 | −0.0826 | 0.2650 |
| C39 | 0.6078 | −0.0715 | 0.2941 |
| C40 | 0.6937 | −0.0843 | 0.4027 |
| C41 | 0.8124 | −0.0650 | 0.3838 |
| C42 | 0.8969 | 0.0402 | 0.4994 |
| C43 | 0.9918 | 0.0223 | 0.6769 |
| C44 | 0.9164 | 0.1178 | 0.5156 |
| C45 | 1.0010 | 0.2152 | 0.6420 |
| C46 | 0.9795 | 0.1403 | 0.6212 |
| C47 | 0.9601 | 0.2664 | 0.5640 |
| C48 | 0.8959 | 0.2447 | 0.4599 |
| C49 | 0.8756 | 0.1715 | 0.4360 |
| C50 | 0.8489 | 0.3015 | 0.3761 |
| N1 | 1.0171 | 0.0906 | 0.7037 |
| N2 | 0.6368 | −0.0622 | 0.6704 |
| N3 | 0.9331 | −0.0075 | 0.5810 |
| N4 | 0.4627 | −0.0749 | 0.5246 |
| N5 | 0.8420 | 0.0126 | 0.4015 |
| N6 | 0.6777 | −0.0849 | 0.2178 |
| N7 | 0.5849 | 0.0426 | 0.0803 |
| N8 | 0.4025 | 0.0106 | −0.1105 |
| N9 | 0.3818 | 0.0211 | 0.4149 |
| N10 | 0.1561 | 0.0378 | 0.2158 |
| N11 | 0.1599 | 0.2000 | 0.1967 |
| N12 | −0.0389 | 0.2585 | 0.0355 |
| O1 | 0.8718 | −0.0902 | 0.2185 |
| O2 | 0.7359 | 0.0910 | 0.2072 |
| O3 | 0.3220 | 0.0019 | 0.1698 |
| O4 | 0.3257 | 0.1671 | 0.3217 |
| F1 | 0.7539 | 0.2815 | 0.3030 |
| F2 | 0.9209 | 0.3190 | 0.3146 |
| F3 | 0.8233 | 0.3648 | 0.4151 |
| F4 | 0.8500 | 0.2791 | 0.2840 |
| F5 | 0.9132 | 0.3571 | 0.3931 |
| F6 | 0.7377 | 0.3127 | 0.3710 |
| F7 | 0.6225 | 0.2634 | 0.5011 |
| F8 | 0.7150 | 0.2806 | 0.6609 |
| F9 | 0.5345 | 0.2749 | 0.6173 |
| F10 | 0.6186 | 0.2737 | 0.7242 |
| F11 | 0.7090 | 0.2767 | 0.6039 |
| F12 | 0.5230 | 0.2690 | 0.5624 |
| H10A | −0.0413 | 0.1190 | 0.1459 |
| H10B | −0.0615 | 0.0409 | 0.0911 |
| H11 | 0.0996 | 0.2283 | 0.1837 |
| H12 | 0.3217 | −0.0767 | 0.3481 |
| H13A | 0.1891 | −0.0144 | 0.4538 |
| H13B | 0.1378 | −0.0726 | 0.3618 |
| H14A | 0.0237 | 0.0225 | 0.2848 |
| H14B | 0.1156 | 0.0818 | 0.3457 |
| H16A | 0.1608 | 0.2374 | 0.4116 |
| H16B | 0.1652 | 0.3007 | 0.3293 |
| H16C | 0.2789 | 0.2786 | 0.4183 |
| H17 | 0.5477 | −0.1488 | 0.6244 |
| H1A | −0.1774 | 0.3007 | 0.0757 |
| H1B | −0.1761 | 0.2143 | 0.0756 |
| H1C | −0.2111 | 0.2575 | −0.0344 |
| H21 | 0.4899 | 0.1433 | 0.4990 |
| H22 | 0.7832 | 0.0354 | 0.7676 |
| H23 | 0.7779 | 0.1599 | 0.7473 |
| H26A | 0.3405 | 0.0047 | −0.3327 |
| H26B | 0.3247 | 0.0893 | −0.3570 |
| H26C | 0.2382 | 0.0477 | −0.3035 |
| H27A | 0.2885 | 0.1420 | −0.1496 |
| H27B | 0.3753 | 0.1801 | −0.2063 |
| H27C | 0.4198 | 0.1537 | −0.0857 |
| H28A | 0.2347 | 0.0287 | −0.1160 |
| H28B | 0.2875 | −0.0400 | −0.0457 |
| H28C | 0.2545 | −0.0451 | −0.1725 |
| H29 | 0.4782 | 0.0723 | −0.2025 |
| H2A | −0.0589 | 0.3951 | 0.1087 |
| H2B | 0.0389 | 0.4330 | 0.0656 |
| H2C | 0.0717 | 0.3696 | 0.1516 |
| H3 | 0.0704 | 0.3241 | −0.0167 |
| H30 | 0.4704 | −0.0619 | −0.1962 |
| H31A | 0.3871 | −0.1351 | −0.0819 |
| H31B | 0.5139 | −0.1595 | −0.0817 |
| H32A | 0.6629 | −0.0594 | −0.0989 |
| H32B | 0.6212 | 0.0230 | −0.1096 |
| H33 | 0.7326 | −0.0036 | 0.0683 |
| H34 | 0.6810 | −0.1261 | 0.0750 |
| H35A | 0.4983 | −0.1624 | 0.0944 |
| H35B | 0.4564 | −0.0799 | 0.0866 |
| H37A | 0.5607 | 0.1528 | 0.2573 |
| H37B | 0.4700 | 0.1346 | 0.1467 |
| H37C | 0.5650 | 0.1957 | 0.1521 |
| H39A | 0.5425 | −0.1055 | 0.2823 |

TABLE 7-continued

Atomic Coordinates for Example 2f, Form N-2

| Atom | X | Y | Z |
|---|---|---|---|
| H39B | 0.5781 | −0.0214 | 0.2880 |
| H40A | 0.6920 | −0.1353 | 0.4251 |
| H40B | 0.6765 | −0.0527 | 0.4577 |
| H41 | 0.8743 | −0.0960 | 0.4288 |
| H43 | 1.0183 | −0.0115 | 0.7327 |
| H45 | 1.0440 | 0.2303 | 0.7105 |
| H47 | 0.9746 | 0.3161 | 0.5795 |
| H49 | 0.8344 | 0.1575 | 0.3664 |
| H4A | −0.1020 | 0.3231 | −0.1600 |
| H4B | −0.0560 | 0.4033 | −0.1288 |
| H4C | −0.1627 | 0.3731 | −0.0908 |
| H5 | 0.8235 | 0.0422 | 0.3470 |
| H5A | −0.0340 | 0.2128 | −0.1069 |
| H6A | 0.1414 | 0.1536 | −0.0548 |
| H6B | 0.1615 | 0.2319 | −0.0017 |
| H7 | 0.5113 | 0.0460 | 0.0488 |
| H7A | −0.1528 | 0.1327 | −0.0337 |
| H7B | −0.0576 | 0.0910 | −0.0759 |
| H8 | 0.2540 | 0.1393 | 0.1202 |
| H9 | 0.3825 | 0.0671 | 0.3986 |
| H9A | 0.1212 | 0.0462 | 0.0565 |

TABLE 8

Atomic Coordinates for Example 2g, Form AN-3

| Atom | X | Y | Z |
|---|---|---|---|
| N1 | 0.3835 | 0.0757 | 0.0375 |
| N2 | 0.7286 | −0.0185 | 0.1260 |
| N3 | 0.2667 | 0.0953 | −0.1106 |
| O4 | 0.4406 | 0.1041 | 0.2348 |
| C6 | 0.1693 | 0.2426 | 0.1013 |
| N7 | 0.6875 | 0.0647 | 0.3206 |
| C8 | 0.0362 | 0.2388 | −0.0548 |
| O9 | 0.5030 | −0.1317 | 0.1098 |
| C10 | 0.5797 | −0.0561 | 0.0855 |
| N11 | 0.9744 | 0.0244 | 0.4480 |
| C12 | 0.0569 | 0.3162 | 0.1260 |
| C5 | 0.1605 | 0.2026 | 0.0109 |
| C13 | 0.2745 | 0.1240 | −0.0211 |
| N14 | 0.0255 | 0.2060 | −0.1450 |
| C15 | −0.0858 | 0.3132 | −0.0252 |
| C16 | 0.5624 | 0.1278 | 0.2890 |
| C17 | 0.5237 | 0.0103 | 0.0054 |
| C18 | 1.1544 | 0.0668 | 0.4534 |
| C19 | 0.8045 | −0.0612 | 0.2107 |
| C20 | 0.1422 | 0.1402 | −0.1658 |
| C21 | −0.0752 | 0.3517 | 0.0617 |
| C22 | 0.9970 | −0.0294 | 0.2320 |
| C23 | 0.7649 | −0.1008 | 0.3793 |
| C24 | 0.7898 | 0.0709 | 0.0816 |
| C25 | 0.6909 | −0.0417 | 0.2964 |
| C26 | 0.6097 | 0.2153 | 0.6473 |
| C27 | 0.9604 | −0.0758 | 0.4035 |
| C28 | 0.6935 | 0.0679 | −0.0147 |
| C29 | 1.0708 | −0.0864 | 0.3149 |
| F30 | 0.1149 | 0.3018 | 0.2839 |
| C31 | 1.1447 | 0.1747 | 0.4843 |
| C32 | 0.0681 | 0.3603 | 0.2194 |
| F33 | −0.0775 | 0.3987 | 0.2482 |
| C34 | 0.5829 | 0.2314 | 0.3240 |
| C35 | 1.2896 | 0.0095 | 0.5118 |
| C36 | 0.8948 | 0.0210 | 0.5396 |
| C37 | 0.6085 | 0.1849 | 0.7418 |
| N38 | 0.6123 | 0.2421 | 0.5722 |
| F39 | 0.1781 | 0.4283 | 0.2274 |
| H21 | −0.1570 | 0.4019 | 0.0806 |
| H6 | 0.2566 | 0.2184 | 0.1457 |
| H15 | −0.1768 | 0.3372 | −0.0677 |
| H20 | 0.1322 | 0.1240 | −0.2309 |
| H1 | 0.3709 | 0.0824 | 0.1036 |

TABLE 8-continued

Atomic Coordinates for Example 2g, Form AN-3

| Atom | X | Y | Z |
|---|---|---|---|
| H17 | 0.4819 | −0.0292 | −0.0463 |
| H28A | 0.7603 | 0.0328 | −0.0600 |
| H28B | 0.6637 | 0.1325 | −0.0383 |
| H24A | 0.7555 | 0.1274 | 0.1175 |
| H24B | 0.9167 | 0.0696 | 0.0774 |
| H19 | 0.8001 | −0.1313 | 0.2000 |
| H22A | 1.0680 | −0.0427 | 0.1790 |
| H22B | 1.0006 | 0.0401 | 0.2458 |
| H29A | 1.0737 | −0.1556 | 0.3001 |
| H29B | 1.1889 | −0.0637 | 0.3299 |
| H27 | 1.0060 | −0.1224 | 0.4487 |
| H23A | 0.6964 | −0.0882 | 0.4334 |
| H23B | 0.7596 | −0.1700 | 0.3643 |
| H25 | 0.5708 | −0.0620 | 0.2829 |
| H7 | 0.7807 | 0.0874 | 0.3623 |
| H34A | 0.6865 | 0.2365 | 0.3642 |
| H34B | 0.4795 | 0.2484 | 0.3581 |
| H34C | 0.5937 | 0.2759 | 0.2722 |
| H36A | 0.7774 | −0.0065 | 0.5345 |
| H36B | 0.8886 | 0.0871 | 0.5638 |
| H36C | 0.9671 | −0.0190 | 0.5809 |
| H18 | 1.1968 | 0.0630 | 0.3910 |
| H35A | 1.4009 | 0.0440 | 0.5102 |
| H35B | 1.3030 | −0.0555 | 0.4859 |
| H35C | 1.2530 | 0.0042 | 0.5751 |
| H31A | 1.2617 | 0.2028 | 0.4883 |
| H31B | 1.0911 | 0.1790 | 0.5441 |
| H31C | 1.0736 | 0.2106 | 0.4391 |
| H37A | 0.5614 | 0.1191 | 0.7457 |
| H37B | 0.5364 | 0.2293 | 0.7767 |
| H37C | 0.7279 | 0.1858 | 0.7670 |

TABLE 9

Atomic Coordinates for Example 2h, Form H4-1, HCl

| Atom | X | Y | Z |
|---|---|---|---|
| N1 | −0.1488 | 0.2098 | −0.0343 |
| O2 | 0.3490 | 0.4972 | 0.0272 |
| N3 | 0.2326 | 0.3477 | 0.0060 |
| N4 | 0.2975 | 0.2676 | 0.0466 |
| N5 | 0.0807 | 0.4627 | 0.0181 |
| N6 | 0.5197 | 0.3793 | 0.0531 |
| F7 | −0.0010 | 0.2280 | 0.0989 |
| O8 | 0.1939 | 0.6851 | 0.0181 |
| C9 | 0.2189 | 0.4432 | −0.0048 |
| C10 | 0.3038 | 0.3881 | 0.0205 |
| N11 | 0.5990 | 0.4425 | 0.0823 |
| C12 | 0.0927 | 0.4487 | −0.0003 |
| C13 | −0.0342 | 0.3317 | −0.0074 |
| C14 | 0.3955 | 0.3262 | 0.0584 |
| C15 | 0.4700 | 0.3861 | 0.0880 |
| C16 | 0.3630 | 0.3248 | 0.0764 |
| C17 | 0.1395 | 0.5810 | 0.0261 |
| C18 | 0.3194 | 0.2774 | 0.0280 |
| C19 | −0.1511 | 0.2151 | −0.0542 |
| C20 | 0.1983 | 0.2123 | 0.0011 |
| C21 | 0.0952 | 0.3112 | −0.0319 |
| C22 | −0.0230 | 0.3271 | −0.0270 |
| C23 | 0.2130 | 0.2691 | 0.1003 |
| C24 | 0.2222 | 0.4228 | −0.0243 |
| C25 | 0.2358 | 0.2673 | 0.0829 |
| C26 | 0.4468 | 0.3881 | 0.1058 |
| C27 | 0.3218 | 0.3305 | 0.1117 |
| C28 | 0.1344 | 0.5769 | 0.0455 |
| C29 | −0.2730 | 0.1906 | −0.0263 |
| F30 | 0.0717 | 0.2300 | 0.1235 |
| C31 | 0.2191 | 0.1567 | 0.0180 |
| C32 | 0.6135 | 0.4326 | 0.0655 |
| F33 | 0.0240 | 0.0760 | 0.1070 |
| C34 | 0.0782 | 0.2012 | 0.1072 |

TABLE 9-continued

Atomic Coordinates for Example 2h, Form H4-1, HCl

| Atom | X | Y | Z |
|---|---|---|---|
| C35 | −0.2346 | 0.0735 | −0.0609 |
| C36 | −0.1999 | 0.3066 | −0.0603 |
| CL37 | 0.0168 | 0.2311 | 0.0469 |
| O38 | −0.1364 | 0.0296 | 0.0183 |
| O39 | 0.3598 | 0.8724 | −0.0063 |
| O40 | −0.2980 | 0.1857 | 0.0261 |
| O41 | −0.1879 | 0.2915 | 0.0585 |
| H42 | 0.3077 | 0.3275 | 0.1257 |
| H43 | 0.1538 | 0.2201 | 0.0743 |
| H44 | 0.5279 | 0.4347 | 0.1149 |
| H45 | 0.7124 | 0.4674 | 0.0613 |
| H46 | 0.4192 | 0.2973 | 0.0255 |
| H47 | 0.2578 | 0.0900 | 0.0153 |
| H48 | 0.1288 | 0.1011 | 0.0254 |
| H49 | 0.0936 | 0.1554 | −0.0028 |
| H50 | 0.2571 | 0.2098 | −0.0092 |
| H51 | 0.3036 | 0.5397 | −0.0022 |
| H52 | 0.2392 | 0.5114 | −0.0309 |
| H53 | 0.2974 | 0.4009 | −0.0274 |
| H54 | 0.0792 | 0.2199 | −0.0265 |
| H55 | 0.1025 | 0.3114 | −0.0456 |
| H56 | −0.0076 | 0.4161 | −0.0330 |
| H57 | −0.0551 | 0.2416 | −0.0013 |
| H58 | −0.1201 | 0.3469 | −0.0044 |
| H59 | 0.0964 | 0.5331 | −0.0071 |
| H60 | 0.1837 | 0.6722 | 0.0512 |
| H61 | 0.0338 | 0.5217 | 0.0502 |
| H62 | 0.1844 | 0.5224 | 0.0503 |
| H63 | −0.2772 | 0.1614 | −0.0127 |
| H64 | −0.2760 | 0.2805 | −0.0267 |
| H65 | −0.3579 | 0.1133 | −0.0329 |
| H66 | −0.0504 | 0.2577 | −0.0592 |
| H67 | −0.1794 | 0.3278 | −0.0737 |
| H68 | −0.3053 | 0.2578 | −0.0581 |
| H69 | −0.1526 | 0.3966 | −0.0528 |
| H70 | −0.2410 | 0.0701 | −0.0746 |
| H71 | −0.1946 | 0.0132 | −0.0562 |
| H72 | −0.3347 | 0.0316 | −0.0554 |
| H73 | −0.1530 | 0.1183 | −0.0305 |
| H74 | 0.0220 | 0.3750 | 0.0260 |
| H75 | 0.1982 | 0.2109 | 0.0512 |
| H76 | 0.2980 | 0.8016 | 0.0030 |
| H77 | 0.4177 | 0.8365 | −0.0131 |
| H78 | −0.2680 | 0.2326 | 0.0385 |
| H79 | −0.2444 | 0.1328 | 0.0235 |
| H80 | −0.2485 | 0.2185 | 0.0683 |
| H81 | −0.1126 | 0.2683 | 0.0544 |
| H82 | −0.0947 | 0.0714 | 0.0059 |
| H83 | −0.0825 | 0.1005 | 0.0284 |

TABLE 10

Characteristic powder x-ray diffraction peak positions (degrees 2θ ± 0.1)@ RT for Examples 2a, b, d, e, f, g, and h, based on a high quality pattern collected with a diffractometer (CuKα) with a spinning capillary with 2θ calibrated with a NIST other suitable standard.

| Exp 2a | Exp 2b | Exp 2d | Exp 2e | Exp 2f | Exp 2g | Exp 2h |
|---|---|---|---|---|---|---|
| 8.1 | 10.0 | 5.5 | 10.1 | 7.2 | 6.3 | 6.9 |
| 11.7 | 11.4 | 9.6 | 11.3 | 8.7 | 9.0 | 8.7 |
| 13.0 | 11.9 | 11.4 | 11.9 | 9.7 | 11.7 | 9.8 |
| 13.9 | 14.3 | 14.5 | 13.3 | 12.5 | 15.0 | 10.3 |
| 16.6 | 15.6 | 15.8 | 14.2 | 12.8 | 17.6 | 11.8 |
| 17.0 | 16.5 | 16.6 | 15.6 | 13.3 | 18.6 | 13.5 |
| 17.6 | 19.1 | 18.4 | 16.8 | 16.0 | 19.7 | 15.0 |
| 21.1 | 19.4 | 19.2 | 19.0 | 16.6 | 20.7 | 18.8 |
| 23.2 | 20.2 | 20.0 | 19.5 | 18.2 | 21.4 | 21.4 |
| 23.9 | 21.2 | 23.6 | 20.4 | 18.8 | 23.8 | 22.9 |

Comparative Pharmacological Characteristics

Assays and data comparing the pharmacological characteristics of Example 1 and compounds found in WO2005021500 (corresponding to U.S. Pat. No. 7,163,937 assigned to present Applicant) are presented below.

Human Peripheral Blood Mononuclear Cell Binding ("CCR2 Binding")

See also: Yoshimura et al., *J. Immunol.* 1990, 145, 292. The human CCR2 binding assay was established with human peripheral blood mononuclear cells (hPBMCs) using $^{125}$I-human MCP-1 as the tracer ligand. hPBMCs were isolated from human leukopak (Biological Specialty Inc.) using a standard protocol with Ficoll-Hypaque (Mediatech Cellgro). Isolated hPBMCs were washed and diluted to $1\times10^7$/ml in binding buffer (RPMI-1640, 0.1% BSA, 20 mM Hepes, pH 7.4). $^{125}$I-MCP-1 (NEN/Perk Elmer) was diluted to 0.45 nM in binding buffer. The compound was diluted in binding buffer at 3-fold the final concentrations used in the binding assay. The binding assay was performed using a 96-well filter plate (Millipore). Total $^{125}$I-MCP-1 binding was assessed as follows: to each reaction of a total volume of 150 μl were added $5\times10^5$ cells, 0.15 nM $^{125}$I-MCP-1, and compound such that the final concentration ranged from 0 to 100 nM. The plate was incubated at room temperature for 30 minutes followed by three washes with RPMI-1640, 0.1% BSA, 0.4 M NaCl, 20 mM Hepes, pH 7.4 using a vacuum manifold filtration (Millipore). After washing, the plate was air-dried for 60 minutes at room temperature. This was followed by adding 25 μl of Microscint 20 into each well. The plate was sealed and counted on the Trilux for 1 minute. Non-specific binding was determined in the presence of 300 nM cold MCP-1 (Pepro-Tech Inc.). Specific $^{125}$I-MCP-1 was calculated as the difference between total and non-specific binding. All conditions were tested in duplicate. The IC50 is defined as the concentration of competing compound required to reduce specific binding by 50%.

hERG Flux

HEK293 cells stably-expressing hERG channels were grown (37° C., 5% $CO_2$) in Dulbecco's Modified Eagle's Media supplemented with 10% Sigma fetal bovine serum, non-essential amino acids, 2 mM L-glutamine and 500 μg/ml G418, at incubator. Cell dissociation buffer was used to extract the cells from flasks, which were then plated into 384-well Corning poly-D-lysine coated black/clear plates at a density of $2\times10^4$ cells per well (20 μl) in 10% serum media, and incubated for 15-24 hours at 37° C. in a 5% $CO_2$ incubator until a confluent monolayer of cells was obtained.

A 2 mM stock of BTC-AM dye (Molecular Probes, Eugene, Oreg.) was prepared in 100% DMSO and then added 1:1 to 10% (w/v) pluronic acid in DMSO on the day of assay. The dye was then diluted in hERG external EP buffer (140 mM NaCl, 4.0 mM KCl, 1.8 mM $CaCl_2$, 1.0 mM $MgCl_2$, 10 mM HEPES, pH 7.3 and 10 mM glucose; all buffer components obtained from Sigma Chemical). This BTC dye mixture (30 μl) was added to the cells and produced a final loading concentration of 2.5 μM. Cells are incubated at 21° C. for 45 minutes.

Test compounds were diluted to 10 mM DMSO in 60 μl. These compounds were then serially-diluted at a 1:2 ratio in DMSO in columns 1-10 and 11-20 of a 384-well plate. Assay-ready plates were generated by stamping 2.5 μl from the DMSO serially diluted plate, which was prepared on the Velocity 11 BioCel. Aqueous plates were created by adding 48 μl of EP buffer and then were diluted 30-45 minutes before the assay was read on the FLIPR. After dye loading, aqueous-diluted compounds were added to the cells of the three replicate plates (10 μl) yielding a ten point concentration range of 80 μM to 0.156 nM. Final DMSO concentration in the assay is 1%. Assay-ready aqueous plates were prepared and diluted on a Cybio liquid handler.

Cells loaded with dye were read on the FLIPR384 (Molecular Devices, Sunnyvale, Calif.), which excites the dye using the 488 nm line of an argon laser. Emission was filtered using a 540±30 nm bandpass filter. hERG channels are stimulated to open by the addition of 20 μl/well EP buffer containing 66 mM $K_2SO_4$ and 1.3 mM $Tl_2SO_4$ (Sigma/Aldrich). For each plate, data were collected every second for a period of 12 seconds, at which time the $Tl^+$-containing stimulus buffer was added. Data collection proceeded every second for 48 seconds, and then continued every three seconds for an additional 2 minutes.

The dynamic range of the assay was determined from blanks and totals wells. The totals wells (columns 21 and 22) define maximal hERG activation for the plate (no test compound present), and the blanks wells (columns 23 and 24) define 100% hERG inhibition. The blanks wells contain 400 nM of either of the standard hERG inhibitors dofetilide (Ficker et al., 1998) or E-4031. Raw data points in each sample well were first corrected for cell/signal variation, negative control (blanks) background, and normalized to the positive controls (totals) using the online FLIPR software. Test compound concentration response curves for the hERG $Tl^+$ flux data were then fit using Excel Fit (ID Business Solutions Limited, Surrey, UK) with a single-site logistic equation, $Y=A+((B-A)/1+((C/X)^D)))$ where A=maximal inhibition. Data were analyzed by fitting maximum amplitudes of change in fluorescence for $Tl^+$ flux for a given condition of test compound. Potencies ($IC_{50}$ values) of compounds were calculated from the average of triplicate wells.

Sodium Channel, Site 2 Binding Assay

See also: W. A. Catterall, et al. *J. Biol. Chem.* 1981, 256, 8922. The standard binding buffer contained 50 mM HEPES, 50 mM Tris-HCl, pH 7.4, 130 mM Choline Chloride, 5.4 mM KCl, 0.8 mM $MgCl_2$, 5.5 mM glucose, 40 μg/mL LqT. Binding reactions were initiated by adding synaptosomes (prepared from Wistar rat brain) to the reaction mixture containing 5 nM [$^3$H]-Batrachotoxin in a standard binding buffer and the compound to be tested at the desirable concentration. Samples were then mixed and incubated at 37° C. for 60 minutes. The reactions were stopped by adding ice-cold washing buffer containing 50 mM HEPES, 50 mM Tris-HCl, pH 7.4, 1.8 mM $CaCl_2$, 0.8 mM $MgCl_2$ and 1 mg/mL bovine serum albumin. The synaptosomes were immediately collected onto glass fiber filters and washed 3 times with washing buffers. The radioactivity of [$^3$H]-Batrachotoxin remaining on the filters was counted using liquid scintillation spectrometers.

Parallel Artificial Membrane Permeability Assay (PAMPA)

The Parallel Artificial Membrane Permeability Assay (PAMPA) consists of a specially formulated lecithin-based lipid combination referred to as the gastrointestinal tract (GIT) lipid. The GIT lipid is used to form a membrane in a sandwich plate assembly similar to that used in the Caco-2 assays. The GIT lipid closely resembles in vivo membrane composition and performance as measured by standard compounds that are known to be passively absorbed in humans. PAMPA is widely used as an in vitro model for permeability screening of discovery compounds. The rate of passage of compounds through the PAMPA membrane is used to determine a permeability coefficient (Pc), which can be related to the in vivo passive permeability of the compound.

The permeability coefficient (Pc) of a particular compound is examined in a pH-dependent setting with apical and basolateral pH of 7.4. All experiments are conducted in triplicate determinations.

Compounds (10 mM stocks in 100% DMSO) were diluted 1:100 in pH 7.4 donor well buffer (pION CAT # 110151), providing a 100 μM assay solution in 1% DMSO. Compound diluted in donor well buffer was transferred to a Whatman Unifilter plate and filtered prior to dispensing 200 μl into the donor well of the assay plate (pION CAT #110163). The PAMPA membrane was formed by pipetting 4 μl of the lipid solution (pION CAT #110169) onto the filter plate (VWR CAT #13503). The membrane was then covered with 200 μl of acceptor well buffer at pH 7.4 (pION CAT #110139). The PAMPA assay plate (donor side and acceptor side) was combined and allowed to incubate at room temperature for 4 hours. The plate was then disassembled and spectrophotometer plates (VWR CAT #655801) were filled (150 μl/well). The donor, acceptor, reference, and blank plates were read in the SpectraMax UV plate reader. Data was captured by the pION software, which analyzes the spectra and generates Pc values.

CCR2 Chemotaxis

The human CCR2 chemotaxis assay was conducted with the human monocytic cell line, THP-1. THP-1 cells were first labeled with the fluorescent dye Calcein-AM in phenol red-free, BSA-free RPMI-1640 (pH 7.4) at 37° C. for 30 minutes with gentle mixing every 15 minutes. The labeled cells were then washed and re-suspended at $1\times10^5$/ml in chemotaxis buffer (phenol red-free RPMI-1640, 0.1% BSA, pH 7.4). The test compound was diluted in chemotaxis buffer such that the final assay concentration ranged from 0.01 nM to 1 μM. The ligand MCP-1 (PeproTech Inc.) was diluted to 20 nM in chemotaxis buffer. To perform the assay, an equal volume of test compound dilutions was mixed with an equal volume of labeled THP-1 cells (Mixture 1), and an equal volume of test compound dilutions was mixed with an equal volume of diluted MCP-1 ligand (Mixture 2). Both mixtures were incubated independently at 37° C. for 10 minutes followed by gentle mixing. MCP-1-induced chemotaxis was then measured in a chemotaxis plate (Becton Dickinson) by placing 50 μl of Mixture 1 in the top chamber and 225 μl of Mixture 2 in the bottom chamber. The plate was covered with a lid and incubated at 37° C. for 30 minutes. 30 minutes later, the plate was read on a Cytofluor. All conditions were tested in duplicate. For signal to noise determination, 50 μl of labeled THP-1 cells alone ($5\times10^4$/well) were placed into the top chamber and 225 μl of ligand MCP-1 alone was placed in the bottom chamber (final concentration of 10 nM). The inhibition achieved by graded concentrations of test compound was calculated as a percentage of the compound-free MCP-1 control. The IC50 is defined as the concentration of test compound required to reach 50% inhibition of cellular chemotaxis.

hERG Patch Clamp

Whole-cell patch-clamp was used to directly measure hERG currents in HEK-293 cells stably expressing the cloned hERG potassium channel α subunit. The compound was tested in an aqueous buffer with pH 7.4 at room temperature. Repetitive test pulses (0.05 Hz) were applied from a holding potential of −80 mV to +20 mV for 2 seconds and tail currents were elicited following the test pulses by stepping the voltage to −65 mV. The effects from the compound were calculated by measuring inhibition of peak tail current Sodium Channel Patch Clamp Whole-cell patch-clamp was used to directly measure inward sodium currents in HEK-293 cells expressing the human cardiac sodium channel, SCN5A. The compound was tested at a protein-free aqueous buffer. For determining steady state inhibition, sodium currents were elicited every 5 seconds using the following voltage protocol: cells were held at a potential of −90 mV and stepped to −20 mV for 60 ms. Effects were calculated by measuring inhibition of peak current during the test pulse to −20 mV. Rate-dependence of inhibition was assessed by stimulation at frequencies of 1 Hz and 4 Hz.

Single-Dose Pharmacokinetics in Rats

Male Sprague-Dawley rats (250-300 g) were used for the pharmacokinetic studies. Rats were fasted overnight prior to PO dosing and fed 4 h post dose. Blood samples (~0.3 mL) were collected from the jugular vein into $K_2$EDTA-containing tubes and then centrifuged at 4° C. (1500-2000×g) to obtain plasma. In an oral bioavailability study, 2 groups of animals (N=2-3 per group) received the test compound either as an intravenous (IV) infusion (over 10 min) via the jugular vein or by oral gavage. Serial blood samples were obtained at 0.17 (for IV only), 0.25, 0.5, 0.75, 1, 2, 4, 6, 8, and 24 h post dose. Plasma samples, obtained by centrifugation at 4° C. (1500-2000×g), were stored at −20° C. until analysis by LC/MS/MS.

Single-Dose Pharmacokinetics in Monkeys

The pharmacokinetics of various test compounds were evaluated in male Cynomolgus monkeys in a crossover-design. Monkeys were fasted overnight prior to PO dosing and fed 4 h post dose. A group of 1-3 animals (3 to 5 kg) received the compound by IV infusion (over 10 min) via a femoral vein and by oral gavage, with a 1-week washout between treatments. Serial blood samples (~0.3 mL) were collected from a femoral artery at 0.17 (IV only), 0.25, 0.5, 0.75, 1, 2, 4, 6, 8, and 24 h post dose, and centrifuged at 4° C. (1500-2000×g) to obtain plasma. Samples were stored at −20° C. until analysis by LC/MS/MS.

Data Analysis for Pharmacokinetic Assays

The pharmacokinetic parameters were obtained by non-compartmental analysis of plasma concentration vs. time data (KINETICA™ software, Version 4.2, InnaPhase Corporation, Philadelphia, Pa.). The peak concentration (Cmax) and time for Cmax were recorded directly from experimental observations. The area under the curve from time zero to the last sampling time (AUC(0-T)) was calculated using a combination of linear and log trapezoidal summations. The total plasma clearance (CLTp), steady-state volume of distribution (Vss), apparent elimination half-life (T½) and mean residence time (MRT) were estimated after IV administration. Estimations of T½ was made using a minimum of 3 time points with quantifiable concentrations. The absolute oral bioavailability (F) was estimated as the ratio of dose-normalized AUC values following oral and IV doses.

Find below data for each compound as measured in the assays described above.

TABLE 11

Comparative In Vitro Data

| Compound | CCR2 Binding $IC_{50}$ (nM) | hERG FLUX $IC_{50}$ (nM) | Na$^+$ channel binding (% inhibition) | PAMPA permeability (nm/sec) |
|---|---|---|---|---|
| Example 12as, WO2005021500 | 0.27 (1) | 2,800 | Not available | Not available |
| Example 12aj WO2005021500 | 0.43 ± 0.06 (2) | 770 | Not available | Not available |
| Example 2k WO2005021500 | 0.88 ± 0.60 (23) | 51,000 | 97%, 10,000 nM | 529 ± 157 (9) |
| Example 12bd WO2005021500 | 1.15 ± 0.07 (2) | >80,000 | 54%, 10,000 nM | 392 |
| Example 8a WO2005021500 | 1.83 ± 0.80 (12) | >80,000 | 3%, 10,000 nM; 33%, 30,000 nM | 94 ± 58 (10) |
| Example 8e, WO2005021500 | 2.20 ± 0.03 (2) | >80,000 | 6%, 10,000 nM | 2 ± 2 (2) |
| Example 9c, WO2005021500 | 0.96 ± 0.26 (19) | >80,000 | 48%, 10,000 nM; 75%, 30,000 nM | 145 ± 71 (8) |
| Example 1 Present Invention | 1.14 ± 0.69 (75) | >80,000 | 0%, 10,000 nM; 21%, 30,000 nM | 443 ± 114 (8) |

TABLE 12a

Additional Comparative In Vitro Data

| Compound | CCR2 Chemotaxis $IC_{50}$ (nM) | hERG patch clamp (% Inhib.) | $Na^+$ channel patch clamp (% Inhib.) |
|---|---|---|---|
| Example 2k U.S. Pat. No. 7,163,937 | 0.24 ± 0.16 (72) | 83%, 10,000 nM 90%, 30,000 nM | 52%, 10,000 nM |
| Example 8a WO2005021500 | 2.63 ± 1.24 (4) | 4%, 10,000 nM | 22%, 10,000 nM 49%, 30,000 nM |
| Example 9c, WO2005021500 | 0.21 | 4%, 10,000 nM | 19%, 10,000 nM 39%, 30,000 nM |
| Example 1, Present Invention | 0.67 ± 0.42 (22) | 33%, 10,000 nM 61%, 30,000 nM | 17%, 10,000 nM 19%, 30,000 nM |

TABLE 12b

Comparative In Vivo Pharmacokinetic Data in the Rat

| Compound | Dose IV/PO (mg/kg) | Cl (mL/min/kg) | F % | Oral AUC (nM*h) |
|---|---|---|---|---|
| Example 2k WO2005021500 | 2.5/25 | 40 | 68 | 9294 |
| Example 8a WO2005021500 | 6/72 | 42 | 1.4 | 690 |
| Example 9c, WO2005021500 | 4/43 | 54 | 14 | 1855 |
| Example 1, Present Invention | 2/10 | 43 | 51 | 3794 |

TABLE 12c

Comparative In Vivo Pharmacokinetic Data in the Monkey

| Compound | Dose IV/PO (mg/kg) | Cl (mL/min/kg) | F % | Oral AUC (nM*h) |
|---|---|---|---|---|
| Example 2k WO2005021500 | 1/1.4 | 25 | 46 | 862 |
| Example 8a WO2005021500 | 1/11 | 14 | 9.4 | 1896 |
| Example 9c, WO2005021500 | 1/10 | 12 | 26 | 6763 |
| Example 1, Present Invention | 1/1.3 | 23 | 47 | 836 |

Utility

Representative compounds of the examples are shown to be modulators of chemokine receptor activity using assays know by those skilled in the art. In this section, we describe such assays and give their literature reference. More assays are described herein in the section titled "Comparative Pharmacological Characteristics", supra. By displaying activity in these assays of MCP-1 antagonism, compounds of the examples are expected to be useful in the treatment of human diseases associated with chemokines and their cognate receptors. The definition of activity in these assays is a compound demonstrating an $IC_{50}$ of 30 µM or lower in concentration when measured in a particular assay.

Antagonism of MCP-1 Binding to Human PBMC (Yoshimura et al., J. Immunol. 1990, 145, 292)

At least one compounds described in the examples have activity in the antagonism of MCP-1 binding to human PBMC (human peripheral blood mononuclear cells) described here.

Millipore filter plates (#MABVN1250) are treated with 100 µl of binding buffer (0.5% bovine serum albumin, 20 mM HEPES buffer and 5 mM magnesium chloride in RPMI 1640 media) for thirty minutes at room temperature. To measure binding, 50 µl of binding buffer, with or without a known concentration compound, is combined with 50 µl of $^{125}$-I labeled human MCP-1 (to give a final concentration of 150 pM radioligand) and 50 µl of binding buffer containing $5 \times 10^5$ cells. Cells used for such binding assays can include human peripheral blood mononuclear cells isolated by Ficoll-Hypaque gradient centrifugation, human monocytes (Weiner et al., J. Immunol. Methods. 1980, 36, 89), or the THP-1 cell line which expresses the endogenous receptor. The mixture of compound, cells and radioligand are incubated at room temperature for thirty minutes. Plates are placed onto a vacuum manifold, vacuum applied, and the plates washed three times with binding buffer containing 0.5M NaCl. The plastic skirt is removed from the plate, the plate allowed to air dry, the wells punched out and counted. The percent inhibition of binding is calculated using the total counts obtained in the absence of any competing compound and the background binding determined by addition of 100 nM MCP-1 in place of the test compound.

Antagonism of MCP-1-Induced Calcium Influx (Sullivan, et al. Methods Mol. Biol., 114, 125-133 (1999)

At least one compounds described in the examples have activity in the antagonism of MCP-1-induced calcium influx assay described here.

Calcium mobilization is measured using the fluorescent $Ca^{2+}$ indicator dye, Fluo-3. Cells are incubated at $8 \times 10^5$ cells/ml in phosphate-buffered saline containing 0.1% bovine serum albumin, 20 mM HEPES buffer, 5 mM glucose, 1% fetal bovine serum, 4 µM Fluo-3 AM and 2.5 mM probenecid for 60 minutes at 37° C. Cells used for such calcium assays can include human monocytes isolated as described by Weiner et al., J. Immunol. Methods, 36, 89-97 (1980) or cell lines which expresses the endogenous CCR2 receptor such as THP-1 and MonoMac-6. The cells are then washed three times in phosphate-buffered saline containing 0.1% bovine serum albumin, 20 mM HEPES, 5 mM glucose and 2.5 mM probenecid. The cells are resuspended in phosphate-buffered saline containing 0.5% bovine serum albumin, 20 mM HEPES and 2.5 mM probenecid at a final concentration of $2-4 \times 10^6$ cells/ml. Cells are plated into 96-well, black-wall microplates (100 µl/well) and the plates centrifuged at 200×g for 5 minutes. Various concentrations of compound are added to the wells (50 µl/well) and after 5 minutes, 50 µl/well of MCP-1 is added to give a final concentration of 10 nM. Calcium mobilization is detected by using a fluorescent-imaging plate reader. The cell monolayer is excited with an argon laser (488 nM) and cell-associated fluorescence measured for 3 minutes, (every second for the first 90 seconds and every 10 seconds for the next 90 seconds). Data are generated as arbitrary fluorescence units and the change in fluorescence for each well determined as the maximum-minimum differential. Compound-dependent inhibition is calculated relative to the response of MCP-1 alone.

Antagonism of MCP-1-Induced Human PBMC Chemotaxis (Bacon et al., Brit. J. Pharmacol. 1988, 95, 966)

At least one compounds described in the examples have activity in the antagonism of MCP-1-induced human PBMC chemotaxis assay described here.

Neuroprobe MBA96-96-well chemotaxis chamber, Polyfiltronics MPC 96 well plate, and Neuroprobe polyvinylpyrrolidone-free polycarbonate PFD5 8-micron filters are warmed in a 37° C. incubator. Human Peripheral Blood Mononuclear Cells (PBMCs) (Boyum et al., Scand. J. Clin. Lab Invest. Suppl. 1968, 97, 31), freshly isolated via the standard ficoll density separation method, are suspended in DMEM at $1 \times 10^7$ c/ml and warmed at 37° C. A 60 nM solution of human MCP-1 is also warmed at 37° C. Dilutions of test compounds are made up at 2× the concentration needed in DMEM. The PBMC suspension and the 60 nm MCP-1 solution are mixed 1:1 in polypropylene tubes with prewarmed DMEM with or without a dilution of the test compounds. These mixtures are warmed in a 37° C. tube warmer. To start the assay, add the MCP-1/compound mixture into the wells of the Polyfiltronics MPC 96 well plate that has been placed into the bottom part of the Neuroprobe chemotaxis chamber. The approximate volume is 400 μl to each well and there should be a positive meniscus after dispensing. The 8 micron filter is placed gently on top of the 96 well plate, a rubber gasket is attached to the bottom of the upper chamber, and the chamber is assembled. A 200 μl volume of the cell suspension/compound mixture is added to the appropriate wells of the upper chamber. The upper chamber is covered with a plate sealer, and the assembled unit is placed in a 37° C. incubator for 45 minutes. After incubation, the plate sealer is removed and all the remaining cell suspension is aspirated off. The chamber is disassembled and the filter gently removed. While holding the filter at a 90 degree angle, unmigrated cells are washed away using a gentle stream of phosphate buffered saline and the top of the filter wiped with the tip of a rubber squeegee. Repeat this wash twice more. The filter is air dried and then immersed completely in Wright Geimsa stain for 45 seconds. The filter is then washed by soaking in distilled water for 7 minutes, and then a 15 second additional wash in fresh distilled water. The filter is again air dried. Migrated cells on the filter are quantified by visual microscopy.

Mammalian chemokine receptors provide a target for interfering with or promoting immune cell function in a mammal, such as a human. Compounds that inhibit or promote chemokine receptor function are particularly useful for modulating immune cell function for therapeutic purposes. Accordingly, the present invention is directed to compounds which are useful in the prevention and/or treatment of a wide variety of inflammatory, infectious, and immunoregulatory disorders and diseases, including asthma and allergic diseases, infection by pathogenic microbes (which, by definition, includes viruses), as well as autoimmune pathologies such as the rheumatoid arthritis and atherosclerosis.

For example, an instant compound which inhibits one or more functions of a mammalian chemokine receptor (e.g., a human chemokine receptor) may be administered to inhibit (i.e., reduce or prevent) inflammation or infectious disease. As a result, one or more inflammatory process, such as leukocyte emigration, adhesion, chemotaxis, exocytosis (e.g., of enzymes, histamine) or inflammatory mediator release, is inhibited.

Similarly, an instant compound which promotes one or more functions of the mammalian chemokine receptor (e.g., a human chemokine) as administered to stimulate (induce or enhance) an immune or inflammatory response, such as leukocyte emigration, adhesion, chemotaxis, exocytosis (e.g., of enzymes, histamine) or inflammatory mediator release, resulting in the beneficial stimulation of inflammatory processes. For example, eosinophils can be recruited to combat parasitic infections. In addition, treatment of the aforementioned inflammatory, allergic and autoimmune diseases can also be contemplated for an instant compound which promotes one or more functions of the mammalian chemokine receptor if one contemplates the delivery of sufficient compound to cause the loss of receptor expression on cells through the induction of chemokine receptor internalization or the delivery of compound in a manner that results in the misdirection of the migration of cells.

In addition to primates, such as humans, a variety of other mammals can be treated according to the method of the present invention. For instance, mammals, including but not limited to, cows, sheep, goats, horses, dogs, cats, guinea pigs, rats or other bovine, ovine, equine, canine, feline, rodent or murine species can be treated. However, the method can also be practiced in other species, such as avian species. The subject treated in the methods above is a mammal, male or female, in whom modulation of chemokine receptor activity is desired. "Modulation" as used herein is intended to encompass antagonism, agonism, partial antagonism and/or partial agonism.

CCR5 Binding and Functional Assays

Cell derivation and cell culture: A pool of HT1080 cells stably expressing endogenous CC chemokine receptor 5 (CCR5) were developed using the methods outlined by Harrington, Sherf, and Rundlett (see U.S. Pat. Nos. 6,361,972 and 6,410,266). The highest-expressing clones were isolated using repetitive flow cytometry, followed by sub-cloning. These cells were then cultured in 6-well dishes at $3 \times 10^5$ cells/well and transfected with a DNA vector containing chimeric HA-tagged G protein Gqi5 (Molecular Devices; 5 micrograms of linearized vector DNA in 15 microl. of Ex-Gen from Fermentes was used for the transfection). Two days after transfection, the wells were combined and plated into P 100 plates. Seven days after plating, colonies were picked, expanded, and analyzed for Gqi5 content by Western blot. A clone (designated as 3559.1.6) having high expression of Gqi5 (from transfection) and of CCR5 (endogenous) was selected and used for the experiments described below. The HT1080 cells (clone 3559.1.6) were cultured with alpha-MEM supplemented with 10% dialyzed fetal bovine serum, 2% penicillin/streptomycin/glutamine, and 500 microgram/mL hygromycin B (final concentration) at 37° C. with 5% $CO_2$ in a humidified atmosphere.

Membrane Preparation: A cell pellet containing $1 \times 10^8$ HT1080 cells (clone 3559.1.6) was resuspended in 5 mL of ice-cold Membrane Prep Buffer (50 mM HEPES, 5 mM $MgCl_2$, 1 mM $CaCl_2$) and homogenized at high-speed on a Polytron homogenizer for 20 sec on ice. The homogenate was diluted with another 25 mL of Membrane Prep Buffer and centrifuged for 12 min (48,000×g at 4° C.). The cell pellet was resuspended in 5 mL of Membrane Prep Buffer before being rehomogenized as described previously. The homogenate was diluted with 5 mL of Membrane Prep Buffer and assayed for CCR5 protein concentration.

Binding assay: The freshly-prepared homogenate from the Membrane Preparation described above was diluted in Binding buffer (50 mM HEPES, 5 mM $MgCl_2$, 1 mM $CaCl_2$, 0.1% BSA; one complete protease inhibitor tablet was added before assay) to achieve a final protein concentration of 10 micrograms/well (solid white 96-well plates from Corning, Inc.). This membrane preparation was mixed with WGA-SPA beads (Amerhsam; pre-soaked in Binding buffer) to give a concentration of 200 micrograms/well. The membrane/SPA bead mix (100 microliters/well) was then added to a plate that had been pre-dotted with 2 microliters DMSO containing various concentrations of test articles (pure DMSO for negative control; various concentrations of examples of this invention for test articles; 500 nM MIP-1 beta as a positive control). The binding assay was initiated through the addition of 50 microliters of $[^{125}I]$-MJP-1 beta (Perkin Elmer; material was diluted in Binding buffer such that the addition of 50 microliters/well gives a final concentration of 0.1 nM $[^{125}I]$-MJP-1 beta). The plate was sealed and allowed to stand at room temperature for 4-6 h before being counted on a Packard TopCount. The percentage bound for the test article was calculated, using negative and positive controls to define the window for each experiment.

Fluorometric Imaging Plate Reader (FLIPR)-based Functional assay: HT1080 cells (clone 3559.1.6) were plated at 10,000 cells/well (30 microliters) in 384-well plates (black/clear bottom Biocoat PDL, Beckton Dickinson) and charged with 30 microliters/well of Fluro-4 AM fluorescent dye (prepared by dissolving 1 mg Fluro-4 AM in 440 microliters DMSO and diluting with 100 microliters of pluronic solution before diluting further with 10 mL of Hanks buffer). The cells were incubated at 37° C. with 5% $CO_2$ for 30 min before being washed three times and suspended in Assay Buffer (20 mM HEPES, 1.2 mM $CaCl_2$, 5 mM $MgC_2$, 2.5 mM Probenecid, 0.5% BSA, 1× Hanks). The test article was serially diluted in DMSO and then diluted 1:10 with Assay Buffer before being added to the cells (10 microliters/well). Using FLIPR, the plates were read (10-70 sec) for induction of flux (i.e. agonist activity). The cells were then further charged with Agonist Solution (30 microliters/well; prepared by diluting 30 microliters of 100 microMolar MIP-1 beta in 100 mL of Assay Buffer; this protocol delivers a final concentration of 5 nM MIP-1 beta in the assay) and the plates were read using FLIPR for one minute. Antagonist activity of the test article was determined relative to 0.4% DMSO/Buffer negative control.

Diseases or conditions of human or other species which can be treated with inhibitors of chemokine receptor function, include, but are not limited to: inflammatory or allergic diseases and conditions, including respiratory allergic diseases such as asthma, allergic rhinitis, hypersensitivity lung diseases, hypersensitivity pneumonitis, eosinophilic cellulitis (e.g., Well's syndrome), eosinophilic pneumonias (e.g., Loeffler's syndrome, chronic eosinophilic pneumonia), eosinophilic fasciitis (e.g., Shulman's syndrome), delayed-type hypersensitivity, interstitial lung diseases (ILD) (e.g., idiopathic pulmonary fibrosis, or ILD associated with rheumatoid arthritis, systemic lupus erythematosus, ankylosing spondylitis, systemic sclerosis, Sjogren's syndrome, polymyositis or dermatomyositis); systemic anaphylaxis or hypersensitivity responses, drug allergies (e.g., to penicillin, cephalosporins), eosinophilia-myalgia syndrome due to the ingestion of contaminated tryptophan, insect sting allergies; autoimmune diseases, such as rheumatoid arthritis, psoriatic arthritis, multiple sclerosis, systemic lupus erythematosus, myasthenia gravis, juvenile onset diabetes; glomerulonephritis, autoimmune thyroiditis, Behcet's disease; graft rejection (e.g., in transplantation), including allograft rejection or graft-versus-host disease; inflammatory bowel diseases, such as Crohn's disease and ulcerative colitis; spondyloarthropathies; scleroderma; psoriasis (including T-cell mediated psoriasis) and inflammatory dermatoses such as an dermatitis, eczema, atopic dermatitis, allergic contact dermatitis, urticaria; vasculitis (e.g., necrotizing, cutaneous, and hypersensitivity vasculitis); eosinophilic myositis, eosinophilic fasciitis; cancers with leukocyte infiltration of the skin or organs. Other diseases or conditions in which undesirable inflammatory responses are to be inhibited can be treated, including, but not limited to, vasculitis, vulnerable plaques, venous neointimal hyperplasia reperfusion injury, dialysis-graft neointimal hyperplasia, artio-venous shunt intimal hyperplasia, atherosclerosis, certain hematologic malignancies, cytokine-induced toxicity (e.g., septic shock, endotoxic shock), polymyositis, dermatomyositis. Infectious diseases or conditions of human or other species which can be treated with inhibitors of chemokine receptor function, include, but are not limited to, HIV.

Diseases or conditions of humans or other species which can be treated with promoters of chemokine receptor function, include, but are not limited to: immunosuppression, such as that in individuals with immunodeficiency syndromes such as AIDS or other viral infections, individuals undergoing radiation therapy, chemotherapy, therapy for autoimmune disease or drug therapy (e.g., corticosteroid therapy), which causes immunosuppression; immunosuppression due to congenital deficiency in receptor function or other causes; and infections diseases, such as parasitic diseases, including, but not limited to helminth infections, such as nematodes (round worms); (Trichuriasis, Enterobiasis, Ascariasis, Hookworm, Strongyloidiasis, Trichinosis, filariasis); trematodes (flukes) (Schistosomiasis, Clonorchiasis), cestodes (tape worms) (*Echinococcosis, Taeniasis saginata*, Cysticercosis); visceral worms, visceral larva migraines (e.g., Toxocara), eosinophilic gastroenteritis (e.g., *Anisaki* sp., *Phocanema* sp.), cutaneous larva migraines (*Ancylostona braziliense, Ancylostoma caninum*). The compounds of the present invention are accordingly useful in the prevention and treatment of a wide variety of inflammatory, infectious and immunoregulatory disorders and diseases.

In addition, treatment of the aforementioned inflammatory, allergic and autoimmune diseases can also be contemplated for promoters of chemokine receptor function if one contemplates the delivery of sufficient compound to cause the loss of receptor expression on cells through the induction of chemokine receptor internalization or delivery of compound in a manner that results in the misdirection of the migration of cells.

In another aspect, the instant invention may be used to evaluate the putative specific agonists or antagonists of a G protein coupled receptor. The present invention is directed to the use of these compounds in the preparation and execution of screening assays for compounds that modulate the activity of chemokine receptors. Furthermore, the compounds of this invention are useful in establishing or determining the binding site of other compounds to chemokine receptors, e.g., by competitive inhibition or as a reference in an assay to compare its known activity to a compound with an unknown activity. When developing new assays or protocols, compounds according to the present invention could be used to test their effectiveness. Specifically, such compounds may be provided in a commercial kit, for example, for use in pharmaceutical research involving the aforementioned diseases.

The compounds of the instant invention are also useful for the evaluation of putative specific modulators of the chemokine receptors. In addition, one could utilize compounds of this invention to examine the specificity of G protein coupled receptors that are not thought to be chemokine receptors, either by serving as examples of compounds which do not bind or as structural variants of compounds active on these receptors which may help define specific sites of interaction.

Compounds disclosed herein are useful to treat or prevent disorders selected from rheumatoid arthritis, osteoarthritis, septic shock, atherosclerosis, aneurism, fever, cardiovascular effects, haemodynamic shock, sepsis syndrome, post ischemic reperfusion injury, malaria, Crohn's disease, inflammatory bowel diseases, mycobacterial infection, meningitis, psoriasis, congestive heart failure, fibrotic diseases, cachexia, graft rejection, autoimmune diseases, skin inflammatory diseases, multiple sclerosis, radiation damage, hyperoxic alveolar injury, HIV, HIV dementia, non-insulin dependent diabetes mellitus, asthma, allergic rhinitis, atopic dermatitis, idiopathic pulmonary fibrosis, bullous pemphigoid, helminthic parasitic infections, allergic colitis, eczema, conjunctivitis, transplantation, familial eosinophilia, eosinophilic cellulitis, eosinophilic pneumonias, eosinophilic fasciitis, eosinophilic gastroenteritis, drug induced eosinophilia, cystic fibrosis, Churg-Strauss syndrome, lymphoma, Hodgkin's disease, colonic carcinoma, Felty's syndrome, sarcoidosis, uveitis, Alzheimer, Glomerulonephritis, and systemic lupus erythematosus, esophageal squamous cell carcinoma, neuropathic pain, and obesity.

In another aspect, the compounds are useful to treat or prevent inflammatory disorders selected from rheumatoid arthritis, osteoarthritis, atherosclerosis, aneurism, fever, cardiovascular effects, Crohn's disease, inflammatory bowel diseases, psoriasis, congestive heart failure, multiple sclerosis, autoimmune diseases, skin inflammatory diseases.

In another aspect, the compounds are used to treat or prevent inflammatory disorders selected from rheumatoid arthritis, osteoarthritis, atherosclerosis, Crohn's disease, inflammatory bowel diseases, and multiple sclerosis.

In another aspect, examples disclosed herein may be useful in for the treatment of a variety of cancers, including, but not limited to, the following:

carcinoma including that of the bladder (including accelerated and metastatic bladder cancer), breast, colon (including colorectal cancer), kidney, liver, lung (including small and non-small cell lung cancer and lung adenocarcinoma), ovary, prostate, testes, genitourinary tract, lymphatic system, rectum, larynx, pancreas (including exocrine pancreatic carcinoma), esophagus, stomach, gall bladder, cervix, thyroid, and skin (including squamous cell carcinoma);

hematopoietic tumors of lymphoid lineage including leukemia, acute lymphocytic leukemia, acute lymphoblastic leukemia, B-cell lymphoma, T-cell lymphoma, Hodgkin's lymphoma, non-Hodgkin's lymphoma, hairy cell lymphoma, histiocytic lymphoma, and Burketts lymphoma;

hematopoietic tumors of myeloid lineage including acute and chronic myelogenous leukemias, myelodysplastic syndrome, myeloid leukemia, and promyelocytic leukemia;

tumors of the central and peripheral nervous system including astrocytoma, neuroblastoma, glioma, and schwannomas;

tumors of mesenchymal origin including fibrosarcoma, rhabdomyoscarcoma, and osteosarcoma; and other tumors including melanoma, xenoderma pigmentosum, keratoactanthoma, seminoma, thyroid follicular cancer, and teratocarcinoma.

In another embodiment, disclosed herein are methods of treating cancer, wherein the cancer is selected from breast cancer, liver cancer, prostate cancer, and melanoma. Additionally, compounds disclosed herein may be useful in the treatment of ovarian cancer, and multiple myeloma.

The present invention provides methods for the treatment of a variety of non-cancerous proliferative diseases.

Combined therapy to prevent and treat inflammatory, infectious and immunoregulatory disorders and diseases, including asthma and allergic diseases, as well as autoimmune pathologies such as rheumatoid arthritis and atherosclerosis, and those pathologies noted above is illustrated by the combination of the compounds of this invention and other compounds which are known for such utilities. For example, in the treatment or prevention of inflammation, the present compounds may be used in conjunction with an anti-inflammatory or analgesic agent such as an opiate agonist, a lipoxygenase inhibitor, a cyclooxygenase-2 inhibitor, an interleukin inhibitor, such as an interleukin-1 inhibitor, a tumor necrosis factor inhibitor, an NMDA antagonist, an inhibitor or nitric oxide or an inhibitor of the synthesis of nitric oxide, a non-steroidal anti-inflammatory agent, a phosphodiesterase inhibitor, or a cytokine-suppressing anti-inflammatory agent, for example with a compound such as acetaminophen, aspirin, codeine, fentaynl, ibuprofen, indomethacin, ketorolac, morphine, naproxen, phenacetin, piroxicam, a steroidal analgesic, sufentanyl, sunlindac, interferon alpha and the like. Similarly, the instant compounds may be administered with a pain reliever; a potentiator such as caffeine, an H2-antagonist, simethicone, aluminum or magnesium hydroxide; a decongestant such as phenylephrine, phenylpropanolamine, pseudophedrine, oxymetazoline, ephinephrine, naphazoline, xylometazoline, propylhexedrine, or levodesoxy-ephedrine; and antitussive such as codeine, hydrocodone, caramiphen, carbetapentane, or dextramethorphan; a diuretic; and a sedating or non-sedating antihistamine. Likewise, compounds disclosed herein may be used in combination with other drugs that are used in the treatment/prevention/suppression or amelioration of the diseases or conditions for which compound of the present invention are useful. Such other drugs may be administered, by a route and in an amount commonly used therefore, contemporaneously or sequentially with a compound of the present invention. When a compound is used contemporaneously with one or more other drugs, a pharmaceutical composition containing such other drugs in addition to the compound of the present invention may be used. Accordingly, the pharmaceutical compositions include those that also contain one or more other active ingredients, in addition to a compound of the present disclosure.

Examples of other active ingredients that may be combined with a compound of the present invention, either administered separately or in the same pharmaceutical compositions, include, but are not limited to: (a) integrin antagonists such as those for selectins, ICAMs and VLA-4; (b) steroids such as beclomethasone, methylprednisolone, betamethasone, prednisone, dexamethasone, and hydrocortisone; (c) immunosuppressants such as cyclosporin, tacrolimus, rapamycin and other FK-506 type immunosuppressants; (d) antihistamines (H1-histamine antagonists) such as bromopheniramine, chlorpheniramine, dexchlorpheniramine, triprolidine, clemastine, diphenhydramine, diphenylpyraline, tripelennamine, hydroxyzine, methdilazine, promethazine, trimeprazine, azatadine, cyproheptadine, antazoline, pheniramine pyrilamine, astemizole, terfenadine, loratadine, cetirizine, fexofenadine, descarboethoxyloratadine, and the like; (e) non-steroidal anti-asthmatics such as b2-agonists (terbutaline, metaproterenol, fenoterol, isoetharine, albuteral, bitolterol, and pirbuterol), theophylline, cromolyn sodium, atropine, ipratropium bromide, leukotriene antagonists (zafirlukast, montelukast, pranlukast, iralukast, pobilukast, SKB-102, 203), leukotriene biosynthesis inhibitors (zileuton, BAY-1005); (f) non-steroidal antiinflammatory agents (NSAIDs) such as propionic acid derivatives (alminoprofen, benxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, pranoprofen, suprofen, tiaprofenic acid, and tioxaprofen), acetic acid derivatives (indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin, and zomepirac), fenamic acid derivatives (flufenamic acid, meclofenamic acid, mefenamic acid, niflumic acid and tolfenamic acid), biphenylcarboxylic acid derivatives (diflunisal and flufenisal), oxicams (isoxicam, piroxicam, sudoxicam and tenoxican), salicylates (acetyl salicylic acid, sulfasalazine) and the pyrazolones (apazone, bezpiperylon, feprazone, mofebutazone, oxyphenbutazone, phenylbutazone); (g) cyclooxygenase-2 (COX-2) inhibitors; (h) inhibitors of phosphodiesterase type IV (PDE-IV); (i) other antagonists of the chemokine receptors; (j) cholesterol lowering agents such as HMG-COA reductase inhibitors (lovastatin, simvastatin and pravastatin, fluvastatin, atorvsatatin, and other statins), sequestrants (cholestyramine and colestipol), nicotonic acid, fenofibric acid derivatives (gemfibrozil, clofibrat, fenofibrate and benzafibrate), and probucol; (k) anti-diabetic agents such as insulin, sulfonylureas, biguanides (metformin), a-glucosidase inhibitors (acarbose) and glitazones (troglitazone ad pioglitazone); (l) preparations of interferons (interferon alpha-2a, interferon-2B, interferon alpha-N3, interferon beta-1a, interferon beta-1b, interferon gamma-1b); (m) antiviral compounds such as efavirenz, nevirapine, indinavir, ganciclovir, lamivudine, famciclovir, and zalcitabine; (o) other compound such as 5-aminosalicylic acid an prodrugs thereof, antimetabolites such as azathioprine and 6-mercaptopurine, and cytotoxic cancer chemotherapeutic agents. The weight ratio of the compound of the present invention to the second active ingredient may be varied and will depend upon the effective doses of each ingredient.

Generally, an effective dose of each will be used. Thus, for example, when a compound is combined with an NSAID the weight ratio of the compound of the present invention to the NSAID will generally range from about 1000:1 to about 1:1000, or alternatively from about 200:1 to about 1:200. Combinations of a compound of the present invention and other active ingredients will generally also be within the aforementioned range, but in each case, an effective dose of each active ingredient should be used.

In treating cancer, a combination of chemotherapeutic agents and/or other treatments (e.g., radiation therapy) is often advantageous. The second (or third) agent may have the same or different mechanism of action than the primary therapeutic agent. It may be especially useful to employ cytotoxic drug combinations wherein the two or more drugs being administered act in different manners or in different phased of the cell cycle, and/or where the two or more drugs have overlapping toxicities or side effects, and/or where the drugs being combined each has a demonstrated efficacy in treating the particular disease state manifested by the patient.

Accordingly, compounds disclosed herein (or other formulae disclosed herein) may be administered in combination with other anti-cancer and cytotoxic agents and treatments useful in the treatment of cancer or other proliferative diseases. The invention herein further comprises use of the compounds herein (or other formulae disclosed herein), in preparing medicaments for the treatment of cancer, and/or it comprises the packaging of the compounds of herein together with instructions that the compounds be used in combination with other anti-cancer or cytotoxic agents and treatments for the treatment of cancer. The present invention further comprises combinations of the compounds of and one or more additional agents in kit form, e.g., where they are packaged together or placed in separate packages to be sold together as a kit, or where they are packaged to be formulated together.

The second (or more) anti-cancer agents may be selected from any one or more of the following:

alkylating agents (including nitrogen mustards, alkyl sulfonates, nitrosoureas, ethylenimine derivatives, and triazenes); anti-angiogenics (including matrix metalloproteinase inhibitors); antimetabolites (including adenosine deaminase inhibitors, folic acid antagonists, purine analogues, and pyrimidine analogues); antibiotics or antibodies (including monoclonal antibodies, CTLA-4 antibodies, anthracyclines); aromatase inhibitors;

cell-cycle response modifiers; enzymes; farnesyl-protein transferase inhibitors;

hormonal and antihormonal agents and steroids (including synthetic analogs, glucocorticoids, estrogens/anti-estrogens [e.g., SERMs], androgens/anti-androgens, progestins, progesterone receptor agonists, and luteinizing hormone-releasing [LHRH] agonists and antagonists); insulin-like growth factor (IGF)/insulin-like growth factor receptor (IGFR) system modulators (including IGFR1 inhibitors); integrin-signaling inhibitors; kinase inhibitors (including multi-kinase inhibitors and/or inhibitors of Src kinase or Src/abl, cyclin dependent kinase [CDK] inhibitors, panHer, Her-1 and Her-2 antibodies, VEGF inhibitors, including anti-VEGF antibodies, EGFR inhibitors, mitogen-activated protein [MAP] inhibitors, MEK inhibitors, Aurora kinase inhibitors, PDGF inhibitors, and other tyrosine kinase inhibitors or serine/threonine kinase inhibitors;

microtubule-disruptor agents, such as ecteinascidins or their analogs and derivatives; microtubule-stabilizing agents such as taxanes, and the naturally-occurring epothilones and their synthetic and semi-synthetic analogs;

microtubule-binding, destabilizing agents (including vinca alkaloids); and topoisomerase inhibitors; prenyl-protein transferase inhibitors; platinum coordination complexes; signal transduction inhibitors; and other agents used as anti-cancer and cytotoxic agents such as biological response modifiers, growth factors, and immune modulators.

Additionally, the compounds of the present invention can be formulated or co-administered with other therapeutic agents that are selected for their particular usefulness in addressing side effects associated with the aforementioned conditions. For example, compounds of the invention may be formulated with agents to prevent nausea, hypersensitivity and gastric irritation, such as antiemetics, and $H_1$ and $H_2$ antihistaminics.

The above other therapeutic agents, when employed in combination with the compounds of the present invention, can be used, for example, in those amounts indicated in the Physicians' Desk Reference (PDR) or as otherwise determined by one of ordinary skill in the art.

The compounds are administered to a mammal in a therapeutically effective amount. By "therapeutically effective amount" it is meant an amount of a compound of the present disclosure that, when administered alone or in combination with an additional therapeutic agent to a mammal, is effective to prevent or ameliorate the disease condition or the progression of the disease.

Dosage and Formulation

The compounds of this disclosure can be administered in such oral dosage forms as tablets, capsules (each of which includes sustained release or timed release formulations), pills, powders, granules, elixirs, tinctures, suspensions, syrups, and emulsions. They may also be administered in intravenous (bolus or infusion), intraperitoneal, subcutaneous, or intramuscular form, all using dosage forms well known to those of ordinary skill in the pharmaceutical arts. They can be administered alone, but generally will be administered with a pharmaceutical carrier selected on the basis of the chosen route of administration and standard pharmaceutical practice.

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. A physician or veterinarian can determine and prescribe the effective amount of the drug required to prevent, counter, or arrest the progress of the disorder.

By way of general guidance, the daily oral dosage of each active ingredient, when used for the indicated effects, will range between about 0.001 to 1000 mg/kg of body weight, or between about 0.01 to 100 mg/kg of body weight per day, or alternatively, between about 1.0 to 20 mg/kg/day. Intravenously, the doses will range from about 1 to about 10 mg/kg/minute during a constant rate infusion. Compounds of this invention may be administered in a single daily dose, or the total daily dosage may be administered in divided doses of two, three, or four times daily. In one embodiment, the daily oral dosage of the active ingredient is between 3 and 600 mg either administered once daily or in divided doses administered twice daily. Alternatively, the active ingredient may be administered in doses of 10-20 mg administered twice daily or 40 to 100 mg administered once daily. Alternatively, the active ingredient may be administered a dose of 12.5 mg twice a day or 75 mg once a day. Alternatively, the active ingredient may be administered in doses of 3, 10, 30, 100, 300, and 600 mg administered either once or twice a day.

Compounds of this invention can be administered in intranasal form via topical use of suitable intranasal vehicles, or via transdermal routes, using transdermal skin patches. When administered in the form of a transdermal delivery system, the dosage administration will, of course, be continuous rather than intermittent throughout the dosage regimen.

The compounds are typically administered in admixture with suitable pharmaceutical diluents, excipients, or carriers (collectively referred to herein as pharmaceutical carriers) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl callulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

Compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Dosage forms (pharmaceutical compositions) suitable for administration may contain from about 1 milligram to about 100 milligrams of active ingredient per dosage unit. In these pharmaceutical compositions the active ingredient will ordinarily be present in an amount of about 0.5-95% by weight based on the total weight of the composition.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration may contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in *Remington's Pharmaceutical Sciences*, Mack Publishing Company, a standard reference text in this field.

Representative useful pharmaceutical dosage-forms for administration of the compounds of this invention can be illustrated as follows:

Capsules

A large number of unit capsules can be prepared by filling standard two-piece hard gelatin capsules each with 100 milligrams of powdered active ingredient, 150 milligrams of lactose, 50 milligrams of cellulose, and 6 milligrams magnesium stearate.

Soft Gelatin Capsules

A mixture of active ingredient in a digestable oil such as soybean oil, cottonseed oil or olive oil may be prepared and injected by means of a positive displacement pump into gelatin to form soft gelatin capsules containing 100 milligrams of the active ingredient. The capsules should be washed and dried.

Tablets

Tablets may be prepared by conventional procedures so that the dosage unit is 100 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

Injectable

A parenteral composition suitable for administration by injection may be prepared by stirring 1.5% by weight of active ingredient in 10% by volume propylene glycol and water. The solution should be made isotonic with sodium chloride and sterilized.

Suspension

An aqueous suspension can be prepared for oral administration so that each 5 mL contain 100 mg of finely divided active ingredient, 200 mg of sodium carboxymethyl cellulose, 5 mg of sodium benzoate, 1.0 g of sorbitol solution, U.S.P., and 0.025 mL of vanillin.

Where the compounds of this invention are combined with other anticoagulant agents, for example, a daily dosage may be about 0.1 to 100 milligrams of the compound of Formula I and about 1 to 7.5 milligrams of the second anticoagulant, per kilogram of patient body weight. For a tablet dosage form, the compounds of this invention generally may be present in an amount of about 5 to 10 milligrams per dosage unit, and the second anti-coagulant in an amount of about 1 to 5 milligrams per dosage unit.

Where two or more of the foregoing second therapeutic agents are administered with the compound of the examples, generally the amount of each component in a typical daily dosage and typical dosage form may be reduced relative to the usual dosage of the agent when administered alone, in view of the additive or synergistic effect of the therapeutic agents when administered in combination.

Particularly when provided as a single dosage unit, the potential exists for a chemical interaction between the combined active ingredients. For this reason, when the compound of the examples and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a material which effects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low viscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or administered in separate forms but at the same time by the same manner, will be readily apparent to those skilled in the art, once armed with the present disclosure.

Additionally, certain compounds disclosed herein may be useful as metabolites of other compounds. Therefore, in one embodiment, compounds may be useful either as a substantially pure compound, which may also then be incorporated into a pharmaceutical composition, or may be useful as metabolite which is generated after administration of the prodrug of that compound. In one embodiment, a compound may be useful as a metabolite by being useful for treating disorders as described herein.

"Substantially pure" as used herein is intended to include a compound having a purity greater than about 90 weight percent, including about 90, 91, 92, 93, 94, 95, 96, 97, 98, 99, and 100 percent.

As one example, a compound disclosed herein may be substantially pure in having a purity greater than about 90 percent (by weight), where the remaining less than about 10 percent of material comprises other metabolite of the compound, a prodrug of the compound, and/or reaction and/or processing impurities arising from its preparation.

Obviously, numerous modifications and variations of the present invention are possible in light of the above teachings. It is therefore to be understood that within the scope of the appended claims, the invention may be practiced otherwise that as specifically described herein.

In Vivo Assays and Efficacy

N-((1R,2S,5R)-5-(isopropyl(methyl)amino)-2-((S)-2-oxo-3-(6-(trifluoromethyl)quinazolin-4-ylamino)pyrrolidin-1-yl)cyclohexyl)acetamide (also referred to as "Example 1") was evaluated in the following in vivo assays as described below.

Section 1. Intradermal (ID) MCP-1 Challenge Model in Cynomolgus Monkey

Methods

Intradermal injection of MCP-1 results in the infiltration of mononuclear cells to the injection site. This model was initially developed to assess the inhibitory effect of CCR2 antagonists on the infiltration of mononuclear cells to the skin tissue injected with human MCP-1.

As described below, each monkey was dosed with Example 1 or its vehicle control (0.5% [w/v] carboxymethylcellulose) once daily for three days. Immediately after dosing on Day 3, all animals received at least 2 intradermal injections of 10 μg (50 μL/injection) of human MCP-1 (R & D Systems) and at least 2 intradermal injections of its DPBS control (50 μl/injection) at separate sites on the dorsal thorax. Dermal biopsies of all sites were obtained at approximately 18 hours following MCP-1 (or DPBS) challenge. Biopsies were processed for semi-quantitative histological evaluation. Representative sections of skin samples were examined by light microscopy, microscopic lesions and cellular infiltration were noted, and their incidences were tabulated.

In Study 1, Example 1 was orally administered at doses of 0, 6.5, 13, or 26 mg/kg to groups of 3 cynomolgus monkeys (1 or 2 per sex per group). In Study 2, naive animals were used to assess Example 1 at 0-, 10-, or 30-mg/kg doses in groups of 2 or 4 animals (1/sex for vehicle-dosed group; 2/sex for Example 1-dosed group).

For both studies, in addition to biopsy analysis, blood was collected and evaluated for complete blood counts and cell differentials. Also evaluated were plasma samples for compound concentrations, and serum samples for systemic inflammatory mediator levels.

Results

In the first study, MCP-1 induced recruitment of mononuclear cells to the skin of vehicle-treated control animals was 2.7±0.3 (on a scale of 0 to 4, Table 13). At 26 mg/kg, Example 1 inhibited the infiltration (56%). Two lower doses of 13 and 6.5 mg/kg achieved lower levels of inhibition. The compound also inhibited the infiltration of other cells types such as eosinophils and neutrophils. The plasma concentrations of the compound at 18 hours and their relationship to levels of inhibition and Cyno chemotaxis IC90 values are summarized in Table 13.

Two methods were used to determine the inhibitory potency of Example 1 in the in vitro chemotaxis assay. The first employs monkey PBMC's while the second uses L1.2 cells stably transfected with Cyno CCR2. The former was found to be highly variable (IC50=5.5±10 nM), the second gave a higher mean value, but was more consistent (IC50=11.4±8 nM). Based on this second value, the 26 mg/kg dose resulted in a free plasma concentration at 18 hours post-dosing of 2× the chemotaxis IC90 (Table 13).

In both studies, evaluation of changes in serum inflammatory mediators showed an increase (~3-fold) in MCP-1 level in Example 1-treated groups relative to vehicle control. In addition, complete blood count (CBC) analysis showed an increase (~3-fold) in neutrophils in Example 1-treated groups relative to vehicle control.

A hCCR2 KI mouse study was conducted to evaluate the effect of Example 1 on monocyte/macrophage infiltration in thioglycollate (TG) peritonitis model with cell differential counting-based and flow cytometry-based methodologies.

Section 2. Characterization of Human CCR2 Knockin (hCCR2 KI) Mouse

Methods

The hCCR2 KI mouse was genetically engineered by replacing the mouse CCR2 gene with the human CCR2 coding sequence. The mouse was obtained from the Gladstone Institute of Cardiovascular Diseases at the University of California San Francisco.

Standard PCR (gene-specific and quantitative) methods were used to distinguish wild type (mouse CCR2 gene) from targeted alleles (human CCR2 gene) and to determine the human CCR2 gene copy number and mouse CCR2 gene copy number with ear or tail samples. RT-PCR analysis of total RNA isolated from blood leukocyte was also conducted to determine the level of expression of human and mouse CCR2 mRNA. Flow cytometric analysis was used to determine the surface expression of human or mouse CCR2 proteins on blood monocytes. FACS analysis of monocyte/macrophage

TABLE 13

Summary of effects of Example 1 on infiltration of mononuclear cells and other cell types in response to MCP-1 challenge in Cynomolgus monkeys

| Doses (mg/kg) | Free plasma conc (nM) | Fold CTX IC90[a] | Fold CTX IC90[b] | MNC score (inh %) | PMN score | Eos score | Total cell score |
|---|---|---|---|---|---|---|---|
| 0 | 0 | 0 | 0 | 2.7 ± 0.3 (0%) | 0.8 ± 0.3 | 1.83 ± 0.3 | 5.3 ± 0.6 |
| 6.5 | 53 | 1.8 | 0.5 | 2.2 ± 0.6 (19%) | 0.8 ± 0.3 | 1.3 ± 0.8 | 4.3 ± 1.6 |
| 13 | 101 | 3.4 | 0.9 | 2.2 ± 0.3 (19%) | 0.7 ± 0.3 | 1.2 ± 0.6 | 4.0 ± 0.5 |
| 26 | 238 | 7.9 | 2.2 | 1.2 ± 0.6 (56%) | 0.2 ± 0.3 | 0.5 ± 0 | 1.8 ± 0.8 |

[a]Cynomolgus PBMC-based chemotaxis
[b]Chemotaxis with L1.2 cells stably expressing Cynomolgus CCR2

A second study was run in naive monkeys. Compared with the first study, Example 1 inhibited mononuclear cell infiltration to a greater degree (91%) at 30 mg/kg (high dose) and gave inhibition of 87% at 10 mg/kg (Table 14).

TABLE 14

Summary of effects of Example 1 on infiltration of mononuclear cells and other cell types in response to MCP-1 challenge in Cynomolgus monkeys

| Doses (mg/kg) | Free plasma conc (nM) | Fold CTX IC90[a] | Fold CTX IC90[b] | MNC score (inh %) | PMN score | Eos score | Total cell score |
|---|---|---|---|---|---|---|---|
| 0 | 0 | 0 | 0 | 1.5 (0%) | 1.3 | 0.4 | 3.2 |
| 10 | 34 | 1.1 | 0.37 | 0.2 ± 0.2 (87%) | 0 | 0.3 ± 0.1 | 0.5 ± 0.2 |
| 30 | 83 | 2.8 | 0.91 | 0.1 ± 0.3 (91%) | 0.1 ± 0.3 | 0.6 ± 0.7 | 0.8 ± 0.8 |

[a]Cynomolgus PBMC-based chemotaxis assay
[b]Chemotaxis assay with L1.2 cells stably expressing Cynomolgus CCR2 accumulation in the peritoneal cavity in TG-induced peritonitis models (see Section 3) were used to determine the functionality of human CCR2 in these mice.

Results

The hCCR2 KI mouse was genetically engineered by replacing the mouse CCR2 gene with the human CCR2 coding sequence. Prior to the use of these animals for in vivo evaluation of Example 1, both genotypic and phenotypic characterization of these mice was conducted. PCR-based genotypic studies (gene-specific and quantitative) of the ear or tail samples detected two copies of human CCR2 gene and varying quantities of PCR product suggesting the presence of 0 to 2 copies of the mouse CCR2 gene. With total cellular RNA isolated from blood leukocytes from these KI mice, relative quantitative RT-PCR analysis detected human CCR2 mRNA, and marginal levels of PCR product with the primer set designed to detect mouse CCR2 mRNA. When flow cytometric analysis was used to detect protein expression in the CCR2 KI mice, human CCR2, but not mouse CCR2, surface protein was detected by staining whole blood cell isolates with specific anti-human CCR2 and anti-mouse CCR2 antibodies, respectively.

The hCCR2-selective antagonists block monocyte infiltration in these hCCR2 KI mice, but not in wild-type mice, when plasma steady-state levels cover the IC90 for human CCR2 chemotaxis, but are below the levels required to inhibit mouse CCR2 chemotaxis. Furthermore, in in vitro assays that mimic hCCR2 KI setting (mouse MCP-1/human CCR2), Example 1 inhibits mouse MCP-1 binding to human CCR2 expressing hPBMCs (IC50=2.2±1.2 nM) and mouse MCP-1-induced/human CCR2 mediated chemotaxis of THP-1 cells (IC50=0.6±0.3 nM).

Section 3. 48-Hour Thioglycollate (TG)-Induced Peritonitis Model in hCCR2 KI Mouse Methods The hCCR2 KI mice (C57BL/6-SVJ129) were injected intraperitoneally with 1 ml of thioglycollate (TG) (Hardy Diagnostics). For each study, eight male mice per group were used. Example 1 was dosed orally 1 hour prior to TG injection. The vehicle used was 0.01 N HCl in water. Forty-eight hours post TG injection, peritoneal lavages were performed by injecting 5 ml PBS/10 mM EDTA/10% BSA into the peritoneal cavity.

For the 48-hour TG peritonitis study, Example 1 was dosed twice a day with the first dose one hour prior to TG injection. Total peritoneal cell counts were obtained on isolated cells by a cell counter. Cytospins were performed to determine differential leukocyte counts. The cells were stained for 3 minutes with Wright-Giemsa Stain (Sigma-Aldrich) and then rinsed with deionized water for 5 minutes. Differential counts were calculated based on a total of 200 cells counted per sample. Blood was also collected from the retro-orbital sinus at the end of each study in EDTA for determination of drug concentration.

For flow cytometric analysis, peritoneal exudate cells ($1\times10^6$) were washed once with FACS buffer (PBS/0.5% BSA) and resuspended in FACS buffer. Cells were incubated with an Fc-blocking antibody (BD Pharmingen) on ice for 15 min followed by addition of the following antibodies (BD Pharmingen): PE conjugated anti-F4/80, FITC conjugated anti-Ly6C, and Alexa 647 conjugated anti-hCCR2. After 45 min on ice, cells were fixed by BD Cytofix for 15 min on ice, washed twice with FACS buffer, and resuspended in 200 μl FACS buffer. Cellular events (40,000) were acquired for each sample and data were analyzed using FloJo software (Tree-Star). A FSC/SSC gate was set to include all monocytes (low SSC, higher FSC) while excluding granulocytes from the analysis. This gated population was then analyzed for Ly6C (FITC), F4/80 (PE) expression. Peritoneal monocytes/macrophage numbers were determined by multiplying total peritoneal cell counts obtained by the cell counter and the percentage of monocytes/macrophages identified by F4/80+ cells from flow cytometry. Statistical significance of differences between means was analyzed using the paired two-tailed t test with significance set at p values below 0.05.

Results

Figure 15:
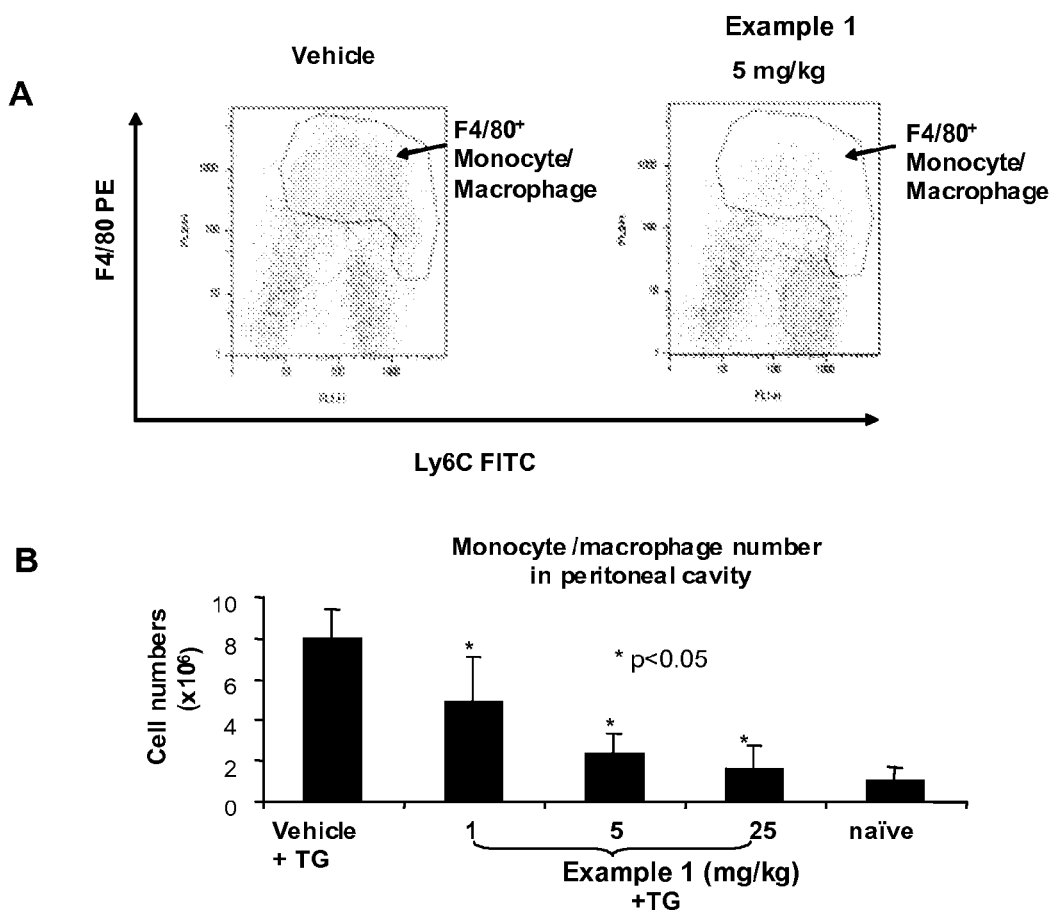
FIG. 15. 48-hour TG peritonitis model in hCCR2 KI mice: Example 1 inhibition of monocyte/macrophage infiltration into peritoneal cavity (FACS analysis).

Example 1 was evaluated in the hCCR2 KI mouse TG peritonitis model to determine its EC50 in inhibiting monocyte/macrophage infiltration. Mice were administered thioglycollate, and dosed orally with Example 1 at 1, 5, or 25 mg/kg BID. Forty eight hours post TG treatment, peritoneal lavage was obtained for cellular infiltrate analysis. Example 1 showed a dose-dependent reduction in the number of total peritoneal leukocytes obtained by cell counter (FIG. 15). Based on differential leukocyte counts by morphological evaluation of lavage samples, Example 1 demonstrated a dose-dependent inhibition of monocyte/macrophage influx. Doses of 1, 5, 25 mg/kg gave an inhibition of 20%, 62% and 69%, respectively. Statistically significant inhibition was reached at 5 and 25 mg/kg (FIG. 15). In two separate studies, the average EC50 for inhibition of monocyte/macrophage infiltration was estimated to be 3.0±0.9 nM.

Figure 16:
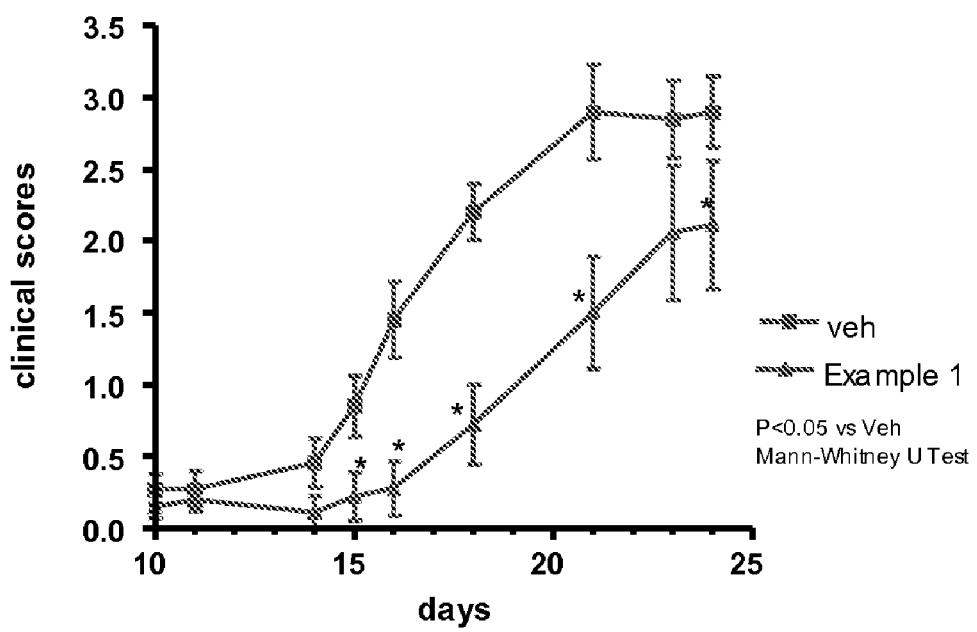
FIG. 16. EAE in hCCR2 KI mice: clinical score of Example 1 treatment

The recruited monocyte/macrophage infiltrate was also quantified by flow cytometry. To distinguish between the recruited monocyte/macrophages versus resident macrophages and granulocytes, staining of both F4/80 and Ly6C monocyte/macrophage surface markers was used to define the recruited monocyte/macrophages. A similar dose-dependent inhibition in monocyte/macrophage infiltration was observed by this method with all three doses showing statistically significant inhibition (FIG. 16). Doses of 1, 5, and 25 mg/kg gave an inhibition of 38%, 71% and 86%, respectively. In two separate studies, the average EC50 for inhibition of monocyte/macrophage infiltration by this analysis was estimated to be 2.2±0.5 nM.

To assess the in vivo level of receptor occupancy by Example 1 in the 48-hour thioglycolate peritonitis model using the hCCR2 knock-in mouse, plasma levels of both Example 1 and mouse CCR2 ligand MCP-1 were measured. The caveat for this estimation is that only CCR2 and its major ligand MCP-1, were taken into consideration. The receptor occupancy of a ligand in the presence of a competitive inhibitor is defined by the Gaddum equation:

$$\frac{[RL]}{[R]} = \frac{1}{1 + (K_d/[L])(1 + [I]/K_i)}$$

Since Example 1 is a competitive inhibitor of MCP-1 binding to CCR2, the amounts of both mouse MCP-1/CCR2 receptor complex and Example 1/CCR2 receptor complex can be determined using the serum levels of both mouse MCP-1 and protein-unbound Example 1 in plasma. The $K_d$ for mouse MCP-1 binding to hCCR2 is 0.91+/−0.08 nM (n=8) which was determined in cold competition ligand binding experiments using $^{125}$I-human MCP-1. The average Ki for Example 1 binding to hCCR2 is 1.2 nM. The fraction of mouse MCP-1/CCR2 receptor complexes is determined using the form of the equation described above. To determine the fraction of Example 1/CCR2 complexes the equation is re-defined as:

$$\frac{[RI]}{[R]} = \frac{1}{1 + (K_i/[I])(1 + [L]/K_d)}$$

Finally, the amount of CCR2 free is determined from:

[CCR2]$_{total}$=[CCR2]$_{free}$+[mouse MCP-1/CCR2]+
(Example 1/CCR2]

As shown in Table 15, the percent inhibition of monocyte/macrophage infiltration into the peritoneum at 48 h reflects the percentage of Example 1/CCR2 receptor complex (Example 1-occupied CCR2).

TABLE 15

Determination of in vivo receptor occupancy in blood of Hccr2 KI mice in the 48-hour TG peritonitis model

| Dose (mg/kg) | Concentration of Mouse MCP-1 in plasma (nM) | Concentration of free Example 1 in plasma (nM) (fold IC90 CCR2 binding) | % mouse MCP-1 bound CCR2 | % of Example 1-bound CCR2 | % free CCR2 | % inhibition of monocyte/ macrophage infiltration[a] |
|---|---|---|---|---|---|---|
| 25 | 0.041 | 24 (1.4) | 0.2 | 95.0 | 4.8 | 86 |
| 5 | 0.043 | 4 (0.2) | 1.1 | 76.1 | 22.8 | 71 |
| 1 | 0.027 | 1 (0.05) | 1.6 | 44.7 | 53.7 | 38 |
| 0 (vehicle) | 0.03 | 0 | 3.2 | 0 | 96.8 | 0 |

[a]FACS-based analysis of total monocyte/macrophages

Section 4. Chronic Efficacy Studies

Methods

To study the effect of Example 1 on EAE (experimental autoimmune encephalomyelositis) a model of multiple sclerosis, 10 mice per group were used. On day 0, hCCR2 KI mice were immunized subcutaneously with a total of 200 µl of 300 µg myelin oligodendrocyte glycoprotein (MOG) 35-55 (Genemed Synthesis) mixed 1:1 with 300 µg Mycobacterium tuberculosis (H37Ra) (Becton-Dickinson) in incomplete Freund's adjuvant (IFA) (Sigma-Aldrich). On day 0 (two hours post-immunization) and day 2, mice were injected intraperitoneally with 100 µl of 400 ng pertussis toxin. Clinical scoring began on day 10, continued three times per week throughout the study, and was based on a scale of 0-5: 0, no signs of disease; 0.5, partial tail weakness; 1, limp tail or waddling gait with tail tonicity; 1.5, waddling gait with partial tail weakness; 2, wadding gait with limp tail (ataxia); 2.5 (ataxia with partial limb paralysis; 3, full paralysis of one limb; 3.5, full paralysis of one limb with partial paralysis of a second limb; 4, full paralysis of two limbs; 4.5, moribund; 5, death. Oral dosing of Example 1 at 55 mg/kg (BID) was initiated on day 1.

Results

In two of the three studies conducted, Example 1 significantly reduced the clinical score (p<0.05) (FIG. 17). The IC50 is 2.2 nM for Example 1 in $^{125}$I-mouse MCP-1 binding to hCCR2-expressing cells, hPBMCs (mimicking hCCR2 KI setting). Based on this IC50 value, the 55 mg/kg doses resulted in a free plasma trough concentration of ~2-fold the binding IC90. Histological evaluation of the spinal cord on Day 22 did not demonstrate a significant difference in total inflammatory cellular infiltrate between mice treated with Example 1 versus vehicle. A marked neutrophil infiltrate was observed in mice treated with compound.

What is claimed is:

1. A crystalline form of a compound, N-((1R,2S,5R)-5-(isopropyl(methyl)amino)-2-((S)-2-oxo-3-(6-(trifluoromethyl)quinazolin-4-ylanlino)pyrrolidin-1-yl)cyclohexyl)acetamide, or a pharmaceutically acceptable salt thereof, wherein the crystalline form is the N-2 form.

2. The crystalline form according to claim 1 characterized by unit cell parameters substantially equal to the following:
   Cell dimensions:
   a=11.8427(3)
   b=18,1503(7)
   c=12.7923(4)
   α=90
   β=105.362(2)
   γ=90
   Space group P2$_1$
   Molecules/unit cell 2
wherein said crystal is at a temperature of about +22° C.

3. The crystalline form according to claim 1 characterized by a powder x-ray diffraction pattern comprising three or more of 2θ values (CuKαλ=1.541 Å) selected from 7.2, 8.7, 9.7, 12.5, 12.8, 13.3, 16.0, 16.6, 18.2, and 18.8, at a temperature of about 22° C.

4. The crystalline form according to claim 3 further characterized by a powder x-ray diffraction pattern comprising four or more of 2θ values (CuKαλ=1.541 Å) selected from the group consisting of 7.2, 8.7, 9.7, 12.5, 12.8, 13.3, 16.0, 16.6, 18.2, and 18.8, at a temperature of about 22° C.

5. The crystalline form according to claim 1 characterized by fractional atomic coordinates as listed in Table 7.

6. A pharmaceutical composition comprising a crystalline form according to claim 1, and a pharmaceutically acceptable carrier or diluent.

7. A compound, N-((1R,2S,5R)-5-(isopropyl(methyl)amino)-2-((S)-2-oxo-3-(6-(trifluoromethyl)quinazolin-4-ylamino)pyrrolidin-1-yl)cyclohexyl)acetamide,or a pharmaceutically acceptable salt thereof.

8. A compound of claim 7 that is a crystalline form of N-((1R,2S,5R)-5-(isopropyl(methyl)amino)-2-((S)-2-oxo-3-(6-(trifluoromethyl)quinazolin-4-ylamino)pyrrolidin-1-yl)cyclohexyl)acetamide, or a pharmaceutically acceptable salt thereof.

9. A pharmaceutical composition comprising a compound according to claim 7, and a pharmaceutically acceptable carrier or diluent.

* * * * *

UNITED STATES PATENT AND TRADEMARK OFFICE
CERTIFICATE OF CORRECTION

PATENT NO.        : 7,671,062 B2                                     Page 1 of 1
APPLICATION NO.   : 11/782704
DATED             : March 2, 2010
INVENTOR(S)       : Michael G. Yang and Robert J. Cherney It is certified that error appears in the above-identified patent and that said Letters Patent is hereby corrected as shown below:

On the Title Page and Column 1 line 1:

Title of the Invention
Line 1, "MODULATORS OF CHEMOKINE RECEPTOR ACTIVITY, CRYSTALLINE FORMS AND PROCESS" should read -- N-((IR,2S,5R)-5-(ISOPROPYL(METHYL)AMINO)-2-((S)-2-0XO-3-(6-TRIFLUOROMETHYL)QUINAZOLIN-4-YLAMINO)PYRROLIDIN-1-YL)CYCLOHEXYL)ACETAMIDE AND OTHER MODULATORS OF CHEMOKINE RECEPTOR ACTIVITY, CRYSTALLINE FORMS AND PROCESS --.

Column 112
Line 4, "ylanlino" should read -- ylamino --.

Signed and Sealed this
Twenty-second Day of February, 2011

David J. Kappos
*Director of the United States Patent and Trademark Office*